(12) United States Patent
Barlow et al.

(10) Patent No.: US 10,974,009 B2
(45) Date of Patent: Apr. 13, 2021

(54) UNOBTRUSIVE NASAL MASK

(71) Applicant: ResMed Pty Ltd, Bella Vista (AU)

(72) Inventors: Adam Francis Barlow, Sydney (AU); Matthew Eves, Sydney (AU); Lochlan Von Moger, Sydney (AU); Phoebe Katherine Hill, Sydney (AU); Kai Stuebiger, Sydeny (AU); Peter Ross Anderson, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 16/922,354

(22) Filed: Jul. 7, 2020

(65) Prior Publication Data

US 2020/0330713 A1    Oct. 22, 2020

Related U.S. Application Data

(63) Continuation of application No. 16/365,090, filed on Mar. 26, 2019, which is a continuation of application
(Continued)

(30) Foreign Application Priority Data

Jun. 2, 2009    (AU) .............................. 2009902524
Dec. 15, 2009   (AU) .............................. 2009906101
(Continued)

(51) Int. Cl.
 *A61M 16/06*   (2006.01)
 *A61M 16/08*   (2006.01)
 *A61M 16/00*   (2006.01)

(52) U.S. Cl.
 CPC .... *A61M 16/0622* (2014.02); *A61M 16/0075* (2013.01); *A61M 16/06* (2013.01);
(Continued)

(58) Field of Classification Search
 CPC ......... A61M 16/06–0694; A62B 18/02; A62B 18/025; A62B 18/06
 See application file for complete search history.

(56) References Cited

U.S. PATENT DOCUMENTS 122,905 A    1/1872   O'Dell
781,516 A *  1/1905   Guthrie, Jr. ............ A62B 23/06
                                                 128/206.18
(Continued)

FOREIGN PATENT DOCUMENTS

AU   PCT/AU2008/906390    12/2008
AU   PCT/AU2009/900327    1/2009
(Continued)

OTHER PUBLICATIONS

U.S. Appl. No. 12/377,801, filed Aug. 31, 2010, Veliss et al.
(Continued)

*Primary Examiner* — Valerie L Woodward
(74) *Attorney, Agent, or Firm* — Fish & Richardson P.C.

(57) ABSTRACT

A patient interface for delivering breathable gas to a patient includes a sealing portion including a nose tip engagement portion adapted to form a seal with the patient's nose tip, an upper lip engagement portion adapted to form a seal with the patient's upper lip and/or base of the patient's nares, and nostril engagement flaps adapted to form a seal with the patient's nares. The nose tip engagement portion, the upper lip engagement portion, and the nostril engagement flaps are all structured to extend or curve outwardly from a supporting wall defining an air path.

28 Claims, 125 Drawing Sheets

Related U.S. Application Data

No. 14/738,977, filed on Jun. 15, 2015, now Pat. No. 10,265,490, which is a continuation of application No. 13/321,981, filed as application No. PCT/AU2010/000684 on Jun. 2, 2010, now Pat. No. 9,095,673.

(60) Provisional application No. 61/222,711, filed on Jul. 2, 2009, provisional application No. 61/272,162, filed on Aug. 25, 2009, provisional application No. 61/272,250, filed on Sep. 4, 2009, provisional application No. 61/263,175, filed on Nov. 20, 2009, provisional application No. 61/282,693, filed on Mar. 18, 2010.

(30) Foreign Application Priority Data

May 28, 2010 (AU) .................................. 201902359
May 28, 2010 (WO) ................ PCT/AU2010/000657

(52) U.S. Cl.
CPC .... *A61M 16/0611* (2014.02); *A61M 16/0616* (2014.02); *A61M 16/0633* (2014.02); *A61M 16/0644* (2014.02); *A61M 16/0666* (2013.01); *A61M 16/0683* (2013.01); *A61M 16/0816* (2013.01); *A61M 16/0825* (2014.02); *A61M 2205/02* (2013.01); *A61M 2210/0618* (2013.01)

(56) References Cited

U.S. PATENT DOCUMENTS

| | | | |
|---|---|---|---|
| 844,097 A | 2/1907 | Caldwell | |
| 1,192,186 A | 7/1916 | Greene | |
| 1,229,050 A | 6/1917 | Donald | |
| 1,362,766 A | 12/1920 | Martin | |
| 1,445,010 A | 2/1923 | Feinberg | |
| 1,710,160 A | 2/1925 | Gibbs | |
| 2,126,755 A | 8/1938 | Dreyfus | |
| 2,130,555 A | 9/1938 | Malcom | |
| 2,228,218 A | 1/1941 | Schwartz | |
| 2,578,621 A | 12/1951 | Yant | |
| 2,706,983 A | 4/1955 | Matheson et al. | |
| 3,330,273 A | 7/1967 | Bennett | |
| 3,424,633 A | 1/1969 | Corrigall et al. | |
| 4,126,131 A | 11/1978 | Davis et al. | |
| 4,248,218 A | 2/1981 | Fischer | |
| 4,263,908 A | 4/1981 | Mizerak | |
| 4,537,192 A | 8/1985 | Foster | |
| 4,641,647 A | 2/1987 | Behan | |
| 4,676,236 A | 6/1987 | Piorkowski et al. | |
| 4,676,241 A | 6/1987 | Webb et al. | |
| 4,782,832 A | 11/1988 | Trimble et al. | |
| 4,919,128 A | 4/1990 | Kopala et al. | |
| 4,938,209 A | 7/1990 | Fry | |
| 4,944,310 A | 7/1990 | Sullivan | |
| 4,989,596 A | 2/1991 | Macris et al. | |
| 5,005,571 A | 4/1991 | Dietz | |
| 5,018,519 A | 5/1991 | Brown | |
| 5,042,478 A | 8/1991 | Kopala et al. | |
| 5,062,421 A | 11/1991 | Burns et al. | |
| D322,318 S | 12/1991 | Sullivan | |
| 5,243,971 A | 9/1993 | Sullivan et al. | |
| 5,265,595 A | 11/1993 | Rudolph | |
| 5,267,557 A | 12/1993 | Her-Mou | |
| 5,375,593 A | 12/1994 | Press | |
| 5,429,683 A | 7/1995 | Le Mitouard | |
| 5,513,634 A | 5/1996 | Jackson | |
| 5,526,806 A | 6/1996 | Sansoni | |
| 5,560,354 A | 10/1996 | Berthon-Jones et al. | |
| 5,657,752 A | 8/1997 | Landis et al. | |
| 5,662,101 A | 9/1997 | Ogden et al. | |
| 5,673,690 A | 10/1997 | Tayebi et al. | |
| 5,724,965 A | 3/1998 | Handke et al. | |
| 5,746,201 A | 5/1998 | Kidd | |
| 5,752,510 A * | 5/1998 | Goldstein | A61M 16/0488 |
| | | | 128/200.24 |
| D397,215 S | 8/1998 | Hoftman | |
| 5,921,239 A | 7/1999 | McCall et al. | |
| 6,016,804 A | 1/2000 | Gleason et al. | |
| D431,077 S | 9/2000 | McGinnis et al. | |
| 6,119,694 A * | 9/2000 | Correa | A61M 16/0666 |
| | | | 128/207.13 |
| 6,123,071 A | 9/2000 | Berthon-Jones et al. | |
| 6,182,660 B1 | 2/2001 | Hopper | |
| 6,192,886 B1 | 2/2001 | Rudolph | |
| 6,263,874 B1 | 7/2001 | LeDez et al. | |
| 6,412,488 B1 * | 7/2002 | Barnett | A61M 16/06 |
| | | | 128/205.25 |
| 6,418,928 B1 | 7/2002 | Bordewick et al. | |
| 6,431,172 B1 | 8/2002 | Bordewick | |
| 6,435,181 B1 | 8/2002 | Jones, Jr. et al. | |
| 6,457,473 B1 | 10/2002 | Brostrom et al. | |
| 6,467,483 B1 | 10/2002 | Kopacko et al. | |
| 6,478,026 B1 | 11/2002 | Wood | |
| 6,530,373 B1 | 3/2003 | Patron et al. | |
| 6,561,190 B1 | 5/2003 | Kwok | |
| 6,581,594 B1 | 6/2003 | Drew et al. | |
| 6,584,975 B1 | 7/2003 | Taylor | |
| 6,631,718 B1 | 10/2003 | Lovell | |
| 6,644,315 B2 | 11/2003 | Ziaee | |
| 6,691,707 B1 | 2/2004 | Gunaratnam et al. | |
| 6,796,308 B2 | 9/2004 | Gunaratnam et al. | |
| 6,823,869 B2 | 11/2004 | Raje et al. | |
| D499,803 S | 12/2004 | Chang | |
| 6,851,425 B2 | 2/2005 | Jaffre et al. | |
| 6,860,270 B2 | 3/2005 | Sniadach | |
| 6,907,882 B2 | 6/2005 | Ging et al. | |
| 6,926,004 B2 | 8/2005 | Schumacher | |
| 6,986,352 B2 | 1/2006 | Frater et al. | |
| 7,007,696 B2 | 3/2006 | Palkon et al. | |
| 7,021,312 B2 | 4/2006 | Cannon | |
| 7,152,602 B2 | 12/2006 | Bateman et al. | |
| 7,178,525 B2 | 2/2007 | Matula, Jr. et al. | |
| 7,178,528 B2 | 2/2007 | Lau et al. | |
| 7,210,481 B1 | 5/2007 | Lovell et al. | |
| 7,219,669 B1 | 5/2007 | Lovell et al. | |
| 7,243,650 B2 | 7/2007 | Thornton | |
| D556,898 S | 12/2007 | Guney et al. | |
| D557,408 S | 12/2007 | Amarasinghe et al. | |
| 7,353,827 B2 | 4/2008 | Geist | |
| 7,357,136 B2 | 4/2008 | Ho et al. | |
| 7,448,386 B2 | 11/2008 | Ho et al. | |
| D585,981 S | 2/2009 | Moore et al. | |
| 7,523,754 B2 | 4/2009 | Lithgow et al. | |
| 7,546,837 B2 | 6/2009 | Busch et al. | |
| 7,658,189 B2 | 2/2010 | Davidson et al. | |
| 7,708,017 B2 | 5/2010 | Davidson et al. | |
| 7,823,589 B2 | 11/2010 | Janbakhsh et al. | |
| 7,827,990 B1 | 11/2010 | Melidis et al. | |
| 7,909,035 B2 | 3/2011 | Thornton | |
| 7,942,148 B2 | 5/2011 | Davidson et al. | |
| 7,975,694 B2 * | 7/2011 | Ho | A61M 16/0633 |
| | | | 128/207.13 |
| 7,992,560 B2 | 8/2011 | Burton et al. | |
| 8,042,539 B2 | 10/2011 | Chandran et al. | |
| 8,210,182 B2 * | 7/2012 | Duquette | A61M 16/0677 |
| | | | 128/207.18 |
| 8,402,971 B2 | 3/2013 | Scheiner et al. | |
| 8,443,806 B2 | 5/2013 | McAuley et al. | |
| 8,479,741 B2 | 7/2013 | McAuley et al. | |
| 8,667,964 B2 | 3/2014 | Ho | |
| 8,714,157 B2 | 5/2014 | McAuley et al. | |
| 8,887,725 B2 | 11/2014 | Hernandez et al. | |
| 8,944,061 B2 | 2/2015 | D'Souza et al. | |
| 8,950,404 B2 | 2/2015 | Formica et al. | |
| 8,960,196 B2 | 2/2015 | Henry | |
| 9,027,556 B2 | 5/2015 | Ng et al. | |
| 9,095,673 B2 | 8/2015 | Barlow et al. | |
| 9,119,931 B2 | 9/2015 | D'Souza et al. | |
| 9,242,062 B2 | 1/2016 | Melidis et al. | |

(56) References Cited

U.S. PATENT DOCUMENTS

| | | |
|---|---|---|
| 9,333,315 B2 | 5/2016 | McAuley et al. |
| 9,339,624 B2 | 5/2016 | McAuley et al. |
| 9,381,316 B2 | 7/2016 | Ng et al. |
| 9,517,317 B2 | 12/2016 | McAuley et al. |
| 9,539,405 B2 | 1/2017 | McAuley et al. |
| 9,737,678 B2 | 8/2017 | Formica et al. |
| 9,878,118 B2 | 1/2018 | Formica et al. |
| 10,441,738 B2 | 10/2019 | Formica et al. |
| 2002/0020416 A1 | 2/2002 | Namey |
| 2002/0029780 A1 | 3/2002 | Frater et al. |
| 2002/0096173 A1 | 7/2002 | Berthon-Jones et al. |
| 2002/0100479 A1 | 8/2002 | Scarberry et al. |
| 2002/0148472 A1 | 10/2002 | Barnett et al. |
| 2003/0005931 A1 | 1/2003 | D. Jaffre et al. |
| 2003/0029454 A1 | 2/2003 | Gelinas et al. |
| 2003/0196655 A1 | 10/2003 | Ging et al. |
| 2003/0196658 A1 | 10/2003 | Ging et al. |
| 2003/0200970 A1 | 10/2003 | Stenzler et al. |
| 2004/0025882 A1 | 2/2004 | Madaus et al. |
| 2004/0041342 A1 | 3/2004 | Frieman |
| 2004/0067333 A1 | 4/2004 | Amarasinghe |
| 2004/0112381 A1 | 6/2004 | Ujihazy et al. |
| 2004/0112384 A1 | 6/2004 | Lithgow et al. |
| 2004/0118406 A1 | 6/2004 | Lithgow et al. |
| 2004/0182398 A1 | 9/2004 | Sprinkle et al. |
| 2004/0211428 A1 | 10/2004 | Jones, Jr. et al. |
| 2004/0221850 A1 | 11/2004 | Ging et al. |
| 2004/0226566 A1* | 11/2004 | Gunaratnam ..... A61M 16/0683 128/207.18 |
| 2004/0255949 A1 | 12/2004 | Lang et al. |
| 2005/0001152 A1 | 1/2005 | Stewart et al. |
| 2005/0011524 A1 | 1/2005 | Thomlinson et al. |
| 2005/0016544 A1 | 1/2005 | Thornton |
| 2005/0028822 A1 | 2/2005 | Sleeper et al. |
| 2005/0121030 A1 | 6/2005 | Bateman et al. |
| 2005/0150497 A1 | 7/2005 | Eifler et al. |
| 2005/0155604 A1 | 7/2005 | Ging et al. |
| 2005/0199242 A1* | 9/2005 | Matula, Jr. ........ A61M 16/0816 128/207.13 |
| 2005/0205096 A1 | 9/2005 | Matula, Jr. et al. |
| 2006/0042629 A1 | 3/2006 | Geist |
| 2006/0060200 A1 | 3/2006 | Ho et al. |
| 2006/0118117 A1 | 6/2006 | Berthon-Jones et al. |
| 2006/0124131 A1 | 6/2006 | Chandran et al. |
| 2006/0137690 A1 | 6/2006 | Gunaratnam et al. |
| 2006/0201514 A1 | 9/2006 | Jones et al. |
| 2006/0207597 A1 | 9/2006 | Wright |
| 2006/0207599 A1 | 9/2006 | Busch et al. |
| 2006/0231103 A1 | 10/2006 | Matula, Jr. et al. |
| 2006/0237017 A1 | 10/2006 | Davidson et al. |
| 2006/0272646 A1 | 12/2006 | Ho et al. |
| 2006/0283461 A1 | 12/2006 | Lubke et al. |
| 2007/0006879 A1 | 1/2007 | Thornton |
| 2007/0044804 A1 | 3/2007 | Matula, Jr. et al. |
| 2007/0125384 A1 | 6/2007 | Zollinger et al. |
| 2007/0125385 A1 | 6/2007 | Ho et al. |
| 2007/0131230 A1* | 6/2007 | Giroux ................ A61M 15/08 128/207.13 |
| 2007/0144525 A1 | 6/2007 | Davidson et al. |
| 2007/0163600 A1 | 7/2007 | Hoffman |
| 2007/0175480 A1 | 8/2007 | Gradon et al. |
| 2007/0186930 A1 | 8/2007 | Davidson et al. |
| 2007/0209663 A1* | 9/2007 | Marque ............. A61M 16/0683 128/207.11 |
| 2007/0277828 A1 | 12/2007 | Ho et al. |
| 2008/0006277 A1 | 1/2008 | Worboys et al. |
| 2008/0047560 A1 | 2/2008 | Veliss et al. |
| 2008/0060649 A1 | 3/2008 | Veliss et al. |
| 2008/0060657 A1 | 3/2008 | McAuley et al. |
| 2008/0072910 A1 | 3/2008 | Janbakhsh et al. |
| 2008/0121235 A1 | 3/2008 | Janbakhsh et al. |
| 2008/0110464 A1 | 5/2008 | Davidson et al. |
| 2008/0110466 A1 | 5/2008 | Armitstead |
| 2008/0190432 A1* | 8/2008 | Blochlinger ...... A61M 16/0683 128/205.25 |
| 2008/0210241 A1 | 9/2008 | Schulz et al. |
| 2008/0257354 A1 | 10/2008 | Davidson et al. |
| 2009/0032026 A1 | 2/2009 | Price et al. |
| 2009/0044808 A1 | 2/2009 | Guney et al. |
| 2009/0065005 A1* | 3/2009 | Ades ................. A61M 16/0816 128/205.25 |
| 2009/0078259 A1 | 3/2009 | Kooj et al. |
| 2009/0095301 A1 | 4/2009 | Hitchcock et al. |
| 2009/0114229 A1 | 5/2009 | Frater et al. |
| 2009/0133696 A1 | 5/2009 | Remmers et al. |
| 2009/0159084 A1 | 6/2009 | Sher et al. |
| 2009/0241961 A1 | 10/2009 | McAuley et al. |
| 2009/0277452 A1 | 11/2009 | Lubke et al. |
| 2010/0000534 A1 | 1/2010 | Kooij |
| 2010/0000537 A1 | 1/2010 | McAuley et al. |
| 2010/0006101 A1 | 1/2010 | McAuley et al. |
| 2010/0018534 A1 | 1/2010 | Veliss et al. |
| 2010/0132717 A1 | 6/2010 | Davidson et al. |
| 2010/0199992 A1 | 8/2010 | Ho et al. |
| 2010/0229868 A1 | 9/2010 | Rummery |
| 2010/0307502 A1 | 12/2010 | Rummery et al. |
| 2010/0313891 A1 | 12/2010 | Veliss et al. |
| 2011/0000492 A1 | 1/2011 | Veliss et al. |
| 2011/0056497 A1 | 3/2011 | Scheiner et al. |
| 2011/0072553 A1 | 3/2011 | Ho |
| 2011/0088699 A1 | 4/2011 | Skipper et al. |
| 2011/0146685 A1 | 6/2011 | Allan et al. |
| 2011/0197341 A1 | 8/2011 | Formica et al. |
| 2011/0209709 A1 | 9/2011 | Davidson et al. |
| 2011/0232647 A1 | 9/2011 | Ho |
| 2012/0067349 A1 | 3/2012 | Barlow et al. |
| 2013/0112206 A1 | 5/2013 | Buddharaju |
| 2013/0199537 A1 | 8/2013 | Formica et al. |
| 2014/0083430 A1 | 3/2014 | Matula, Jr. et al. |
| 2018/0318540 A1 | 11/2018 | Barlow et al. |
| 2019/0091431 A1 | 3/2019 | Formica et al. |
| 2019/0091432 A1 | 3/2019 | Barlow et al. |
| 2019/0091433 A1 | 3/2019 | Barlow et al. |
| 2020/0330715 A1 | 10/2020 | Formica et al. |
| 2020/0345964 A1 | 11/2020 | Formica et al. |

FOREIGN PATENT DOCUMENTS

| | | |
|---|---|---|
| AU | PCT/AU2009/902731 | 6/2009 |
| AU | PCT/AU2009/904236 | 9/2009 |
| AU | 2010902359 | 5/2010 |
| CA | 2380430 | 2/2001 |
| CN | 2102118 | 4/1992 |
| CN | 1131915 | 9/1996 |
| CN | 2721141 | 8/2005 |
| CN | 1750853 | 3/2006 |
| CN | 1901961 | 1/2007 |
| CN | 101237902 | 8/2008 |
| CN | 101301505 | 11/2008 |
| CN | 101227947 | 4/2011 |
| CN | 101242866 | 5/2011 |
| CN | 1886167 | 9/2012 |
| DE | 4004157 | 4/1991 |
| DE | 29723101 | 5/1998 |
| EP | 0747078 | 6/1996 |
| EP | 0998319 | 7/1998 |
| EP | 1020201 | 7/2000 |
| EP | 1057494 | 12/2000 |
| EP | 2359888 | 8/2011 |
| FR | 2775905 | 9/1999 |
| GB | 0108522 | 4/2001 |
| GB | 2385533 | 8/2003 |
| JP | H056-5539 | 3/1993 |
| JP | H09-10311 | 1/1997 |
| JP | 2002-526180 | 8/2002 |
| JP | 2005-537906 | 12/2005 |
| JP | 2006-518230 | 8/2006 |
| JP | 2007-516750 | 6/2007 |
| JP | 2008-501438 | 1/2008 |
| JP | 2008-526391 | 7/2008 |
| JP | 2008-264026 | 11/2008 |
| JP | 2008-541955 | 11/2008 |

(56) References Cited

FOREIGN PATENT DOCUMENTS

| | | |
|---|---|---|
| JP | 2009-527260 | 7/2009 |
| JP | 6-508272 | 5/2019 |
| WO | WO 99/04842 | 2/1999 |
| WO | WO 00/20072 | 4/2000 |
| WO | WO 00/50122 | 8/2000 |
| WO | WO 01/32250 | 5/2001 |
| WO | WO 01/97893 | 12/2001 |
| WO | WO 2002/047749 | 6/2002 |
| WO | WO 03/076020 | 9/2003 |
| WO | WO 03/090827 | 11/2003 |
| WO | WO 2004/022146 | 3/2004 |
| WO | WO 2004/022147 | 3/2004 |
| WO | WO 2004/041341 | 5/2004 |
| WO | WO 2004/041342 | 5/2004 |
| WO | WO 2004/052438 | 6/2004 |
| WO | WO 2004/073778 | 9/2004 |
| WO | WO 2004/078231 | 9/2004 |
| WO | WO 2004/096332 | 11/2004 |
| WO | WO 2005/021075 | 3/2005 |
| WO | WO 2005/023334 | 3/2005 |
| WO | WO 2005/046776 | 5/2005 |
| WO | WO 2005/051468 | 6/2005 |
| WO | WO 2005/063328 | 7/2005 |
| WO | WO 2005/079726 | 9/2005 |
| WO | WO 2005/118042 | 12/2005 |
| WO | WO 2005/123166 | 12/2005 |
| WO | WO 2006/000046 | 1/2006 |
| WO | WO 2006/000770 | 1/2006 |
| WO | WO 2006/074513 | 7/2006 |
| WO | WO 2006/074515 | 7/2006 |
| WO | WO 2006/130903 | 12/2006 |
| WO | WO 2007/006089 | 1/2007 |
| WO | WO 2007/008725 | 1/2007 |
| WO | WO 2007/014088 | 2/2007 |
| WO | WO 2007/041751 | 4/2007 |
| WO | WO 2007/045008 | 4/2007 |
| WO | WO 2007/048174 | 5/2007 |
| WO | WO 2007/064665 | 6/2007 |
| WO | WO 2007/130067 | 11/2007 |
| WO | WO 2007/139531 | 12/2007 |
| WO | WO 2007/147088 | 12/2007 |
| WO | WO 2008/007985 | 1/2008 |
| WO | WO 2008/011682 | 1/2008 |
| WO | WO 2008/028092 | 3/2008 |
| WO | WO 2008/030831 | 3/2008 |
| WO | WO 2008/043134 | 4/2008 |
| WO | WO 2008/068966 | 6/2008 |
| WO | WO 2008/070929 | 6/2008 |
| WO | WO 2009/026627 | 3/2009 |
| WO | WO 2009/052560 | 4/2009 |
| WO | WO 2009/059353 | 5/2009 |
| WO | WO 2009/062265 | 5/2009 |
| WO | WO 2009/108994 | 9/2009 |
| WO | WO 2009/139647 | 11/2009 |
| WO | WO 2010/059592 | 5/2010 |
| WO | WO 2010/066004 | 6/2010 |
| WO | WO 2010/067235 | 6/2010 |
| WO | WO 2010/135785 | 12/2010 |
| WO | WO 2010/139014 | 12/2010 |
| WO | WO 2011/060479 | 5/2011 |
| WO | WO 2012/040791 | 4/2012 |
| WO | WO 2013/066195 | 5/2013 |

OTHER PUBLICATIONS

U.S. Appl. No. 12/478,537, filed Jun. 4, 2009, Kooij et al.
ACP Composites—Large Stock of Ready to Use Composite Plate, Tube, Sheet, Fabrics and Core Materials, https://www.acpsakes.com/Core-Materials-nd-Foam.html, dated Oct. 5, 2015, 4 pages.
Flexifit instructions, http://web.archive.org/web/19970126045828/http:/www.archive.org/ dated Jan. 26, 1997, Affidavit of Christopher Butler dated Sep. 6, 2016, 23 pages.
Guidelines for Sandwich Core Materials, http://fibreglast.com/product/guidelines-for-sandwich-core-materials/Learning_Center, dated Oct. 5, 2015, 3 pages.
Malloy, Plastic Part Design for Injection Molding, New York: Hanser Publishers, 1994, 14 pages.
Opus Brochure, Fisher & Paykel Healthcare, www.fphcare.com, 2 pages.
Philips Respironics, "ComfortLite 2", 2 pages, (2009).
Philips Respironics, "OptiLife", 2 pages, (2008).
ResMed Mask Frames, Nasal Cushions and Headgear, http: //web.archive.org/web/19970 1 26045828 /http ://www.a rchive.org/ dated Jan. 26, 1997, Affidavit of Christopher Butler dated Jul. 6, 2017, 8 pages.
ResMed Mirage Swift Nasal Pillows System, www.resmed.com, 2004, 6 pages.
ResMed Mirage Vista Nasal Mask—Component Cards, www.resmed.com Reference No. 1010279/30502, dated 2005, 1 page.
ResMed Origins Brochure dated Apr. 17, 2016, 64 pages.
U.S. Appl. No. 29/380,213, filed Dec. 1, 2010.
Ultra Mirage Full Face Mask brochure, http://web.archive.org/web/19970 1 26045828/http://www.archive.org/ dated Jan. 26, 1997, Affidavit of Christopher Butler dated Sep. 6, 2016, 9 pages.
Users Guide ResMed Mirage Swift Nasal Pillows System, www.myresmed.com dated May 6, 2004, 11 pages.

* cited by examiner

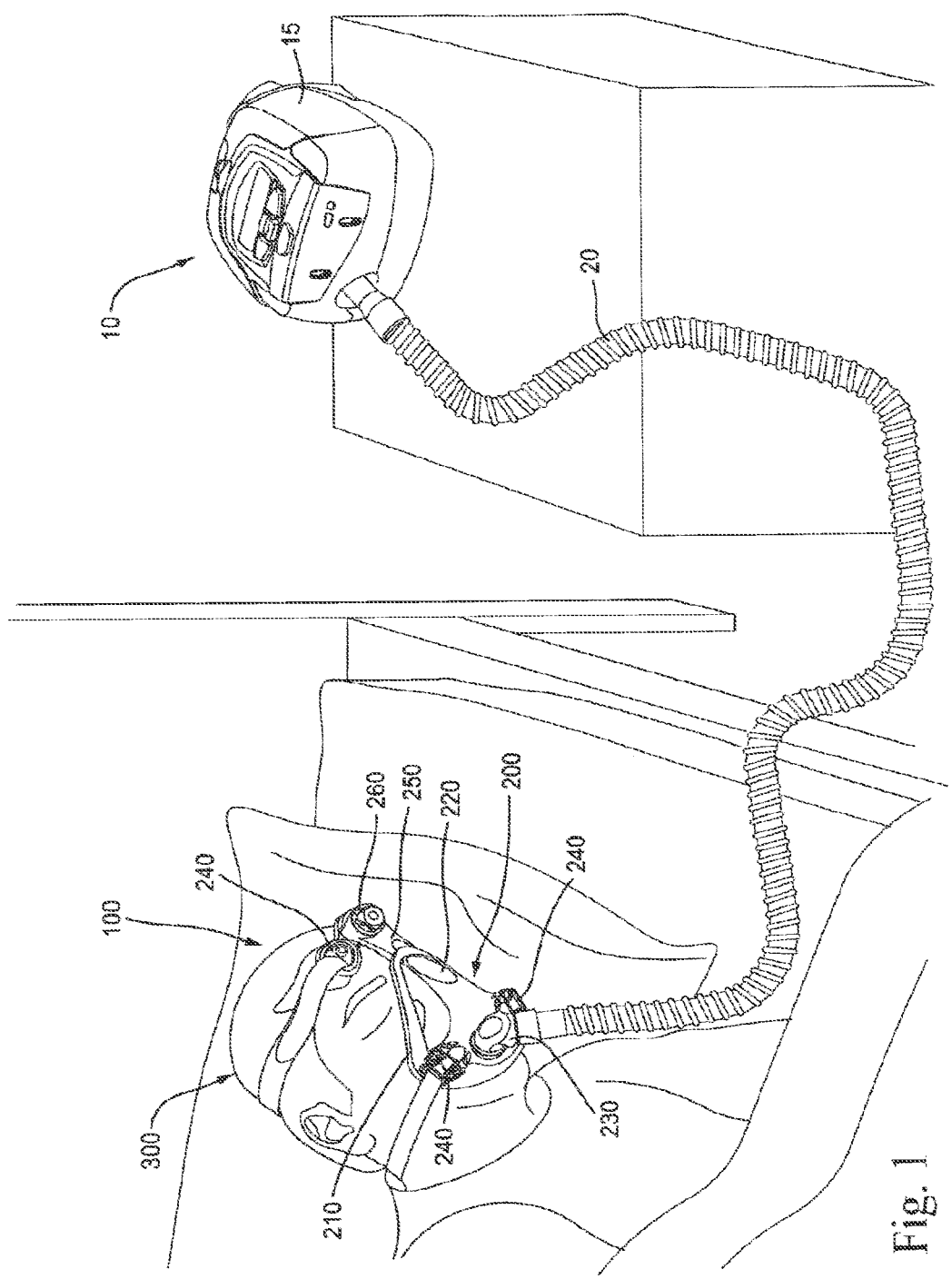

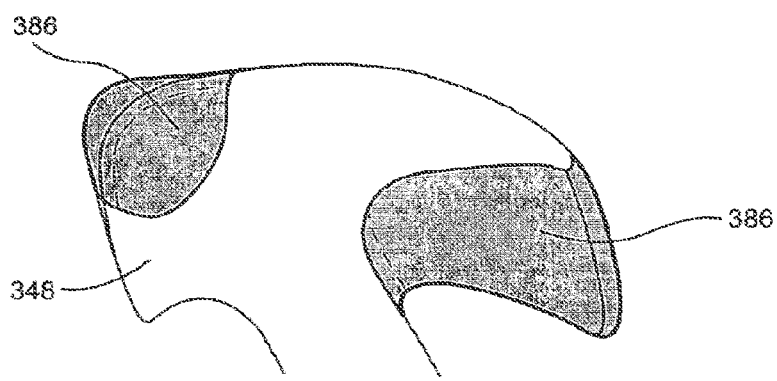
Fig. 34-2
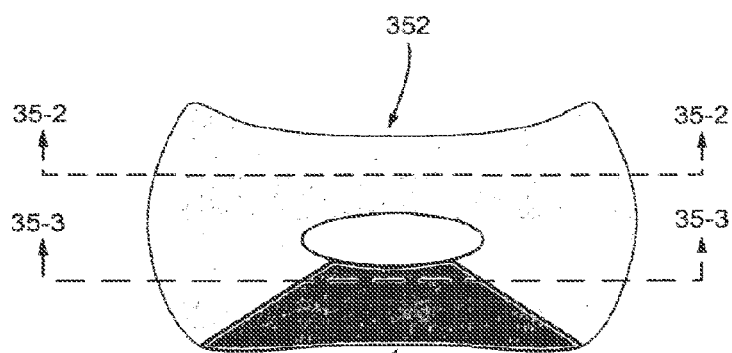
Fig. 35-1
Fig. 35-2
Fig. 35-3
 Higher Hardness    Low Hardness

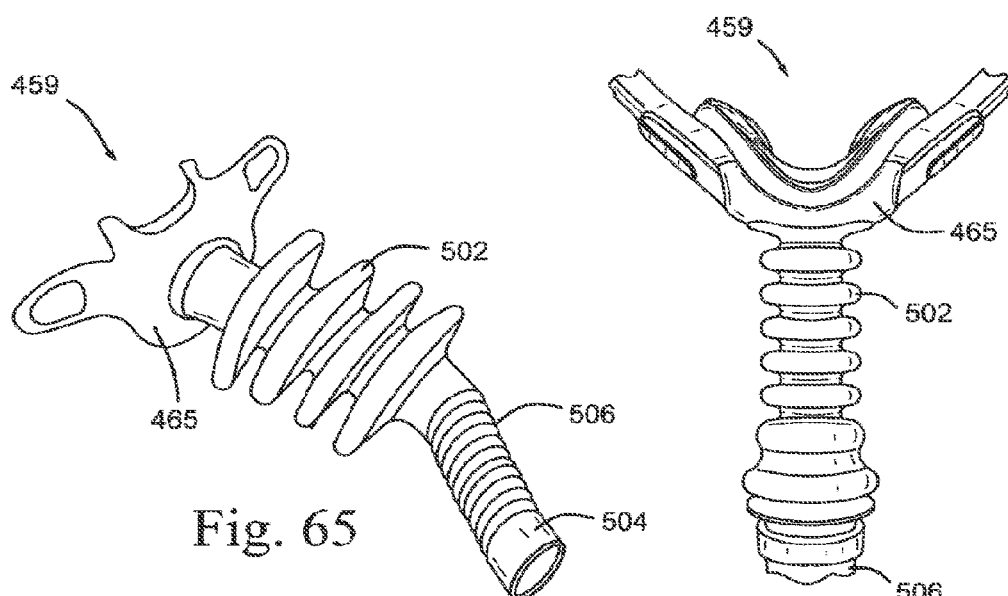
Fig. 65
Fig. 66
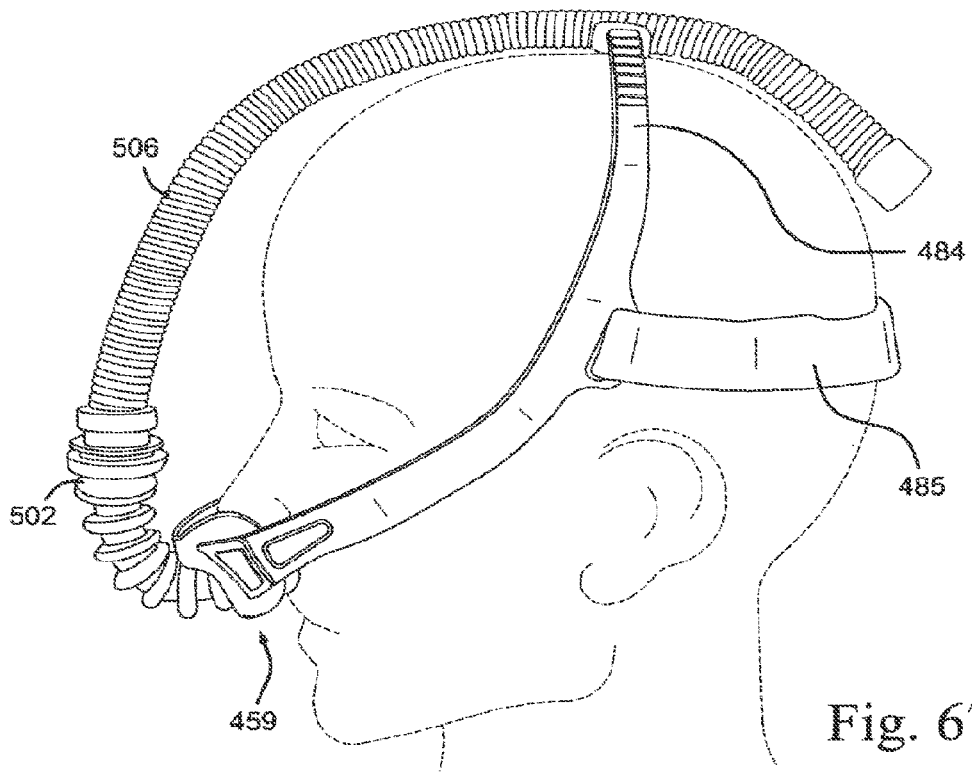
Fig. 67

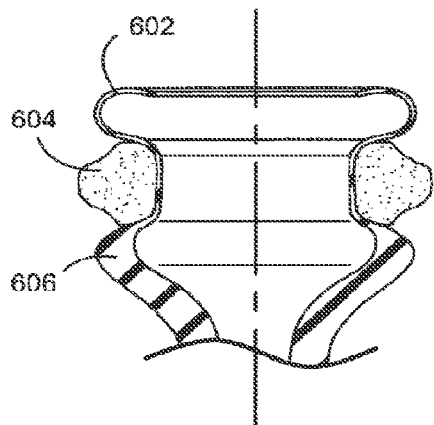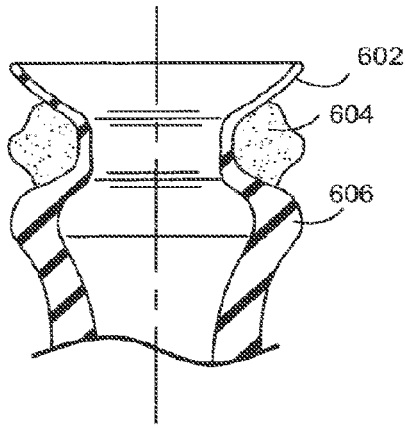
Fig. 122-1    Fig. 122-2
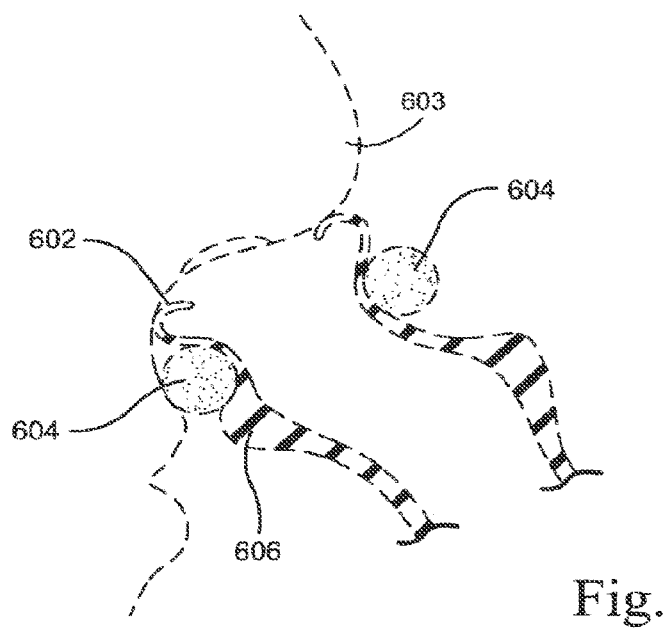
Fig. 122-3

UNOBTRUSIVE NASAL MASK

CROSS-REFERENCE TO RELATED APPLICATIONS

This application is a continuation of U.S. application Ser. No. 16/365,090, filed Mar. 26, 2019, which is a continuation of U.S. application Ser. No. 14/738,977, now issued as U.S. Pat. No. 10,265,490, filed Jun. 15, 2015, which is a continuation of application Ser. No. 13/321,981, filed Nov. 22, 2011, now issued as U.S. Pat. No. 9,095,673, which is the U.S. national phase of International Application No. PCT/AU2010/000684, filed Jun. 2, 2010, which designated the U.S. and claims the benefit of Australian Provisional Application No. 200902524, filed Jun. 2, 2009; Australian Provisional Application No. 2009906101, filed Dec. 15, 2009; Australian Provisional Application No. 2010902359, filed May 28, 2010; U.S. Provisional Application 61/222,711, filed Jul. 2, 2009; U.S. Provisional Application 61/272,162, filed Aug. 25, 2009; U.S. Provisional Application 61/272,250, filed Sep. 4, 2009; U.S. Provisional Application 61/263,175, filed Nov. 20, 2009; U.S. Provisional Application 61/282,693, filed Mar. 18, 2010; and PCT Application No. PCT/AU2010/000657, filed May 28, 2010, each of which is incorporated herein by reference in its entirety.

FIELD OF THE INVENTION

The technology relates to a nasal respiratory mask for use with an air delivery system for treatment, e.g., of Sleep Disordered Breathing (SDB) with Continuous Positive Airway Pressure (CPAP) or Non-Invasive Positive Pressure Ventilation (NIPPY). In particular, the technology relates to a respiratory mask that is unobtrusive.

BACKGROUND OF THE INVENTION

Apparatus to deliver breathable gas to a patient typically includes a positive airway pressure (PAP) device, an air delivery conduit or tube, and a patient interface, wherein the patient interface contacts the patient's face in use to deliver pressurized breathable gas to the patient from the PAP device.

In use, the patient interface can appear bulky and as such may discourage patients from using treatment as it is too obtrusive. This in turn may lead to lower therapy compliance and thus failed treatment.

Patients using nasal pillows or puffs may dislike the placement of the pillows in the nares and/or the sensation of pressurized air being directed up the nares (also known as the 'air jetting' affect).

Therefore, a need has developed in the art to provide alternative patient interfaces that are less obtrusive, may not include placement of pillows up the nares and/or may reduce the sensation of pressurized air being directed up the nares.

SUMMARY OF THE INVENTION

One aspect of the present technology relates to a patient interface for delivering breathable gas to a patient. Another aspect of the present technology is a patient interface that forms a seal on an underside of a patient's nose. Another aspect of the present technology is a patient interface that avoids contact with a nasal bridge region of a patient's nose. Another aspect of the present technology is a patient interface that forms a seal on an underside of a patient's nose in a region surrounding both nares. Another aspect of the present technology is a patient interface that avoids contacting the nasal septum. Another aspect of the present technology is a patient interface defining a single breathing chamber that provides a supply of air at positive pressure for both nostrils.

One form of patient interface in accordance with the present technology includes a sealing portion including a nose tip engagement portion adapted to form a seal with the patient's nose tip, an upper lip engagement portion adapted to form a seal with the patient's upper lip and/or base of the patient's nares, and nostril engagement flaps adapted to form a seal with the patient's nares. In one form, the nose tip engagement portion, the upper lip engagement portion, and the nostril engagement flaps are all structured to extend or curve outwardly from a supporting wall defining an air path.

In accordance with one form of the present technology, a patient interface is provided that makes use of different seal-forming mechanisms in different regions of the patient interface. Preferably, in a region adapted to form a seal with a nasal crease region of a face, a portion of the seal acts in compression. Preferably, in a region adapted to form a seal with a tip of the nose region of a face, a portion of the seal acts in tension in use. Preferably in an alar sidewall region intermediate of the crease region of the face and a tip of the nose region of a face, a seal portion of the patient interface is arranged to form a cantilever. Preferably in a region intermediate of a left crease region and a right crease region of a face, a seal portion of the patient interface is constructed and arranged to be in tension in use.

In accordance with one form of the present technology, a patient interface is provided that includes a nose tip seal forming portion in the form of a membrane. Preferably the membrane is constructed and arranged to be held relatively fixed at its ends and in tension against a tip of a nose in use.

In accordance with one form of the present technology, a patient interface is provided that comprises a seal forming portion constructed and arranged to have regions of different stiffnesses. In one form, the seal forming portion has a region of relatively high stiffness arranged in use adjacent a nasal crease region of the face, or adjacent the base of the nose near the junction between the top lip and a side of the nose. In one form, the seal forming portion may include respective left and right regions of relatively high stiffness. In one form, the seal forming portion includes a region of relatively low stiffness adapted to form a seal on an underside of a tip of the nose region of a face. In one form, the seal forming portion has a region of intermediate stiffness arranged in use adjacent a side portion of a nose.

In one form, a seal forming portion of a patient interface in accordance with the present technology defines front and rear lateral portions on both a left side and a right side. In one form, a seal forming portion of a patient interface in accordance with the present technology defines front and rear medial portions. Preferably, the respective left and right lateral portions are constructed and arranged to hinge about the front and rear medial portions in use. With reference to FIGS. 19 to 21 of International Patent Application PCT/AU2004/000207 published as WO 2004/073778, a seal forming portion in accordance with an aspect of the present technology is adapted to hinge about a medial portion to accommodate an alar angle of a patient. In one form, the sealing portion is adapted to hinge outwardly to accommodate a wider nose. In one form the sealing portion is adapted to hinge inwardly to accommodate a narrower nose.

In one form of the present technology, a patient interface is provided that includes headgear and a seal forming portion. The seal forming portion is adapted to flex about a medial portion thereof to define an angle therebetween. The patient interface is constructed and arranged so that the angle may be adjusted by altering a headgear tension. In one form, the patient interface includes lateral headgear connectors arranged at an angle with respect to an orifice through which a supply of breathable gas is delivered to the patient. The patient interface is constructed and arranged in one form so that the angle of the headgear connector is adjustable. In a preferred form, adjustment of the angle of the headgear connector may be used to adjust an angle of the seal-forming portion. In one form, adjustment of headgear may be used to increase or decrease a lateral or pinch force of a seal-forming portion. In one form, headgear is connected close to an underside of a seal-forming portion. Preferably the patient interface is arranged so that flexure of a seal-forming portion about a medial portion thereof may be achieved by altering a headgear tension. In one form, a top surface of a headgear connector is configured to push against an underside of a seal-forming portion, preferably a rear-lateral portion thereof, to increase a lateral or pinch force.

In one form, a patient interface is provided that includes a seal-forming portion adapted to form a seal on an underside of a nose of a patient, the patient interface includes a flexible body that defines a breathing chamber. Headgear is connected to sides of the flexible body. The body is constructed and arranged to flex in response to a changed headgear tension to alter a lateral or pinch force on a side of a nose to effect a seal. In one form the flexible body is formed from a rubber, preferably silicone. In one form the flexible body is formed from a rubber having a Type A durometer of about 35 to about 45, preferably about 40.

In one form of the present technology, a patient interface is provided that comprises a seal forming portion, headgear, an air delivery conduit and a decoupling arrangement. The headgear is connected to a region of the patient interface close to the seal forming portion. The air delivery conduit is connected to the decoupling portion. The decoupling portion is located between a point of connection of the headgear and a point of connection of the air delivery conduit.

Another aspect of the present technology relates to a patient interface for delivering breathable gas to a patient, the patient interface including a sealing portion structured to extend or curve outwardly from a supporting wall defining an air path. In one form of the present technology, a seal-forming portion is arranged in a trumpet or horn shape in cross-section. In one form, a seal-forming portion has a bell-shape in cross-section. In one form, a seal-forming portion lies on an inside surface of a cushion. In one form, certain regions of the seal forming portion have a trumpet, horn or bell shape, while other regions have a different shape. For example, a region of the seal forming portion adapted to form a seal with an underside of a tip of the nose may have a trumpet, horn or bell shape.

In one form of the present technology, a seal forming portion is formed from a low durometer rubber, preferably a silicone having a Type A durometer in the range of 1 to 15.

In one form of the present technology, a patient interface is provided that comprises a mask body formed from a rubber having a Type A durometer in the range of about 35 to about 45, and a seal-forming portion formed from a rubber having a Type A durometer in the range of 1 to 15. In one form, the patient interface further comprises headgear connectors formed from a flexible material, preferably a rubber having a Type A durometer in the range of about 35 to about 45. Preferably the rubber is silicone rubber.

Another aspect of the present technology relates to a patient interface for delivering breathable gas to a patient, the patient interface including a sealing portion structured to curve outwardly and form at least one hanging membrane.

Another aspect of the present technology relates to a patient interface for delivering breathable gas to a patient. The patient interface includes a sealing portion including a nose tip engagement portion adapted to form a seal with the patient's nose tip, an upper lip engagement portion adapted to form a seal with the patient's upper lip and/or base of the patient's nares, and nostril engagement flaps adapted to form a seal with the patient's nares, and a supporting portion supporting one or more portions of the sealing portion, wherein the supporting portion supports different portions of the sealing portion with varying degrees of support. The supporting portion may include one or more thickened portions, have cored out portion or recesses, or portions having variable hardness to provide the varying degrees of support.

Another aspect of the present technology relates to a patient interface for delivering breathable gas to a patient, a supporting portion supporting one or more portions of the sealing portion, wherein the supporting portion supports different portions of the sealing portion with varying degrees of support.

Another aspect of the present technology relates to a patient interface for delivering breathable gas to a patient. The patient interface includes a sealing portion including a nose tip engagement portion adapted to form a seal with the patient's nose tip, an upper lip engagement portion adapted to form a seal with the patient's upper lip and/or base of the patient's nares, and nostril engagement flaps adapted to form a seal with the patient's nares, and a supporting portion supporting the sealing portion, the sealing portion being connected to the supporting portion on side portions of the sealing portion, and the sealing portion being spaced apart from the supporting portion on front and rear portions of the sealing portion.

Another aspect of the present technology relates to a patient interface for delivering breathable gas to a patient. The patient interface includes a sealing portion including a nose tip engagement portion adapted to form a seal with the patient's nose tip, an upper lip engagement portion adapted to form a seal with the patient's upper lip and/or base of the patient's nares, and nostril engagement flaps adapted to form a seal with the patient's nares, and a supporting portion supporting the sealing portion, the sealing portion being connected to the supporting portion, and the sealing portion being attached to the supporting portion, wherein the supporting portion is compliant.

Another aspect of the present technology relates to a patient interface for delivering breathable gas to a patient. The patient interface includes a sealing portion and a supporting portion supporting the sealing portion, the sealing portion being connected to the supporting portion in some regions, and being spaced apart from the supporting portion in other regions.

Another aspect of the present technology relates to a patient interface for delivering breathable gas to a patient. The patient interface includes a sealing portion including a nose tip engagement portion adapted to engage with the patient's nose tip, and a supporting portion supporting the sealing portion, the supporting portion being connected to the sealing portion on two side portions of the sealing portion, and the supporting portion being spaced apart by a gap from the sealing portion at the nose tip engagement portion, the nose tip engagement portion being adapted to stretch to fit and seal with the patient's nose tip.

Another aspect of the present technology relates to a patient interface for delivering breathable gas to a patient. The patient interface includes a sealing portion adapted to form a seal with a patient's face in use, the sealing portion including a front stretch portion adapted to form a seal with the patient's nose tip, a rear stretch portion adapted to for a seal with the patient's upper lip, side push portions adapted to anchor the sealing portion at regions of the patient's nose adjacent the nasal labial creases by applying a force normal to a plane of the patient's face, and side wrap portions adapted to form a seal with the patient's nares by applying a pinching force normal to the patients nares. The side wrap portions and side push portions may have a greater thickness than the front stretch portion or the rear stretch portion. The front stretch portion may stretch to seal with the patient's nose tip in use and the rear stretch portion may stretch to seal with the patient's upper lip in use.

Another aspect of the present technology relates to a patient interface for delivering pressurized breathable gas to a patient. The patient interface includes a sealing portion adapted to form a seal with the patient's face, the sealing portion having an opening adapted to receive the pressurized breathable gas, an outer sealing margin to seal with the patient's face, and a transition region between the opening and the outer sealing margin that gradually increases in size from the opening to the outer sealing margin.

Another aspect of the present technology relates to a patient interface for delivering breathable gas to a patient. The patient interface includes a sealing portion adapted to form a seal with the patient's face, a supporting portion supporting one or more portions of the sealing portion, headgear connectors extending from the supporting portion, the headgear connectors adapted to connect to headgear to secure the patient interface to the patient, wherein the headgear causes the headgear connectors to bend towards the supporting portion in use, and a bending force from the headgear connectors is transferred to the sealing portion as a sealing force. The bending force may be applied as a pinch force to sides of the patient's nose, and/or as an anchor force to regions of the patient's nose adjacent the nasal labial creases.

Another aspect of the present technology relates to a patient interface for delivering breathable gas to a patient. The patient interface includes a sealing portion, and a multi-axis elbow assembly operatively coupled between the sealing portion and a flexible tube, wherein the multi-axis elbow assembly allows movement of the flexible tube in two separate planes while substantially isolating drag forces from the flexible tube from being transferred to the sealing portion.

Another aspect of the present technology relates to a multi-axis elbow assembly that allows movement of a connected tube in two separate planes while substantially isolating drag forces from the tube.

Other aspects, features, and advantages of the present technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various embodiments of this technology. In such drawings:

FIG. 1-1 shows a patient interface according to an embodiment of the technology in use;

FIG. 1-2 is an isometric view of a sealing portion and suspension system of the patient interface of FIG. 1-1;

FIG. 1-3 is another isometric view of the sealing portion and suspension system of FIG. 1-2;

FIG. 1-4 is a top view of the sealing portion and suspension system of FIG. 1-2;

FIG. 1-5 is a bottom view of the sealing portion and suspension system of FIG. 1-2;

FIG. 1-6 is a front view of the sealing portion and suspension system of FIG. 1-2;

FIG. 1-7 is a rear view of the sealing portion and suspension system of FIG. 1-2;

FIG. 1-8 is a side view of the sealing portion and suspension system of FIG. 1-2;

FIG. 1-9 is an isometric view of a suspension system and frame of the patient interface of FIG. 1-1;

FIG. 1-10 is a bottom view of the suspension system and frame of FIG. 1-9;

FIG. 1-11 is a top view of the suspension system and frame of FIG. 1-9;

FIG. 1-12 is a front view of the suspension system and frame of FIG. 1-9;

FIG. 1-13 is a rear view of the suspension system and frame of FIG. 1-9;

FIG. 1-14 is a side view of the suspension system and frame of FIG. 1-9;

FIG. 1-15 is an isometric view of a sealing portion, suspension system, and frame of the patient interface of FIG. 1-1;

FIG. 1-16 is a rear view of the sealing portion, suspension system, and frame of FIG. 1-15;

FIG. 1-17 is a front view of the sealing portion, suspension system, and frame of FIG. 1-15;

FIG. 1-18 is a side view of the sealing portion, suspension system, and frame of FIG. 1-15;

FIG. 2-1 is a rear view of a sealing portion and frame according to an embodiment of the present technology;

FIG. 2-2 is a front view of the sealing portion and frame of FIG. 2-1;

FIG. 2-3 is a side view of the sealing portion and frame of FIG. 2-1;

FIG. 2-4 is a top view of the sealing portion and frame of FIG. 2-1;

FIG. 2-5 is a bottom view of the sealing portion and frame of FIG. 2-1;

FIG. 2-6 is an isometric view of the sealing portion and frame of FIG. 2-1;

FIGS. 2-7A and 2-7B are top views illustrating alternative shapes of the sealing portion according to embodiments of the present technology;

FIGS. 2-8A and 2-8B are side views illustrating alternative shapes of the sealing portion according to embodiments of the present technology;

FIGS. 2-9A and 2-9B are rear views illustrating alternative shapes of the sealing portion according to embodiments of the present technology;

FIG. 2-10 is an isometric view of a sealing portion and frame in use according to an embodiment of the present technology;

FIG. 2-11 is a rear view illustrating an alternative shape of the sealing portion according to an embodiment of the present technology;

FIG. 3-1 shows a patient interface according to another embodiment of the technology in use;

FIG. 3-2 is an isometric view of a sealing portion and suspension system of the patient interface of FIG. 3-1;

FIG. 3-3 is a rear view of the sealing portion and suspension system of FIG. 3-2;

FIG. 3-4 is a top view of the sealing portion and suspension system of FIG. 3-2;

FIG. 3-5 is a bottom view of the sealing portion and suspension system of FIG. 3-2;

FIG. 3-6 is a side view of the sealing portion and suspension system of FIG. 3-2;

FIG. 4-1 shows a patient interface according to another embodiment of the technology in use;

FIG. 4-2 is an isometric view of a sealing portion of the patient interface of FIG. 4-1;

FIG. 4-3 is another isometric view of the sealing portion of FIG. 4-2;

FIG. 4-4 is a rear view of the sealing portion of FIG. 4-2;

FIG. 4-5 is a front view of the sealing portion of FIG. 4-2;

FIG. 4-6 is a side view of the sealing portion of FIG. 4-2;

FIG. 4-7 is a top view of the sealing portion of FIG. 4-2;

FIGS. 4-8 and 4-9 show alternative self-adjusted shapes of the sealing portion of FIG. 4-2;

FIGS. 5-1 and 5-2 are cross-sectional views illustrating sealing portions with gel beading according to embodiments of the present technology;

FIGS. 6-1 and 6-2 are schematic views illustrating nostril engagement flaps for sealing portions according to embodiments of the present technology;

FIGS. 7-1, 7-2, and 7-3 show sealing portions with fingers or ridges according to embodiments of the present technology;

FIG. 8-1 illustrates a mask with a gel suspension system according to an embodiment of the present technology;

FIGS. 8-2 and 8-3 show a mask with a gel suspension system according to another embodiment of the present technology;

FIGS. 9-1 and 9-2 show sealing portions with stiffening ribs according to embodiments of the present technology;

FIG. 10 shows a sealing portion with headgear connectors according to an embodiment of the present technology;

FIG. 11 shows a suspension system with headgear connectors according to an embodiment of the present technology;

FIG. 12 shows headgear for a mask according to an embodiment of the present technology;

FIGS. 13-1, 13-2, 13-3, 13-4, and 13-5 shows headgear according to an embodiment of the present technology;

FIGS. 14-1, 14-2, 14-3, and 14-4 show elbows for a mask according to embodiments of the present technology;

FIG. 15 shows a sealing portion with adhesive strips according to an embodiment of the present technology;

FIGS. 16-1 and 16-2 show sealing portions with flexible tubing according to embodiments of the present technology;

FIGS. 17-1 and 17-2 illustrate sealing portions with a gusset-type suspension system according to embodiments of the present technology;

FIGS. 18-1 and 18-2 illustrate a sealing portion provided to an exoskeleton according to an embodiment of the present technology;

FIGS. 20-1 to 20-7 show cross sections of a sealing portion according to an embodiment of the present technology;

FIG. 21-1 is a side view of a lower portion of an embodiment of the present technology;

FIG. 21-2 is a rear view of a lower portion of an embodiment of the present technology;

FIG. 21-3 is a front view of a lower portion of an embodiment of the present technology;

FIG. 21-4 is a top view of a lower portion of an embodiment of the present technology;

FIG. 21-5 is another top view of a lower portion of an embodiment of the present technology;

FIG. 21-6 is a bottom view of a lower portion of an embodiment of the present technology;

FIG. 22-1 is a side view of an upper portion of an embodiment of the present technology;

FIG. 22-2 is a rear view of an upper portion of an embodiment of the present technology;

FIG. 22-3 is a front view of an upper portion of an embodiment of the present technology;

FIG. 22-4 is a top view of an upper portion of an embodiment of the present technology;

FIG. 23-1 is a side view of an embodiment of the present technology;

FIG. 23-2 is a rear view of an embodiment of the present technology;

FIG. 23-3 is a front view of an embodiment of the present technology;

FIG. 23-4 is a top view of an embodiment of the present technology;

FIG. 23-5 is a bottom view of an embodiment of the present technology;

FIG. 23-6 is a cross section through a side view of an embodiment of the present technology;

FIG. 23-7 is a cross section through a front view of an embodiment of the present technology;

FIG. 24-1 is a top view of a sealing portion according to an embodiment of the present technology;

FIGS. 24-2 and 24-3 are front views of the sealing portion of FIGS. 24-1;

FIG. 24-4 is bottom view of the sealing portion of FIGS. 24-1;

FIGS. 25-1, 25-2 and 25-3 are cross sections of sealing portions according to alternative embodiments of the present technology;

FIG. 25-4 is a top view of a sealing portion according to an embodiment of the present technology;

FIGS. 27-1 and 27-2 are isometric views of an embodiment of the present technology;

FIG. 32-1 is a rear view showing headgear attachment to a sealing portion according to an embodiment of the present technology;

FIG. 32-2 is a front view showing headgear attachment to a sealing portion according to another embodiment of the present technology;

FIGS. 33-1 and 33-2 are top views of supporting members for sealing portions according to alternative embodiment of the present technology;

FIGS. 34-1 and 34-2 show membrane support for a sealing portion according to an embodiment of the present technology;

FIG. 35-1 is a top view of a sealing portion with flexible portions according to an embodiment of the present technology;

FIGS. 35-2 and 35-3 are cross-sectional views of the sealing portion of FIG. 35-1;

FIGS. 37-1 and 37-2 illustrate a vent according to an embodiment of the present technology;

FIG. 42-1 is a top view of a swivel ring with vents according to an embodiment of the present technology;

FIG. 42-2 is an isometric view of the swivel ring of FIG. 42-1;

FIG. 42-3 is a side view of a swivel ring according to an embodiment of the present technology;

FIGS. 42-4, 42-5, 42-6 and 42-7 are top views of swivel rings including vents according to alternative embodiments of the present technology;

FIG. 42-8 is a cross section of the swivel ring of FIG. 42-7;

FIGS. 47-1, 47-2 and 47-3 are isometric views of a patient interface according to the present technology including a sealing portion and a supporting portion;

FIG. 48-1 is a top view of the sealing portion and supporting portion of FIG. 47-1;

FIG. 48-2 is a schematic top view of the sealing portion of FIG. 47-1;

FIG. 51-1 is a cross-sectional side view of the sealing portion and supporting portion of FIG. 49;

FIG. 51-2 is a cross-sectional side view of the sealing portion and supporting portion of FIG. 49, with a second membrane;

FIG. 52-1 is a side view of the supporting portion of FIG. 47-1;

FIG. 52-2 is a cross-sectional front view of the sealing portion and supporting portion of FIG. 49;

FIG. 52-3 is a partial cross-sectional front view of the sealing portion and supporting portion of FIG. 49;

FIG. 52-4 is a cross-sectional side view of the sealing portion and supporting portion of FIG. 49 on the patient in use;

FIG. 52-5 is a side view of the sealing portion and supporting portion of FIG. 49 on the patient in use;

FIG. 52-6 is a cross-sectional side view of the sealing portion and supporting portion of FIG. 49 on the patient in use;

FIG. 52-7 is a front perspective view of the sealing portion and supporting portion of FIG. 49 on the patient in use;

FIG. 53 is a front view of the supporting portion of FIG. 47-1;

FIG. 54 is a front view of the supporting portion of FIG. 47-1 and headgear connectors;

FIG. 55 is a top view of the supporting portion and headgear connectors of FIG. 54;

FIG. 56-1 is a side view of the supporting portion and headgear connectors of FIG. 54;

FIG. 56-2 is a cross-sectional view of the supporting portion of FIG. 54;

FIG. 56-3 is a cross-sectional view of the supporting portion of FIG. 54;

FIG. 57 is a front perspective view of a patient interface according to an embodiment of the present technology;

FIG. 58 is a front perspective view of a patient interface in a bent position according to an embodiment of the present technology;

Figure 1:
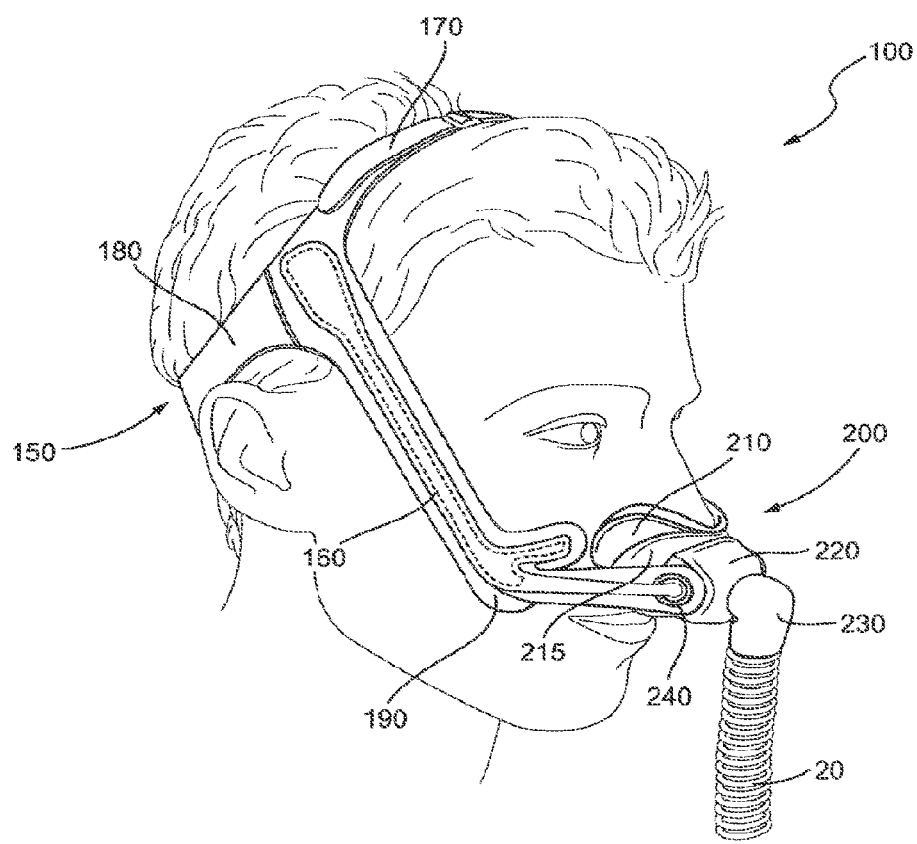
FIG. 1 shows a PAP system with a prior art patient interface.
Figures 1, 2:
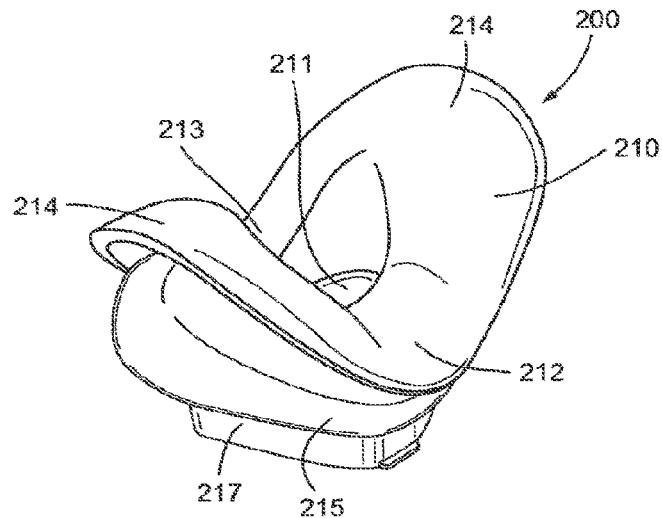
Figure 59:
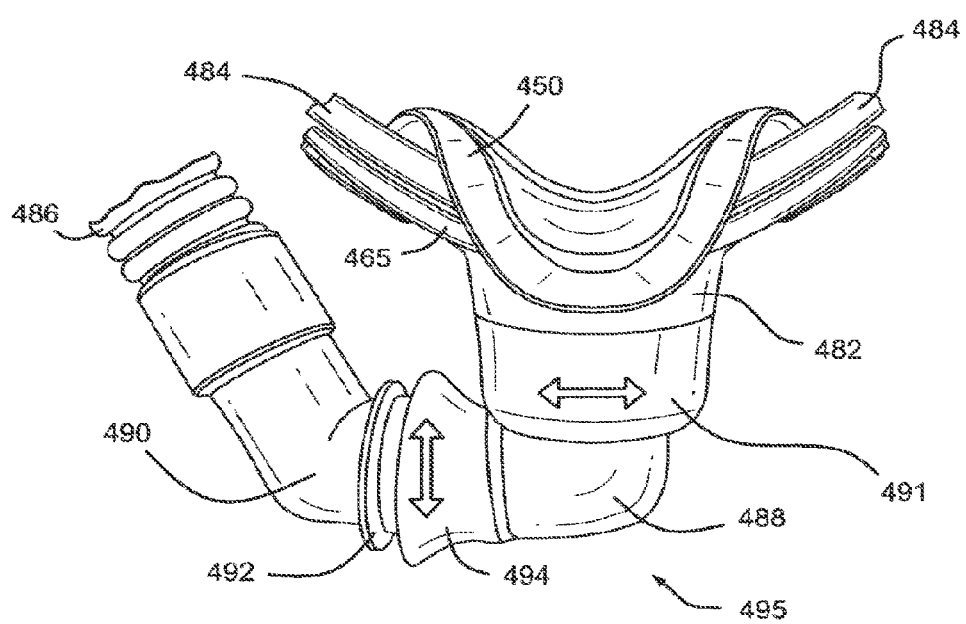
Figure 60:
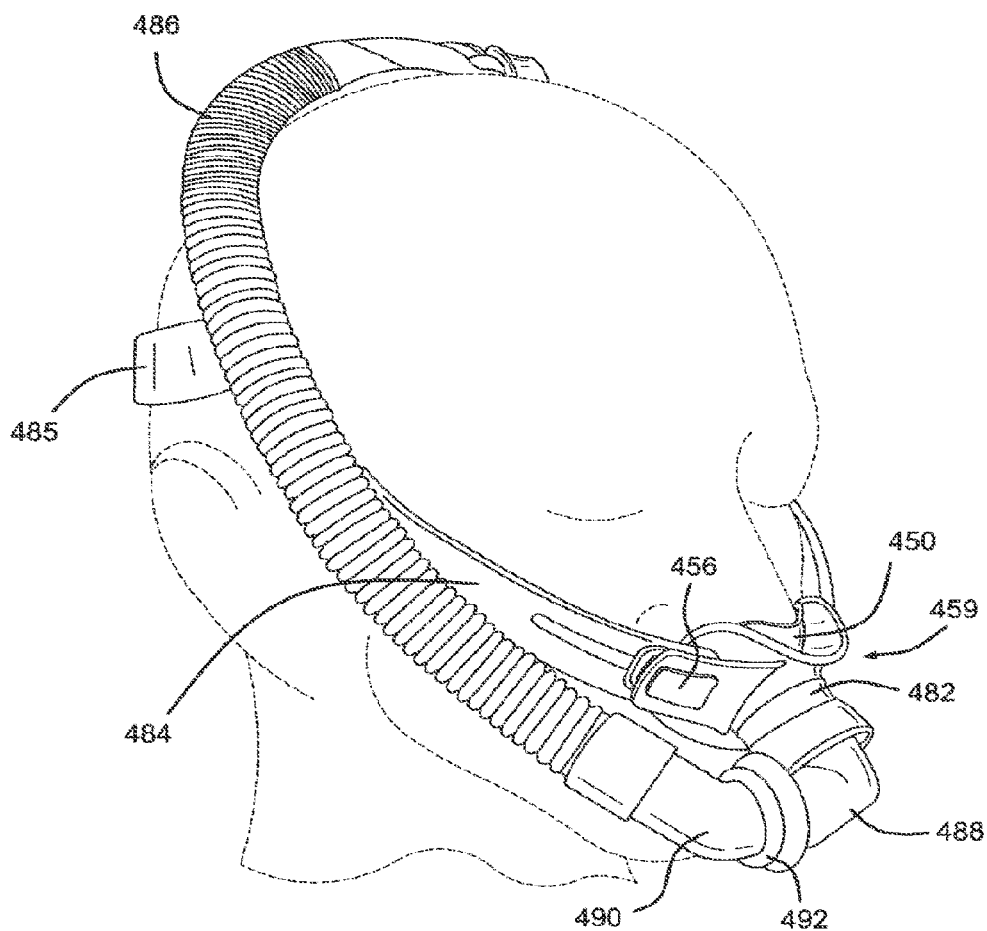
Figure 61:
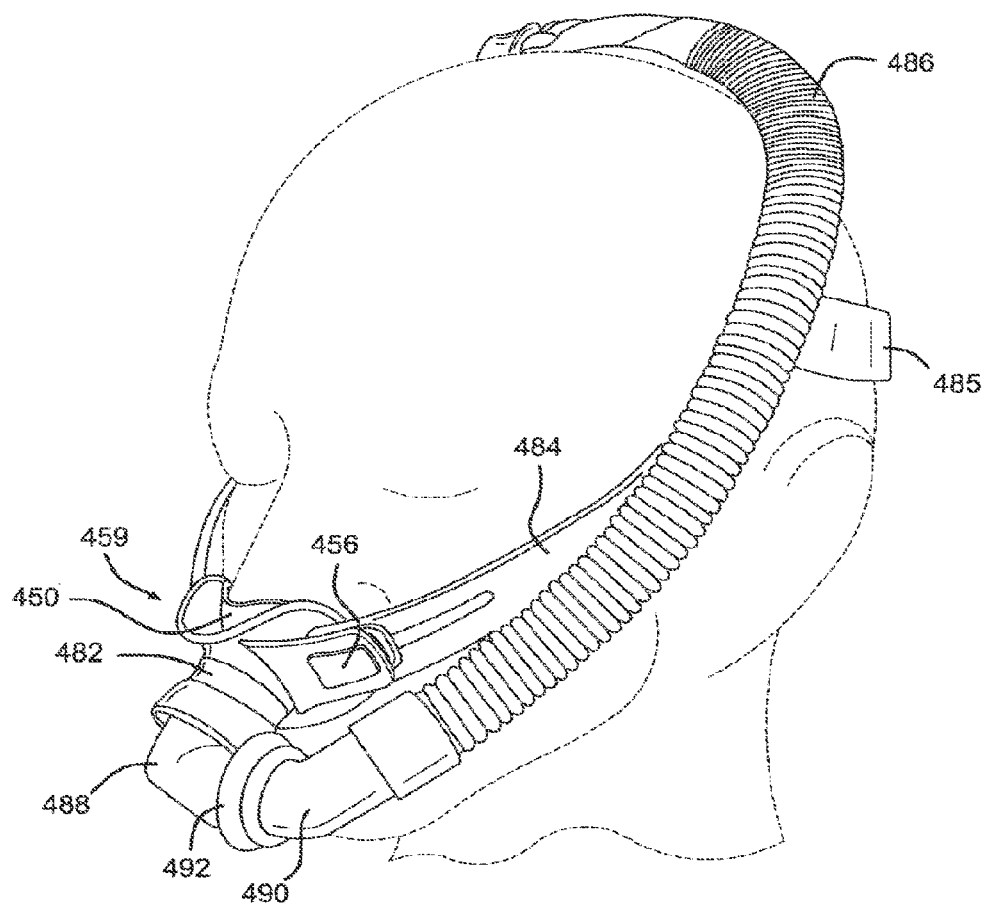
Figure 62:
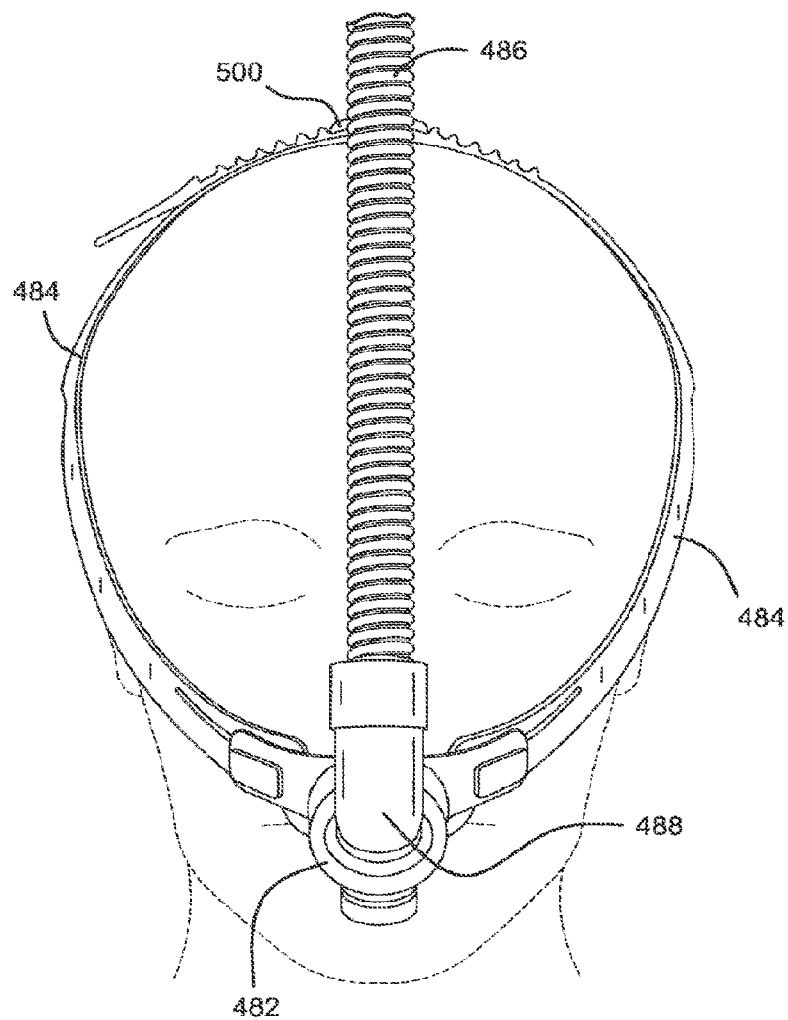
Figure 63:
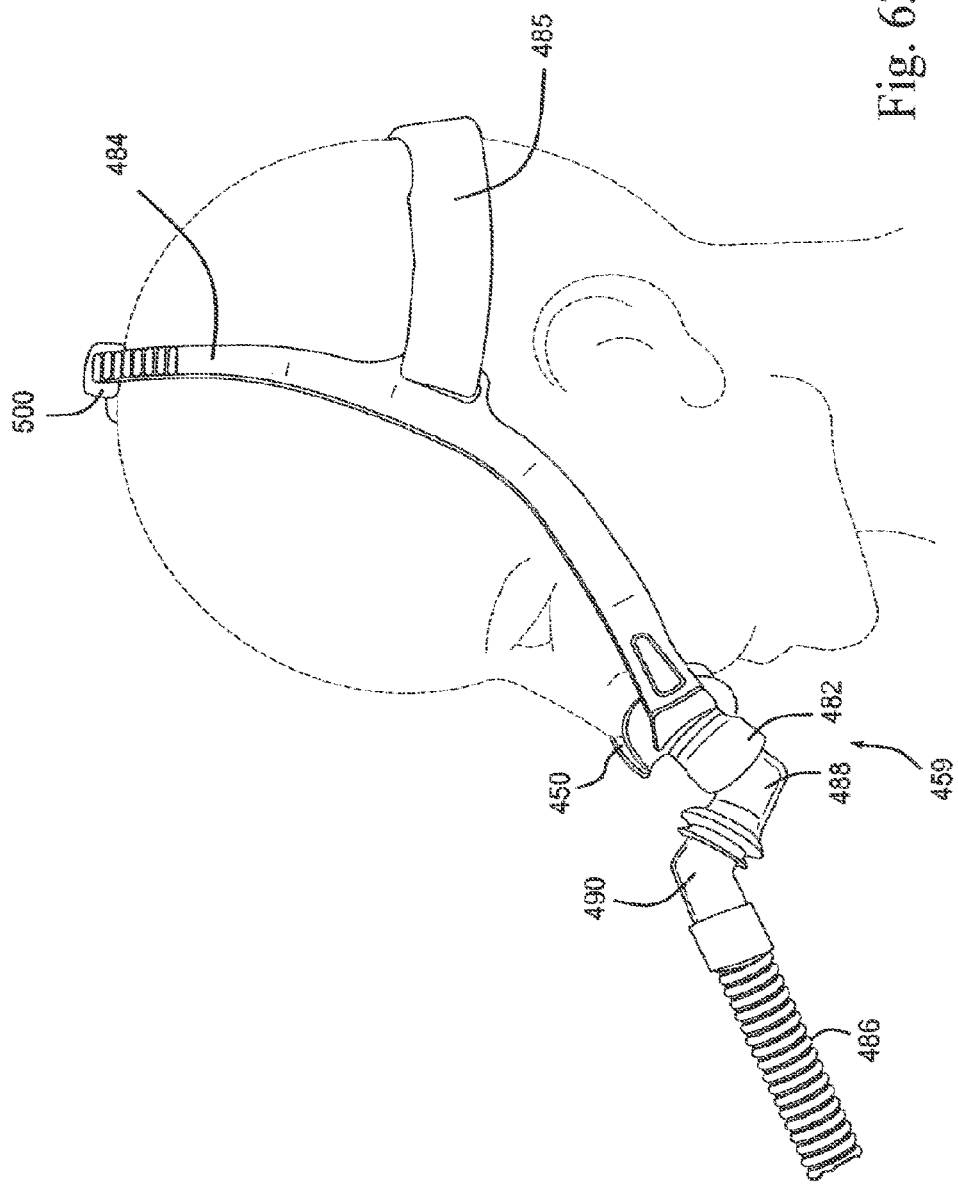
Figure 64:
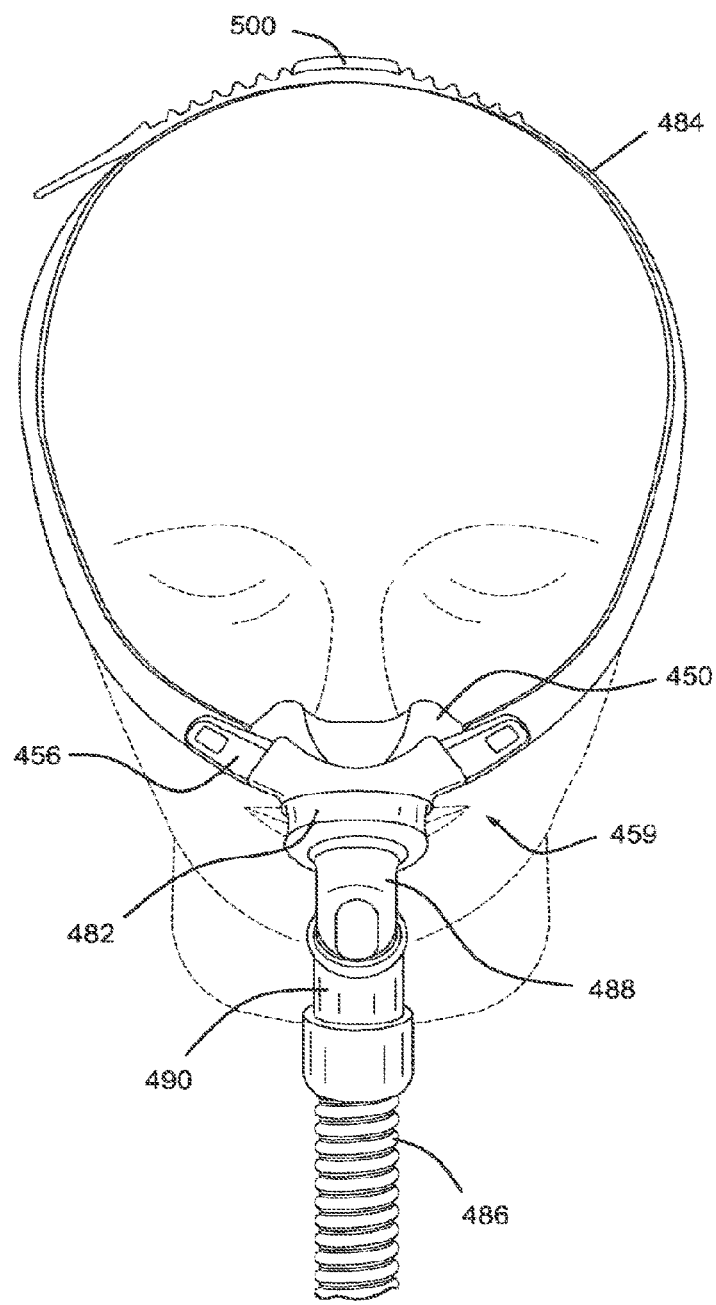
Figure 68:
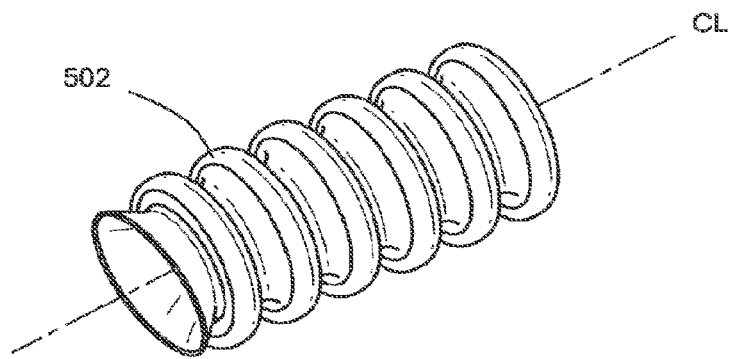
Figure 69:
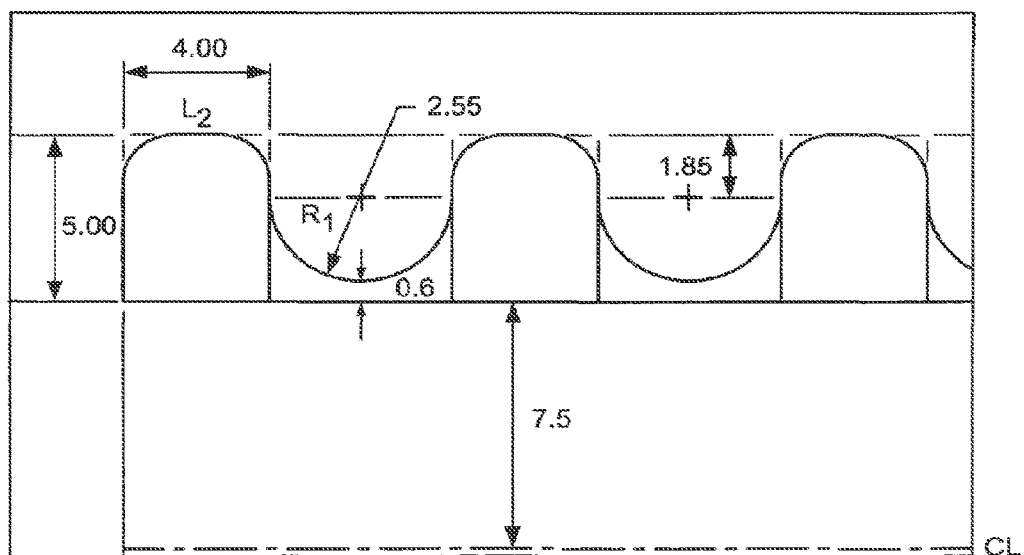
Figure 70:
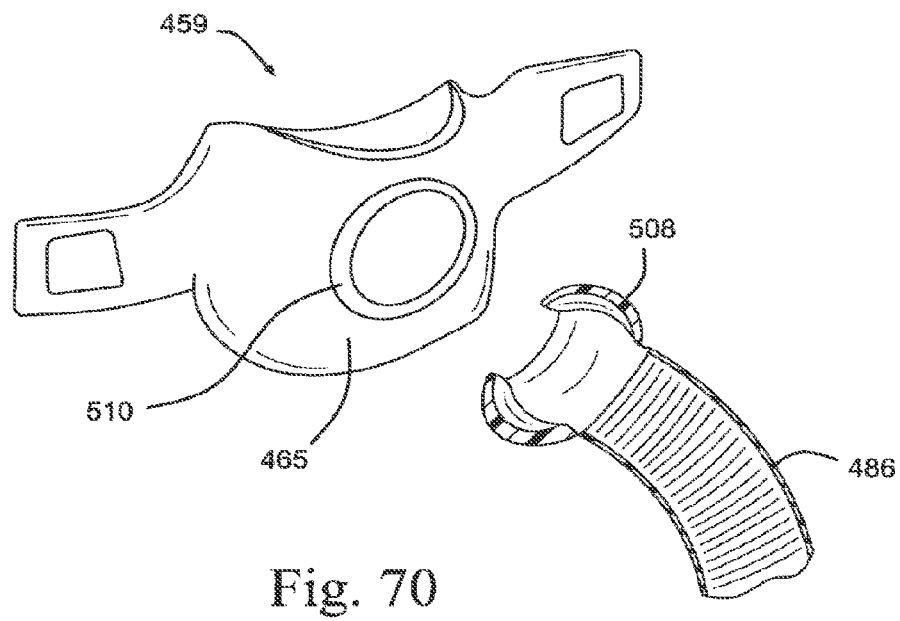
Figure 71:
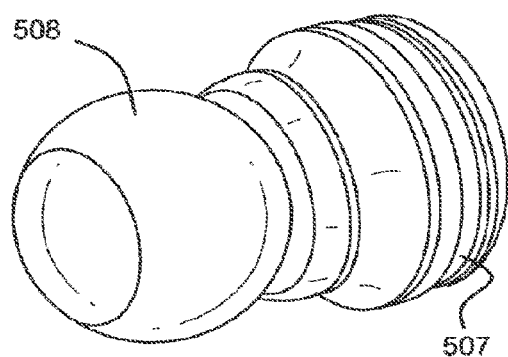
Figure 72:
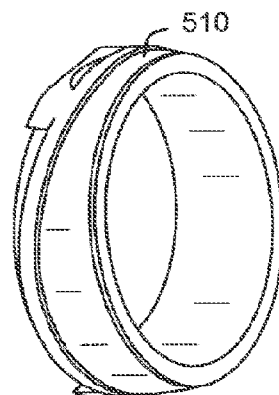
Figure 73:
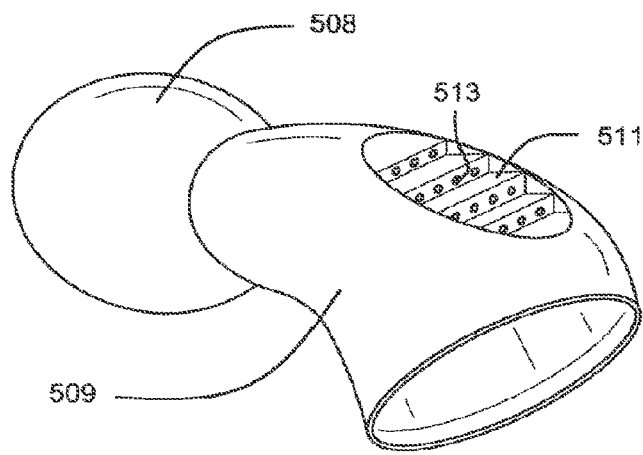
Figure 74:
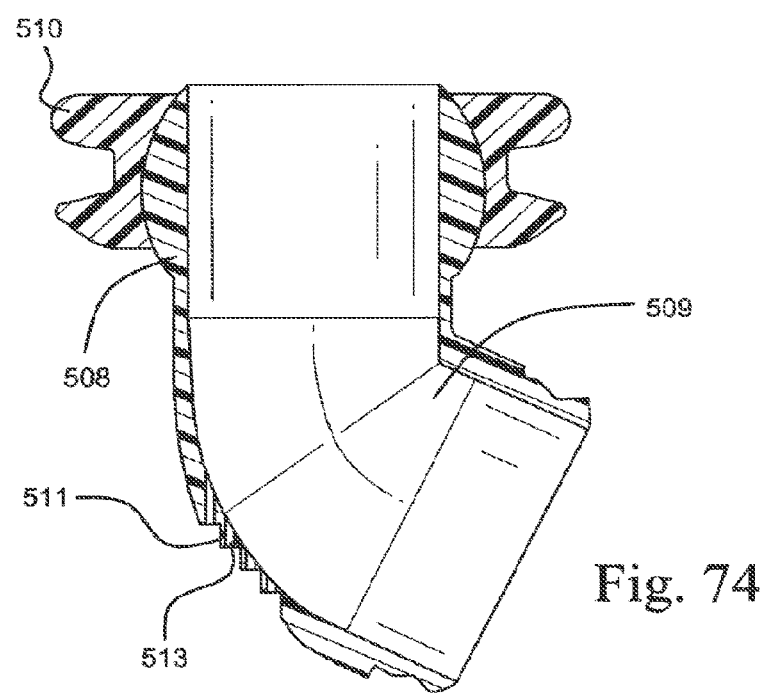
Figure 75:
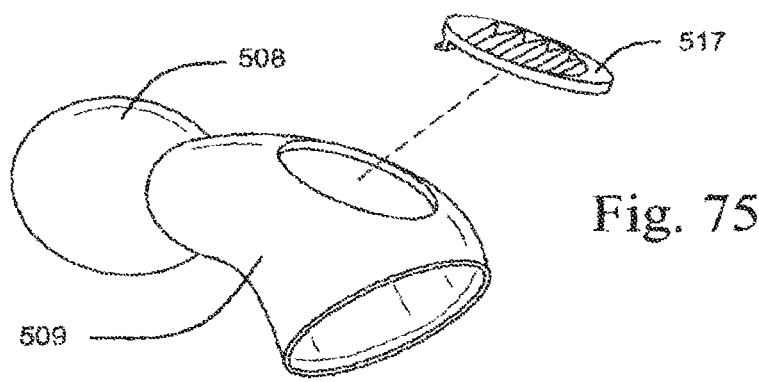
Figure 76:
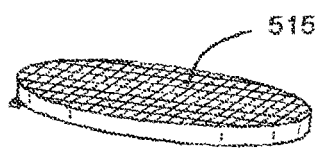
Figure 77:
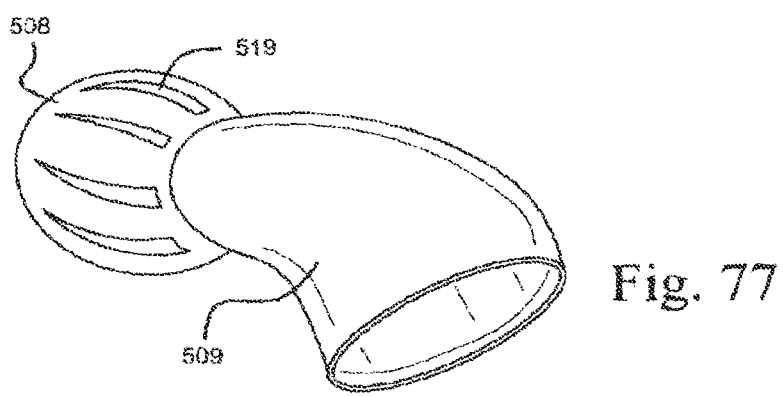
Figure 78:
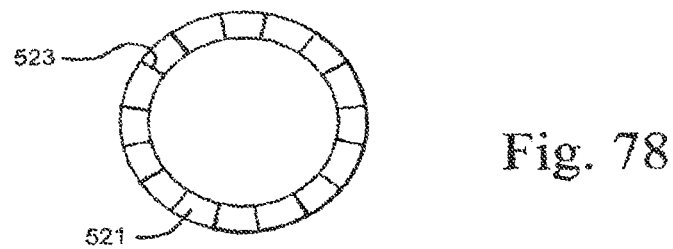
Figure 79:
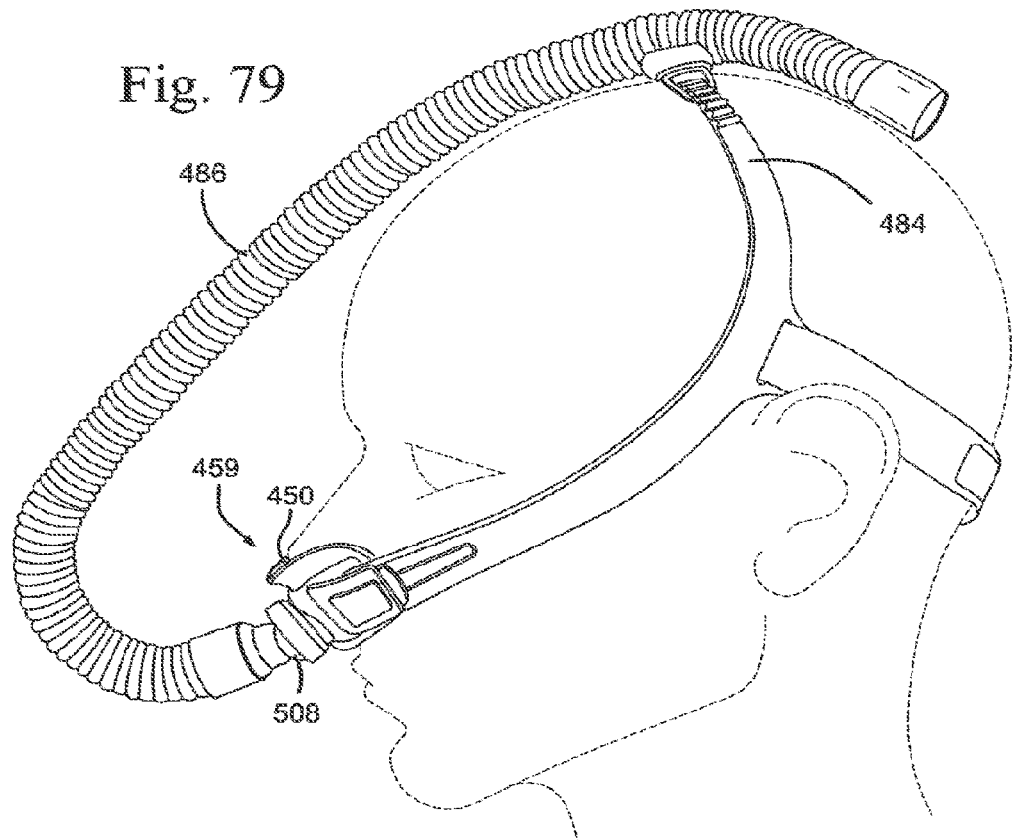
Figure 80:
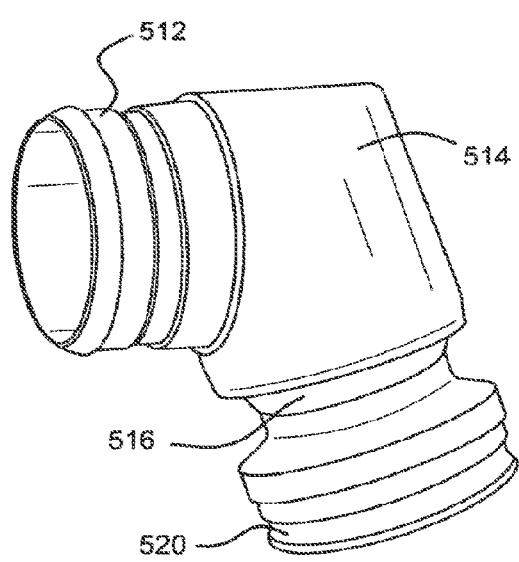
Figure 81:
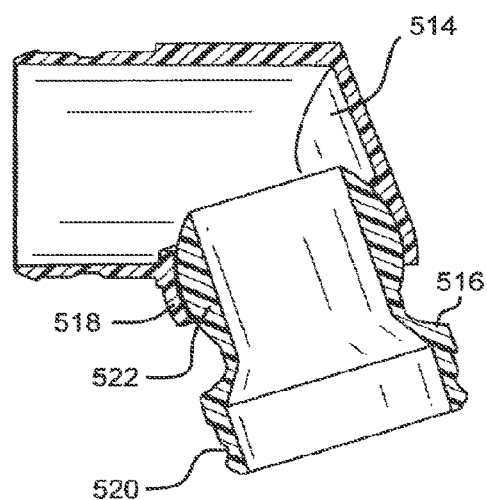
Figure 82:
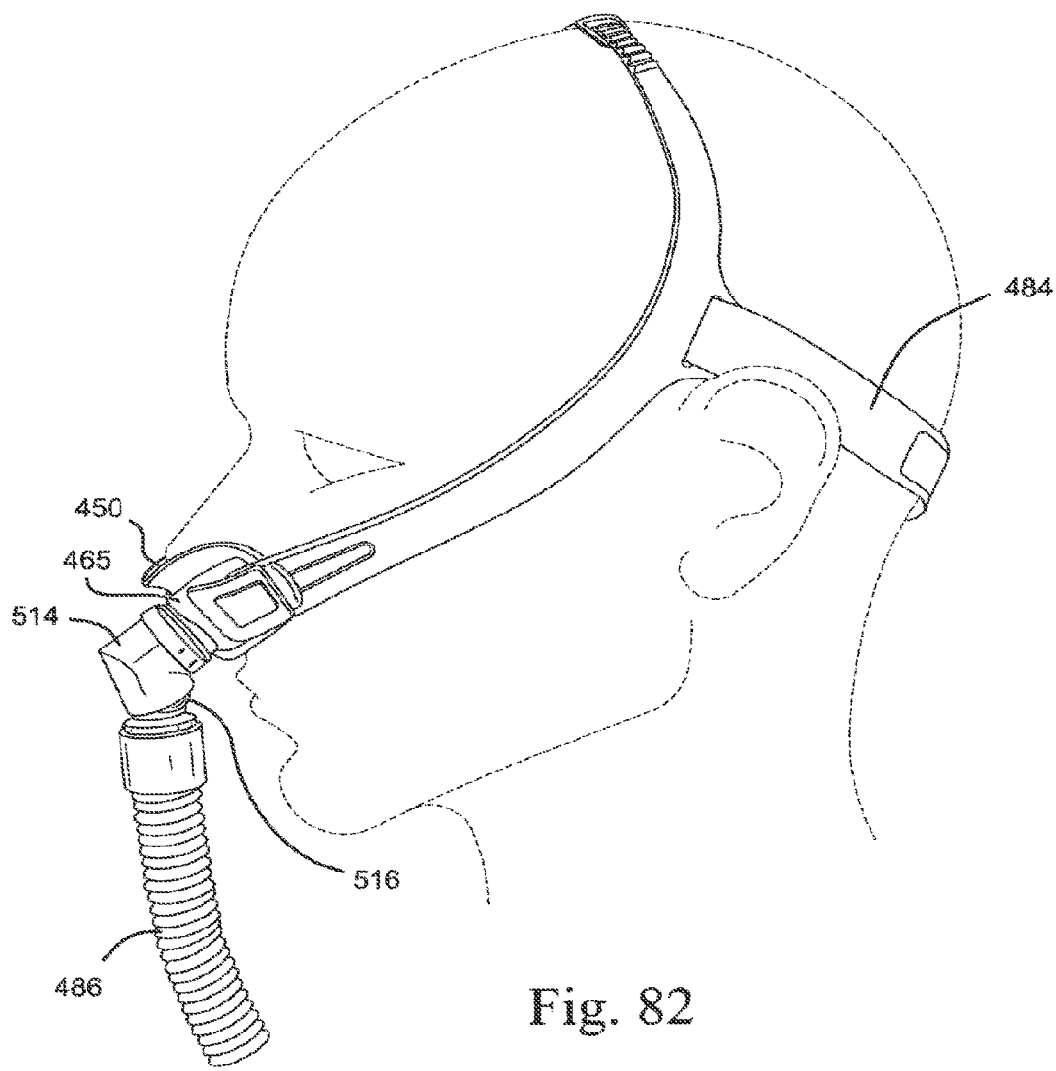
Figure 83:
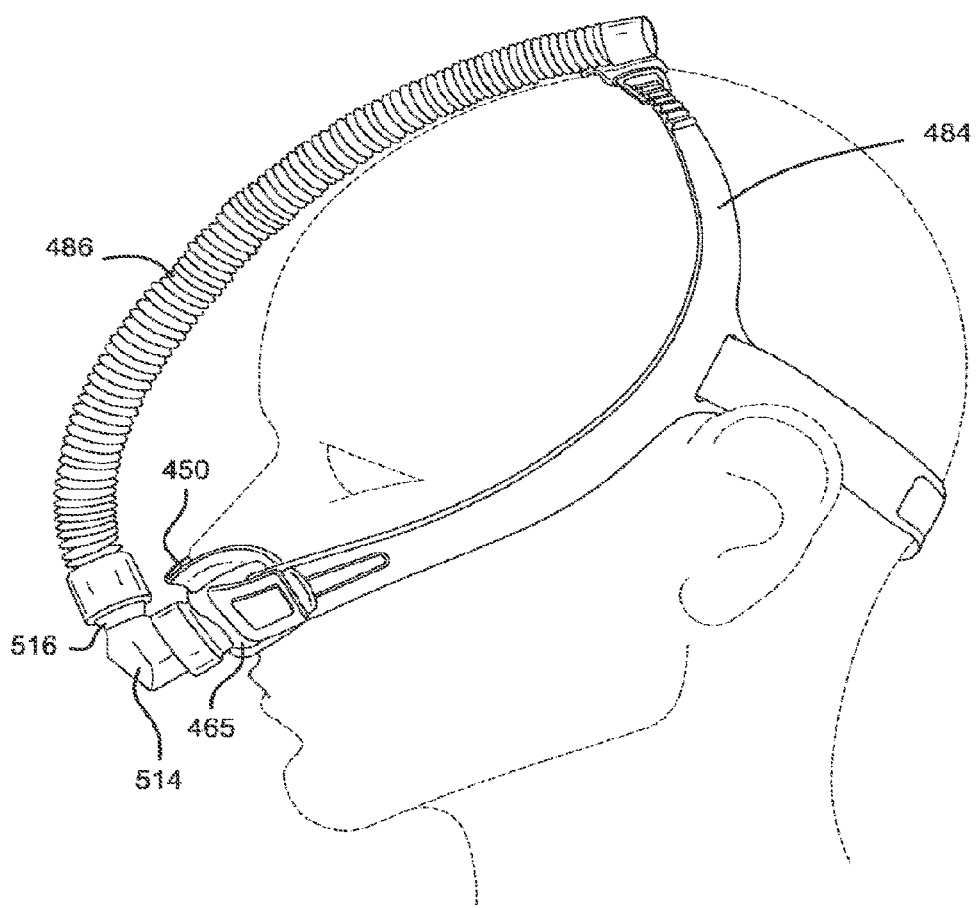
Figure 84:
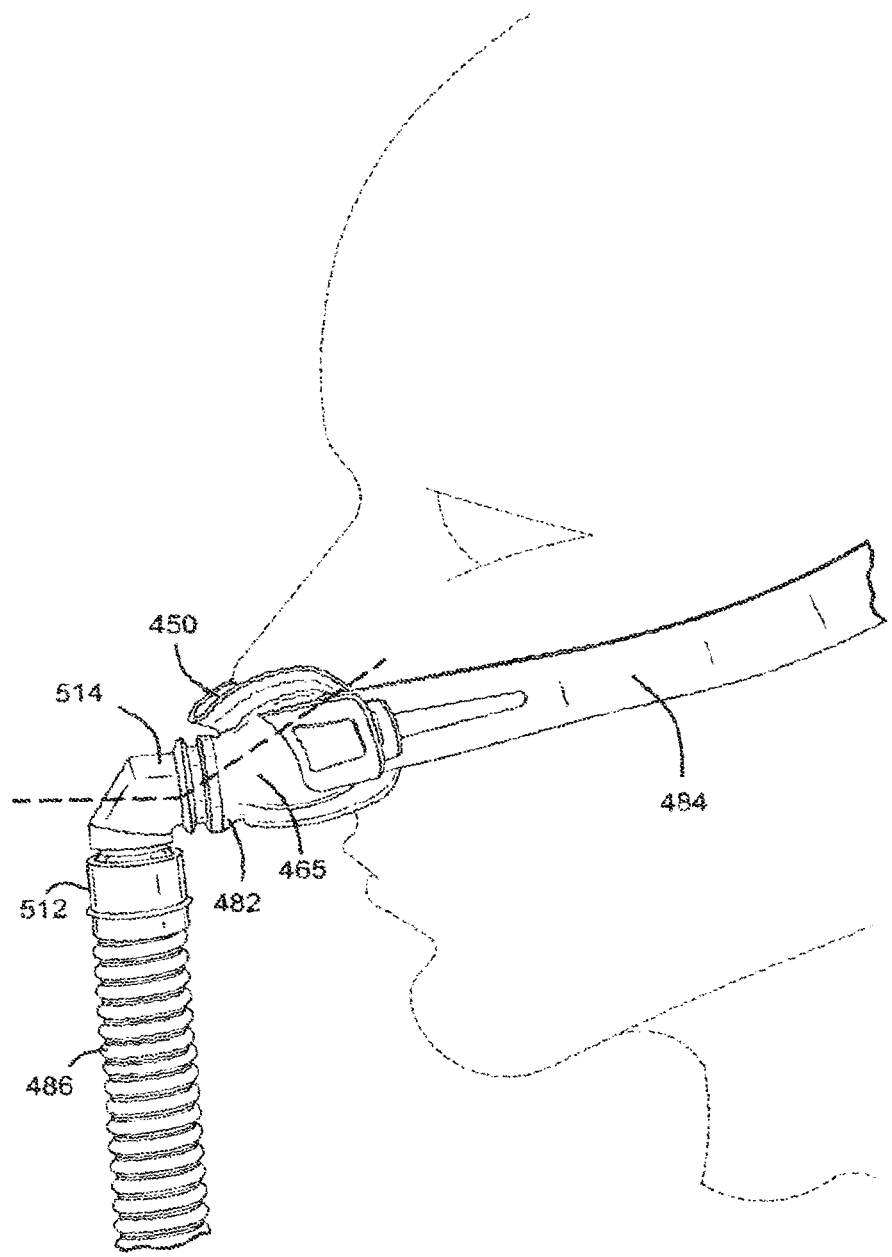
Figure 85:
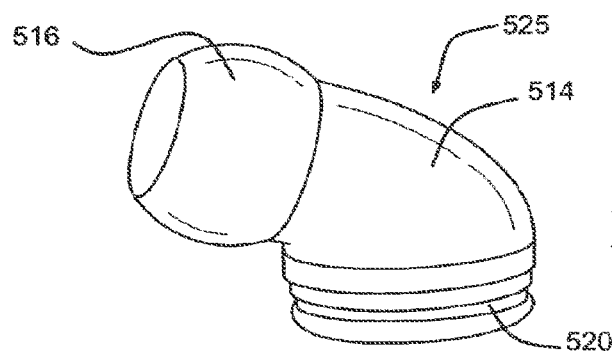
Figure 86:
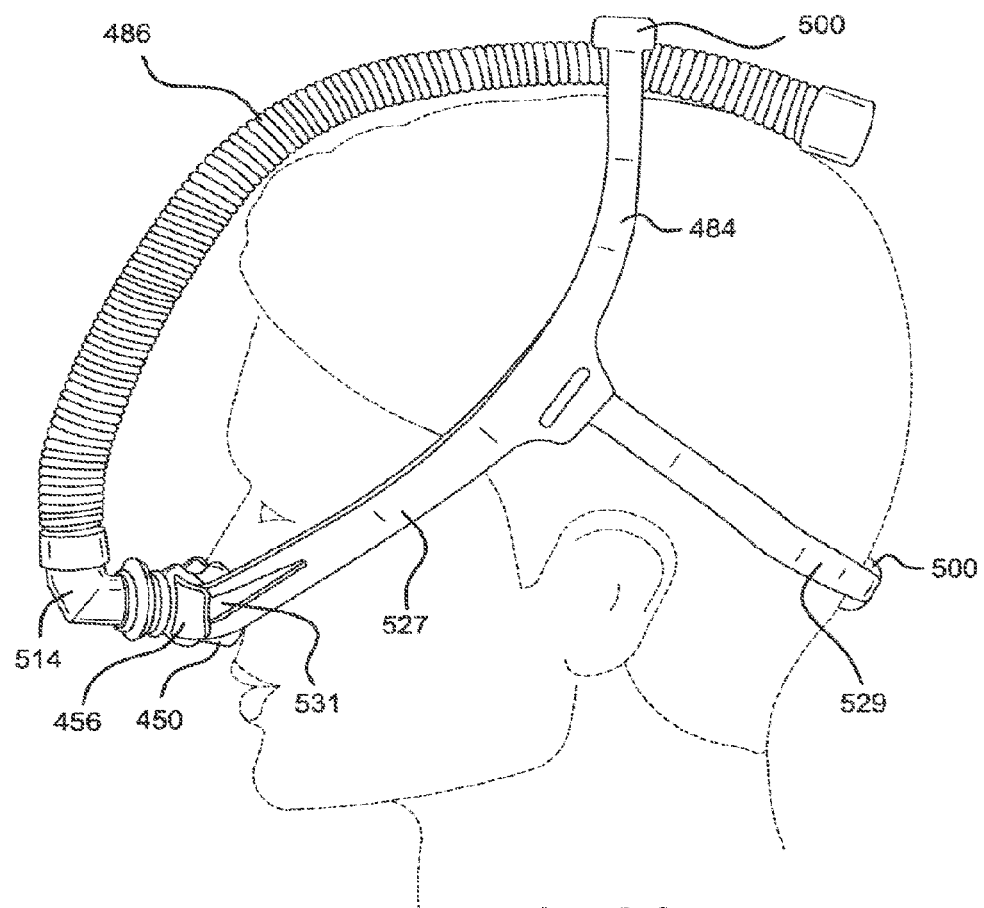
Figure 87:
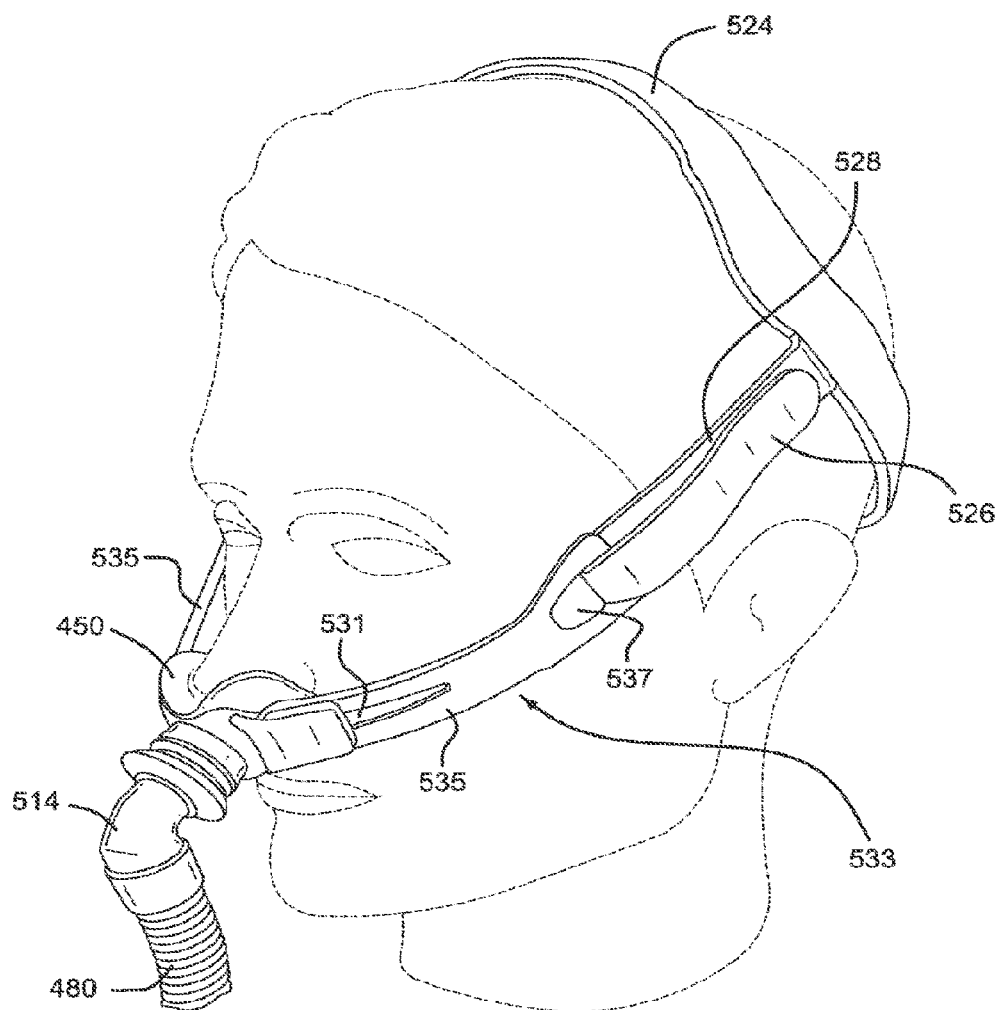
Figure 88:
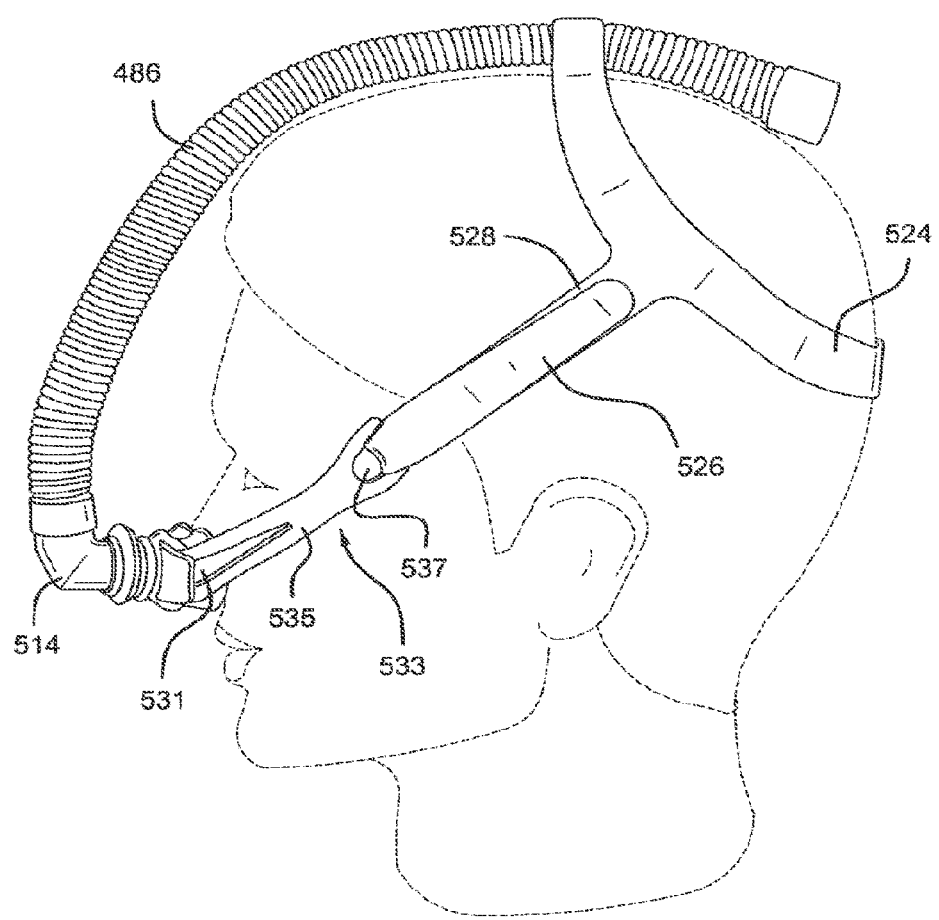
Figure 89:
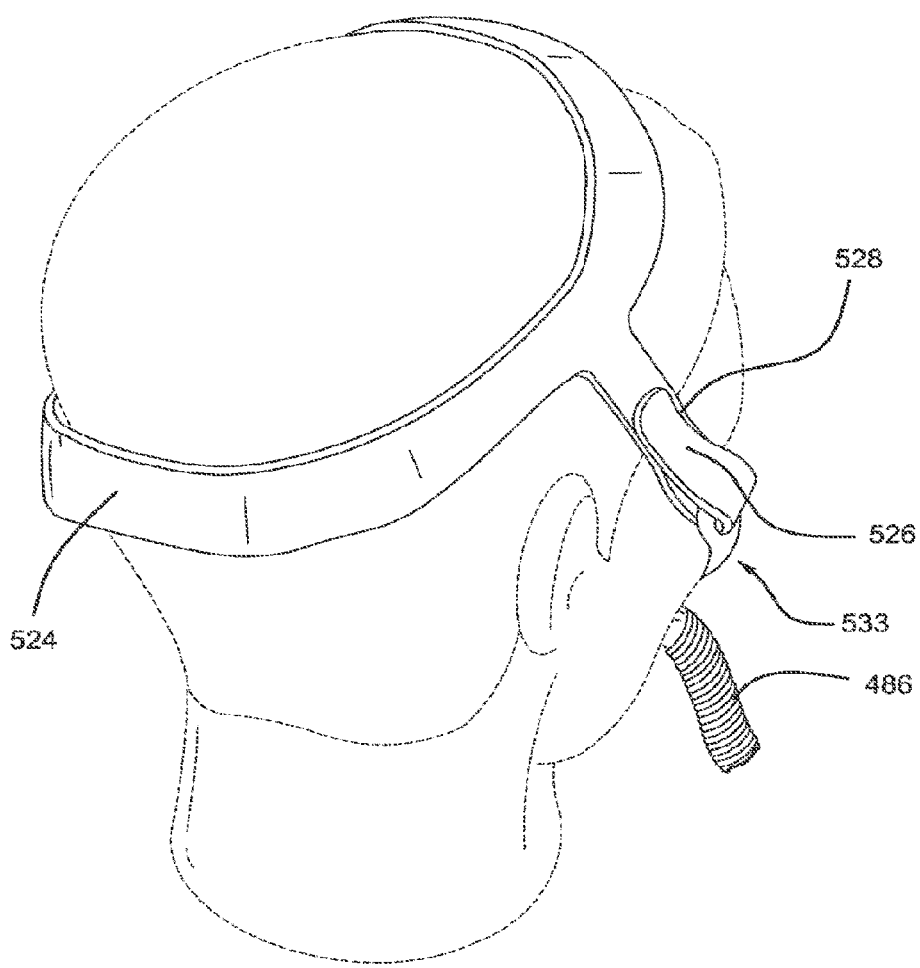
Figure 90:
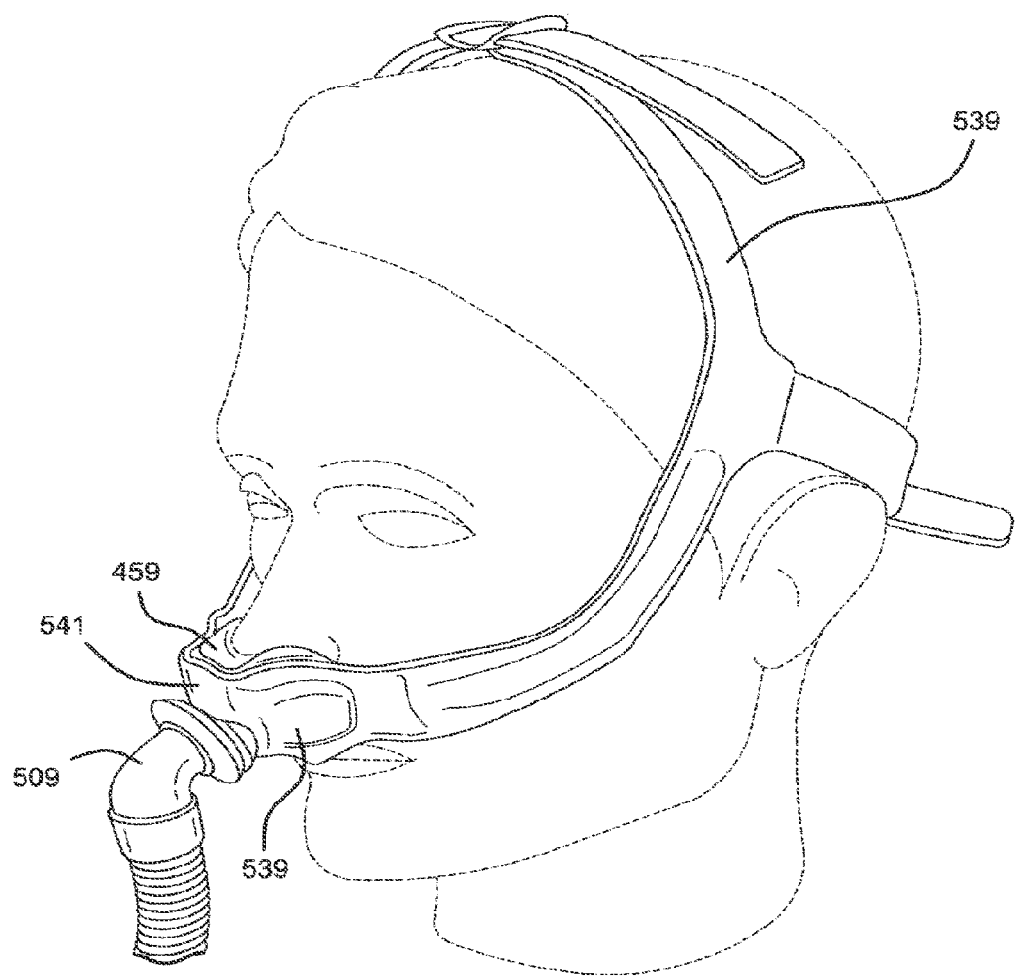
Figure 91:
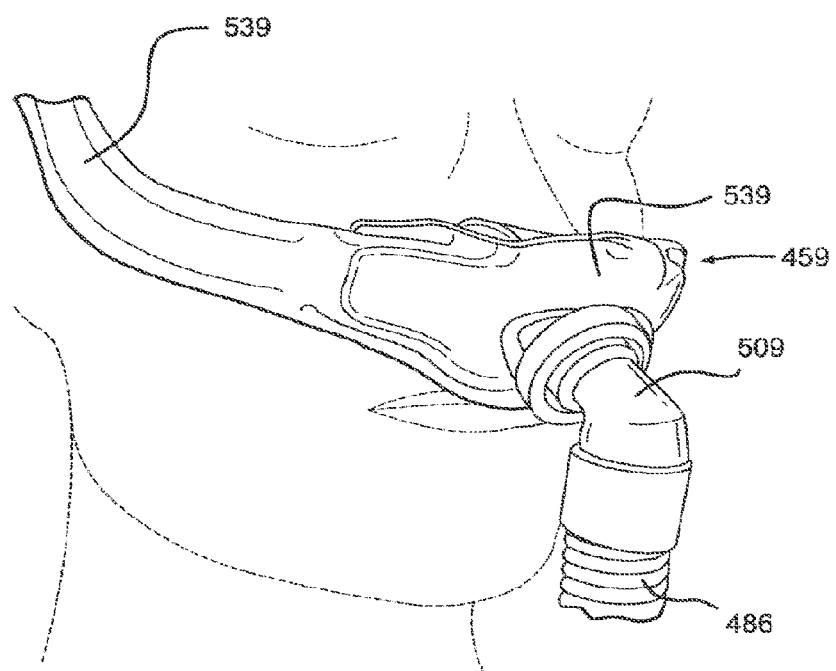
Figure 92:
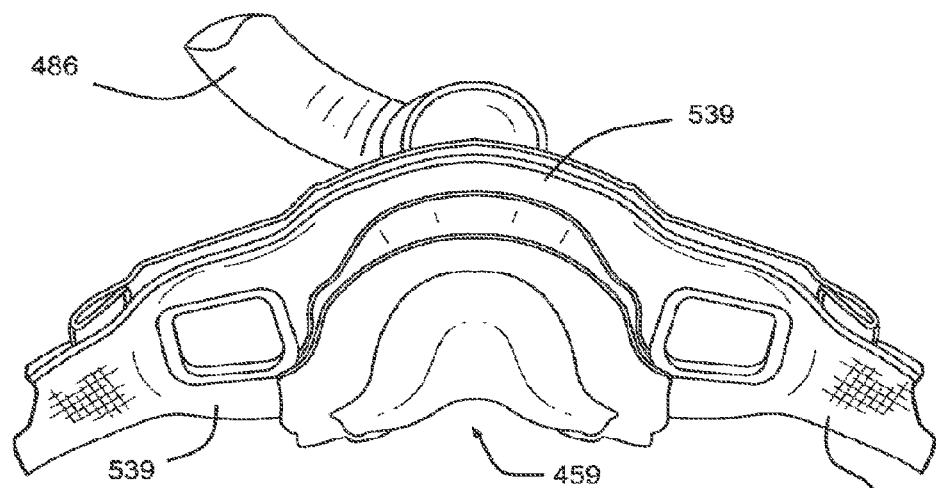
Figures 1, 92:
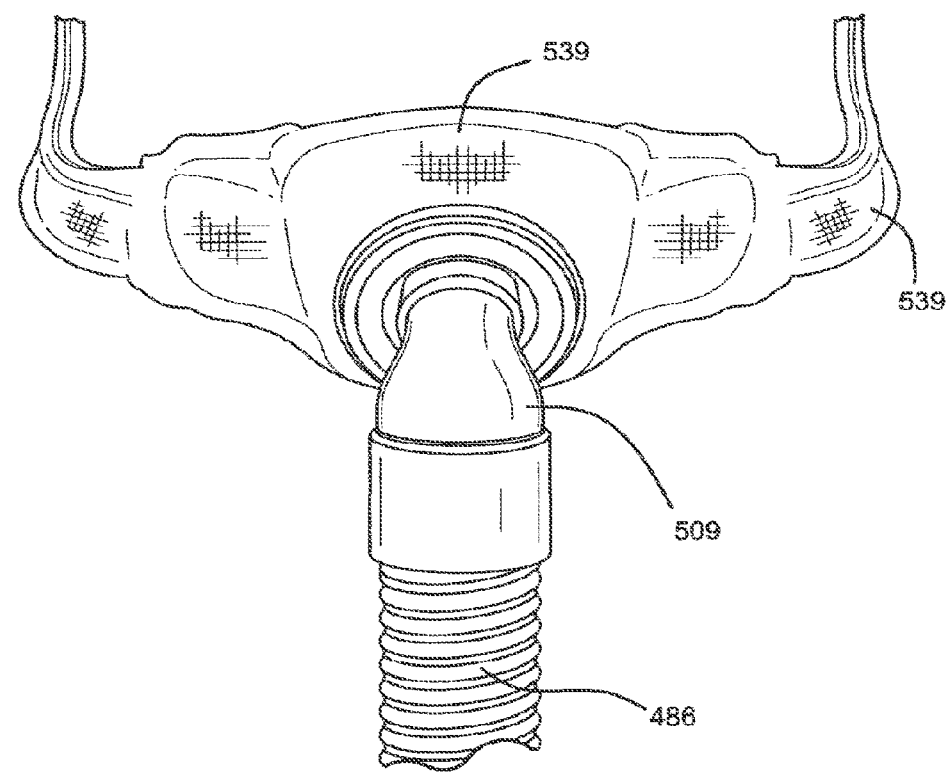
Figure 93:
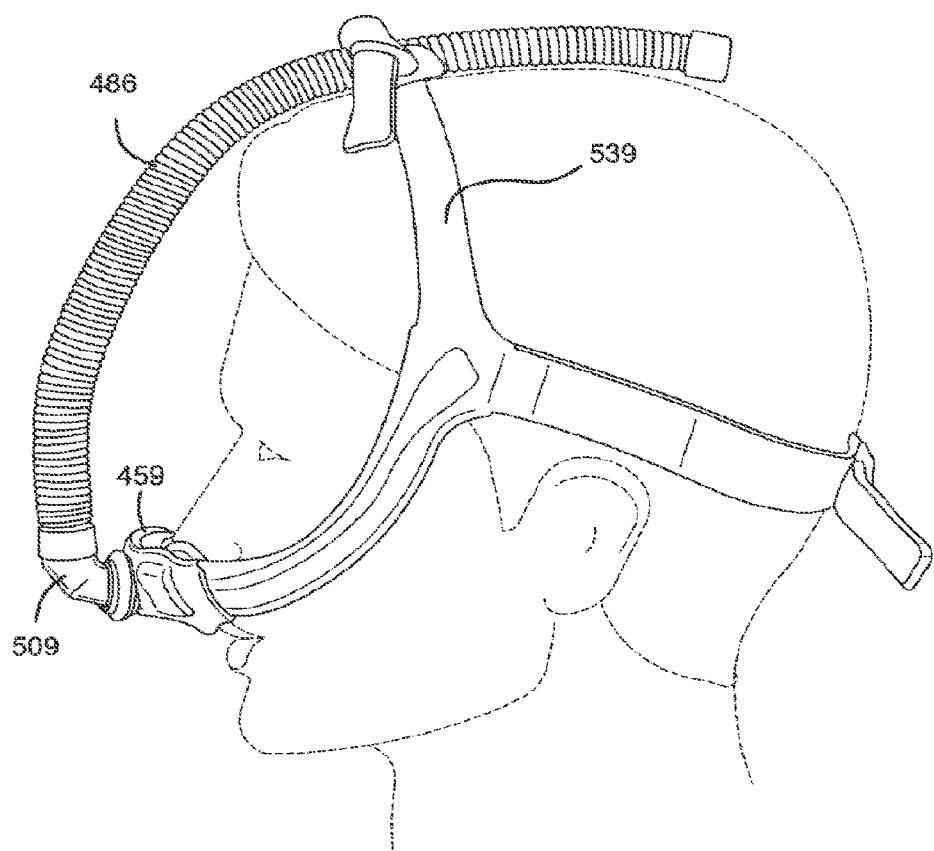
Figure 94:
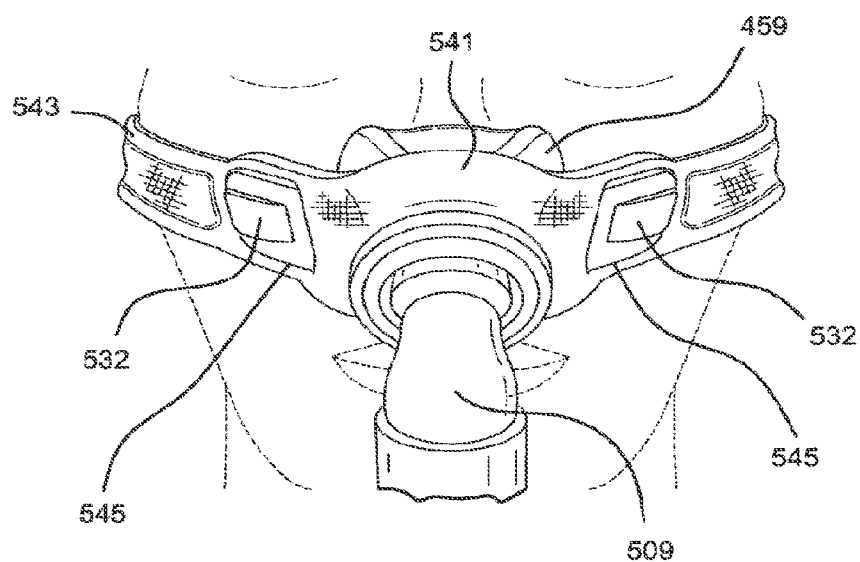
Figure 95:
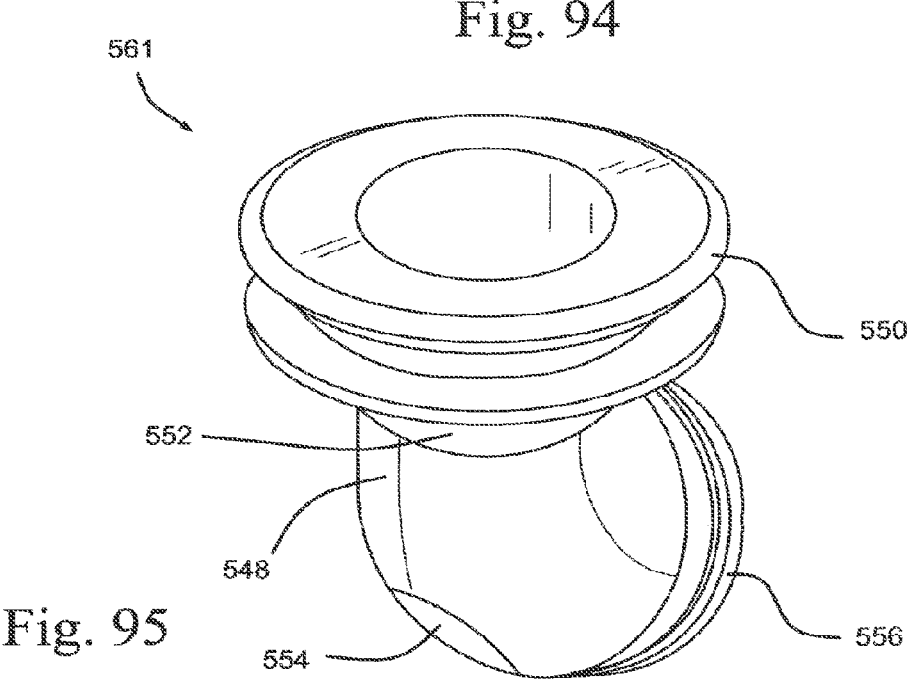
Figure 96:
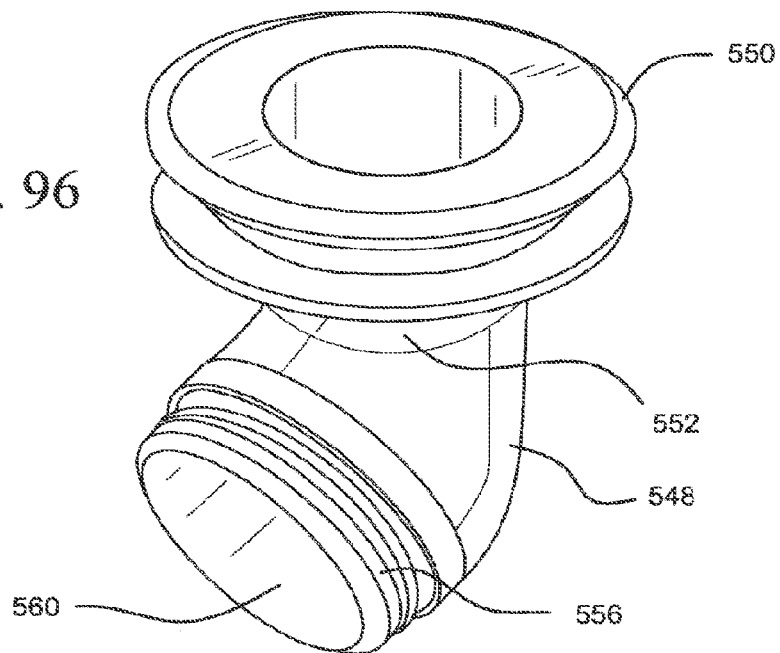
Figure 97:
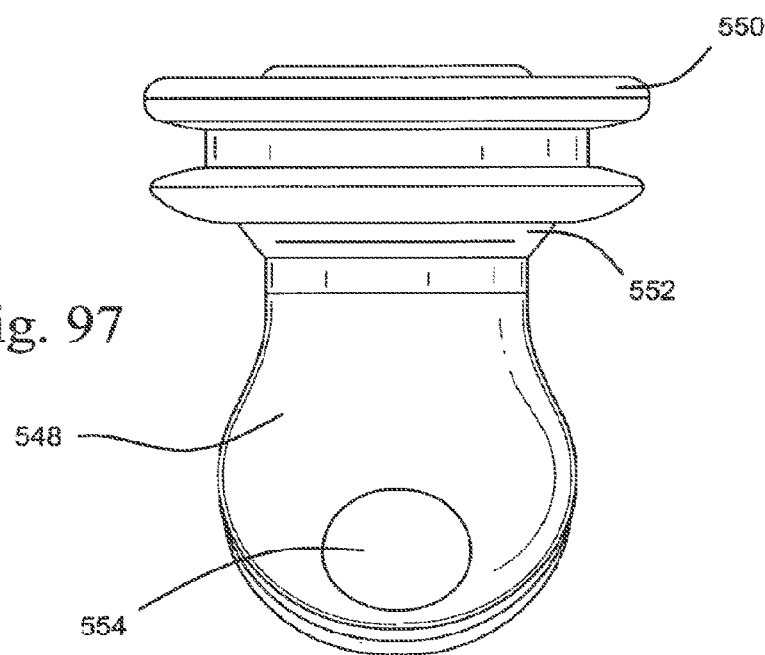
Figure 98:
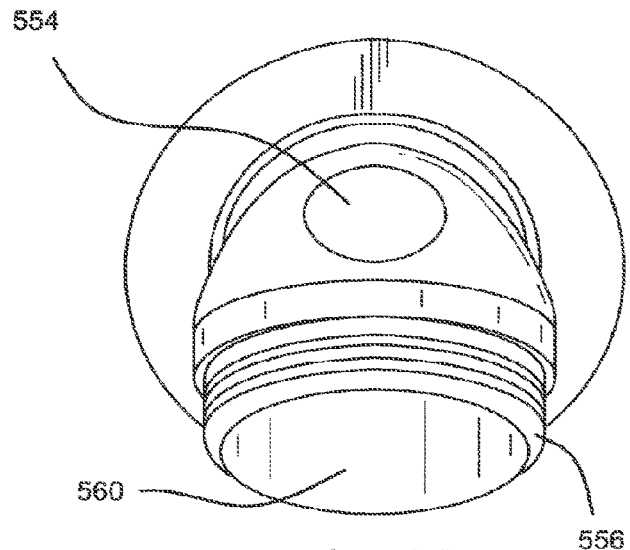
Figure 99:
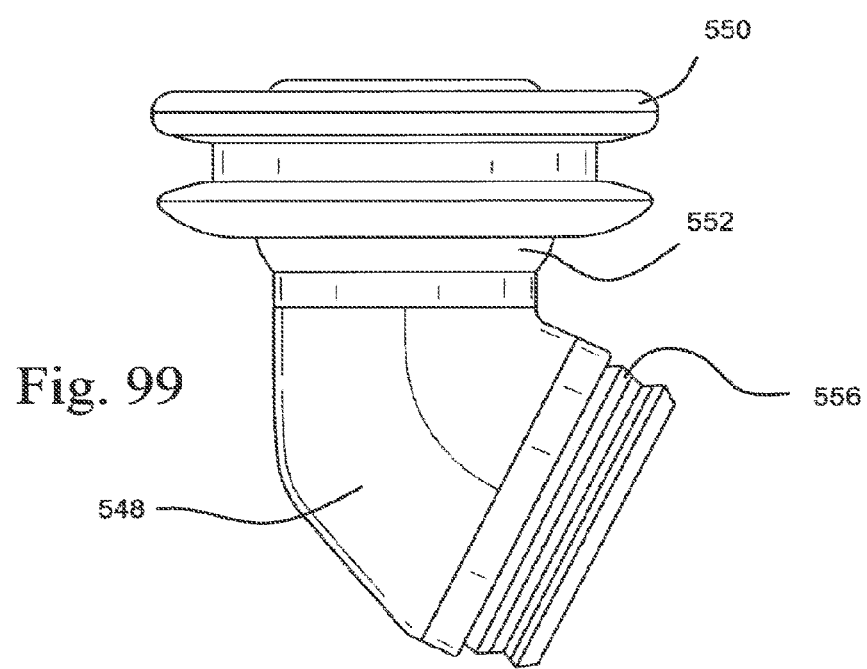
Figure 100:
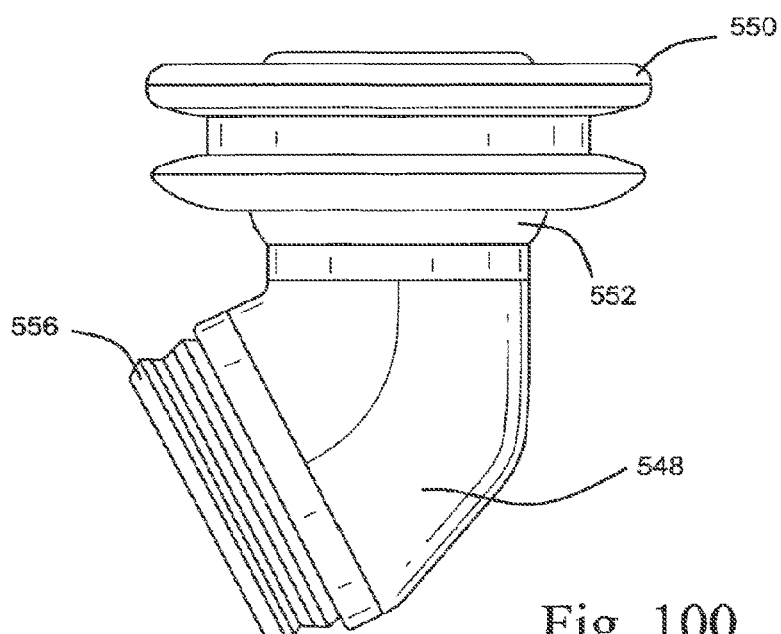
Figure 101:
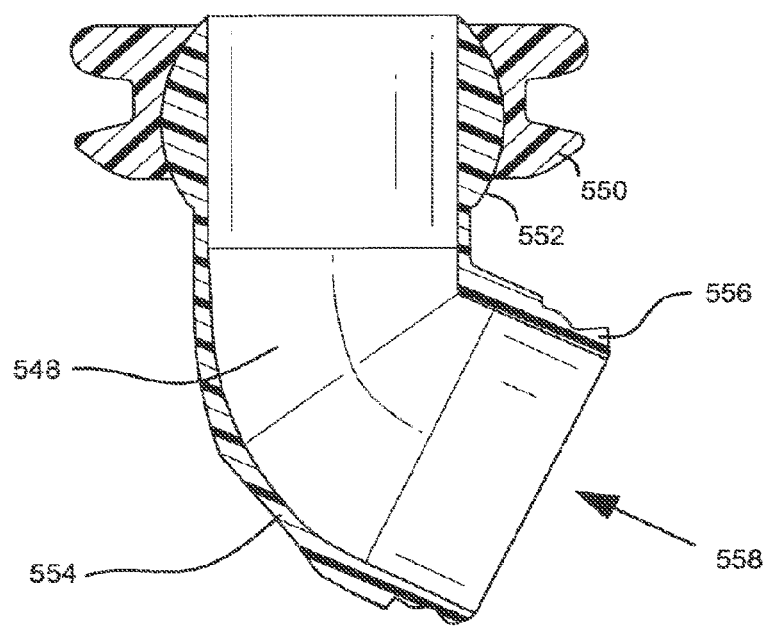
Figure 102:
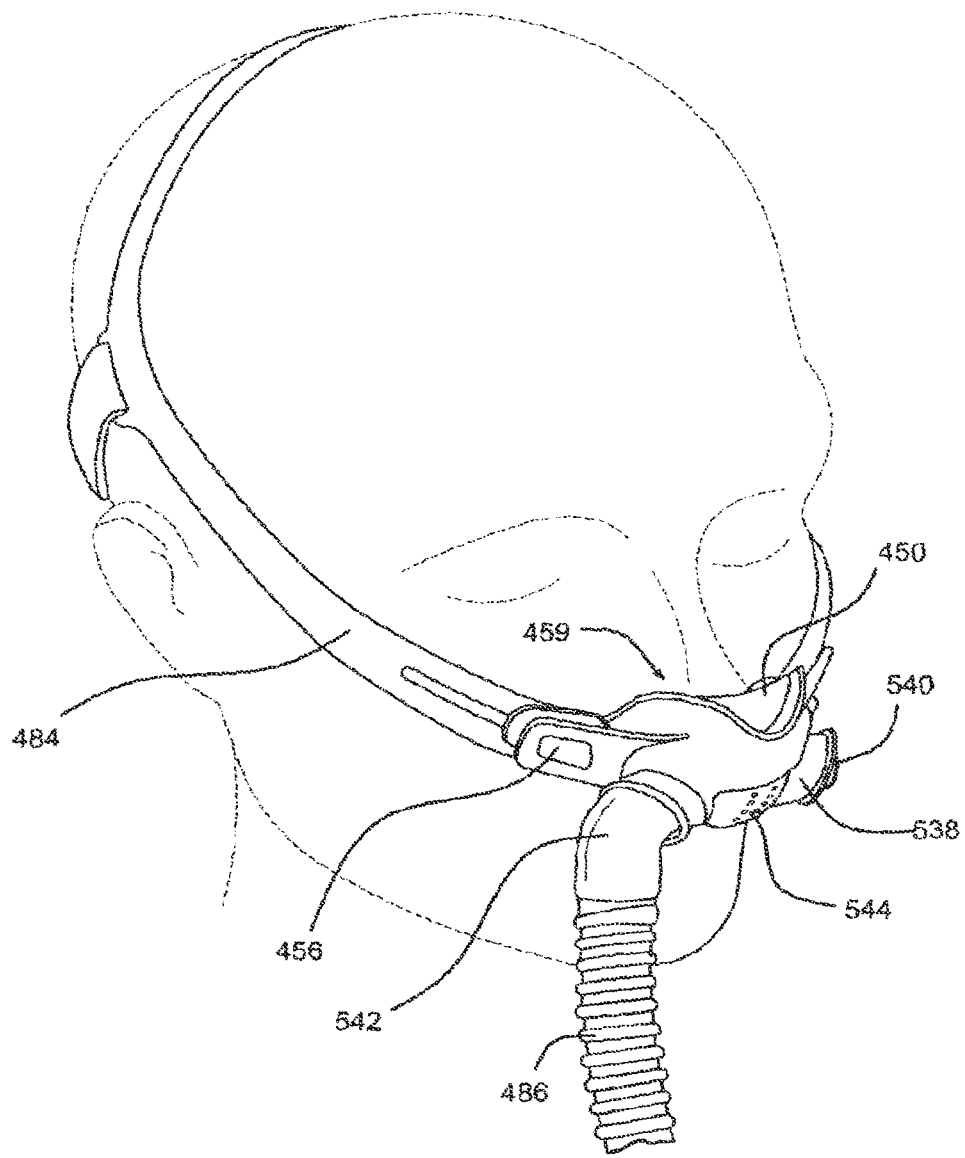
Figure 103:
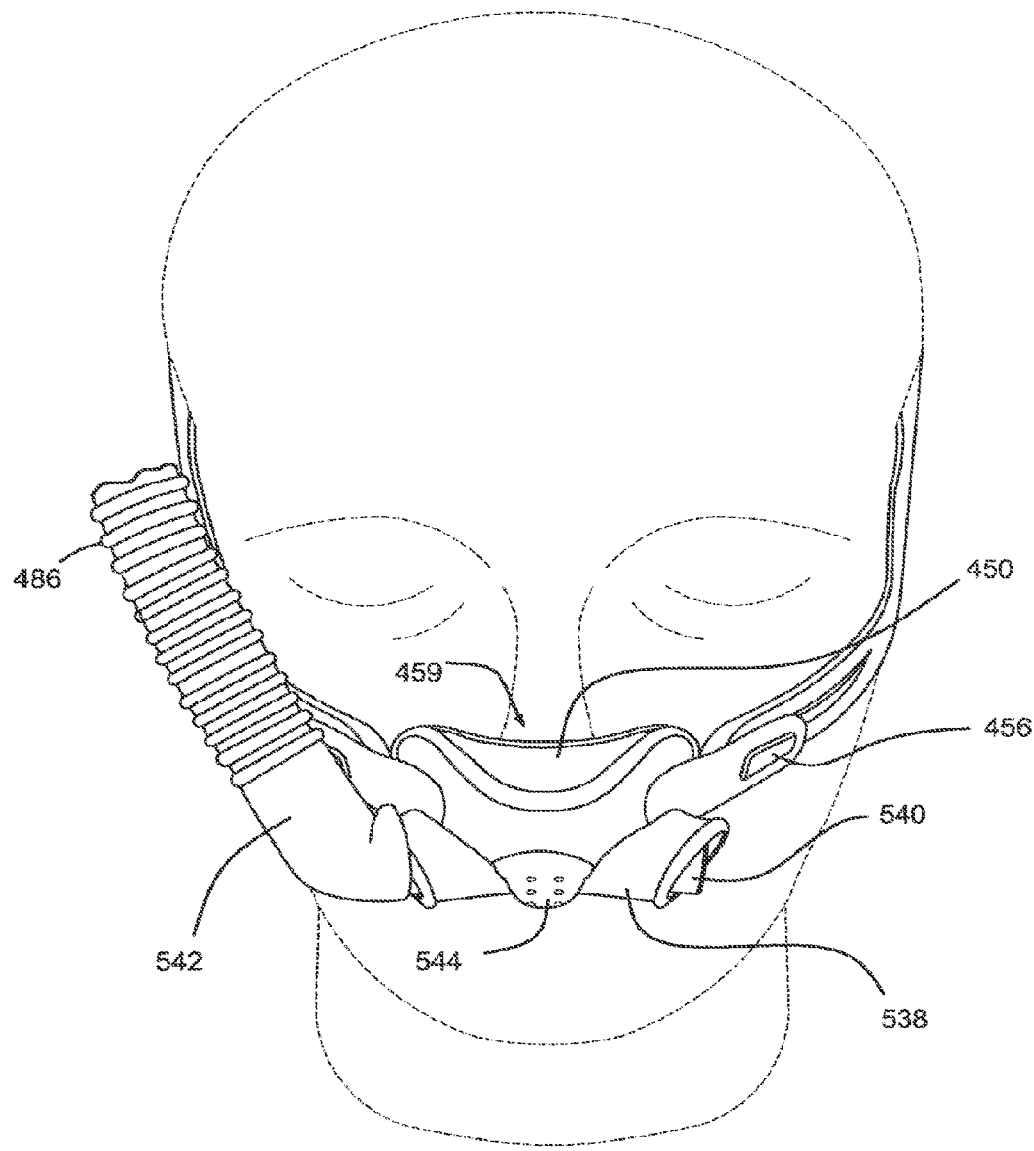
Figure 104:
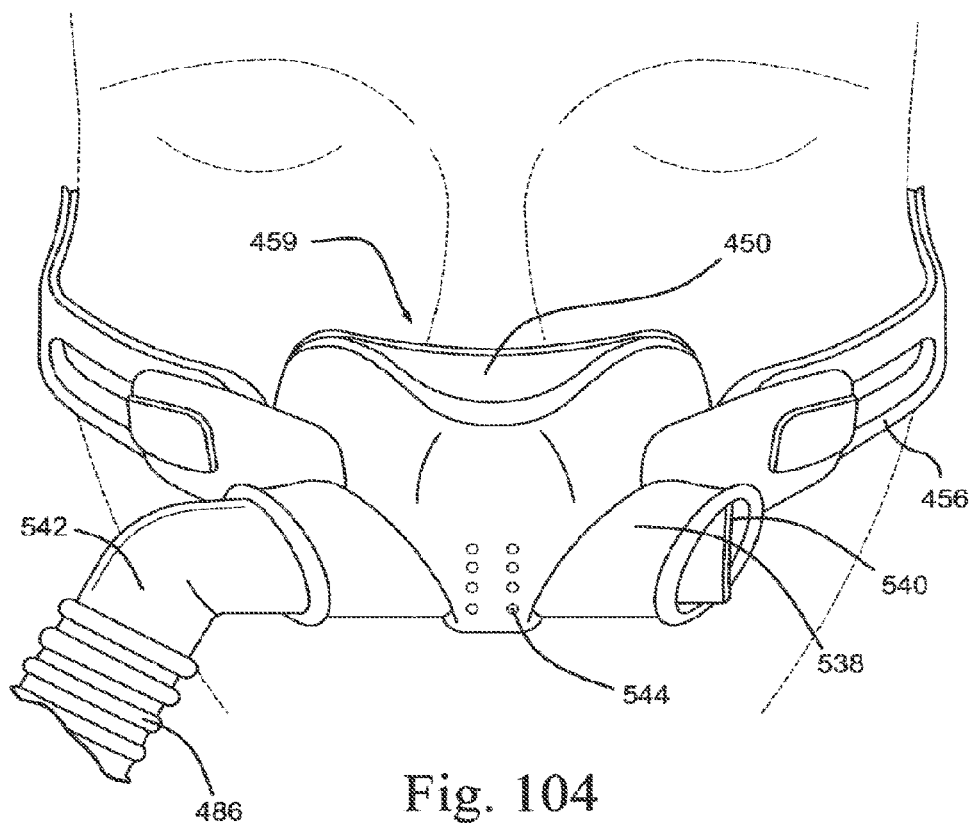
Figure 105:
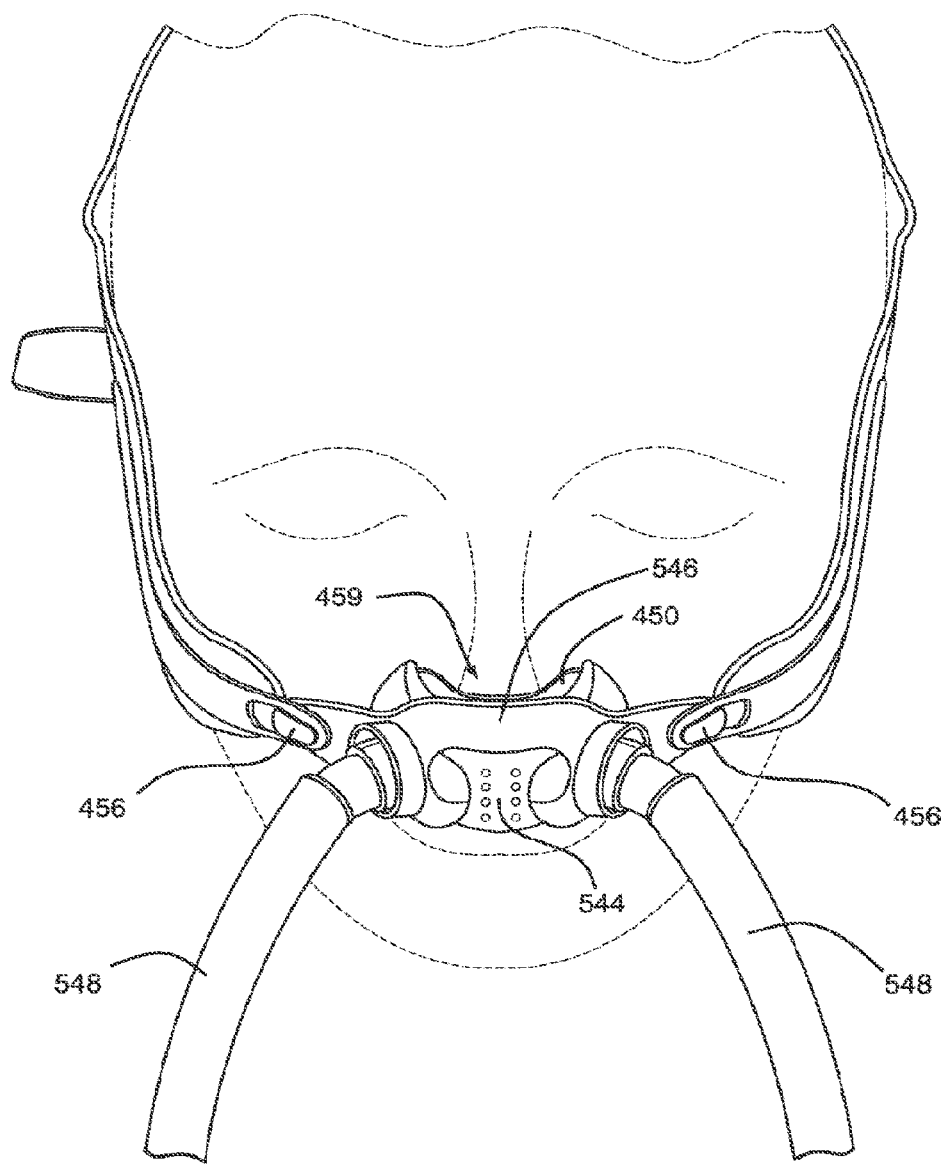
Figure 106:
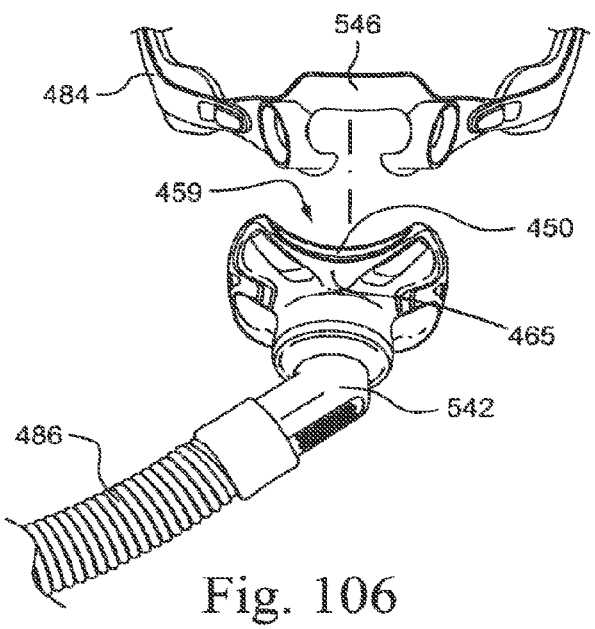
Figure 107:
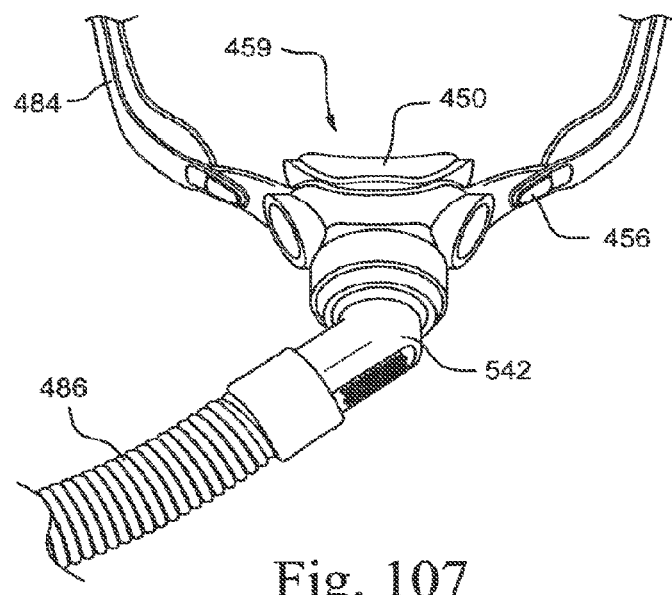
Figure 108:
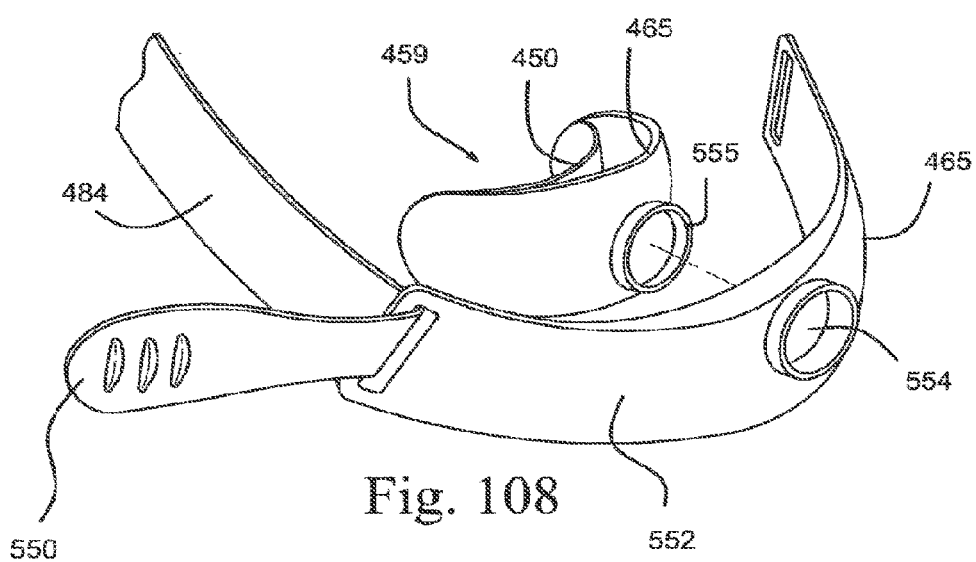
Figure 109:
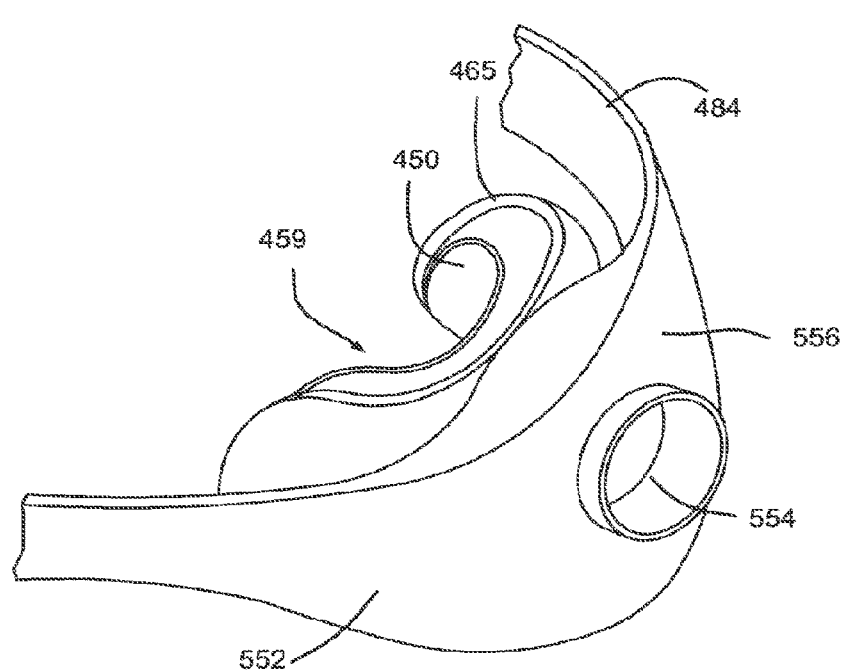
Figure 110:
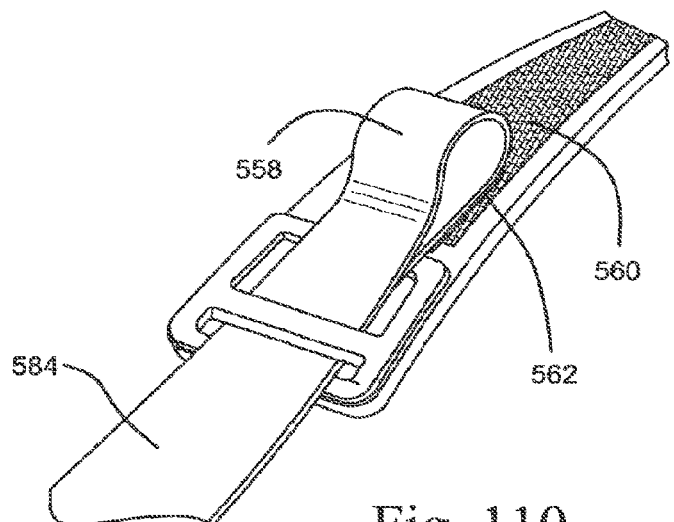
Figure 111:
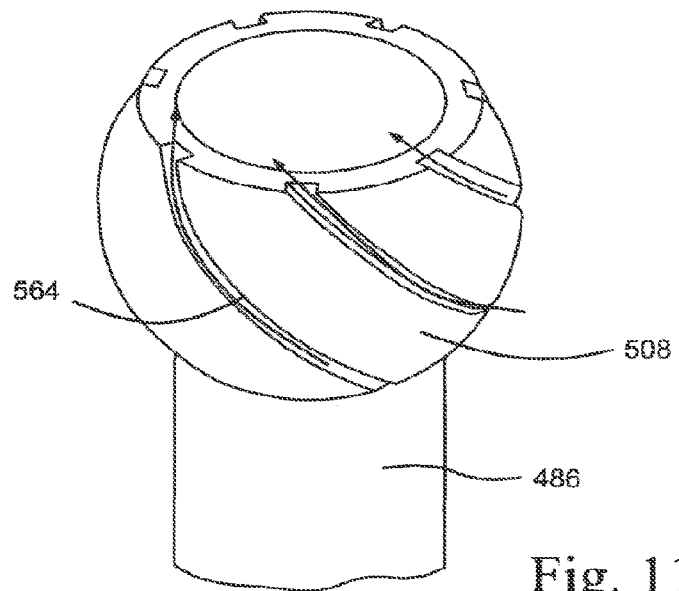
Figure 112:
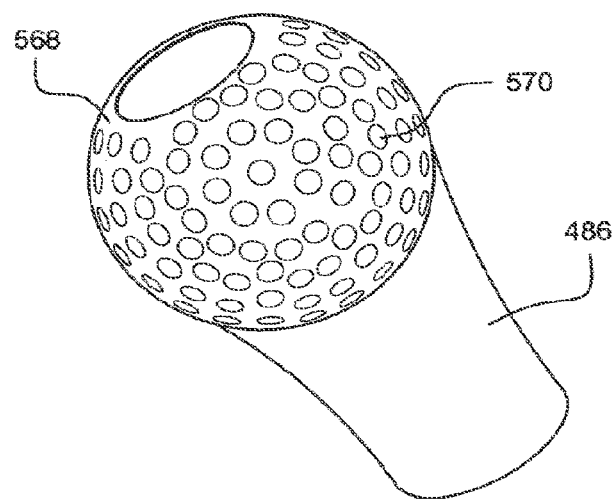
Figures 1, 113:
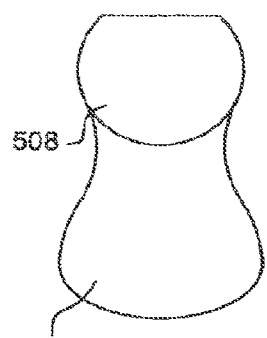
Figures 2, 113:
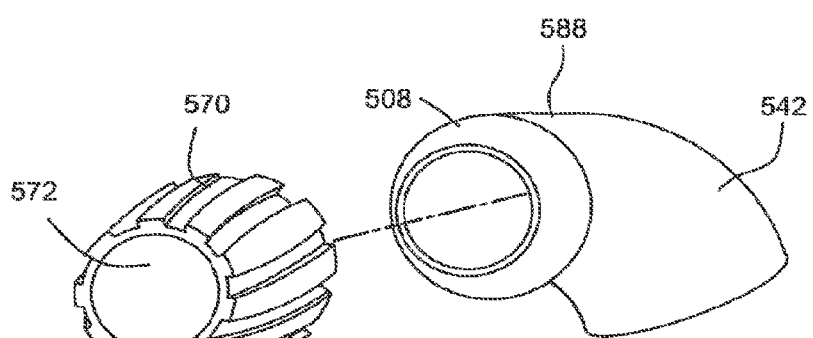
Figure 114:
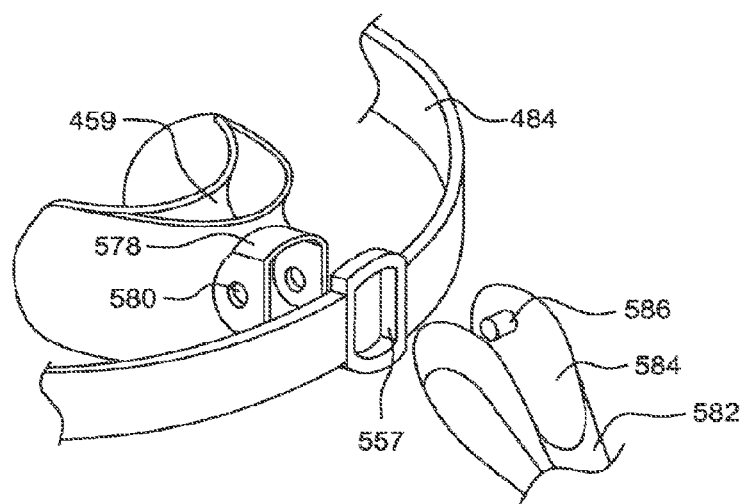
Figure 115:
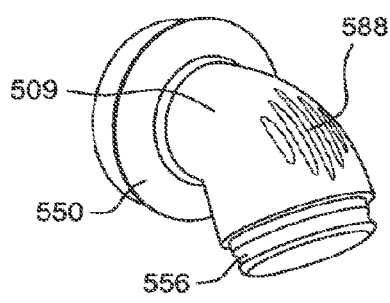
Figure 116:
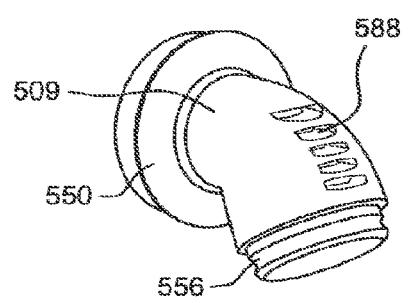
Figure 117:
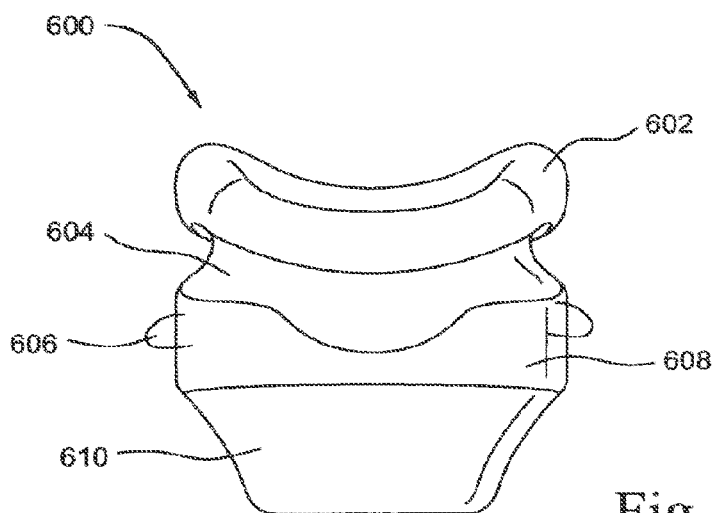
Figure 119:
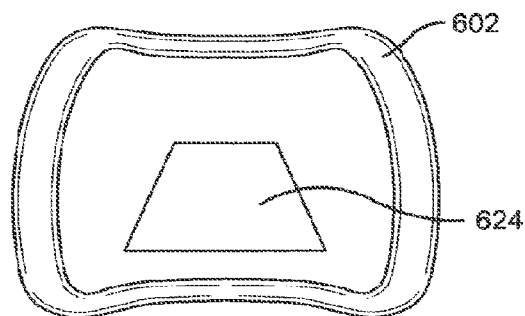
Figure 120:
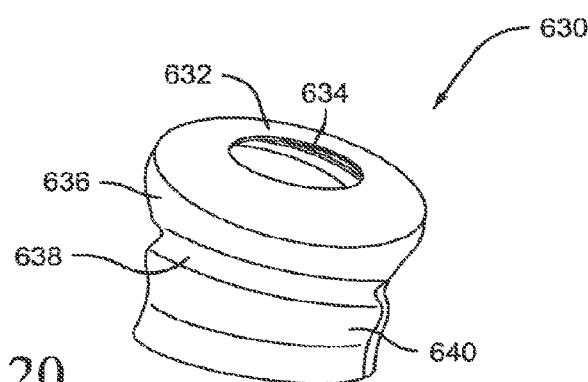
Figure 121:
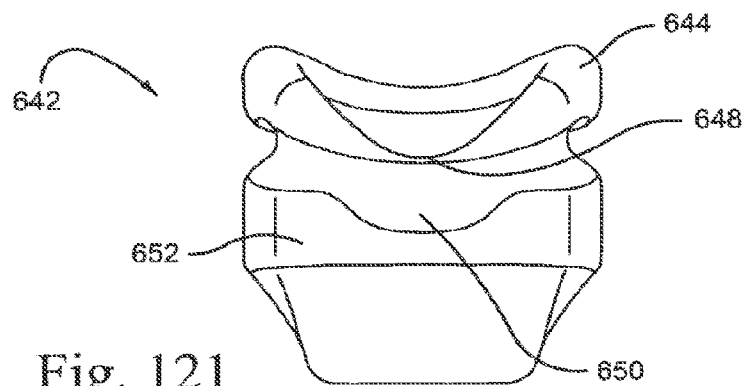
Figure 123:
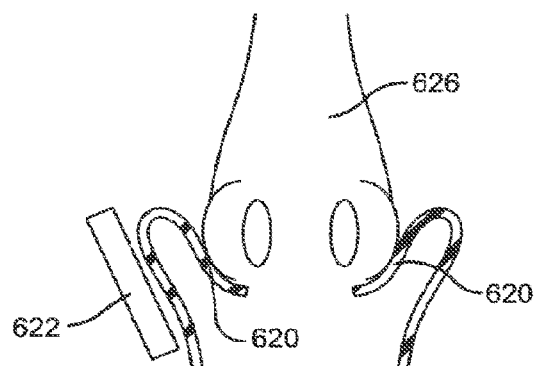
Figure 124:
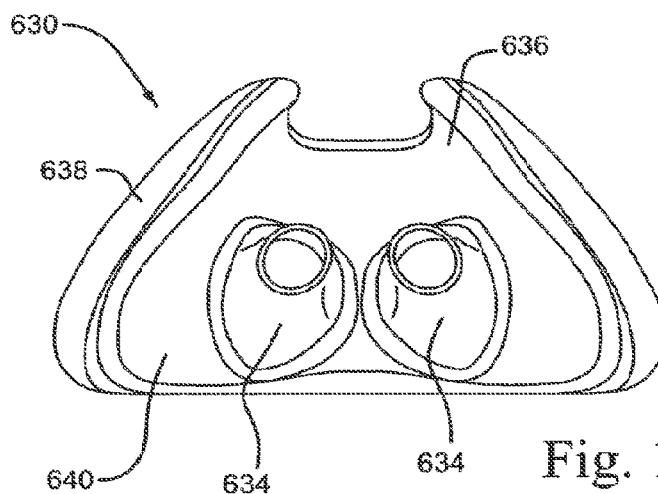
Figure 125:
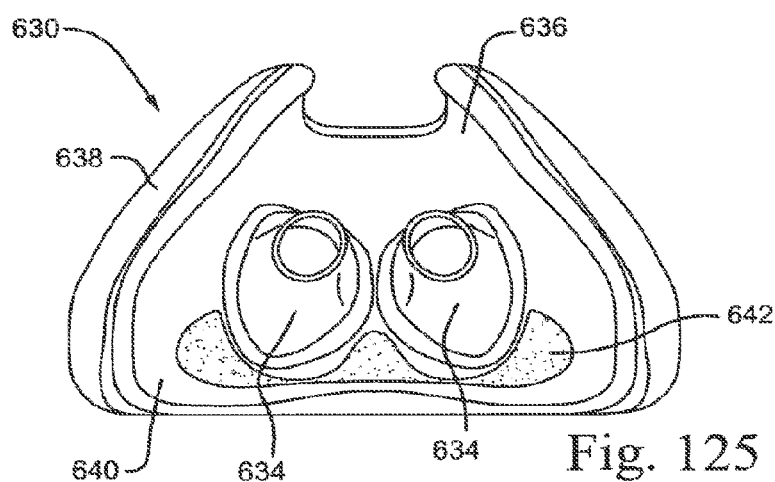

FIG. 59 is a perspective view of a multi-axis elbow assembly according to an embodiment of the present technology;

FIG. 60 is a right side perspective view of a patient interface on the patient in use according to an embodiment of the present technology;

FIG. 61 is a left side perspective view of a patient interface on the patient in use according to an embodiment of the present technology;

FIG. 62 is a front perspective view of a patient interface on the patient in use according to an embodiment of the present technology;

FIG. 63 is a left side perspective view of a patient interface on the patient in use according to an embodiment of the present technology;

FIG. 64 is a front perspective view of a patient interface on the patient in use according to an embodiment of the present technology;

FIG. 65 is a perspective view of a patient interface with a bellows according to an embodiment of the present technology;

FIG. 66 is a perspective view of a patient interface with a bellows according to an embodiment of the present technology;

FIG. 67 is a left side perspective view of a patient interface with headgear on the patient in use according to an embodiment of the present technology;

FIG. 68 is a perspective view of a bellows according to an embodiment of the present technology;

FIG. 69 is a graph illustrating various dimensions of the bellows of FIG. 68;

FIG. 70 is a perspective view of a patient interface with a ball joint and socket connector according to an embodiment of the present technology;

FIG. 71 is a perspective view of a ball joint and connector according to an embodiment of the present technology;

FIG. 72 is a perspective view of a socket connector according to an embodiment of the present technology;

FIG. 73 is a perspective view of a ball joint and elbow with a vent according to an embodiment of the present technology;

FIG. 74 is a cross-sectional view of a ball joint and elbow with vent according to an embodiment of the present technology;

FIG. 75 is a perspective view of a ball joint and elbow with removable vent insert according to an embodiment of the present technology;

FIG. 76 is a perspective view of a mesh vent according to an embodiment of the present technology;

FIG. 77 is a view of a ball joint and elbow with vents according to an embodiment of the present technology;

FIG. 78 is a perspective view of a socket connector with vent grooves according to an embodiment of the present technology;

FIG. 79 is a left side perspective view of a patient interface with headgear on the patient in use according to an embodiment of the present technology;

FIG. 80 is a perspective view of a hybrid elbow and ball joint according to an embodiment of the present technology;

FIG. 81 is a cross-sectional view of the hybrid elbow and ball joint of FIG. 80 according to an embodiment of the present technology;

FIG. 82 is a perspective side view of a patient interface with the hybrid elbow and ball joint of FIG. 80 on the patient in use according to an embodiment of the present technology;

FIG. 83 is a perspective side view of a patient interface with the hybrid elbow and ball joint of FIG. 80 on the patient in use according to an embodiment of the present technology;

FIG. 84 is a perspective side view of a patient interface with a thin membrane and elbow assembly on the patient in use according to an embodiment of the present technology;

FIG. 85 is a perspective view of an angled elbow ball joint assembly according to an embodiment of the present technology;

FIG. 86 is a left side perspective view of a patient interface with headgear on the patient in use according to an embodiment of the present technology;

FIG. 87 is a perspective view of a patient interface with headgear on the patient in use according to an embodiment of the present technology;

FIG. 88 is a left side perspective view of a patient interface with headgear on the patient in use according to an embodiment of the present technology;

FIG. 89 is a rear perspective view of headgear on the patient in use according to an embodiment of the present technology;

FIG. 90 is a perspective view of a patient interface with headgear on the patient in use according to an embodiment of the present technology;

FIG. 91 is a perspective view of a patient interface with headgear on the patient in use according to an embodiment of the present technology;

FIG. 92 is a rear perspective view of a patient interface with headgear according to an embodiment of the present technology;

FIG. 92-1 is a front perspective view of a patient interface with headgear according to an embodiment of the present technology;

FIG. 93 is a left side perspective view of a patient interface with headgear on the patient in use according to an embodiment of the present technology;

FIG. 94 is a perspective view of a patient interface with headgear on the patient in use according to an embodiment of the present technology;

FIG. 95 is a perspective view of a ball and socket assembly incorporated with a ball joint portion, vent and swivel ring according to an embodiment of the present technology;

FIG. 96 is a perspective view of a swivel ring and ball joint according to an embodiment of the present technology;

FIG. 97 is a front perspective view of a ball and socket assembly incorporated with a ball joint portion, vent and swivel ring according to an embodiment of the present technology;

FIG. 98 is a perspective view of a ball and socket assembly incorporated with a ball joint portion, vent and swivel ring according to an embodiment of the present technology;

FIG. 99 is a side perspective view of a ball and socket assembly incorporated with a ball joint portion and swivel ring according to an embodiment of the present technology;

FIG. 100 is a side perspective view of a ball and socket assembly incorporated with a ball joint portion and swivel ring according to an embodiment of the present technology;

FIG. 101 is a cross-sectional side view of a ball and socket assembly incorporated with a ball joint portion, vent and swivel ring joint according to an embodiment of the present technology;

FIG. 102 is a perspective view of a patient interface with a side connected tube on the patient in use according to an embodiment of the present technology;

FIG. 103 is a front perspective view of a patient interface with a side connected tube on the patient in use according to an embodiment of the present technology;

FIG. 104 is a front perspective view of a patient interface with a side connected tube on the patient in use according to an embodiment of the present technology;

FIG. 105 is a front perspective view of a patient interface with a two side connected tubes according to an embodiment of the present technology;

FIG. 106 is a front perspective view of a patient interface with a frame and headgear according to an embodiment of the present technology;

FIG. 107 is a front perspective view of a patient interface with a frame and headgear on the patient in use according to an embodiment of the present technology;

FIG. 108 is a perspective view of a patient interface with a headgear cradle according to an embodiment of the present technology;

FIG. 109 is a perspective view of a patient interface with a headgear cradle according to an embodiment of the present technology;

FIG. 110 is a perspective view of headgear with hook and loop material and a finger loop according to an embodiment of the present technology;

FIG. 111 is a perspective view of a flexible tube and ball having curved vent grooves according to an embodiment of the present technology;

FIG. 112 is a perspective view of a flexible tube and ball having vent holes according to an embodiment of the present technology;

FIGS. 113-1 and 113-2 are perspective views of an elbow and ball having vent grooves and a removable barrier according to an embodiment of the present technology;

FIG. 114 is a perspective view of a patient interface with a headgear connecting cradle and connecting elbow according to an embodiment of the present technology;

FIG. 115 is a perspective view of an elbow with vent grooves and a swivel connector according to an embodiment of the present technology;

FIG. 116 is a perspective view of an elbow with vent grooves and a swivel connector according to an embodiment of the present technology;

FIG. 117 is a front perspective view of a sealing portion of a patient interface according to an embodiment of the present technology;

FIGS. 118-1, 118-2 and 118-3 are perspective views of a sealing portion of a patient interface according to an embodiment of the present technology;

FIG. 119 is a top view of a sealing portion of a patient interface according to an embodiment of the present technology;

FIG. 120 is a perspective view of a sealing portion of a patient interface according to an embodiment of the present technology;

FIG. 121 is a front view of a sealing portion of a patient interface according to an embodiment of the present technology;

FIGS. 122-1, 122-2 and 122-3 are cross-sectional views of a sealing portion of a patient interface according to an embodiment of the present technology;

FIG. 123 is a cross-sectional view of a sealing portion of a patient interface according to an embodiment of the present technology;

FIG. 124 is a top view of a sealing portion of a patient interface according to an embodiment of the present technology; and FIG. 125 is a top view of a sealing portion of a patient interface according to an embodiment of the present technology.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the PAP devices or blowers described herein may be designed to pump fluids other than air.

1. PAP System

As shown in FIG. 1, a PAP system 10 generally includes a PAP device 15, an air delivery conduit 20 (also referred to as an air delivery tube or tubing), and a patient interface 100. In use, the PAP device 15 generates a supply of pressurized air that is delivered to the patient via the air delivery conduit 20 that includes one end coupled to the outlet of the PAP device 15 and an opposite end coupled to the patient interface 100. The patient interface 100 comfortably engages the patient's face and provides a seal.

2. Patient Interface

Patient interface 100 may include a mask 200 and a headgear 300 structured to maintain the mask in position on the patient's face in use, as shown in FIG. 1. As illustrated, mask 200 may include a sealing portion 210, a frame 220, an elbow 230 (e.g., with swivel) adapted to be connected to the air delivery tube 20, headgear attachments 240 (e.g., slots or clips on the frame and/or forehead support adapted to engage headgear straps), forehead support 250 and forehead adjustment 260.

In prior art patient interfaces such as ResMed's Mirage Quattro™ (as shown in FIG. 1), the mask is bulky and obtrusive on the face of the patient. The substantially rigid frame 220 combined with the headgear 300 encompasses a large portion of the patient's face. Such a configuration can psychologically discourage patients from treatment and thus negatively impact their compliance.

Another prior art patient interface is ResMed's Mirage Swift™, a nasal pillows or puff mask that seals in or around the nares of the patient. Such a configuration can cause discomfort due to the contact of the nasal pillows in or around the nares. Additionally, the "air jetting" affect can cause discomfort—this is due to laminar flow being directed up into the nares at higher velocities, thereby causing more pressure on small areas within the nasal passage and drying out the mucosal membrane.

A patient interface disclosed in one or more embodiments of the following description overcomes this by being less obtrusive and more comfortable. The proposed patient interface does not seal in the nares so overcomes this discomfort. Also, the proposed patient interface has a single opening or aperture that directs breathable gas into the patient airways, unlike a nasal pillows patient interface~The single opening can cause more turbulence in the airflow, thereby reducing the "air jetting" affect.

3. Mask

FIGS. 1-1 to 1-18 illustrate a mask 200 including a sealing portion 210, a suspension system 215, and frame 220 according to an embodiment of the present technology. The mask 200 may be either a full face mask or a nasal only mask. The mask 200 may also be a mouth only mask. Whilst a preferred mask is in an under the nose configuration, aspects of the present technology may be incorporated into other forms of mask, such as one surrounding a nose, or both a nose and a mouth.

3.1 Sealing Portion

Sealing portion 210 interfaces with the patient in use, allowing delivery of breathable gas to the patient. In the illustrated embodiment, sealing portion 210 may form a seal with the nares of the patient in use. For example, sealing portion 210 may interface and thus seal with the external portion of each of the alar or nostril flares, the upper lip and/or base of the nares, and the tip of the nose. Sealing portion 210 may be made from materials including but not limited to: silicone, thermoplastic elastomer, gel, foam, or any other suitably conformable material. The material may have a durometer of about 1 to 15 Shore A. Preferably, the material may have a durometer of about 3 to 10 Shore A. Preferably, the material may have a durometer of about 5 to 12 Shore A. Most preferably, the material may have a durometer of about 5 Shore A. Thus, the preferred sealing portion provides a noninvasive arrangement that does not extend into the patient's nostrils in use. The preferred sealing portion 210 does not inflate, and thus does not require inflation pressure to form a seal. Preferably, the seal is not pressure assisted, although it could be modified for such. In one form, the sealing portion could use a gusset (e.g., having a projected area greater than the area of the sealing portion) to help provide a seal as disclosed in U.S.

Pat. No. 7,523,754 or WO 01/97893 A1, which are incorporated herein by reference in their entirety.

In an embodiment, the sealing portion may include a wall thickness of about 0.1-15 mm. Preferably, the sealing portion may have a wall thickness of about 2 to 10 mm. Preferably, the sealing portion may have a wall thickness of about 7 to 12 mm. Preferably, the sealing portion may have a wall thickness of about 1-5 mm. Most preferably, the sealing portion may have a wall thickness of about 1-3 mm. Most preferably, the sealing portion may have a wall thickness of about 1.5 mm. The wall thickness may vary in different regions of the sealing portion, e.g., thickness of about 0.5 mm in thinner regions and ranging up to about 2-10 mm in thicker regions. Alternatively, the sealing portion may include a constant wall thickness, e.g., about 1.2 mm. The walls may be constructed of various layers of material, each layer of material having a different hardness and/or thickness (e.g., two layers each being 1.2 mm thick but having different durometer silicones).

3.1.1 Shape

Figure 19:
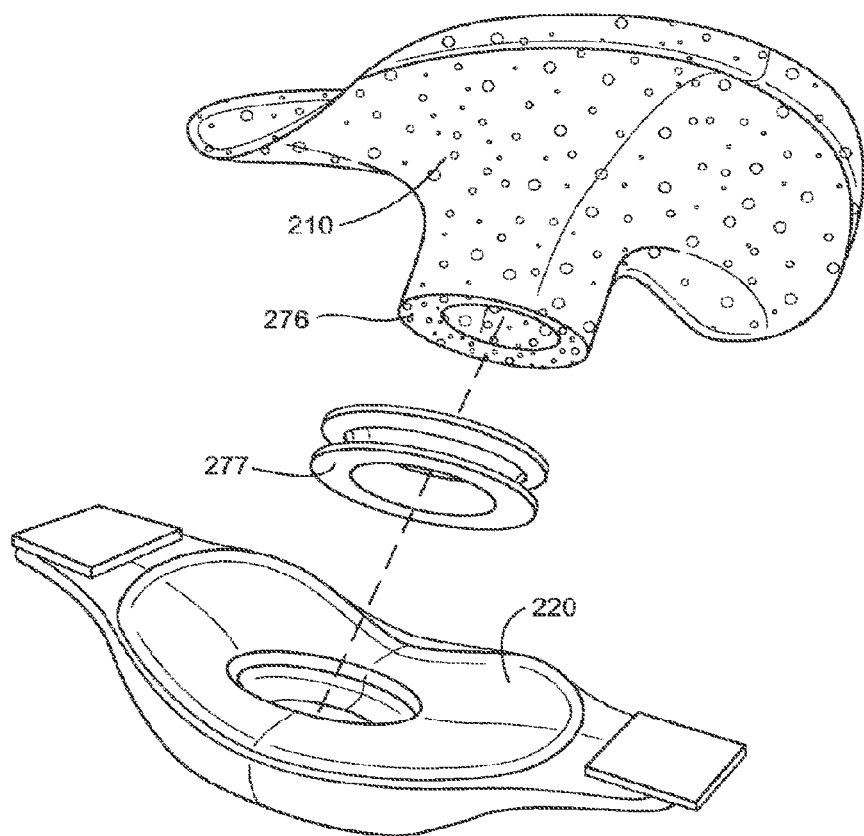
FIG. 19 illustrates a gel sealing portion according to an embodiment of the present technology.
Figures 1, 20:
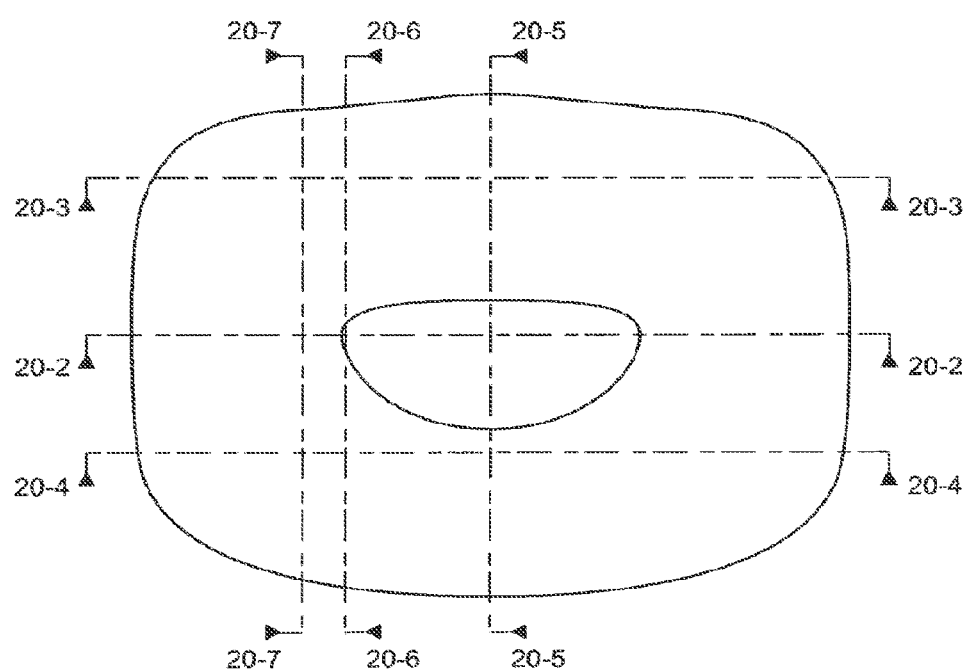
Figures 2, 20:
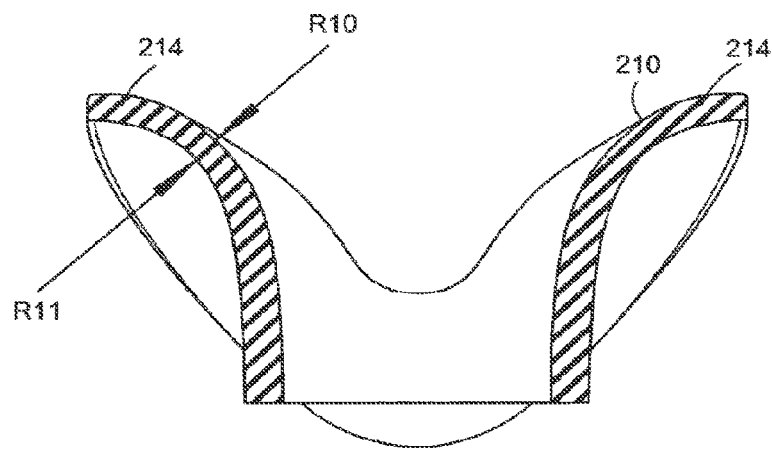
Figures 3, 20:
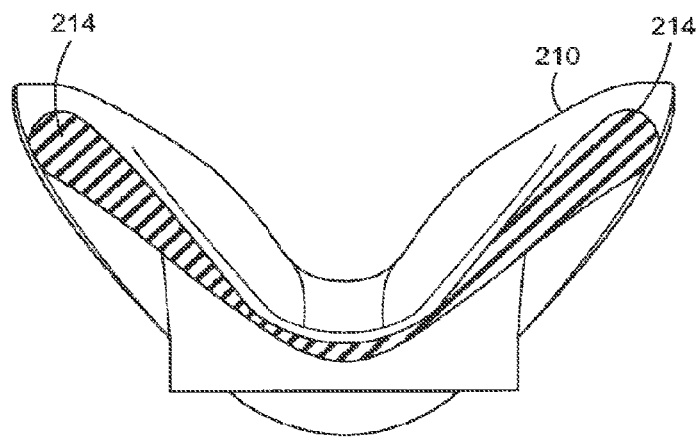
Figures 4, 20:
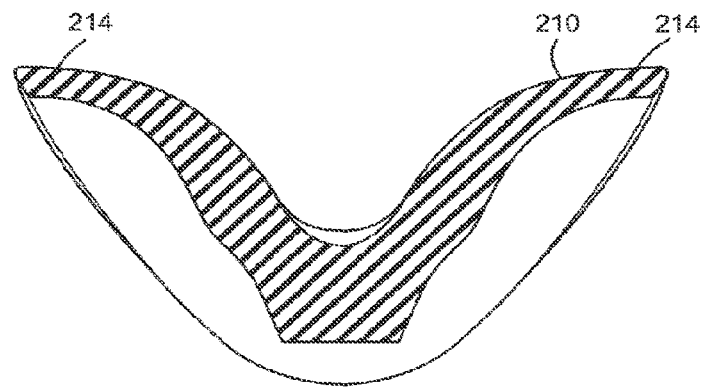
Figures 5, 20:
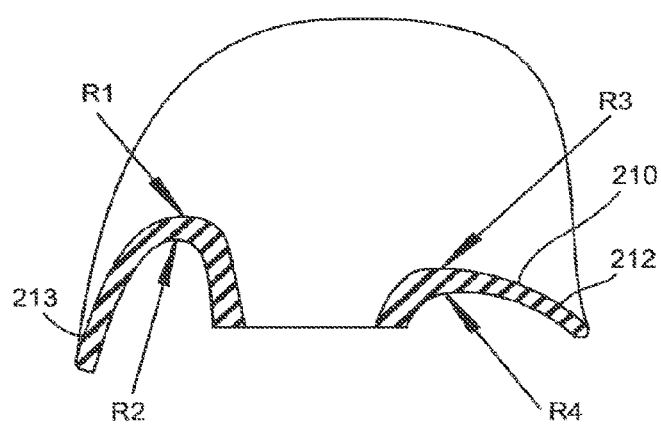
Figures 6, 20:
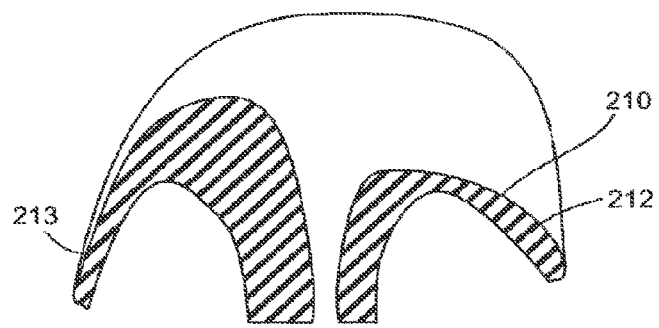
Figures 7, 20:
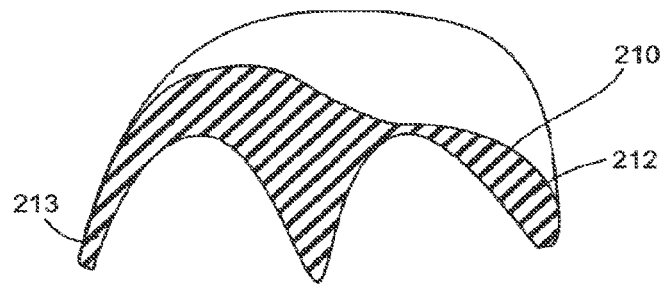
Figures 1, 21:
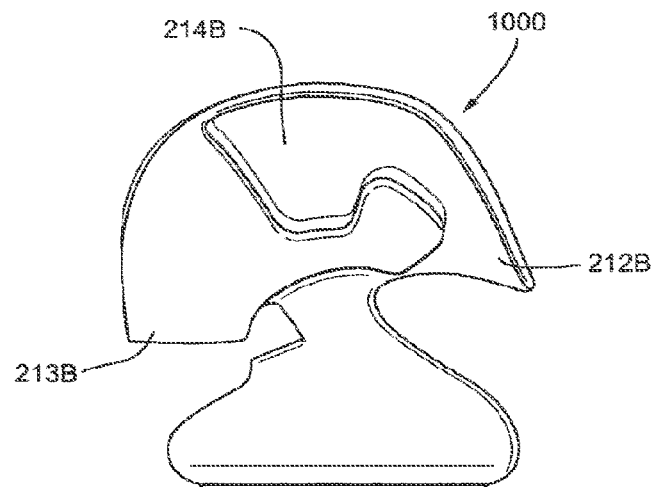
Figures 2, 21:
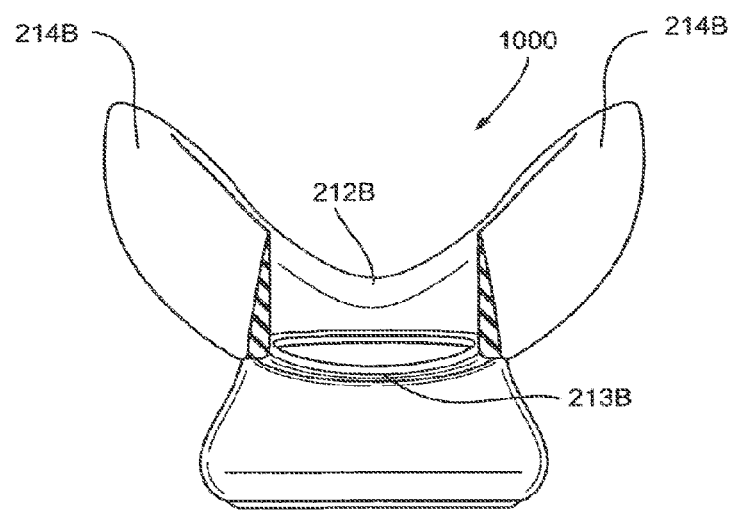
Figures 3, 21:
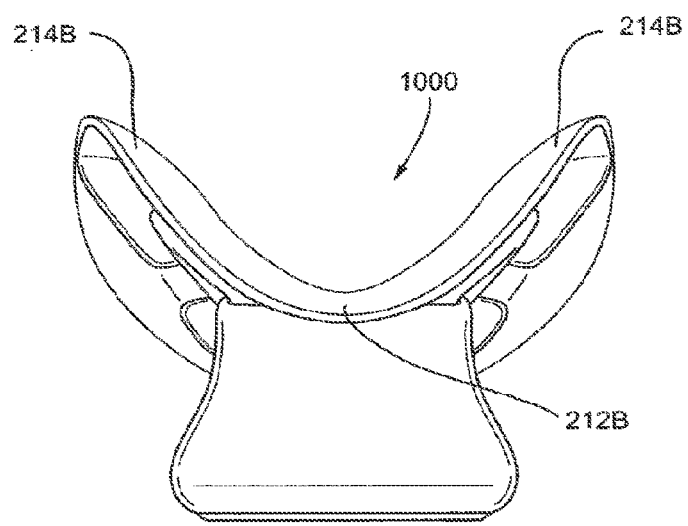
Figures 4, 21:
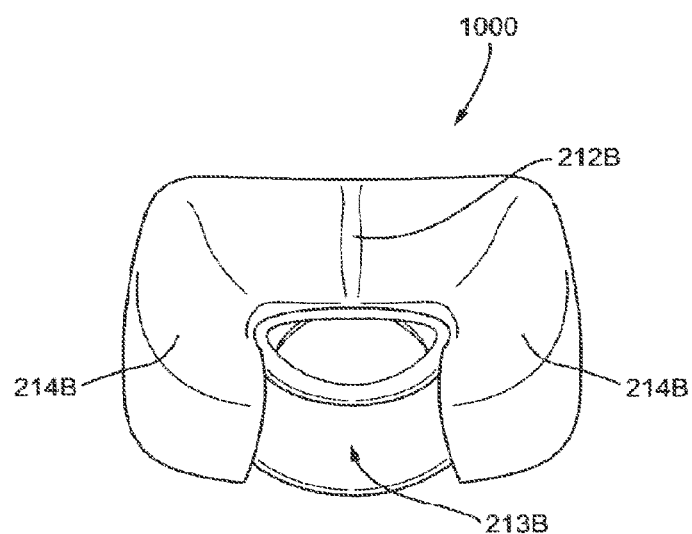
Figures 5, 21:
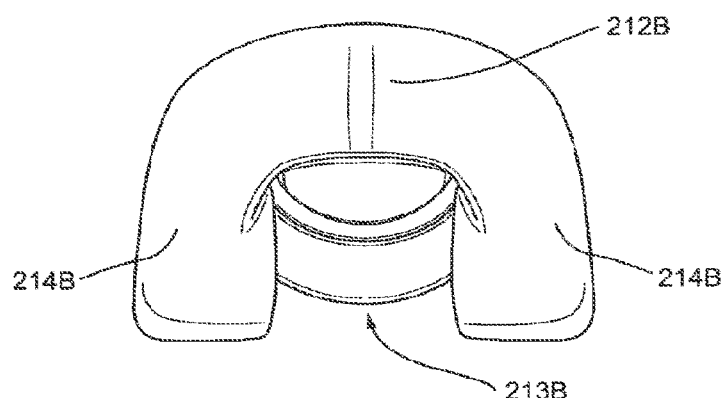
Figures 6, 21:
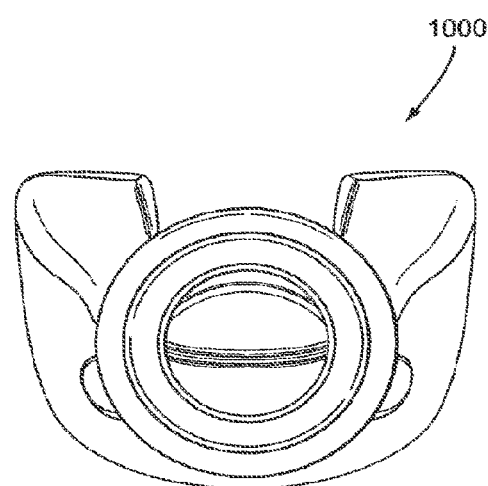

In the illustrated embodiment, sealing portion 210 (also referred to as a nasal cradle) may have a generally cradle, cup or U shape such that when positioned under the nose of the patient, it is conformed or generally shaped to the alar angle of the patient (e.g., see FIG. 1-1; see also FIGS. 19 to 21 of International Patent Application PCT/AU2004/000207 published as WO 2004/073 778 and the related description).

The generally smooth curvature or undulating shape of sealing portion 210 may be comfortable as it can flex to accommodate a variety of nose shapes and sizes. The general shape of sealing portion 210 may also infer comfort and unobtrusiveness to the patient, thereby increasing compliance.

Alternatively, sealing portion 210 may be generally flat yet be able to flex into the desired alar angle of the patient. This may be achieved by providing sealing portion 210 with portions of reduced thickness to encourage bending and/or constructing sealing portion 210 from a flexible material or incorporating portions of flexible material.

3.1.2 Aperture

As best shown in FIGS. 1-2 to 1-7, sealing portion 210 may have an aperture 211 that allows the passage of breathable gas from the air delivery conduit 20 to the patient. Aperture 211 may be generally circular, rectangular, or any other desired shape (e.g., trapezoidal or oval shaped as shown in FIGS. 1-4, 1-5 and 48). In an embodiment, aperture 211 may be shaped so as to indicate the alignment or orientation of the sealing portion 210 with the patient's nose in use, e.g., trapezoidal or triangular shapes.

The aperture 211 of the sealing portion may be larger when compared to that of a nasal pillows or prongs mask. This means that the velocity of the air may be lower when exiting aperture 211 compared to a nasal prongs or pillows mask. The lower velocity of air exiting the aperture 211 makes it easier for the patient to exhale against the incoming air and also reduces irritation due to high velocity air flow in and around the nose.

Figures 1, 48:
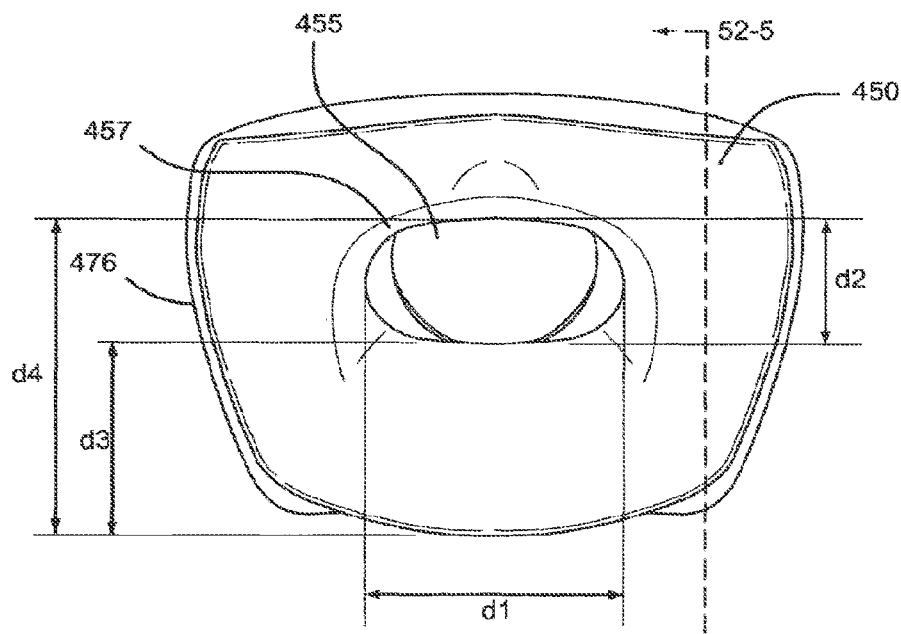
Figures 2, 48:
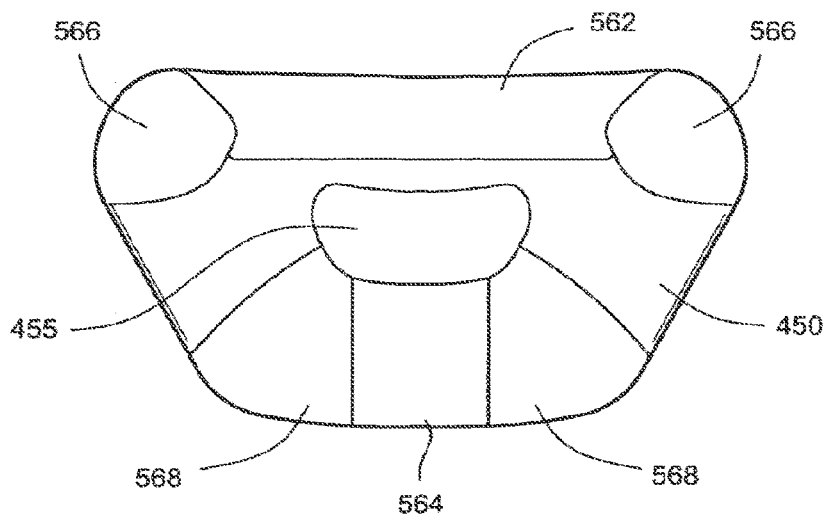

As shown in the embodiment of FIG. 48-1, the aperture 455 may have dimensions di (width) to accommodate the width of the nares on a range of patients with varying anthropometry and d2 (height) to accommodate nose tip height or distance from the top lip on a range of patients with varying anthropometry. Preferably, dimension d1 may be about 10-60 mm. Preferably, dimension d1 may be about 15-40 mm. Most preferably, dimension d1 may be about 21 mm. Most preferably, dimension d1 may be about 38 mm. Most preferably, dimension d1 may be about 58 mm. Preferably, dimension d2 may be about 1-20 mm. Most preferably dimension d2 may be about 5-15 mm. Most preferably, dimension d2 may be about 1 mm. Any other values of d1 and d2 may be used to provide a sufficient flow of gas without unduly high impedance and to fit noses of different sizes. The radius of curvature at corner portion 457 may be 5 mm, although different radius of curvature may be used.

3.1.3 Engagement Portions

Figures 1, 2, 3:
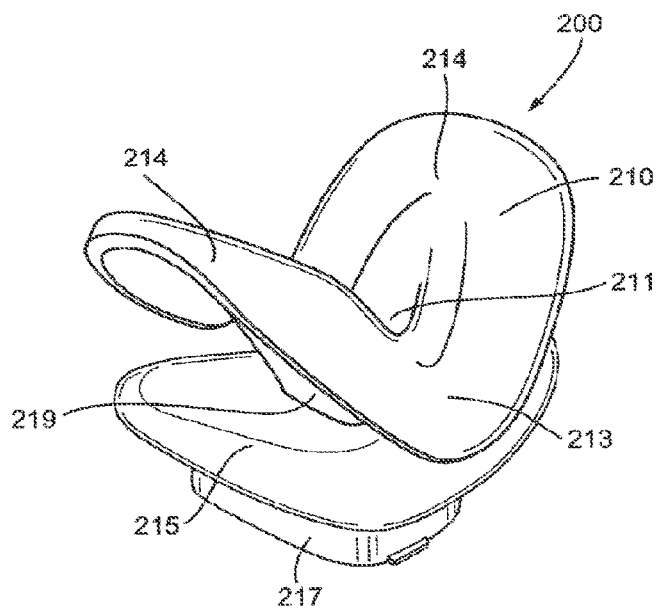

In the illustrated embodiment, sealing portion 210 may include a nose tip engagement portion 212 and an upper lip engagement portion 213. As shown in FIGS. 1-2 to 1-4 and 1-8, nose tip engagement portion 212 is generally flat or planar along its length so as to provide a sufficiently long sealing surface to accommodate various sized noses. The upper lip engagement portion 213 is generally curved along its length so as to minimize contact with the patient's upper lip in use. FIG. 20-1 shows a top view of another embodiment and indicates sections shown in FIGS. 20-2 to 20-7. In an embodiment and as shown in FIG. 20-5, the radius of curvature R4 of the external or non-patient contacting side of the nose tip engagement portion 212 is larger than the radius of curvature R2 of the external or nonpatient contacting side of the upper lip engagement portion 213. In an embodiment, the radius of curvature R3 of the internal or patient contacting side of the nose tip engagement portion 212 is larger than the radius of curvature R1 of the internal or patient contacting side of the upper lip engagement portion 213. The radius of curvature of the non-patient contacting side (e.g., R2, R4) may be different (e.g., larger or smaller) than the radius of curvature of the patient contacting side (e.g., RI, R3). The radius of curvature of RI, R2, R3 and R4 may be 1-5 mm, e.g. 2 mm, 3 mm, 4 mm. In an example, R1 may be about 3-3.75 mm, R2 may be about 2 mm, R3 may be about 3.25-4.5 mm, and R4 may be about 3.25-4.25 mm. As shown on FIG. 20-2, the radius of curvature R10 and R11 may be about 8-13 mm, e.g. 9 mm, 11.5 mm. In an example, RIO may be about 9.5-11.5 mm and R11 may be about 9-10.5 mm.

3.1.4 Nostril Engagement Flaps

In the illustrated embodiment, sealing portion 210 may include nostril engagement flaps 214 structured to align next to or against the nostrils of the patient. In use, flaps 214 seal with the nares (e.g., either directly at the entrance to the nares or along the nostrils of the patient) and flex or bias inwards towards the nose of the patient to stabilize or anchor the seal and enable the sealing portion 210 to fit a variety of nose sizes and shapes.

As demonstrated in FIG. 1-6, nostril engagement flaps 214 may be angled in a generally V-shaped orientation, indicated by angle a (measured from the center of aperture 211 and plotting the general linear path along each nostril engagement flap 214).

In an embodiment, angle a is in the range of about 0-180°, e.g., about 90-180°, about 90-120°, about 120-180°, about 0-90°, about 0-45°, about 45-90°, about 90°, about 75°-95°. Angle a demonstrates the angle of the engagement flaps when not in use or in a relaxed form. Angle a may increase when in use, that is, when the patient places the mask on their nose and their nose exerts a force on the mask, and may thus cause the engagement flaps to flex outwards to an in use position. This may include angles of about 75o-200°. The radius of curvature as indicated by the general area bound by a may be approximately 5-8 mm.

The nostril engagement flaps may include alternative configurations to enhance the seal. For example, as shown in FIG. 6-1, the nostril engagement flaps 214 may be more narrow (e.g., decrease the angle a) so that the flaps "pinch" the nose, i.e., nose flexes flaps outwardly in use. As shown in FIG. 6-2, the flaps 214 may include hook-shaped end portions 214(1) structured to "hook" onto and seal over the patient's nares in use.

3.1.5 Flared Sealing Portion

As shown in FIGS. 1-2 to 1-8, the nose tip engagement portion 212, the upper lip engagement portion 213, and the nostril engagement flaps 214 are all structured to curve or extend outwardly from an annular supporting wall or base 219. That is, the nose tip engagement portion 212, the upper lip engagement portion 213, and the nostril engagement flaps 214 are hung or cantilevered from the supporting wall such that they extend or curve outwardly from the supporting wall defining the air path to outer edges of the sealing portion 210 in a continuous, uninterrupted and smooth manner.

3.1.6 Sealing Portion with Malleable Wire

FIGS. 4-1 to 4-7 show a sealing portion 210 provided with a malleable wire 270. As illustrated, the malleable wire 270 is provided to the underside or non-face contacting portion of the sealing portion and extends about the perimeter of the sealing portion (e.g., spaced inwardly from the edge of the sealing portion to avoid any contact with the patient's face in use). However, the malleable wire may be provided to one or more selected portions of the sealing portion (e.g., only along the flaps). The malleable wire allows the patient to deform the sealing portion 210 to their specific nose shape (i.e., self-adjust the geometry of the sealing portion) and maintain such deformed sealing portion shape during use. For example, FIG. 4-8 shows the sealing portion 210 deformed into a general V-shape, and FIG. 4-9 shows the sealing portion 210 deformed into a general flat or planar shape.

In this embodiment, the sealing portion 210 with malleable wire 270 is provided to a base 271 adapted to attach to a frame. However, such sealing portion may be provided to a suspension system or directly to the frame as described below.

The malleable wire may be attached or otherwise provided to the sealing portion in any suitable manner, e.g., co-molded with sealing portion, retrofit, etc.

The sealing portion may be deformable in other suitable manners, e.g., similar effect may be achieved by constructing the sealing portion of a thermo-formable plastic material.

3.1.7 Gel Beading

As shown in FIGS. 5-1 and 5-2, gel beading 272 (e.g., tear-drop shaped) may be provided around the perimeter of the sealing portion 210 or one or more portions of the sealing portion (e.g., along the nostril engagement flaps) to support the sealing portion, provide compliance, and/or provide tactility in use. The gel beading 272 may be positioned along the edge of the sealing portion (FIG. 5-1), along a portion of the edge, and/or within the edge (FIG. 5-2).

3.1.8 Fingers or Ridges

In an embodiment, fingers or ridges may be provided along the face-contacting surface of the sealing portion to enhance the seal and prevent leak in use. FIG. 7-2 illustrates an embodiment of fingers 273 and FIG. 7-3 illustrates an embodiment of ridges 274. As shown in FIG. 7-1, the fingers 273/ridges 274 may be provided in concentric rings around the sealing portion 210. However, the fingers/ridges may be arranged in other suitable manners, e.g., provided in one or more selected regions of the sealing portion. In each embodiment, the fingers/ridges extend outwardly (e.g., height of about 0.5 mm) from the face-contacting surface of the sealing portion, and are structured to deform and conform to the various contours of the patient's face and nose in use. Such fingers/ridges may especially improve sealing in awkward positions, e.g., along the joint of the nose to the upper lip. Such fingers/ridges may also improve tactility or maintaining location as the fingers/ridges may create a friction/stabilizing interface with the patient's skin in use.

3.1.9 Stiffening Ribs

In an embodiment, stiffening ribs 275 (e.g., thickened portions integrally formed with the sealing portion) may be provided to one or more portions of the sealing portion 210 (e.g., nostril engagement flaps 214) to support the sealing portion in use. For example, as shown in FIG. 9-1, the stiffening ribs 275 may be provided in one or more concentric rings around the sealing portion to add strength around the entire perimeter and support the outer edges of the sealing portion 210 from collapsing away from the patient's nose in use. As shown in FIG. 9-2, stiffening ribs 275 may extend radially from the aperture 211 (e.g., with one or more "branches" of ribs) to add support and reduce flexing in selected regions of the sealing portion, e.g., regions most susceptible to leak or deformation. In another embodiment, the stiffening ribs or thickened portions may be provided at discrete points of the sealing portion, e.g., points most susceptible to leak or deformation. Stiffening ribs 275 may be thicker than the sealing portion 210. Alternatively, stiffening ribs may be made from a different hardness material than the sealing portion 210, e.g., a durometer of silicone higher than that of the sealing portion 210.

3.1.10 Gel Sealing Portion

FIG. 19 illustrates an embodiment of a sealing portion 210 constructed of gel, i.e., gel-filled bladder or membrane (e.g., wall thickness of about 0.3-5 mm, e.g., 0.7 mm). As illustrated, the membrane or bladder 276 is filled with one or more layers of gel, and a cap 277 (e.g., constructed of polycarbonate, silicone, polypropylene, nylon) is provided to close and seal the opening into the bladder. In addition, the cap 277 helps to locate and maintain the gel-filled bladder to the frame 220. The gel sealing portion enhances comfort and compliance in use.

3.1.11 Color Changing Material

In an embodiment, the sealing portion may be constructed of a material adapted to change color, e.g., heat sensitive. For example, the sealing portion may be constructed of a color changing silicone that is heat sensitive, e.g., starts off blue (or any first color) at room temperature and turns white/clear (or any second color different from the first color) with added heat, e.g.; body temperature.

This color changing material may be used by the patient to size their sealing portion. For example, the patient may be provided with a sealing portion for the largest size nose, and when the patient fits the sealing portion to their nose they will be able to see exactly how much excess material is on the sealing portion, e.g., contact with patient's face will heat material and change from first to second color. The patient could then trim off the excess material to customize the mask to their nose.

Also, the color changing material may be used for leak indication, e.g., leaking air will be colder than body temperature so the color changing material will maintain its first or original color where any leak path exists.

The color changing material may have other applications, e.g., for the sealing portion and/or other portions of the patient interface or PAP system.

For example, the color changing material may be used for sterilization. If the cleaning substance to be used (e.g., water) is most effective at cleaning the mask at a certain temperature, the silicone could change color at this certain temperature to indicate the required sterilization conditions have been met, e.g., the mask could turn from colored to white/clear at 100 degrees Celsius if the best method of sterilizing the mask is to boil it in hot water. Alternatively, if cleaning the mask with alcohol is preferable, the reaction of latent heat with the applied alcohol could cause the silicone to change color.

The color changing material may be used as an end of life indicator. If the color changing silicone will only change colour a certain number of times before breaking down, this could be used to indicate that it's time for a new mask.

The color changing material may be used for enhanced invisibility. For example, the silicone changing color to a clear silicone makes the mask becomes less obtrusive.

The color changing material may be used as a locator. For example, the color of the silicone may be useful to locate parts that have been dropped or lost.

The color changing material may be used for mask asymmetry. For example, if the patient has an asymmetric nose, this could be a useful indicator of alignment. It could suggest that the patient needs to position the mask off-center to accommodate their asymmetric nose. The silicone will change color where their nose is currently contacting the mask, and they could adjust the position of the mask in use to ensure both nostrils are able to receive the flow of breathable gas from the mask.

The color changing material may be used on the PAP device, humidifier, and/or tubing (e.g., heated tube) to indicate that the temperature of the PAP device, humidifier, and/or tubing is at its limit or desired temperature.

In another embodiment, the sealing portion may be constructed of a color changing material that is pressure sensitive. In such embodiment, the patient would be able to identify pressure points and then update the mask accordingly.

An exemplary material may be Chromazone® Free Flowing Powder available from Thermographic Measurements Ltd, Devon, UK.

Another exemplary material may be Thermochromatic and Liquid Crystal products available from B&H Colour Change Ltd, London, UK.

Another exemplary material may be Thermochromatic Inks available from Siltech Ltd, Nottingham, UK.

3.1.12 Sizing Indicator

Figures 1, 27:
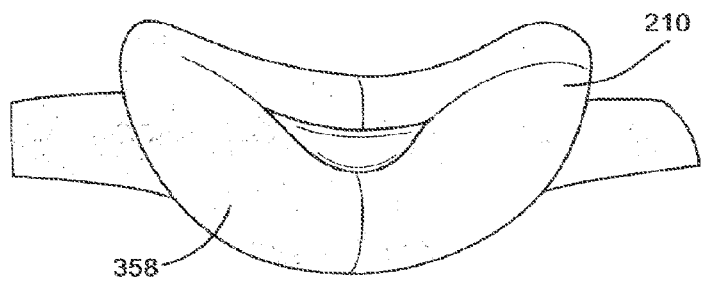
Figures 2, 27:
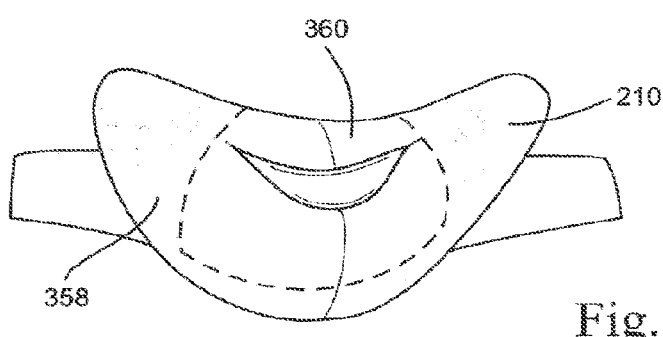

FIGS. 27-1 and 27-2 illustrate the sealing portion 210 with thermo-chromic sizing indicators. FIG. 27-1 shows the sealing portion 210 before use with the sealing portion 210 all being color region 358. FIG. 27-2 shows an exemplary sealing portion 210 after use, where the region touched by the patient has changed color, as shown by color region 360. The color change indicates the portions of the sealing portion 210 that have been contacted by the patient, and may enable the patient to remove excess material after use (i.e., color region 360 in FIG. 27-2). The color changing portions could also be used by people fitting the sealing portion to the patient, whereby the change in color would indicate the ideal selection from among pre-made sealing portions of various sizes.

3.1.13 Sizing Options

Figure 28:
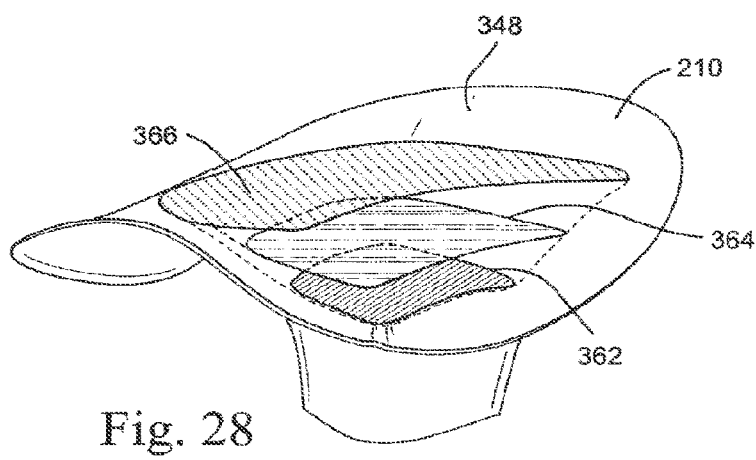
FIG. 28 is an isometric view of a sealing portion with sizing options according to an embodiment of the present technology.

The sealing portion 210 may be arranged such that a single size cradle may be produced that is able to be trimmed down or cut back into smaller sizes. For example, as shown in FIG. 28, sizing of the sealing portion for different sized patients may relate to the size of the orifice, such that orifice opening 362, orifice opening 364 or orifice opening 366 may be used depending on the nose size of the patient, i.e., orifice opening 366 for larger noses and orifice opening 362 for smaller noses. The extra membrane material of membrane 348 may also be trimmed off by the patient or a clinician. Perforations or cutting lines may be incorporated into the sealing portion 210 to indicate sizing ranges.

3.1.14 Protrusions

Figures 1, 2, 3, 4:
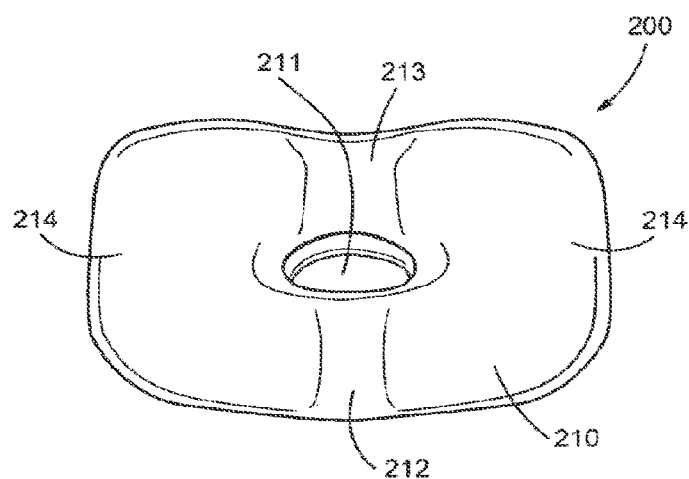
Figures 1, 2, 3, 4, 5:
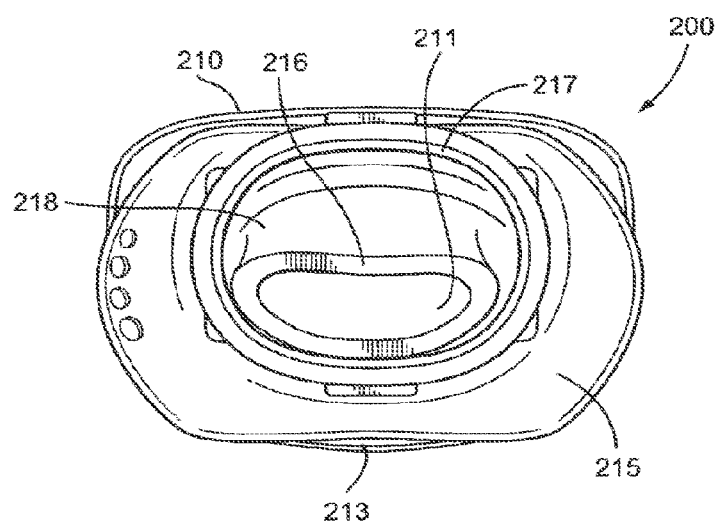
Figures 1, 2, 3, 4, 5, 6:
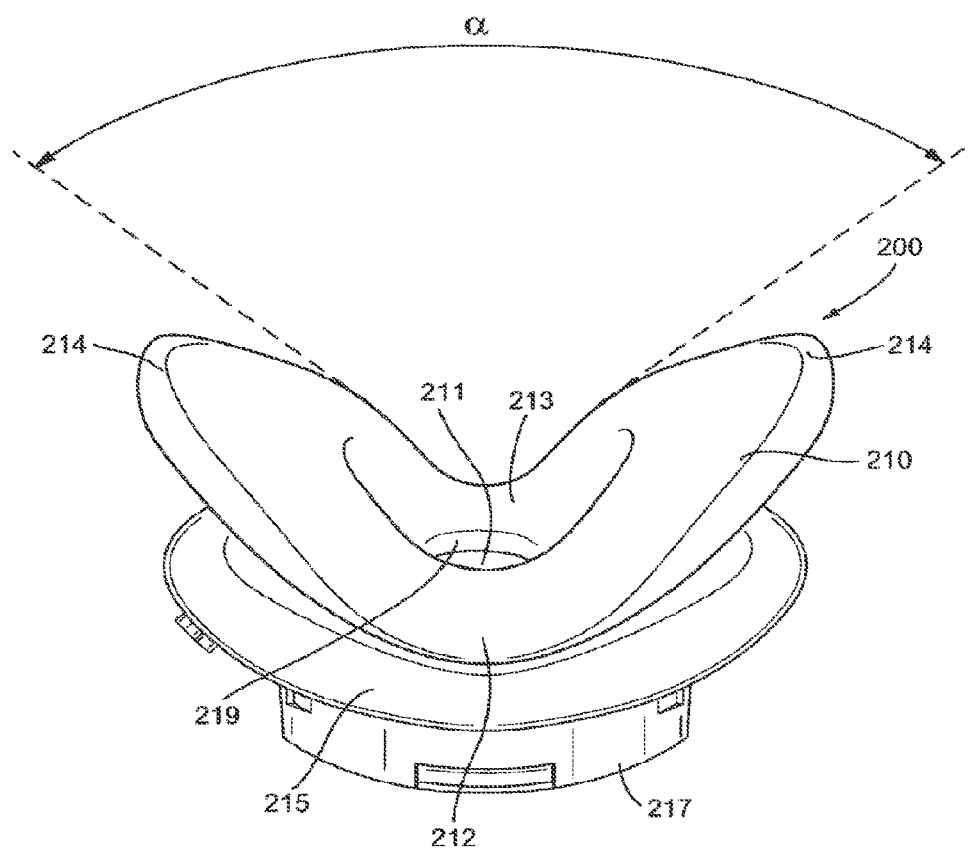
Figures 1, 2, 3, 4, 5, 6, 7:
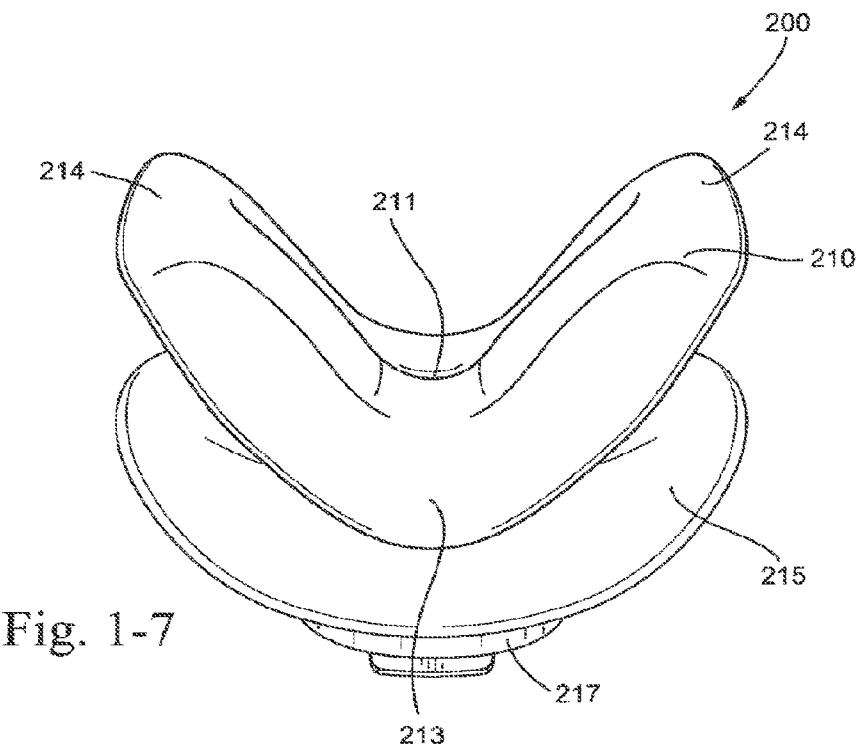
Figures 1, 24:
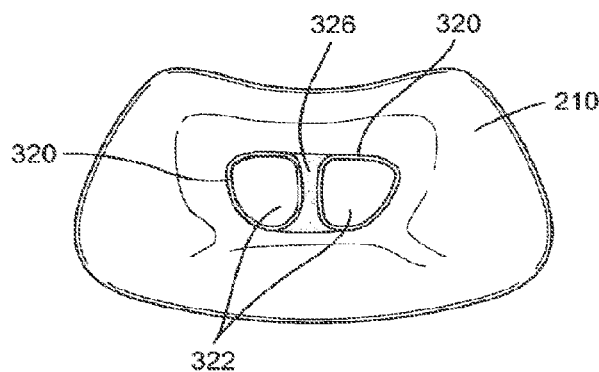
Figures 2, 24:
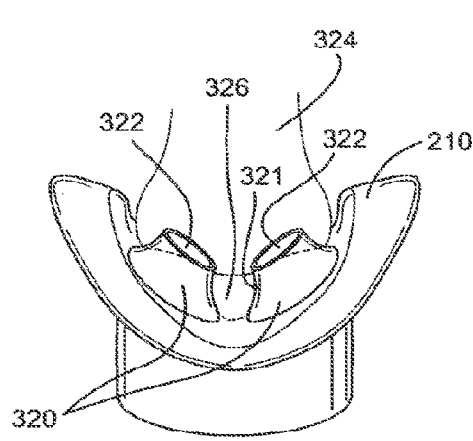
Figures 3, 24:
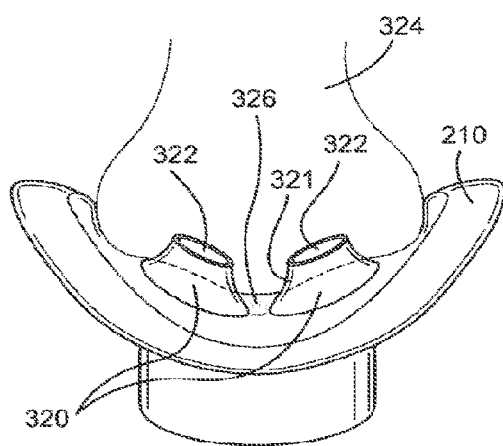
Figures 4, 24:
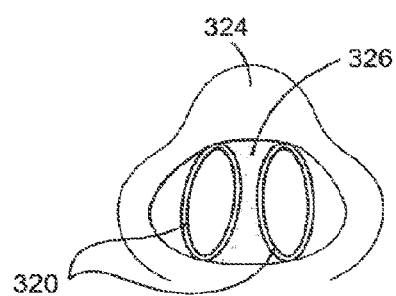

FIGS. 24-1 through 24-4 show a sealing portion 210 (also referred to as a nasal cradle) provided with nozzles or protrusions 320. The nozzles 320 are positioned on the sealing portion 210 so as to be located in or near the patient's nares and position the sealing portion under the patient's nose 324 when in use. The nozzles 320 position the sealing portion 320 to enable an effective seal and provide adequate therapy to the patient.

The nozzles 320 are provided with orifices 322 which are used to expel gas into the patient's nose 324. The nozzles 320 may not necessarily seal with the patient's nares, instead the sealing portion 210 may seal with the underside of the patient's nose, e.g., in a manner as described above. In the illustrated embodiment, the sealing portion 210 is provided with a septum locator 326, where the patient's septum can be located between the nozzles 320. The septum locator 326 may include a cushioning material to provide comfort to the patient at this sensitive region of the nose. Alternative alignment protrusions or mechanisms may be used to position the sealing portion in relation to the patient.

The nozzles 320 are configured to have a curved or concave outer surface 321 that gradually increases in width from a top of the nozzles 320 to a bottom of the nozzles 320 to provide a comfortable fit to different sized noses and nares. As illustrated in FIG. 24-2, a patient with a relatively small nose 324 and nares may utilize the curved surface of the nozzles 320 in a way that the patient's nose extends part of the way down the curved outer surface 321 to provide a comfortable seal. As illustrated in FIG. 24-3, a patient with a relatively larger nose 324 and nares may utilize the curved surface of the nozzles 320 in a way that the patient's nose extends further down the curved outer surface 321 to also provide a comfortable seal. At the same time, the sealing portion 210 may resistively flex to accommodate noses of different size, e.g., width.

3.1.12 Sealing Portion Comfort

Figures 1, 25:
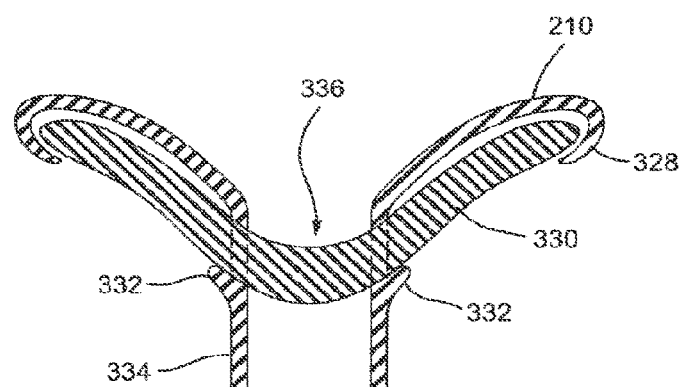
Figures 2, 25:
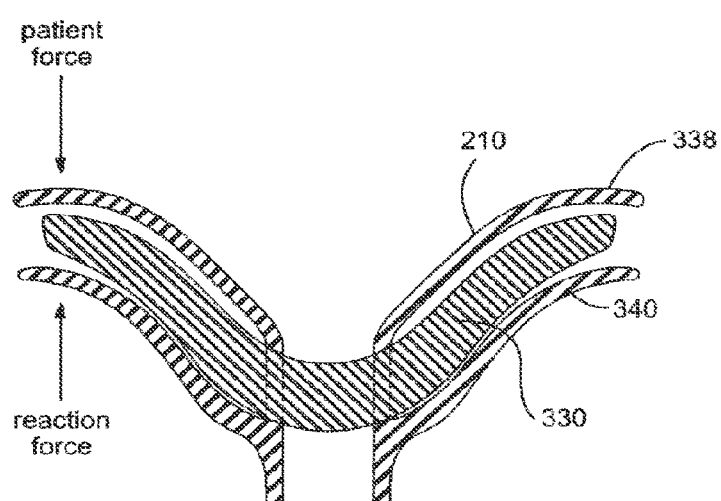
Figures 3, 25:
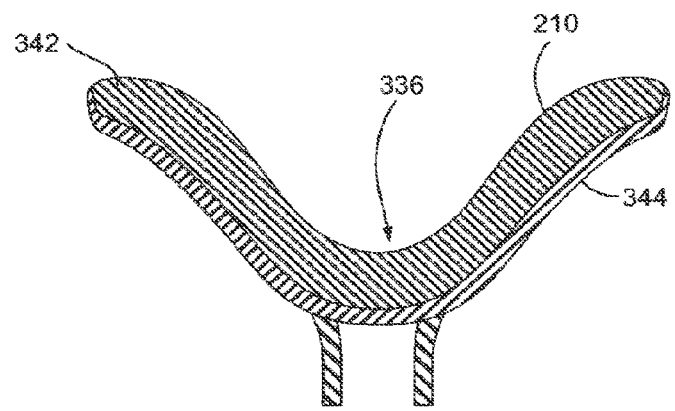
Figures 4, 25:
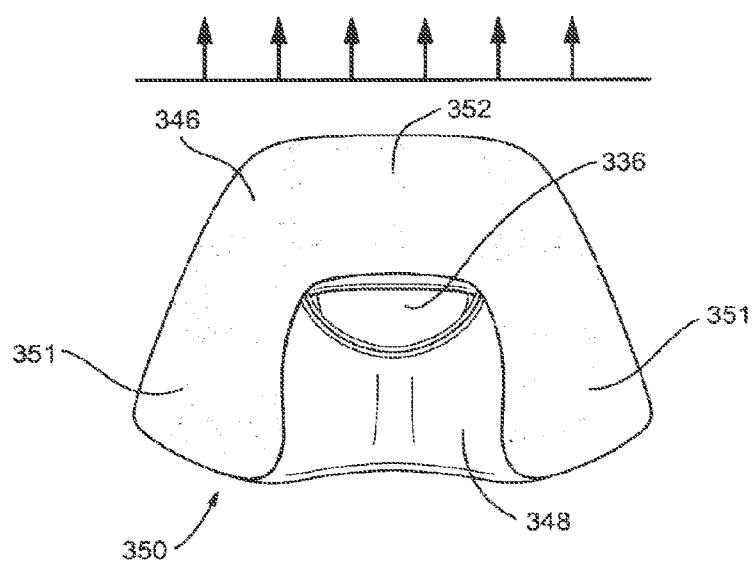

FIGS. 25-1 through 25-4 show a sealing portion 210 including elements structure to provide comfort to the patient. For example, the sealing portion 210 may be provided with a soft, conforming cushion to enhance comfort and thus compliance with therapy. The cushion may be constructed of a low durometer material, such as a material having a hardness of less than 40 Shore A (or Type A). For example, the material may have a hardness of about 5-60 Shore A. Preferably, the material may have a hardness of less than 20 Shore A. Most preferably, the material may have a hardness of less than 10 Shore A.

In FIG. 25-1, a cushion 330 or pocket of soft material is positioned under a sealing membrane 328. The membrane 328 may be constructed of silicone or other suitable material. The cushion 330 may be a molded thermoplastic elastomer (TPE), a gel filled bladder, foam, or another conformable material or a combination of these. As illustrated, the membrane 328 includes an end portion that hooks or wraps over an outer edge of the cushion 330, such that the membrane 328 positions and retains the cushion 330 underneath the membrane 328. Locking bumps 332 on a stem 334 of the sealing portion 210 may also be provided to maintain the cushion 330 in position by preventing it from slipping downward, i.e., locking bumps 332 provide interference to prevent movement of the cushion in the downwards direction.

The sealing portion 210 includes an orifice 336 through which breathable gas may be delivered to the patient. The membrane 328 interfaces with the patient, and preferably prevents the cushion 330 from interfacing with the patient, so that there are fewer constraints in material choice of the cushion 330 due to patient safety.

FIG. 25-2 shows a similar arrangement to FIG. 25-1, but further includes a lower membrane 340 to support the cushion, i.e., an upper membrane 338 and a lower membrane 340 are provided to support the cushion 330 in position. As the patient positions the sealing portion 210 in use, the patient will impart a patient force (as indicated by the arrow) on the sealing portion 210 and the cushion 330. In order for the cushion 330 to provide sufficient reaction force (as indicated by the arrow) at an appropriate displacement, the lower membrane 340 supports the cushion 330 in position to enable a seal with the patient and to provide comfort to the patient.

In FIG. 25-3, the sealing portion includes an upper cushion 342 provided over a lower cushion 344. In this embodiment, the sealing portion may or may not include a sealing membrane as described above. The upper cushion 342 may have one hardness and the lower cushion 344 may have another hardness, e.g., the upper cushion 342 may have a lower hardness than the lower cushion 344. In one example, the upper cushion 342 may have a hardness of about 5-20 Shore A (for example, about 7-15 Shore A, preferably about 7 Shore A) and the lower cushion 344 may have a hardness of about 20-80 Shore A (for example about 40-70 Shore A, preferably about 40 Shore A). However, other suitable hardnesses are possible. The upper cushion 342 and the lower cushion 344 may be made from silicone, TPE, gel, foam, nylon, or a combination thereof, for example. The lower cushion 344 may support the sealing portion 210 in a position to be comfortable and able to seal with the patient in use. An orifice 336 is provided through the upper and lower cushions to allow the delivery of gas to the patient.

In FIG. 25-4, the sealing portion 210 may have a horseshoe shape 346 (when viewed from the top) to cushion the nose tip portion 352 and nostril engagement flaps. This arrangement allows for molding of a bladder as the cushion, since the line of draw of the molding tool (as indicated by the arrows) is straight and therefore easier to mold. The bladder may be filled with gel, foam, TPE or any other suitable material. A membrane 348 may be provided to the cushion 346 and positioned to contact the patient's upper lip in use. The membrane 348 may be stretchable and/or flexible to accommodate various upper lip configurations. The membrane may also seal with less force on the patient's face, and therefore be more comfortable at the upper lip position.

Figures 1, 47:
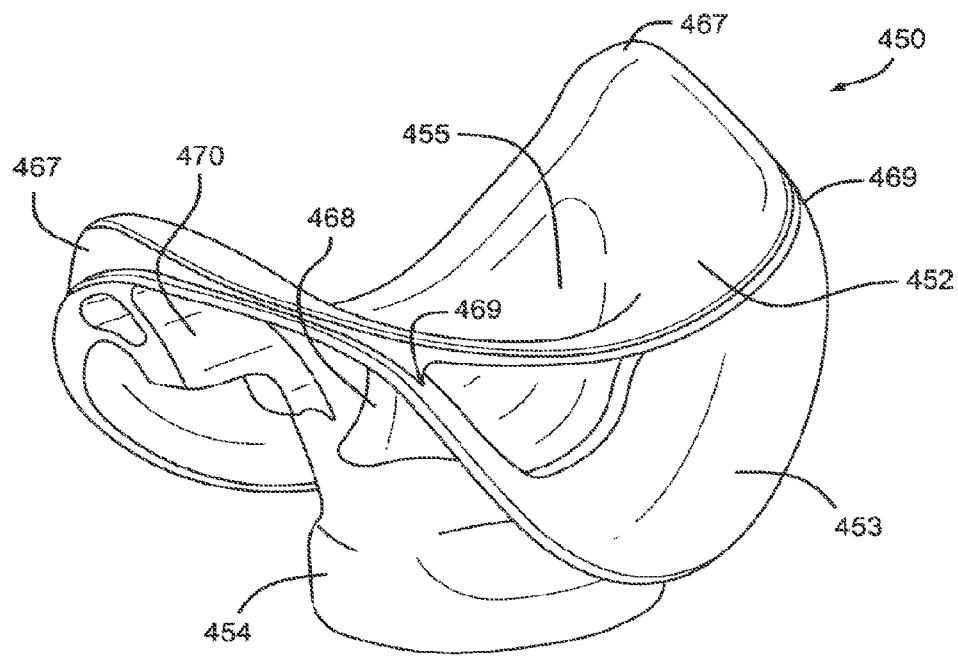
Figures 2, 47:
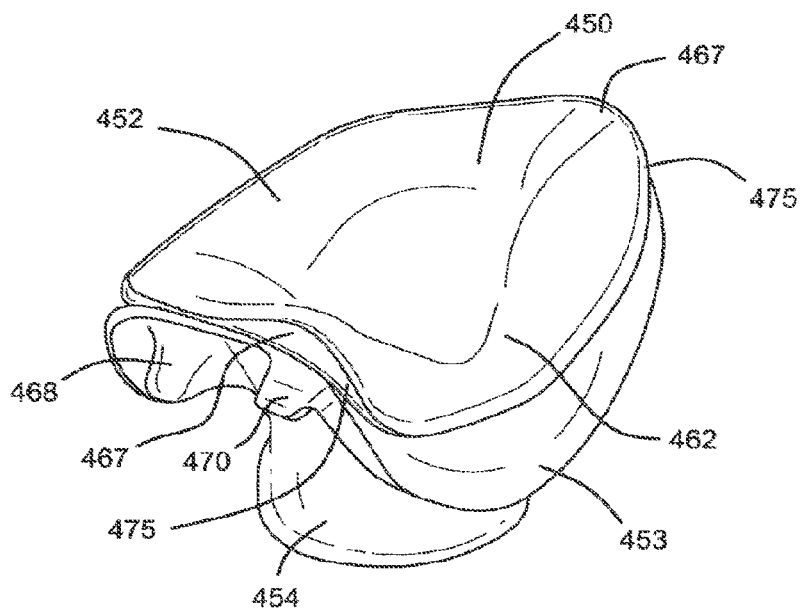
Figures 3, 47:
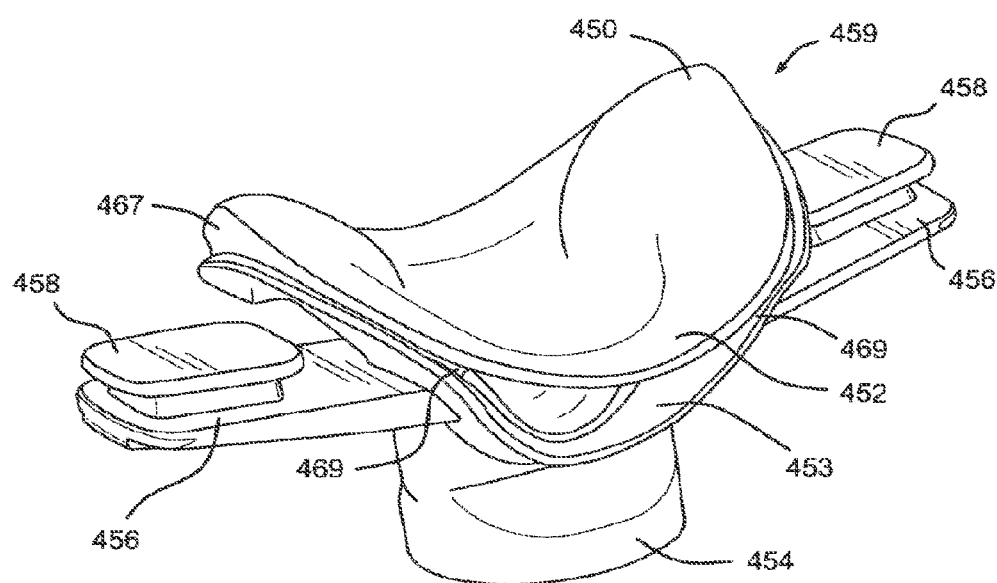
Figure 50:
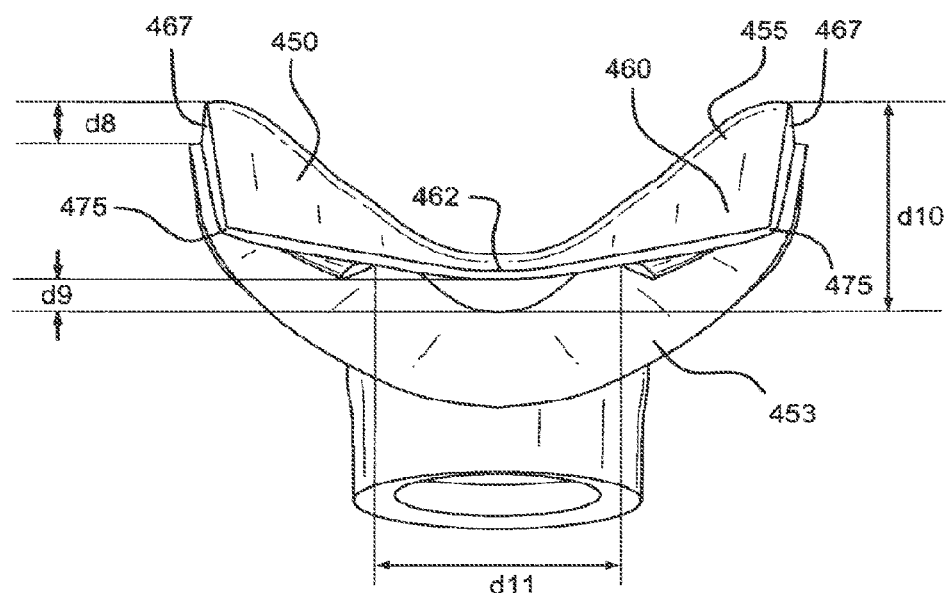
FIG. 50 is a rear view of the sealing portion and supporting portion of FIG. 47-1.

In the embodiment illustrated in FIGS. 47-1 to 50, the sealing portion 450 may be formed from a material and with a softness to provide patient comfort, and to readily conform to the patient's face. For example, the sealing portion 450 may be a liquid silicone rubber material or another elastomeric material, e.g. TPE. The sealing portion may have a durometer of about 5-40 Shore A (preferably about 5-15 Shore A, most preferably about 5 Shore A) to provide comfort to the patient.

3.1.15 Membrane Flexing

Figure 29:
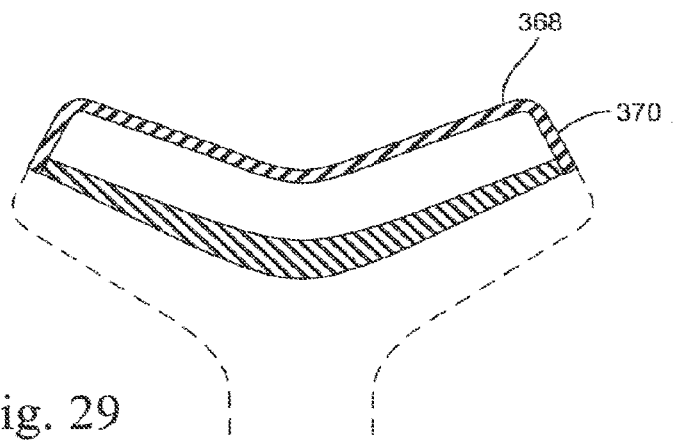
FIG. 29 is a cross section of a prior art sealing portion.
Figure 30:
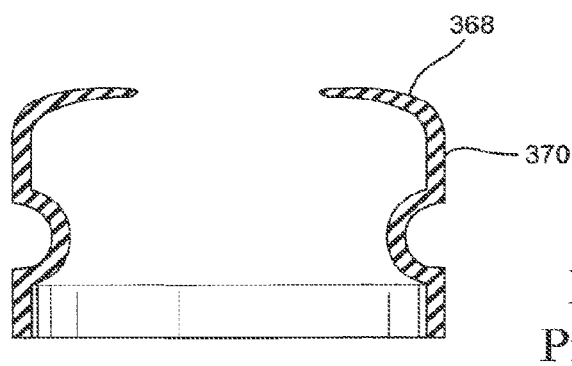
FIG. 30 is a cross section of a prior art sealing portion.

In prior art cradles such as shown in FIGS. 29 and 30 in cross section, the membrane 368 is rolled in or curves inwards from the support wall 370. Such an arrangement permits the patient's nose to travel into the cushion, and the membrane rolls or moves downwards to create a seal. The supporting walls 370 ensure that the membrane 368 is supported and has enough room to roll or bend inwards. Such rolling may cause occlusion of the patient's nares, as the excess material may cover the patient's airway.

Figure 31:
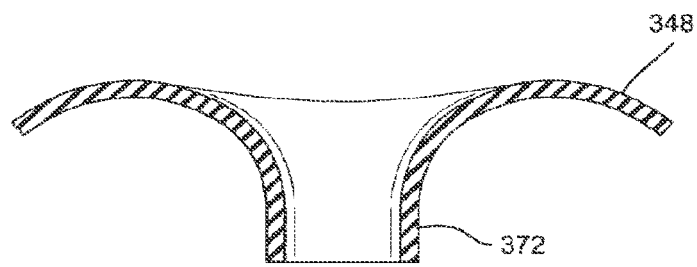
FIG. 31 is a cross section of a sealing portion according to an embodiment of the present technology.

In contrast, in embodiments of the present technology such as illustrated in FIG. 31, the membrane 348 is structured to flex outwards or away from a center of the patient's nose in use. Alternatively this configuration may be described as a trumpet or bell shape. The supporting wall 372 maintains the membrane 348 in its non-use position and prevents the membrane 348 from flexing outwards beyond its intended limit. Since the excess material of the membrane 348 is flexing outwards, it reduces the chance of material occluding the patient's nostrils. The excess material of the membrane 348 reduces the chances of occlusion by removing or reducing pinch forces created by a collapsible outer wall.

3.1.16 Membrane Support

The headgear may be attached to the membrane so as to support the outer walls of the membrane in an upwards position, i.e., to prevent the membrane from flexing outwards into a flat position which may occlude the patient's nares or break the seal of the mask with the patient. As illustrated in the rear view of FIG. 32-1, headgear straps 378 may attach to the sealing portion at headgear attachment points 376. As illustrated, the headgear attachment points 376 are at a position close to orifice 374, so that the straps 378 may support the length of the sealing portion 210 and support the membrane 348 in an upwards position in use. The membrane 348 therefore cannot excessively flex outwards, preventing occlusion of a patient's nares or breaking the seal of the mask with the patient. The headgear straps 378 may flex and move underneath the sealing portion 210 at portions where the headgear straps 378 are not attached via the headgear attachment, to enable greater fit range due to the headgear being able to rest in multiple positions under the membrane.

Figures 1, 32:
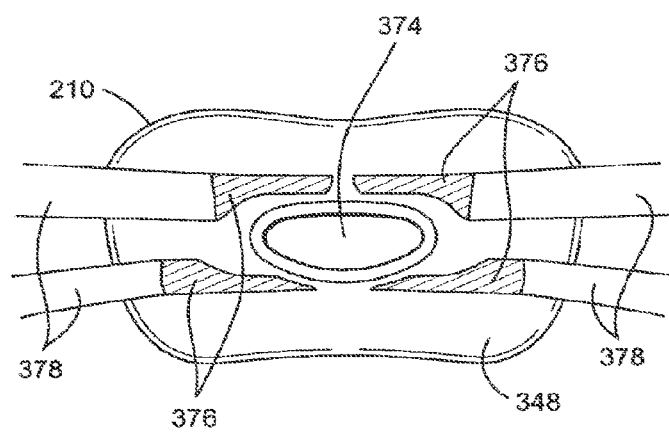
Figures 2, 32:
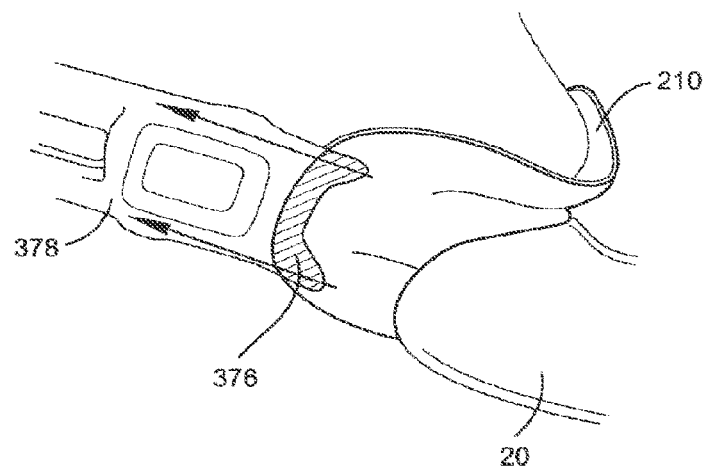

As illustrated in FIG. 32-2, the headgear 378 may alternatively be attached via headgear attachment points 376 at a portion farther away from orifice 374, and closer to an edge of a membrane. This allows greater flexibility of the membrane to accommodate various shapes of noses (e.g., pointy noses versus flat noses).

Figures 1, 33:
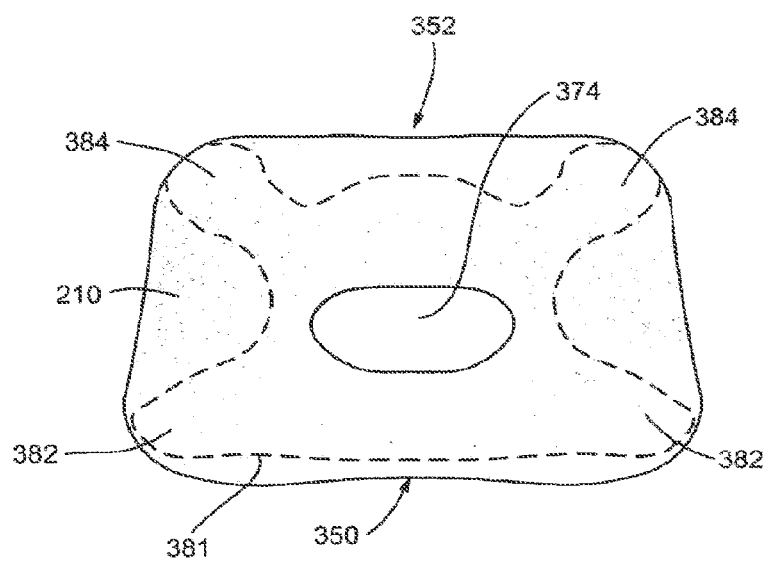
Figures 2, 33:
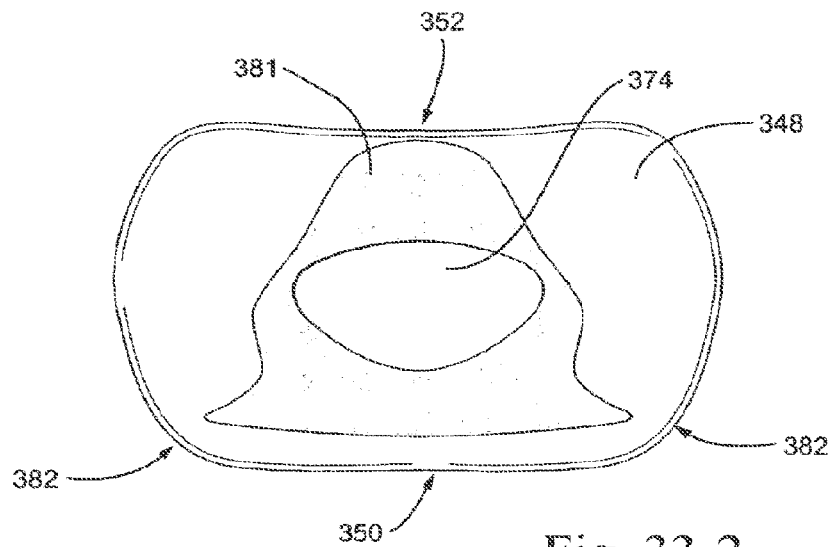

FIG. 33-1 illustrates a supporting member 381 (e.g., a substantially rigid member) positioned under, within or as a part of the sealing portion 210 (the supporting member 381 is shown by the dotted line). The supporting member 381 is structured to force the membrane of the sealing portion 210 into contact with regions of the patient's face that are difficult to seal in. For example, the corner of the nose and the nostril flare may be difficult to seal in as patient's have widely varying geometries in these regions. The supporting member 381 may be more rigid or stiff than the membrane, thereby anchoring the sealing portion at the top lip region, corner of the nose regions 382 and the nostril flare regions 384, also ensuring that the membrane is held in sealing engagement with the patient in these regions. As the tip of the nose is quite sensitive, there may be no supporting member positioned at the nose tip region 352. The supporting member 381 may at least partially extend into the top lip region 350.

The supporting member 381 may be co-molded with the sealing portion 210, and may include a malleable wire or other rigid element. The supporting member 381 may include integrally molded thickened regions to provide support.

FIG. 33-2 illustrates an alternative supporting member 381 that does not include the nostril flare regions so as to allow the membrane 348 to flex in these regions. The support member 381 further extends to the nose tip region 352 to anchor the sealing portion in position with the patient's nares. The supporting member 381 may also at least partially extend into the top lip region 350 and the corner of the nose regions 382.

The supporting member may be co-molded or separately attached to the membrane. The support member may be made from a material with greater hardness than the membrane 384. For example, the membrane may be about IO Shore A and the support member may be about 40 Shore A. However, other suitable hardnesses are possible.

Figures 1, 34:
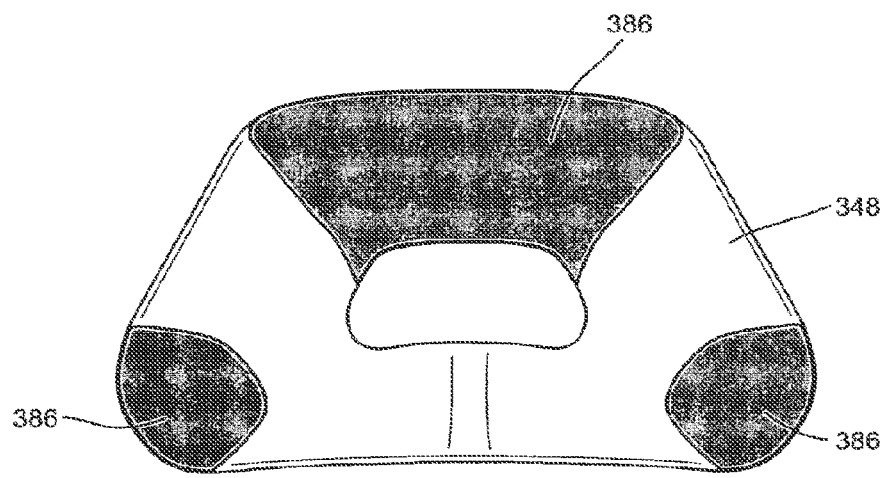

As illustrated in FIGS. 34-1 and 34-2, regions of the sealing portion may include material that is able to support the membrane 348 as well as provide comfort to sensitive regions of the face. For example, stabilizing portions 386 may be providing at the corners of the nose and tip of the nose. The stabilizing portions should be stiff enough to maintain the shape of the sealing portion and support the membrane 348 attached or adjacent to it, while providing sufficient flexibility to be comfortable when in use. The stabilizing regions 386 may be constructed of gel, foam, TPE, silicone or any other suitable material.

3.1.17 Flexible Membrane Portions

FIG. 35-1 illustrates an alternative arrangement to FIGS. 34-1 and 34-2 where the flexible or cushioning region is in the upper lip region 350. As shown in FIGS. 35-2 and 35-3, this flexible or cushioning region has a lower durometer or lower hardness than other regions of the sealing portion, such as the nose tip region 352. In addition, the rest of the sealing portion has two layers—a lower durometer or hardness top layer L1 (i.e. layer contacting the patient's face) and a higher durometer or hardness bottom layer L2. The lower durometer material may have a higher tack or stickiness than the bottom, harder layer and may therefore provide a friction fit with the patient's face.

3.1.18 Membrane Support

Figure 36:
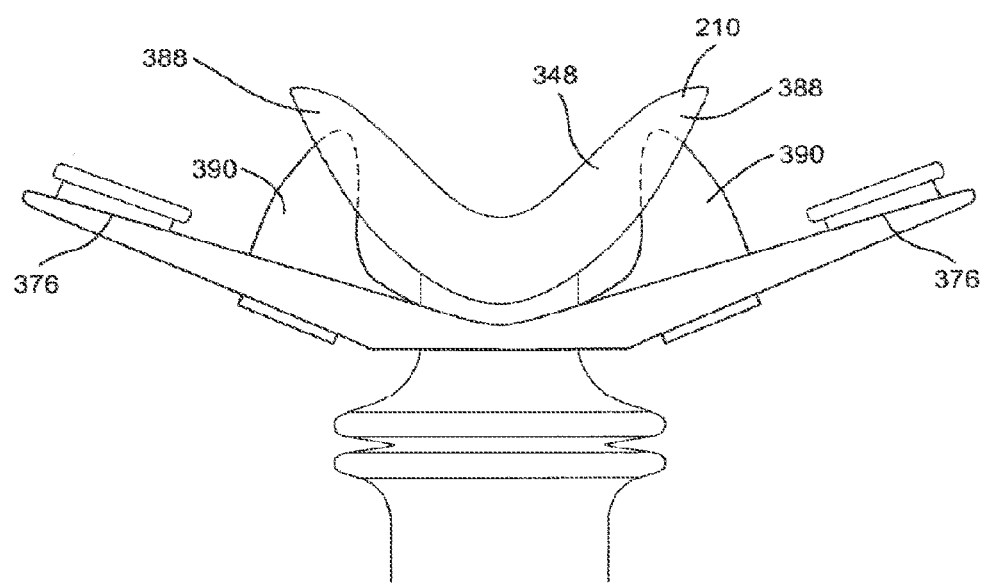
FIG. 36 is a side view of a membrane support according to an embodiment of the present technology.

The membrane 348 may be supported by struts or tabs 390 (FIG. 36) positioned underneath the outer flaps (nostril engagement flaps) 388 of the sealing portion 210. The struts 390 may be attached to or positioned with headgear connectors 376. The struts 390 prevent the outer flaps 388 of the sealing portion 210 from collapsing away from the patient's face, enabling a more effective seal by maintaining the sealed position of the sealing portion 210 on the patient's face.

3.1.20 Diffuse Venting

Figures 1, 37:
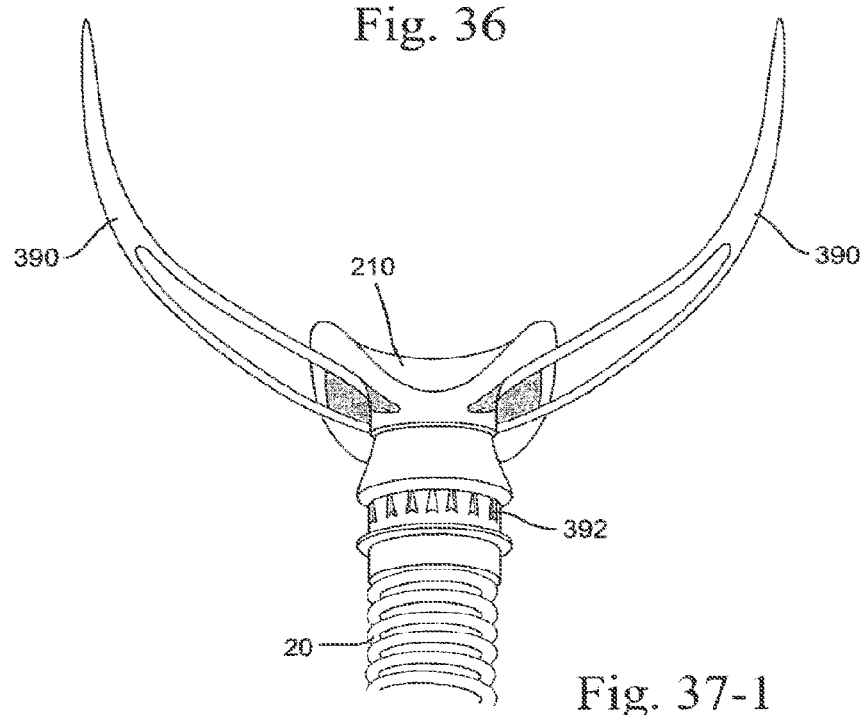
Figures 2, 37:
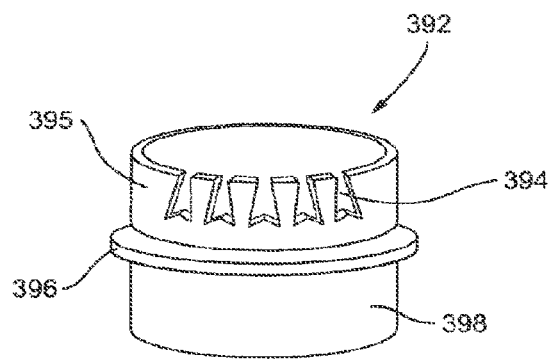

As illustrated in FIGS. 37-1 and 37-2, the sealing portion 210 may be secured in position on the patient's head with one or more headgear straps 390. The sealing portion 210 may also be connected to a tube 20 for the delivery of breathable gas to the patient. The tube 20 may connect to the sealing portion 210 by a vent ring 392. As shown in FIG. 37-2, the vent ring 392 includes a tube connector 398 adapted to attach the tube 20 at one end, with a step or flange 396 to prevent the tube 20 from being positioned on one or more gas washout vents 394. The vent ring 392 includes a sealing portion connector 395 adapted to attach to the sealing portion at its other end. The connector 395 provides the one or more gas washout vents 394, which align with vent holes or tracks along the end of the sealing portion, allowing exhaled gases to pass from the sealing portion 210, through the gas washout vents and out to atmosphere. The gas washout vents or pathways advantageously direct air away from the patient's face. The gas washout vents or pathways also disperse air around the perimeter of the vent ring 392, thereby diffusing the exhaled gases and thus preventing jetting.

3.1.21 Support of Stem

Figure 39:
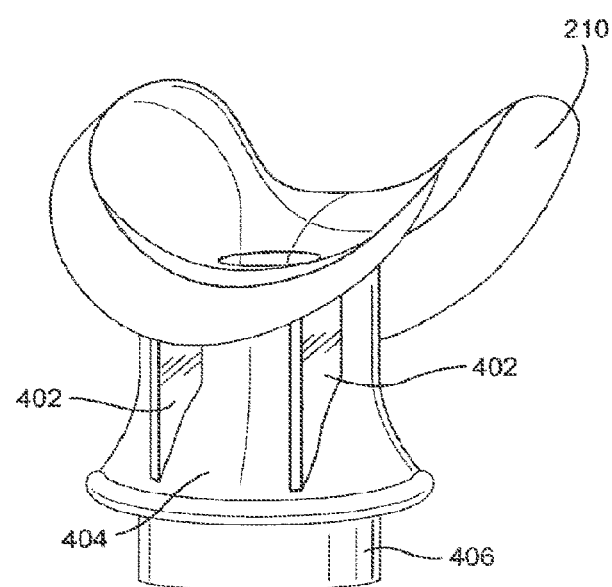
FIG. 39 is an isometric views of support mechanism for a stem of the sealing portion according to an embodiment of the present technology.

FIG. 39 illustrates a sealing portion 210 having a stem 404 for allowing breathable gas to flow through the mask to the patient. The stem 404, which is attached to tube connection 406, may include one or more ribs 402 or other supporting mechanisms to support the stem 404 and prevent it from possibly collapsing and occluding the flow of gas in use. The ribs may be thickened regions or separately attachable or embedded struts to maintain the stem 404 in an open position. Ribs 402 may also support the sealing portion 210 such that it may maintain an open position thereby preventing occlusion of the orifice delivering breathable gas to the patient.

3.1.22 Supported Sealing Portion

The sealing portion 210 may be supported by a supporting portion. The sealing portion may be totally separated from the supporting portion by a gap, or one or more portions of the sealing portion may be in contact with the supporting portion, while other portions of the sealing portion may be separated from the supporting portion by one or more gaps. When such gaps are utilized, the corresponding portions of the sealing portion 210 may be able to stretch to fit the patient's face.

3.1.22.1 Separated Sealing Portion

Figure 40:
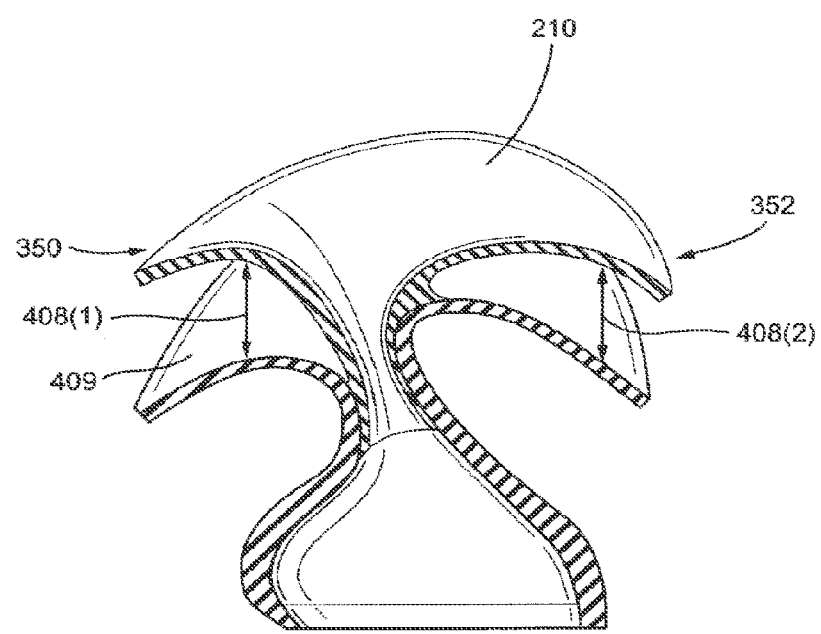
FIG. 40 is a cross section of a sealing portion according to an embodiment of the present technology.

FIG. 40 illustrates a sealing portion 210 that is separated from supporting portion 409 by a space or gap 408(1), 408(2), allowing the sealing portion 210 to flex downwards until it reaches the supporting portion 409. The supporting portion 409 prevents the sealing portion 210 from losing its shape or collapsing and thus assist in maintaining a seal to the patient. The patient contacting portion 407 preferably has a lower hardness than the supporting portion 409, and may be thinner than the supporting portion 409. The patient contact portion 407 and the supporting portion 409 may be formed by multiple shot molding, gluing, or any other suitable method.

The top lip portion 350 of the sealing portion 210 may have a gap 408(1) between the patient contacting portion 407 and the supporting portion 409 to allow for varying anthropometrics of patient upper lips. This also allows flexibility of the patient contacting portion 407 near the septum of a patient, which is a highly sensitive region. The nose tip region 352 of the sealing portion 210 may also have a gap 408(2) between the patient contacting portion 407 and the supporting portion 409 to allow for varying anthropometrics of patient nose tips. The flexibility also enables the patient contacting layer 407 to flex around the nose tip and thereby enhance the sealability of the sealing portion 210.

3.1.22.2 Partially Separated Sealing Portion

FIG. 47-1 shows a view of a sealing portion 450 that is supported or positioned by supporting portion 453. The sealing portion 450 is separated from the supporting portion 453 by a front gap in an area of a nose tip engagement portion 452 between front anchor points 469, and the sealing portion 450 is connected to the supporting portion on sides of the sealing portion 450 outside the front anchor points 469.

The nose tip engagement portion 452 is flexible and can extend downward when contacted by a patient's nose, but will be limited in how far it can extend if it reaches the supporting portion 453. The nose tip engagement portion is extended in length from the aperture 455 to fit nose tips of different size, so that the nose tip of different patients may engage the nose tip engagement portion at different locations. Stem 454 supports the supporting portion 453 and the sealing portion 450. Stem 454 is also adapted to receive the air delivery tube to supply pressurized breathable gas to the patient.

The sealing portion 450, the stem 454, and the supporting portion 453 may be a liquid silicone rubber material or another material, e.g., TPE, gel or foam. The sealing portion 450 may be formed from a material having different properties than the material forming the supporting portion 453 and the stem 454. The stem 454 and the supporting portion 453 may be formed together such as in a mold, and the sealing portion 450 may be formed separately and then joined together with the supporting portion 453, e.g. such as by gluing. Alternatively, the stem 454 and the supporting portion 453 may be formed together such as in a mold, and then the sealing portion 450 may be bonded to the supporting portion 453 and the stem 454 in the mold.

The sealing portion 450 may have different properties than the supporting portion 453 and the stem 454. For example, the sealing portion 450 may be formed from different (or the same) materials, have a different geometry, have a different hardness, than the supporting portion 453 and the stem 454.

The supporting portion 453 and the stem 454 have a hardness that is greater than the hardness of the sealing portion 450 (which as described above may have a hardness of about durometer 5 Shore A), because the supporting portion 453 and the stem 454 both support the sealing portion 450, and provide a reactive force to stabilize the sealing portion 450 in position on the patient's face. For example, the supporting portion 453 and the stem 454 have a hardness of about durometer 20-80 Shore A. Preferably, the supporting portion 453 and the stem 454 have a hardness of about durometer 30-65 Shore A. Most preferably, the supporting portion 453 and the stem 454 have a hardness of about 40 Shore A.

The hardness of the sealing portion 450, the supporting portion 453, and the stem 454 may vary from the hardness levels described, but if so then a thickness of material may need to change to ensure a seal is provided with the patient. For example, the nose tip engagement portion 452 of the sealing portion 450 may have a thickness of 1.2 mm with a hardness of about durometer 5-20 Shore A (preferably about 5-10 Shore A, most preferably about 5 Shore A), but if a harder material is used for the sealing portion 450, then the nose tip engagement portion 452 should have a thickness reduced to, for example, 0.3 mm, so that the same stiffness or reactive force is applied to the patient's face to provide an effective seal.

FIG. 47-2 illustrates another view of the sealing portion 450. The sealing portion 450 is separated from the supporting portion 453 by a rear gap in an area of an upper lip engagement portion 462 between rear anchor points 475, and the sealing portion 450 is connected to the supporting portion 453 on sides of the sealing portion 450 outside the rear anchor points 475. The upper lip engagement portion 462 is flexible and can extend downward when contacted by a patient's upper lip, but will be limited in how far it can extend if it reaches the supporting portion 453.

Figure 49:
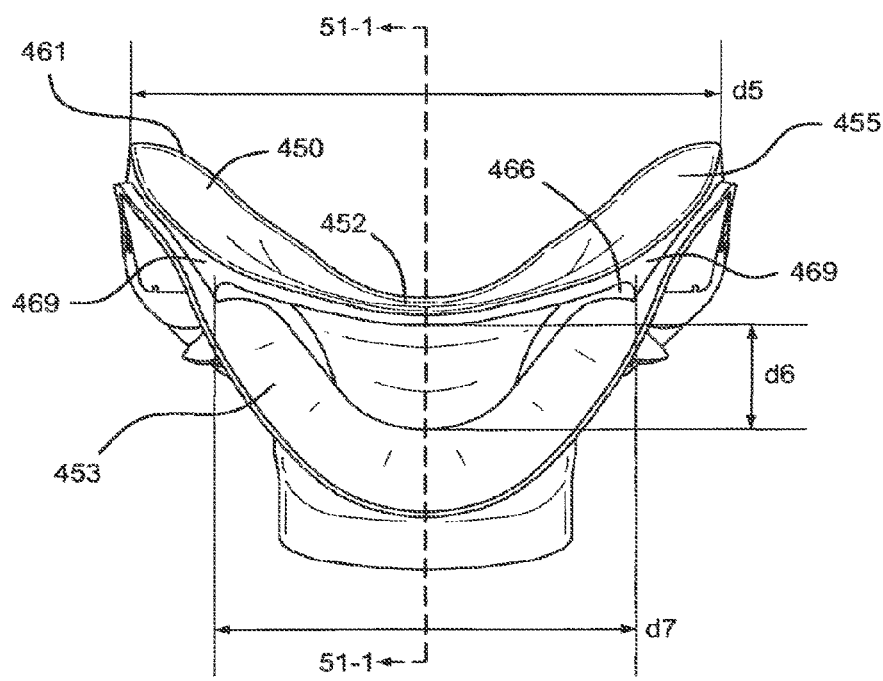
FIG. 49 is a front view of the sealing portion and supporting portion of FIG. 47-1.

FIGS. 49 (and 48-2) illustrates a front view of the sealing portion 450. The nose tip engagement portion 452 is formed as a hanging, flexible membrane. The sides of the sealing portion 450 are connected to or bonded to the supporting portion 453, while there is a front gap between a central portion of the sealing portion 450 and the supporting portion 453 between front anchor points 469. By utilizing this hanging, flexible membrane, the nose tip engagement portion 452 provides a flexible surface that remains in tensile contact with the nose during patient interface movement, and better accommodates varying nose geometries. Different sized noses are provided with a comfortable and effective seal by utilizing a wide nose tip engagement portion 452, which allows the nose tip to be positioned at various locations between the aperture 455 and a front edge of the nose tip engagement portion 452. The nose tip engagement portion 452 may stretch downwards towards the supporting portion depending on the size of the patient's nose.

The sealing portion 450 includes two thickened corner regions 467 positioned on each side of the upper lip engagement portion 462. The thickened corner regions 467 are adapted to seal with the patients face in use at regions of the patient's nose adjacent the nasal labial creases. The two thickened corner regions 467 protrude outward to provide an effective seal in this area. The two thickened corner regions 467 may each have a radius of curvature of between about 2.4 mm and about 6 mm. A radius of curvature of the upper lip engagement portion may be about 5 mm.

A width d5 of the sealing portion 450 may be about 48 mm to fit noses up to about 45 mm in width. A larger width d5 such as 60 mm could be used to fit noses up to 60 mm in width. A distance d6 between the nose tip engagement portion 452 and the supporting portion 453 may be about 5-20 mm, preferably about 5-15 mm and most preferably about 10 mm. This distance d6 has provided effective sealing of the patient interface 451 with patients having nasal alar angles of up to about 135°, but may also fit patients have nasal alar angles of up to about 200°. Distance d7, a width of the nose tip engagement portion (and a distance (width) of the portion of the sealing portion 450 not bonded to the supporting portion 453) may be about 38 mm, but for larger noses could be another value such as about 48 mm, or up to about 60 mm.

A radius of curvature of the nose tip engagement portion 452 may be about 30-45 mm, preferably about 30-40 mm and most preferably about 35 mm, but to fit flatter noses, could be about 35 to 50 mm, preferably about 40-50 mm, and most preferably about 40 mm. At protruding edge 476 in FIG. 48, an at least 1 mm bond contact radius may be used to aid tooling, where the protruding edge 476 may be clamped in a tool while the sealing portion is molded. A distance (height) d3 of the nose tip engagement portion is about 10 to 30 mm, preferably about 12-18 mm and most preferably about 17 mm. A distance d4 of the nose length region is about 20-40 mm, preferably about 25-35 mm and most preferably about 27 mm, which covers nose lengths of about 12 mm to about 25 mm. The distance d4 could be reduced to about 17 mm for wide/shallow noses (over 40 mm wide and less than 15 mm long).

FIG. 48-2 illustrates a schematic top view of the sealing portion 450. The sealing portion 450 includes an aperture 455, a front stretch portion 564, a rear stretch portion 562, side push or compression portions 566 and side wrap or cantilever portions 568. The front stretch portion 564 and the rear stretch portion 562 are flexible portions of the sealing portion that can stretch or flex, when they come into contact with the nose tip and upper lip of a patient. In these regions, sealing portion 450 is a thin membrane that is in tension and thus hugs or closely follows the geometry of the nose tip and top lip of the patient. Preferably the respective front and rear stretch portions are held at their ends, and unsupported in their middle. The flexibility minimizes the force for a given displacement on the top lip and nose tip as these areas can be sensitive.

The side wrap or cantilever portions 568 are adapted to provide a substantially horizontal or lateral force that is substantially normal to the plane of the flares of the patient's nose. As the flares of the patient's nose fill with pressurized air, the flares are urged outwards due to the air pressure. The side wrap or cantilever portions 458 provide a reactive force to this outwards force of the flares, ensuring a good seal in this region. Reinforcement or greater stiffness of the side wrap or cantilever portions 568 (when compared to the stretch portions 562, 564) may be required to ensure the reactive force is sufficient to maintain the seal and avoid blow out or broken seal. Reinforcement may be provided by additional thickness of the sealing portion 450 in these side wrap portions, such as by utilizing a higher stiffness material, or additional structure such as a headgear attachment or ribs underlying the side wrap or cantilever portions 568.

The side push or compression portions 566 are adapted to anchor or support the sealing portion 450 in position. In use, the portions 566 may be largely in compression. The force provided from the side push portions 566 may be normal to the plane of the patient's face, in a substantially horizontal direction. Since this region of the sealing interface of the patient's face is the least sensitive, tension from headgear is substantially transmitted to the side push portions 566. Preferably, this is the stiffest region of the sealing portion 450. The side push portions 566 may have a greater thickness than the front stretch portion 562 or the rear stretch portion 564.

The sealing portion 450 has varying stiffness in different portions, i.e. front stretch portion versus rear stretch portion versus side push portions versus side wrap portions. A stiffness of these portions is varied by varying the materials, the hardness of the materials, the thickness of the materials, or by using supporting portions.

FIG. 50 illustrates a rear view of the patient interface 451. The sealing portion 450 is connected to the supporting portion 453 on both sides of the patient interface 451, and includes an upper lip engagement portion 462 that engages with a patient's upper lip in use. The upper lip engagement portion 462 is formed as a hanging, flexible membrane, with a rear gap between the upper lip engagement portion 462 of the sealing portion 450 and the supporting portion 453. The rear gap is positioned between rear anchor points 475 that anchor the sealing portion 450 to the supporting portion 453. The flexible, hanging membrane provides a flexible surface that remains in tensile contact with the upper lip of the patient during patient interface movement, and can stretch to accommodate varying facial geometries by allowing movement of the upper lip engagement portion 462.

A thickness d8 of the thickened corner regions 467 of the sealing portion 450 could be about 1 to 5 mm, preferably about 2 to 4 mm, most preferably about 3.5 mm with a relatively low durometer Shore A hardness for comfort. The thickness d8 could be increased up to about 5 to 10 mm, preferably about 5 to 8 mm, most preferably about 5 mm depending on the thickness of the underlying supporting portion 453, and could be decreased to a same thickness as the upper lip engagement portion 462, about 0.25 to 3 mm, preferably less than 2 mm, most preferably about 1.2 mm.

The distance d9 between the unbonded region of the sealing portion 450 at the upper lip engagement portion 462 and the supporting layer 453 may be about 1 to 15 mm, preferably about 5 to 10 mm, most preferably about 7 mm when not in use, and may vary between 0 mm and 15 mm, preferably up to 7 mm in use based on contact seal force to the philtrum of the patient. The distance d10 between the top edge of the sealing portion 450 and the supporting portion 453 may be about 10 to 30 mm, preferably about 15 to 20 mm, most preferably about 18 mm. The width of the upper lip engagement portion 462 (and a distance (width) d11 of the unbonded portion of the sealing portion 450) may be about 10 to 30 mm, preferably about 15 to 25 mm, most preferably about 20 mm, but this could be varied between about 14 mm and about 22 mm depending on nose width. A radius of curvature at the center of the upper lip engagement portion 462 may be about 5 to 20 mm, preferably about 10 to 15 mm, most preferably about 12.5 mm when not in use, but will lessen when in use and with inwards flex of the patient interface 451.

The sealing portion 450 is thus connected to the supporting portion 453 on both sides, but is separated by gaps from the supporting portion 453 between the front and rear anchor points 469, 475. These gaps allow the sealing portion 450 to flex in use at the nose tip and upper lip regions of the patient to provide a good fit and comfort to the patient.

Figures 1, 51:
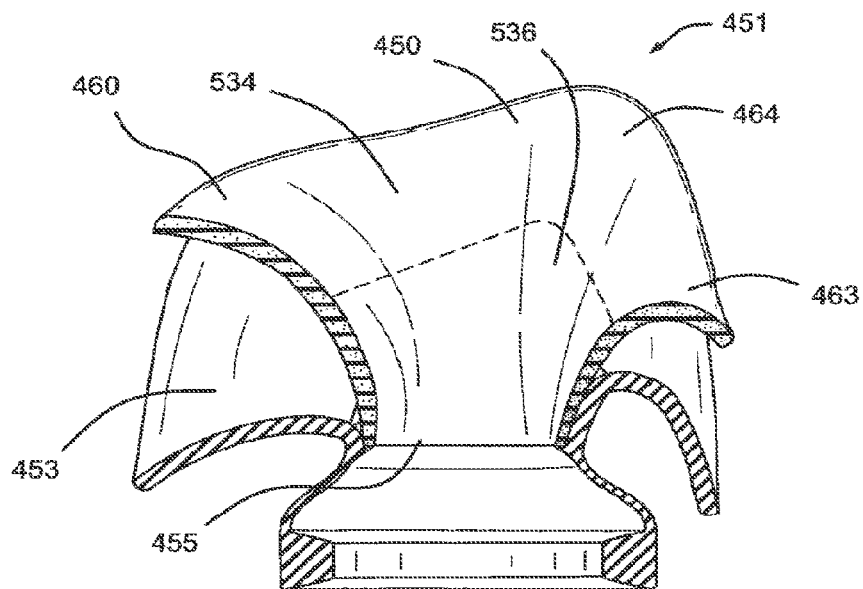
Figures 2, 51:
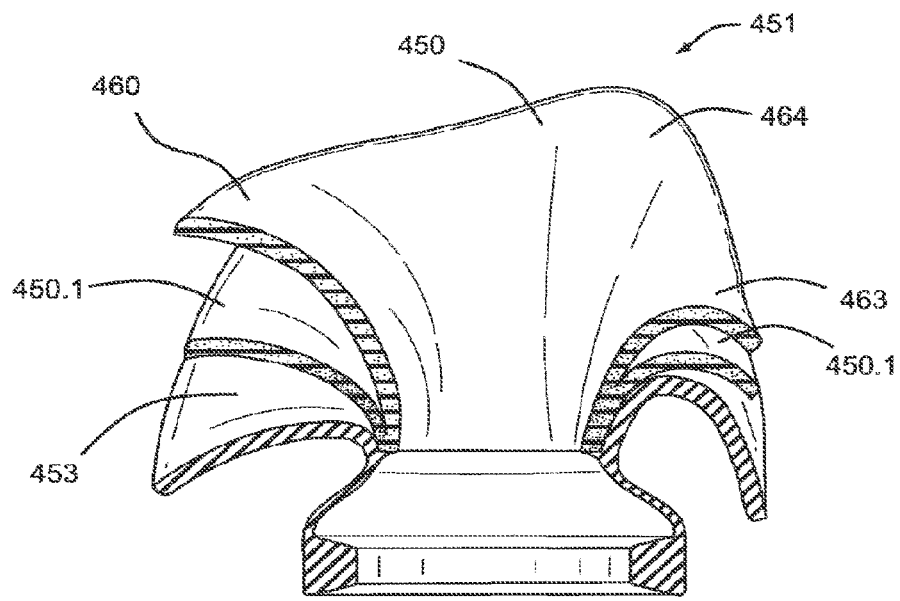

FIG. 51-1 illustrates a cross-sectional side view of the patient interface 451. A front unbonded region 460 of the sealing portion 450 may have a radius of curvature of about 8 to 15 mm, preferably about 10 to 13 mm, most preferably about 12.5 mm. A rear corner portion 464 of the sealing portion 450 may have a radius of curvature of about 1 to 7 mm, preferably about 3 to 6 mm, most preferably about 4 mm. A rear unbonded region 463 of the sealing portion 450 may have a radius of curvature of about 2 to 8 mm, preferably about 3 to 6 mm, most preferably about 5 mm, but this value can vary to almost flat at the outer edge.

The sealing portion 450 may include an outer sealing margin 534 above the dotted line to seal with the patient's face, and a transition region 536 between the opening 455 and the outer sealing margin that gradually increases in size from the opening to the outer sealing margin 534. The opening 455 defines an interior surface in communication with the breathable gas, and the outer sealing margin 534 is formed as a continuous extension of the interior surface. Outer edges of the sealing portion 450 are oriented away from the opening 455 and/or a direction of flow of the breathable gas. The outer sealing margin 534 is substantially convex as seen from its top view.

FIG. 51-2 illustrates a cross-sectional side view of the patient interface 451. This embodiment includes an intermediate portion 450.1 disposed between the sealing portion 450 and the supporting portion 450. The intermediate portion 450.1 may be formed as a hanging membrane. The intermediate portion 450.1 may be molded together with the sealing portion 450, may be molded together with the supporting portion 453, or may be molded separately from the sealing portion 450 and the supporting portion 453. The intermediate portion 450.1 may provide support to the sealing portion 450. The entire intermediate portion 450.1 may be separated from the sealing portion 450 by a gap, such as shown in FIG. 51-2, or portions of the intermediate portion 450.1 may be in contact with the sealing portion 450 while other portions of the intermediate portion 450.1 may be separated from the sealing portion 450 by a gap.

Figures 1, 52:
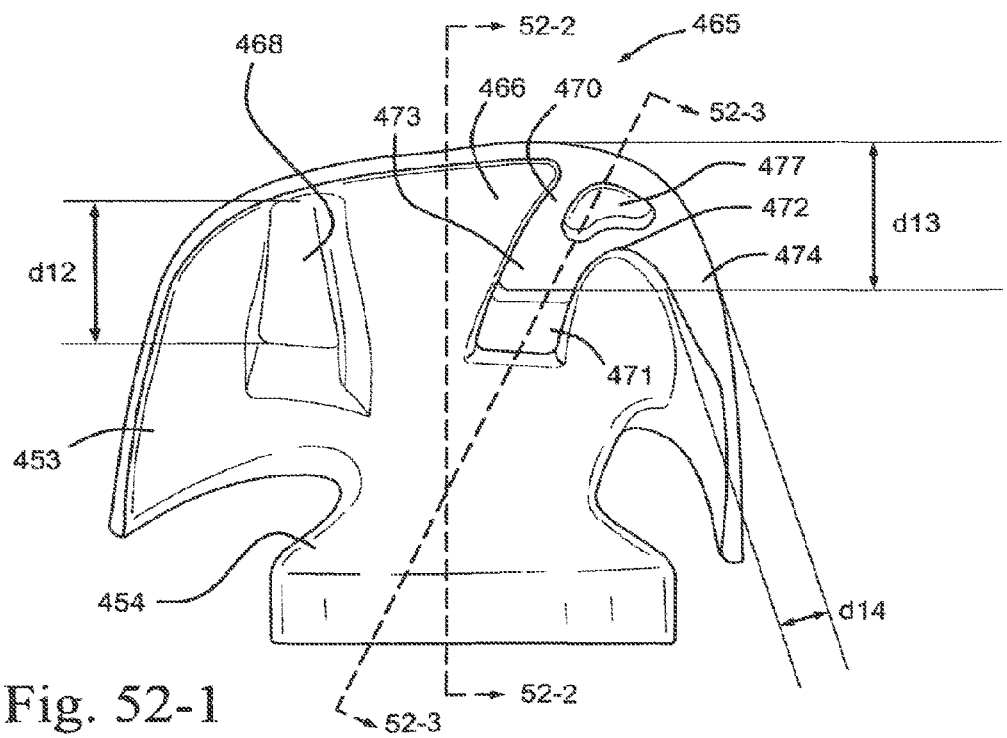
Figures 2, 52:
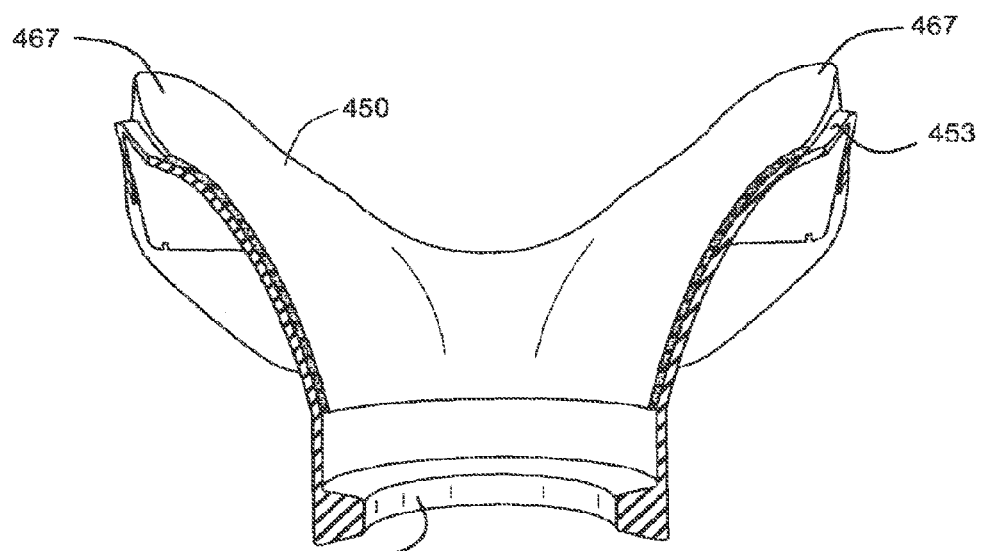
Figures 3, 52:
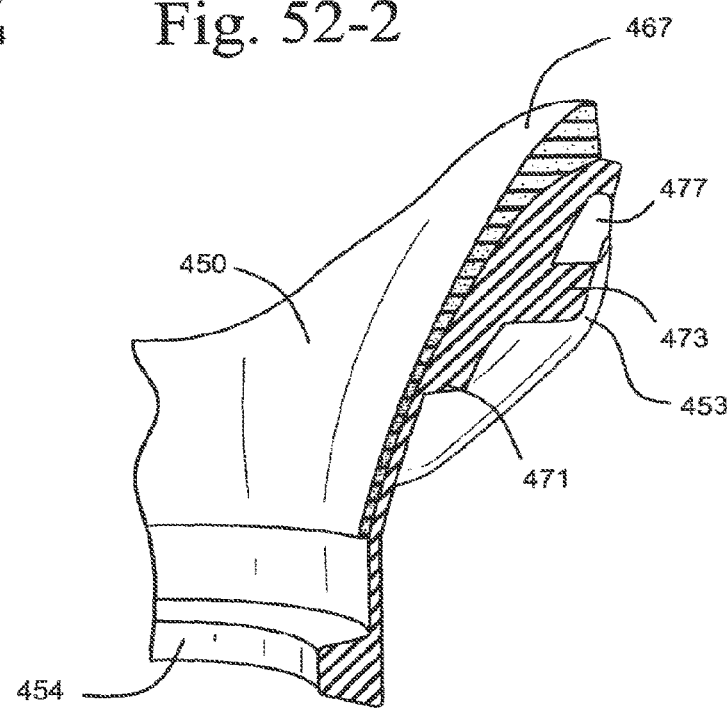
Figures 4, 52:
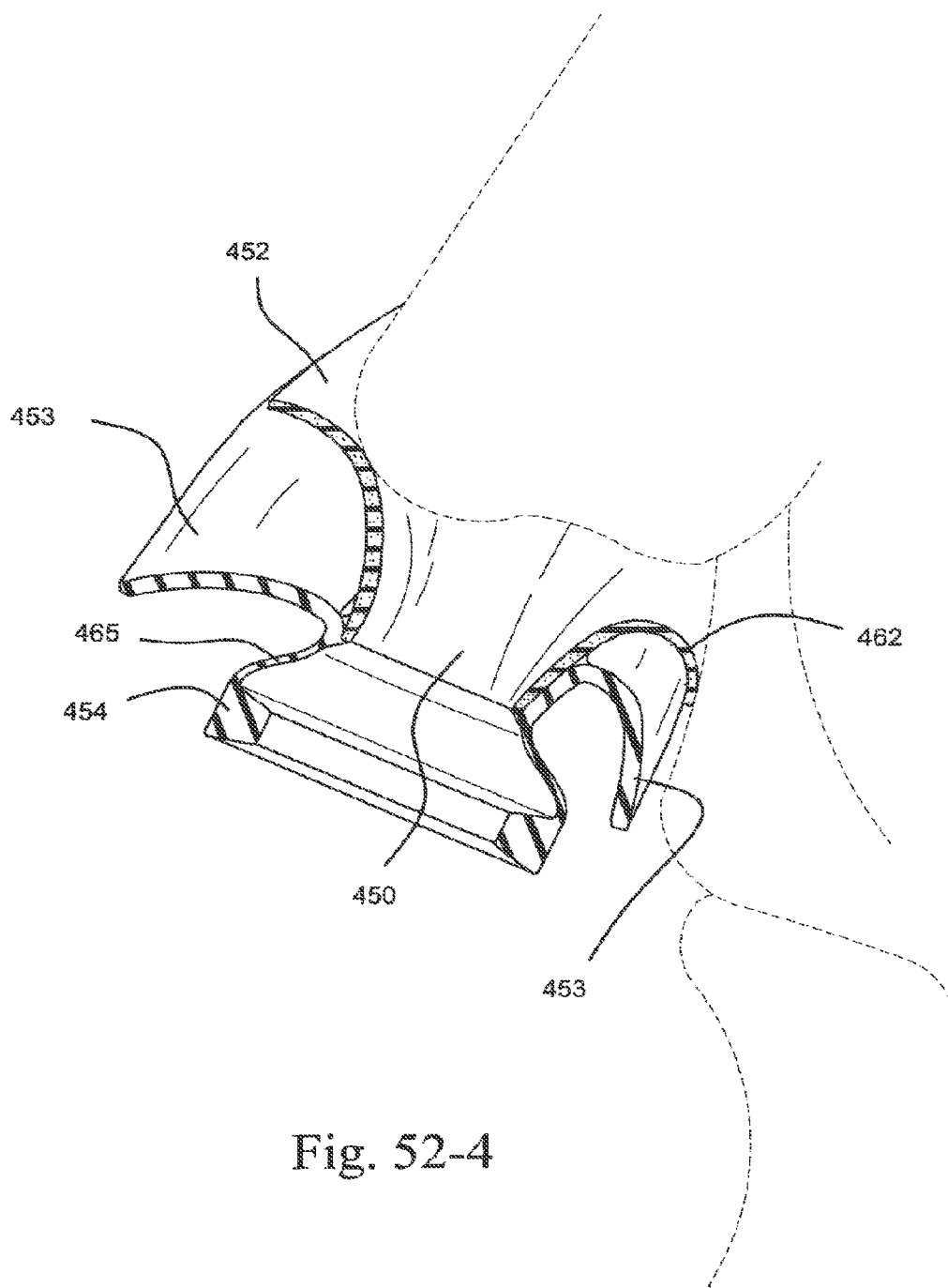
Figures 5, 52:
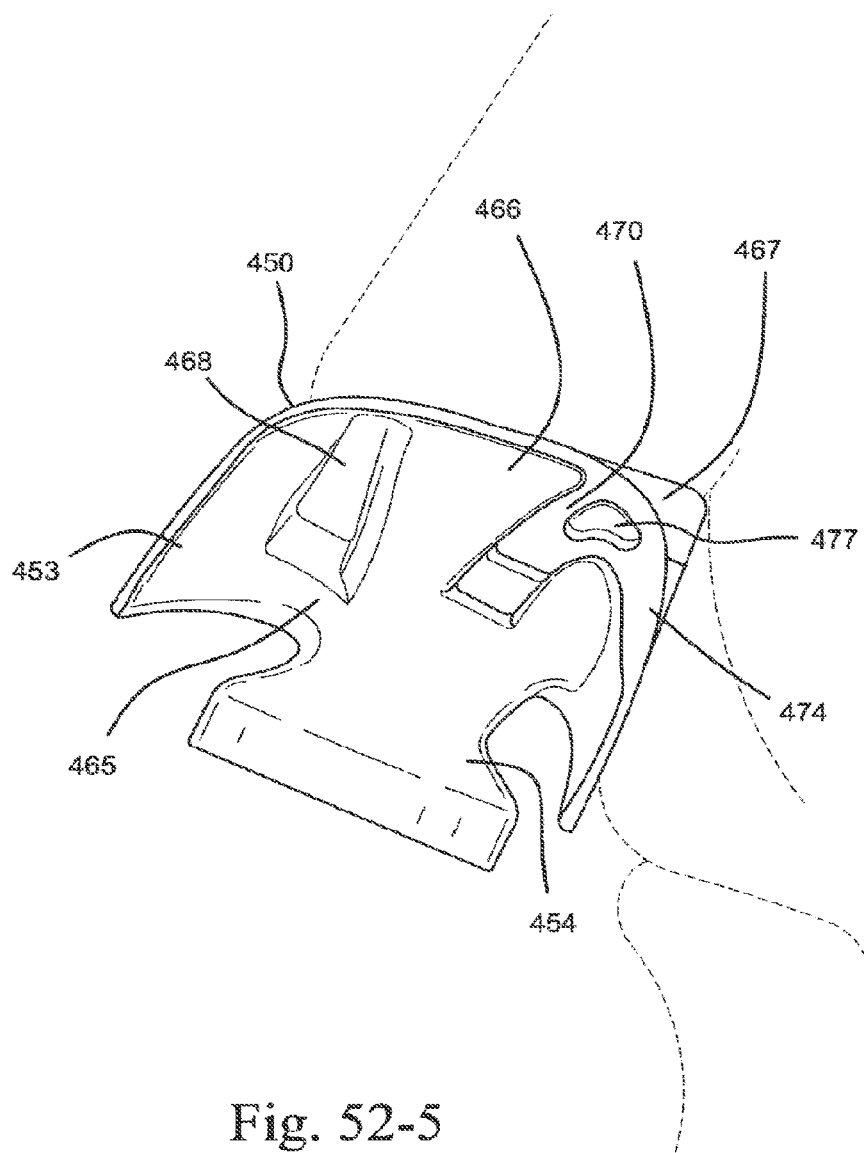
Figures 6, 52:
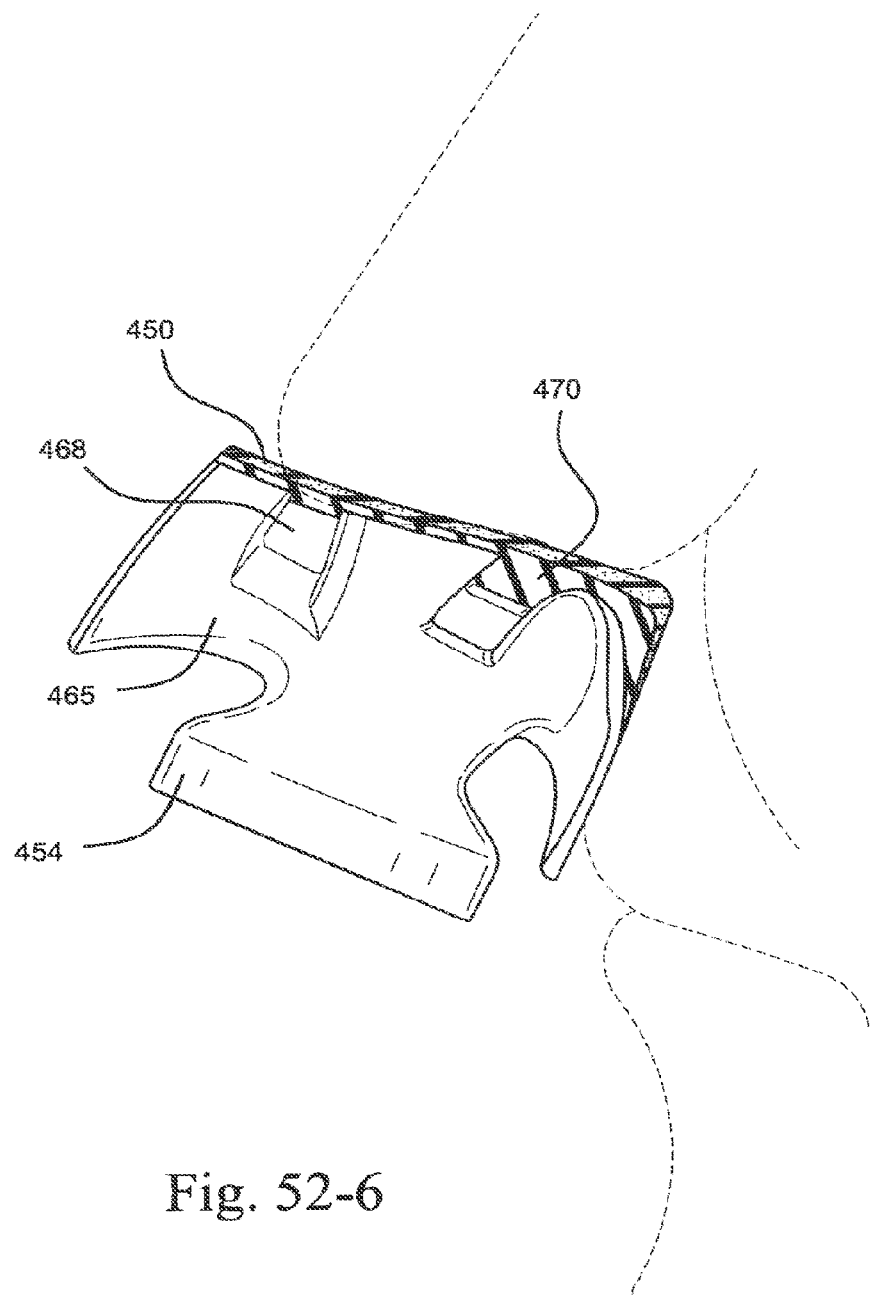
Figures 7, 52:
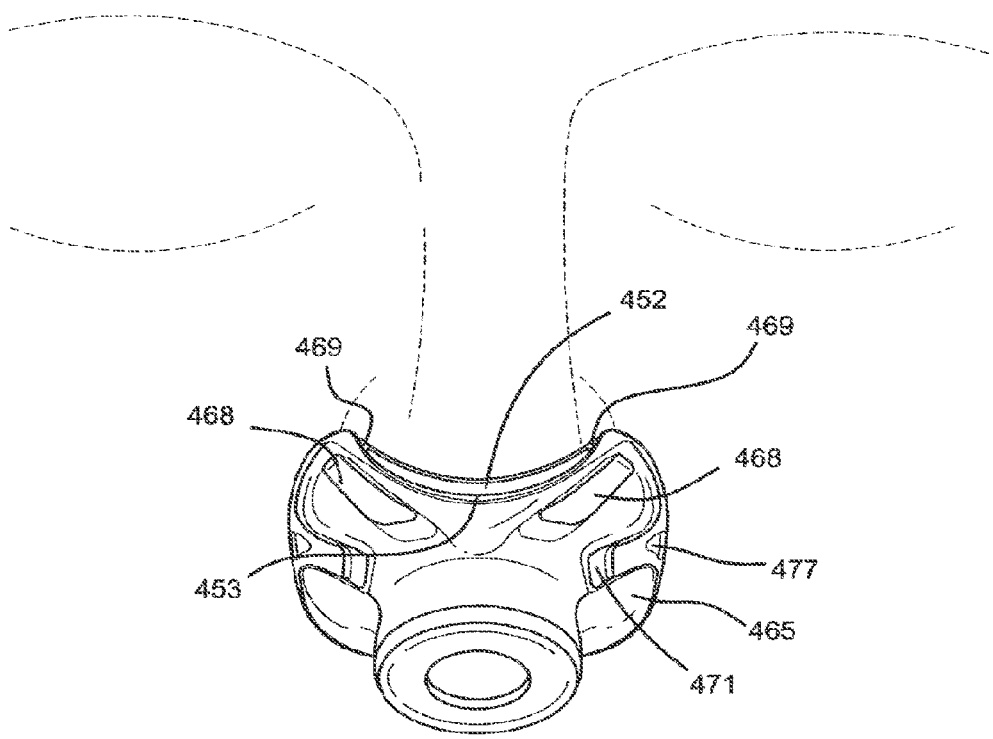

FIG. 52-1 illustrates a support membrane 465, which may include the supporting portion 453 and the stem 454. The supporting portion 453 and the stem 454 may be formed as a single unitary element. The support membrane 465 may have a general wall section 466, a front thickened portion 468, and a rear thickened portion 470. A front thickened portion 468 and a rear thickened portion 470 are formed on each side of the supporting portion 453. The front thickened portion 468 and the rear thickened portion 470 provide varying degrees of support to the sealing portion 450 when assembled. Support membrane 465 may be constructed of a silicone with a hardness of about 20 to 90 Shore A, preferably about 20 to 60 Shore A, and most preferably about 40 Shore A. The support membrane 465 could also be made from polycarbonate, polypropylene, nylon, thermoplastic elastomer (TPE), Hytrel™, etc.

The front thickened portion 468 is positioned adjacent to an area of the sealing portion that contacts with sides of the patient's nose in use as seen in FIG. 47-2, and transfers headgear load into a pinch force on the sides of a patient's nose to provide an effective seal. The front thickened portion 468 may have a thickness that increases from a top to a bottom, and have a height d12 of about 5 to 20 mm, preferably about 7 to 14 mm, most preferably about 11 mm.

The rear thickened portion 470 may include a lower portion 471 having a first thickness and an upper portion 473 having a second thickness greater than the first thickness. A height d 13 of the upper portion 473 may be about 7 to 20 mm, preferably about 8 to 12 mm, most preferably about 9.5 mm, although it could be reduced to about 4 mm to reduce loading. The rear thickened portion 470 may have a curved portion 472, which may have a radius of curvature of about 0.5 to 3 mm, preferably about 2 mm, although it could be increased to about 4 mm to increase stiffness against the upper lip of the patient. The rear thickened portion 470 may include a cored out portion 477 to reduce a bulk of the silicone and to reduce a curing time.

The rear thickened portions 470 are positioned directly below the thickened corner regions 467 of the sealing portion 450, as may be seen in FIG. 47-3. The rear thickened portions 470 transfer a load from the headgear connectors to the thickened corner regions 467 and to the lower corners of the patient's nose to aid in providing an effective seal, and when the headgear is tensioned, the transfer of load to the lower corners of the patient's nose is increased. The bending force from the headgear connectors 456 is transferred in use by the rear thickened portions 470 to the thickened corner regions 467 of the sealing portion 450 to apply a sealing force as an anchor force to regions of the patient's nose adjacent the nasal labial creases. The transfer of force from the headgear connectors 456 to the rear thickened portions 470 may occur by due to the stiffened headgear connector arms, which when bent, cause the bending force, and/or by actual contact of the headgear connectors 456 with the rear thickened portions 470.

A side upper lip portion 474 may also be thickened as compared to general wall section 466, and have a width d 14 that varies from about 3.5 mm to 1.2 mm, to vary the amount of resistance force against the upper lip of the patient.

FIG. 52-2 illustrates a cross-sectional view of the support membrane 465 and the sealing portion 450. The cross-section illustrates how the supporting portion 453 supports and is in contact with the sealing portion 450 on the sides of the sealing portion.

FIG. 52-3 illustrates another cross-sectional view of the of the support membrane 465 and the sealing portion 450. The cross-section illustrates the difference in thickness between the lower portion 471 and upper portion 473 of the rear thickened portion 470, and illustrates the cored out portion 477.

FIG. 52-4 illustrates a cross-sectional view of the support membrane 465 and the sealing portion 450 as it interfaces with and seals with a patient. The nose tip engagement portion 452 engages with and seals with the patient's nose tip. When the nose tip engagement portion 452 and upper lip engagement portion 462 are fitted to the patient's nose tip and upper lip, the nose tip engagement portion 452 and the upper lip engagement portion 462 are stretched towards the supporting portion 453.

FIG. 52-5 illustrates a side view of the support membrane 465 and the sealing portion 450 as it interfaces with and seals with a patient. The sides of the sealing portion 450 and the supporting portion 453 pinch with and seal with the sides of the patient's nose. The thickened corner regions 467 seal with the patient at regions of the patient's nose adjacent the nasal labial creases. The rear thickened portion 470 is positioned adjacent to and below the thickened corner region 467 to provide additional sealing force.

FIG. 52-6 illustrates another cross-sectional view of the support membrane 465 and the sealing portion 450 as it interfaces with and seals with a patient. The sides of the sealing portion 450 seal with the sides of the patient's nose, and are supported in this area by the supporting portion 453, the front thickened portion 468 and the rear thickened portion 470.

FIG. 52-7 illustrates a front view of the support membrane 465 and sealing portion 450 as it interfaces with the patient's face. The nose tip engagement portion 452 engages with and seals with the patient's nose, and stretches towards the supporting portion 453. The front anchor points anchor the sealing portion 450 to the supporting portion 453 on both sides of the nose tip engagement portion 452. The sides of the sealing portion 450 engage with and seal with the sides of the patient's nose.

Figure 53:
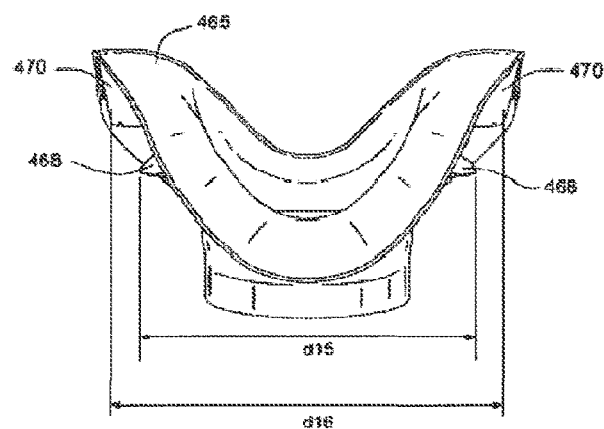

FIG. 53 illustrates a front view of the support membrane 465. The distance d15 between the front thickened portions 468 may be about 25 to 45 mm, preferably about 35 to 42 mm, and most preferably may be about 40 mm. The distance d15 may be varied to change stiffness of contact between the headgear and side walls of the membrane to increase a pinch load on sides of the patient's nose. Distance d16 between the rear thickened portions 470 may be about 35 to 55 mm, preferably about 40 to 50 mm, most preferably about 46 mm. Varying d16 varies the point at which the headgear contacts the rear thickened portion 470 to increase or reduce load.

Figure 54:
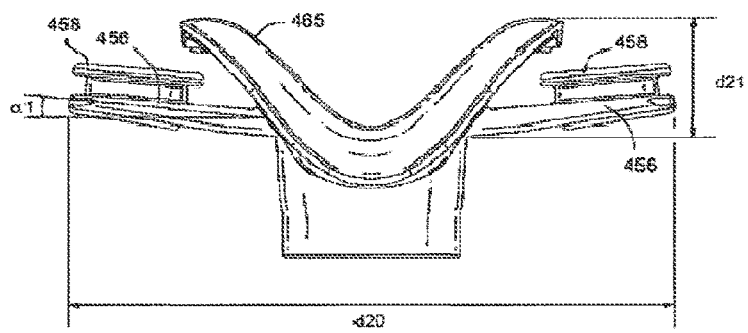

FIG. 54 illustrates a front view of the support membrane 465 with headgear connectors 456. The headgear connectors 456 may be formed as a single unitary element molded with the support membrane 465, or could be formed separately and attached to the support membrane 465. The headgear connectors 456 may include headgear tabs 458 for connecting the headgear. The distance d21 from a bottom of the headgear connectors 456 to a top of the support membrane may be about 10 to 25 mm, preferably about 12 to 20 mm, most preferably about 17 mm. The distance d20 between the outer ends of the headgear connectors may be about 60 to 100 mm, preferably about 70 to 90 mm, most preferably about 80 mm. The headgear connectors 456 may be angled upwards at an angle a1, which may be about 2 to 15°, preferably about 5° to 8°, most preferably about 6.5°. The higher the angle a1, the lower the moment of pinch force applied by the patient interface.

Figure 55:
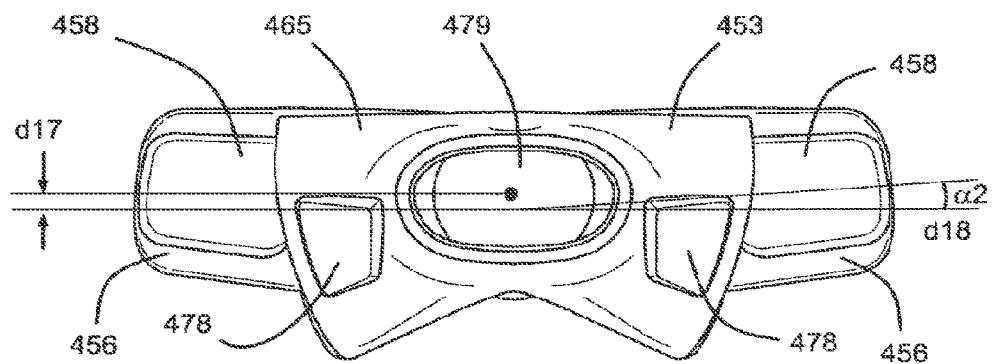

As shown in FIG. 55, the headgear connectors 456 are placed towards the base of the sealing portion 450 in order to create a moment force on the side walls. As the headgear force is applied by tightening the headgear straps, a load is placed on the headgear connectors 456 and the tabs 458, which promotes an inward force on the sides of the sealing portion 450, to provide a seal force to the sides of the patient's nose. When the headgear straps are tightened, the pinch load moment force applied to the sealing portion 450 may cause the inward displacement of the sealing portion 450 to reduce a width of the sealing portion by almost one half from an initial width without the headgear straps in place. The bending force from the headgear connectors 456 is transferred in use by the supporting portion 453 to the sealing portion 450 as a pinch force to sides of the patient's nose.

The stiffness of the side walls of the support membrane 465, the stiffness of the headgear connectors 456, and the connection point of the headgear connectors 456 all affect the amount of pinch force transferred to the sealing portion 450. The headgear connectors 456 may have a thickness of about 2.5 mm to 4.0 mm, with the side walls of the support membrane 465 having a thickness of about 1.2 mm to 5.0 mm, with both using silicone having a hardness of about durometer 40 Shore A to durometer 65 Shore A. The headgear connectors 456 and the side walls of the support membrane 465 do not have to be a constant thickness, but the thickness can vary along their length and width or they may have localized thickened regions to control stiffness in specific regions. Also, there may be additional silicone at the point where the headgear connectors 456 connect to the support membrane 465. Headgear connectors may alternatively be constructed of stiffer material than silicone such as nylon, polycarbonate, polypropylene or other suitable material. This may aid connection of the headgear to the headgear connectors.

FIG. 55 illustrates a top view of the support membrane 465 with headgear connectors 456. The supporting portion 453 may include recessed regions 478 formed in an upper surface of the supporting portion 453, to allow the stiffness of the supporting portion 453 to be reduced by filling the recess with a low hardness filling material, having a lower hardness than the supporting portion. The recess may be about 8 mm by 9 mm inwards from the upper most surface of supporting portion 453, although other size recesses could be used. A reduced stiffness of the supporting portion 453 allows a lesser pinching force to be applied to the patient's nose (when compared to a supporting portion with a higher stiffness), which can provide a more comfortable seal. Distance d17 between a center point of the orifice 479 and a center of the headgear connectors 456 may be adjusted to bias the load on the patient interface from front to back, and d17 may be about 2.7 mm, although values between 0 mm and 4.0 mm may be used. The headgear sweep angle a2 may be varied, and increasing a2 biases a load towards the back (upper lip area) of the patient interface. The headgear sweep angle a.2 may be about 6.6°, although values between 0° and 10° may be used.

Figures 1, 56:
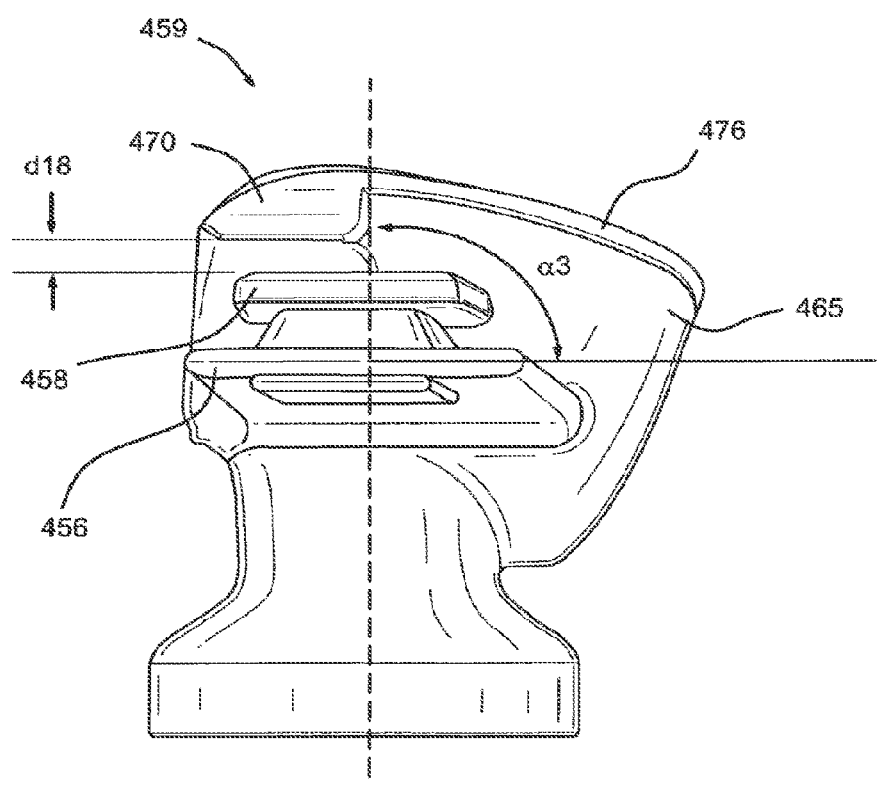
Figures 2, 56:
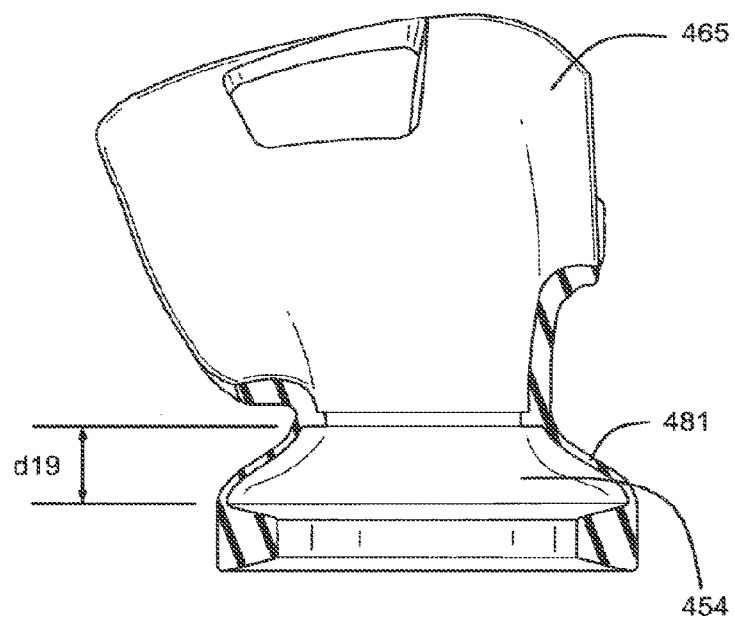
Figures 3, 56:
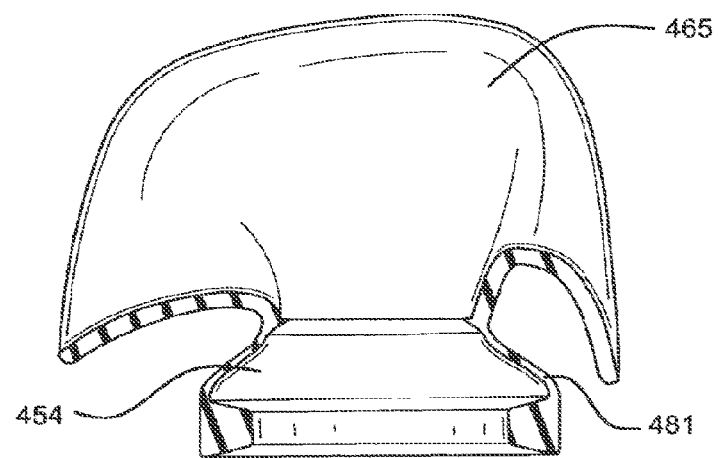

FIG. 56-1 illustrates a side view of the support membrane 465 with headgear connectors 456. Distance d18 between the top of the headgear tab 458 and the rear corner load points formed by rear thickened portion 470 may be about 1-5 mm, preferably about 1-3 mm, most preferably about 2 mm, to allow the headgear tabs 458 a certain amount of movement before they touch the patient interface. This helps to stop the sealing portion from closing while it is first being fitted by the patient. The angle a.3 may be 90°, which could be varied by +/−5° If the headgear connectors 456 are not molded to the support membrane 465, this angle may vary by +/−10°, and varying a3 biases the angle that the patient interface sits under the patient's nose (naso-labial angle).

FIGS. 56-2 and 56-3 illustrate cross-sectional side views of the support membranes 465 illustrated in FIG. 56-1 and FIG. 52, respectively. The stem 454 may be adapted to connect to a ring for connection to an air tube. The ring could have a socket type fitting for a ball joint and/or involve venting. The diameter at the base of the stem 454 has to be sufficient to allow an air path with flow limitations for flow generator compatibility, and could have a diameter of 8 to 25 mm, preferably less than 20 mm and preferably about 1 5 mm. However, different diameters could be used, e.g., 12 mm.

The stem 454 may include a thin walled portion 481, which may have a height d19 of 5.5 mm, although d19 may be varied between, e.g., 2 mm to 10 mm. The thin walled portion 481 allows flex of the decouple region of the stem 454 with drag of a tube connecting thereto. The thin walled portion may have a wall thickness of about 0.3 mm to 1.0 mm depending on flex and strength requirements. The stem 454 may contain stiffening ribs in a radial or circumferential manner, either internal or external, or other stiffening elements.

3.1.23 Seal with Patient

Figure 44:
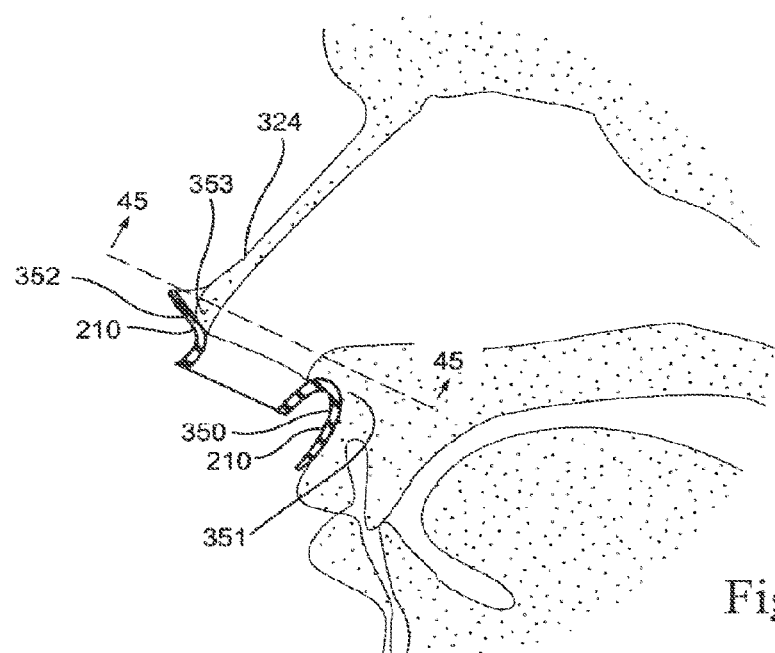
FIGS. 44 to 46 show sealing of a sealing portion with a patient's nose according to an embodiment of the present technology.
Figure 45:
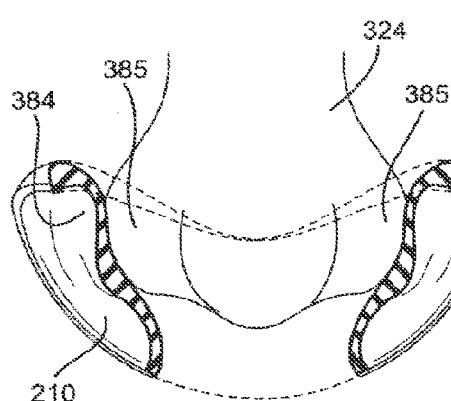
Figure 46:
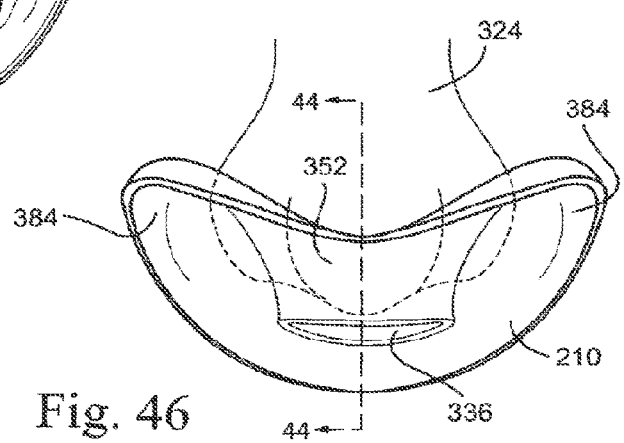

The sealing portion 210 provides an effective seal with a patient's nose 324, as illustrated in FIGS. 44-46. The nostril flare portions 384 of the sealing portion 210 provide a seal with a patient's nostril flares 385. The nose tip portion 352 provides a seal with the patient's nose tip 353. The upper lip portion 350 provides a seal with the patient's upper lip 351. The nostril flare portions 384, nose tip portion 352 and upper lip portion 350 all help provide an effective and comfortable seal with the patient, and help position the orifice 336 adjacent to the patient's nares.

3.2 Suspension System

In FIGS. 1-1 to 1-18 for example, the sealing portion 210 is attached or otherwise provided to a suspension system 215. Attachment may be permanent (e.g., including but not limited to: single component mold (e.g. see FIGS. 1-2 to 1-8), co-molding, insert molding, gluing, or any other suitable means). Alternatively, attachment may be with removable means (e.g., including but not limited to: clips, Velcro™, tongue and groove, or any other suitable means). In an embodiment, attachment of the sealing portion 210 to the suspension system 215 may occur along the perimeter of aperture 211 on sealing portion 210 and aperture 216 on suspension system 215.

Suspension system 215 may be provided to mask 200 to decouple or absorb forces from the sealing portion 210 and the remaining components of patient interface 100 (e.g., air delivery tube 20). Suspension system 215 may be formed from a generally flexible material such as silicone, foam, gel or any other suitable material.

3.2.1 Shape

Suspension system 215 may have a generally wedge or triangular shaped cross section as shown in FIGS. 1-8 and 1-14. Such shape may help to orient the sealing portion with respect to the patient's nose in use.

The surface adjacent aperture 216 of suspension system 215 may be generally U or V shaped as shown in FIGS. 1-12 and 1-13. Such surface may define an angle θ between about 90-180°, e.g., about 110-160°. Alternatively, suspension system 215 may be relatively flat.

In an embodiment, suspension system 215 may be similar to the gusset disclosed in U.S. Patent Application Publication No. 2009/0044808 published 19 Feb. 2009, which is incorporated herein by reference in its entirety. In an embodiment, suspension system 215 may be similar to the decoupling element disclosed in PCT Application No. PCT/AU2009/000240, filed 27 Feb. 2009, which is incorporated herein by reference in its entirety.

3.2.2 Connection to Frame

In the illustrated embodiment of FIGS. 1-1 to 1-18, suspension system 215 includes a connecting ring 217 to sealingly attach suspension system 215 to a frame 220. Connecting ring 217 may interface with a channel 227 provided along the frame perimeter to form an interference fit. The interference fit may be achieved by a tongue and groove, snap fit or any other suitable means. In another embodiment, the connecting ring 217 may be adapted to attach to an elbow 230 and/or an air delivery conduit 20. For example, elbow 230 may interference fit within, around or against connecting ring 217 so as to seal the connection of the elbow 230 or air delivery conduit 20 with the suspension system 215.

The connecting ring 217 defines aperture 218 to allow the passage of breathable gas from frame 220 into suspension system 215. The aperture 216 allows the passage of breathable gas from the suspension system 215 to the sealing portion 210.

3.2.3 Foam or Gel Suspension System

Suspension system 215 may constructed of an alternative material to silicone that may provide greater compliance, resilience, flexibility, comfort, and/or consumer appeal.

For example, the suspension system may be constructed of foam. Foam acts as a spring to support the sealing portion 210 and urge it towards the nares of the patient in use. The compliance of the foam also enables adjustment of the seal position. FIGS. 3-1 to 3-6 show various views of a foam suspension system 215 for use between the sealing portion 210 and the frame 220. The foam may be an open or closed cell foam or a foam with a combination of open and closed cells. The foam may be skinned or un-skinned. The foam may be 1-50 mm thick, e.g., 30 mm thick.

Figures 1, 2, 3, 4, 5, 6, 7, 8:
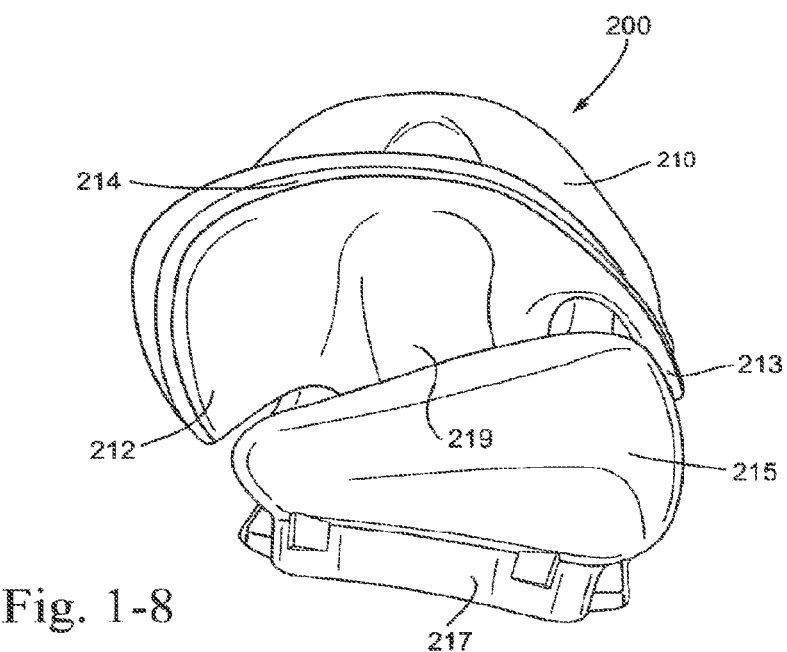
Figures 1, 2, 3, 4, 5, 6, 7, 8, 9:
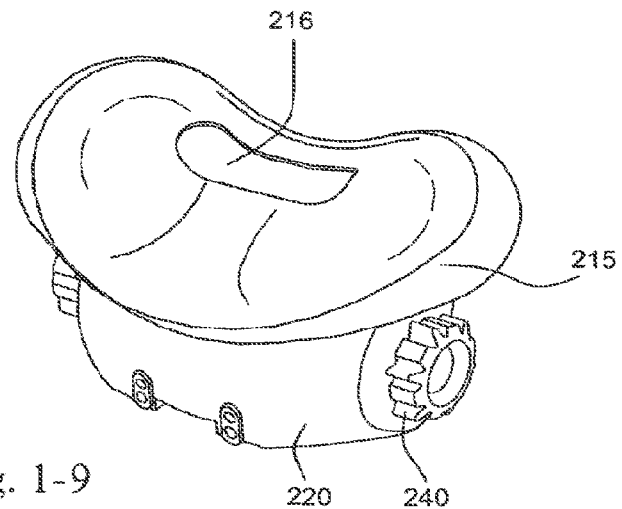

In an alternative embodiment, the suspension system may be constructed of gel. Gel may be conformable, compliant and comfortable. In an embodiment, multiple durometer gels may be used. FIG. 8-1 illustrates a gel suspension system 215 according to an embodiment of the present technology. As illustrated, the gel suspension system 215 is in the form of an encapsulated gel jacket 278 provided between the sealing portion 210 (e.g., silicone) and a base 279 (e.g., plastic). In an embodiment, the gel suspension system may alter the geometry of the sealing portion, e.g., flex thinner regions of the sealing portion (e.g., nose tip engagement portion). The gel may be a silicone gel, polyurethane gel or any other suitable gel. The gel may a gel as disclosed in PCT application No. PCT/AU2008/001711, filed 17 Nov. 2008, which is incorporated herein by reference in its entirety.

In an embodiment, the sealing portion 210 may overhang the foam or gel suspension system to reduce weight and enhance compliance along the edges of the sealing portion 210 to fit a wider range of patient's facial geometries. For example, FIGS. 8-2 and 8-3 illustrate the sealing portion 210 (e.g., silicone) overhanging a gel suspension system 215. Such overhang allows the edges of the sealing portion to "give" or "pinch" depending on orientation to enhance the seal. As illustrated, edges of the sealing portion 210 may include a tear-drop shape gel pocket to facilitate sealing in gaps and corners of the patient's face in use.

In a further embodiment, the suspension system could be constructed from a thermoplastic elastomer (TPE).

3.2.4 Sealing Portion with Flexible Tube

In an alternative embodiment, the suspension system may be in the form of a flexible tube that is provided (e.g., co-molded) or otherwise attached to the base of the sealing portion.

Figures 1, 2, 3, 4, 5, 6, 7, 8, 9, 10:
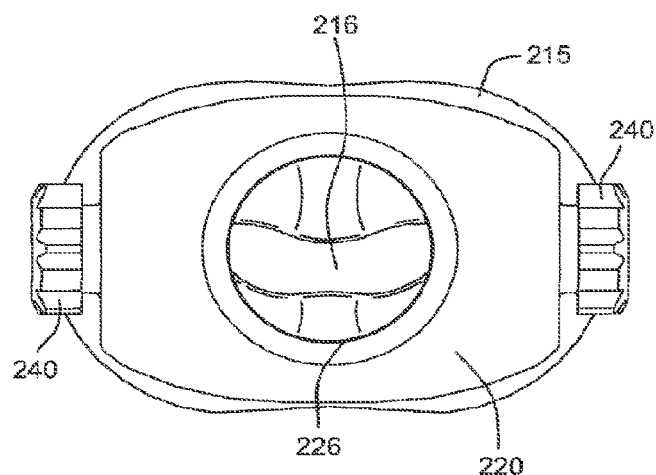
Figures 1, 2, 3, 4, 5, 6, 7, 8, 9, 10, 11:
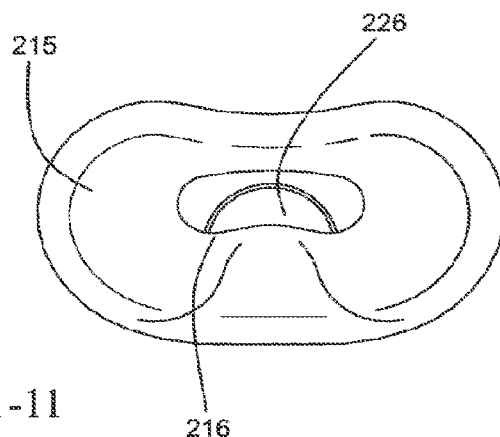
Figures 1, 2, 3, 4, 5, 6, 7, 8, 9, 10, 11, 12:
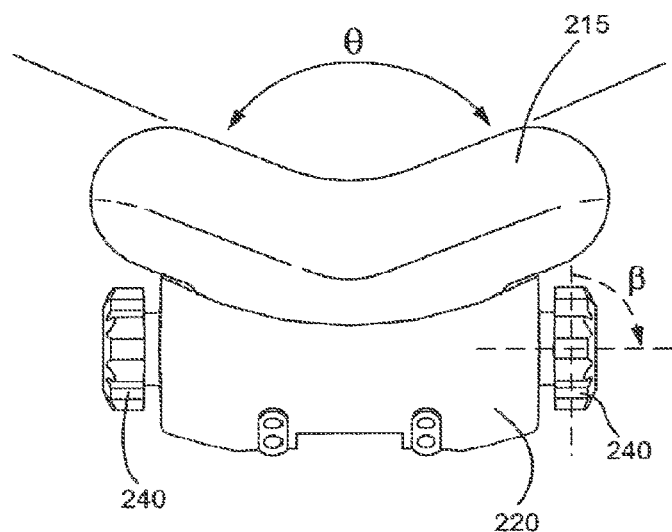
Figures 1, 2, 3, 4, 5, 6, 7, 8, 9, 10, 11, 12, 13:
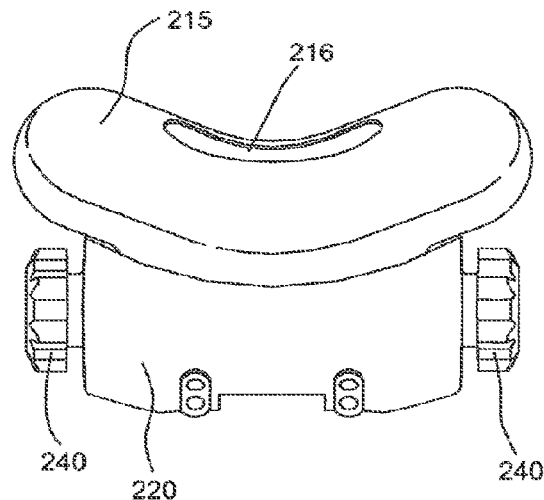
Figures 1, 2, 3, 4, 5, 6, 7, 8, 9, 10, 11, 12, 13, 14:
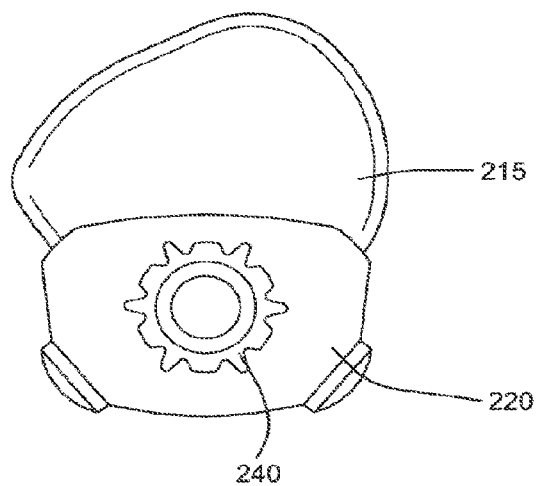
Figures 1, 2, 3, 4, 5, 6, 7, 8, 9, 10, 11, 12, 13, 14, 15:
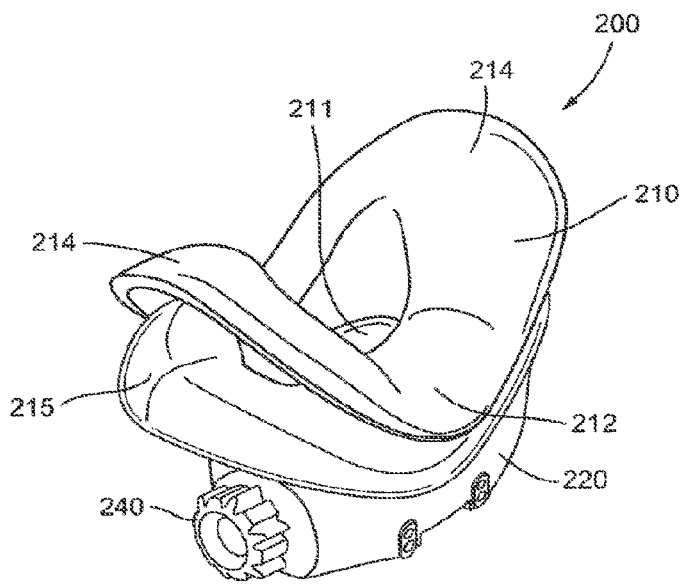
Figures 1, 2, 3, 4, 5, 6, 7, 8, 9, 10, 11, 12, 13, 14, 15, 16:
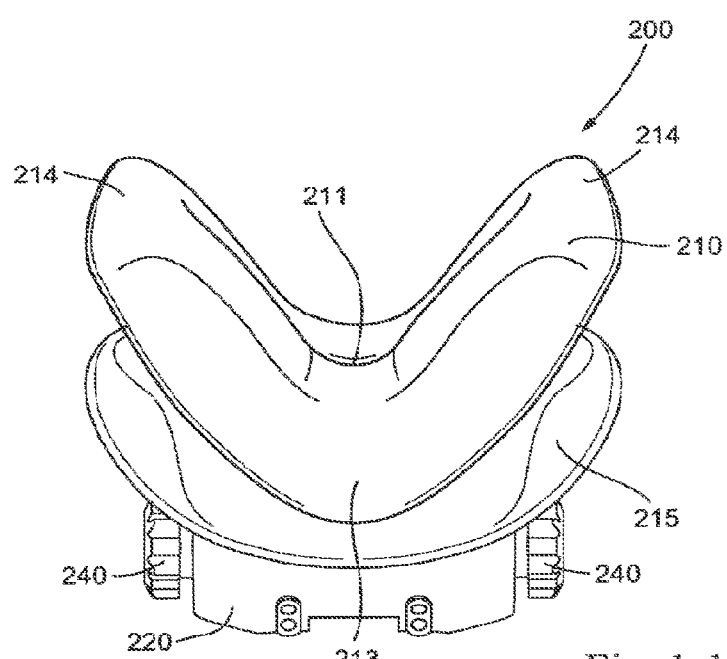

As shown in FIG. 16-1, the flexible tube 280 may be corrugated to allow the tube to move relative to the sealing portion 210 in any direction, e.g., compress, expand, bend, etc., e.g., like a drinking straw As shown in FIG. 16-2, the flexible tube 280 is provided with flexible spiral ribbing which allows the tube to resiliently bend relative to the sealing portion 210.

In each embodiment, the end of the tube may be coupled directly to the air delivery tube in use.

In each embodiment, the flexible tube 280 may have a constant wall section. Alternatively, the flexible tube 280 may have a varying wall thickness to, for example, alter the stretch, elongation or flexibility characteristics of the tube in specific regions.

In an embodiment, one or more vents may be provided to the tube (e.g., molded into tube, insert molded, attached to tube as separate insert) and/or one or more vents may be provided to a swivel on the end of the tube.

Figure 26:
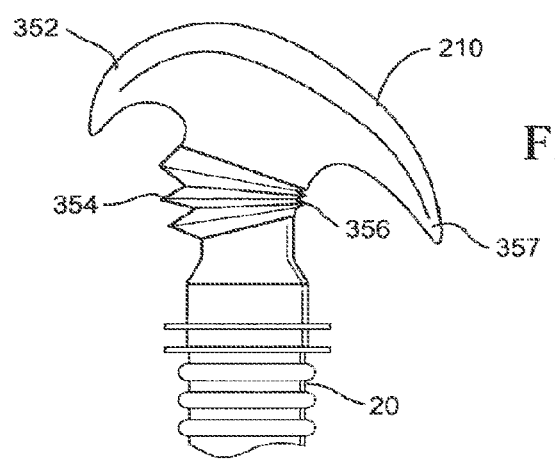
FIG. 26 is a side view of a decoupling arrangement according to an embodiment of the present technology.

As shown in FIG. 26, a concertina portion 354 and a hinge portion 356 may be provided between the sealing portion 210 and the tube 20. The concertina portion 354 absorbs movement of the tube 20 when the tube 20 rotates away from the patient's face in use. That is, when the sealing portion 210 is positioned, the tube 20 cannot flex into the patient's face as the patient's chin or other parts of the patient's face will prevent such movement. When the tube 20 flexes away from the patient's face in use, the hinge portion 356 will transmit the movement of the tube 20 into the concertina portion 354 and thus prevent movement of the sealing portion 210, preserving the seal with the patient. The hinge portion 356 may also prevent the concertina portion 354 from stretching out, preventing the concertina section 354 from losing structural integrity and allowing the concertina section to continue absorbing movement of the tube 20. FIG. 26 also shows the position of the nose tip portion 352 and the upper lip portion 351 of the sealing portion.

3.2.5 Gusset

Figures 1, 2, 3, 4, 5, 6, 7, 8, 9, 10, 11, 12, 13, 14, 15, 16, 17:
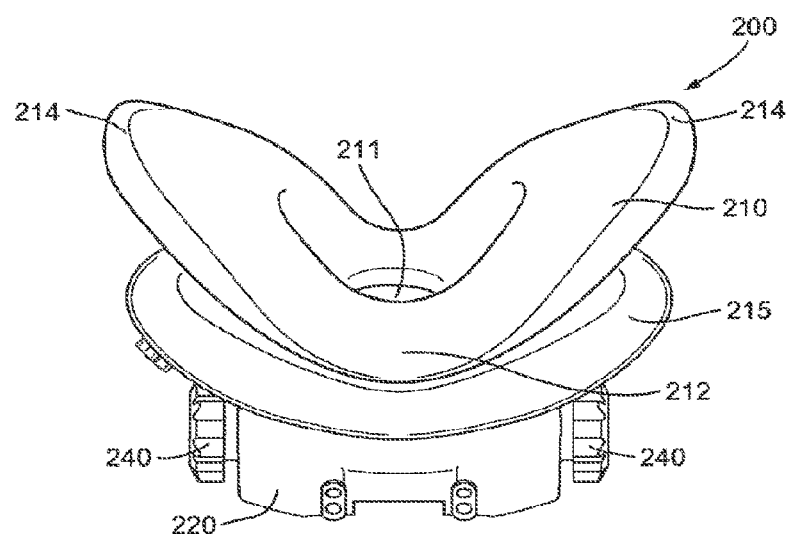

In an embodiment, as shown in FIG. 17-1, the suspension system may be in the form of a gusset or decoupling chamber 281 that is provided (e.g., co-molded) or otherwise attached to the base of the sealing portion 210. In use, the gusset 281 may expand/compress/tilt to enhance the range of adjustability.

The thickness of the gusset side walls may be constant, for example about 0.2 to 3 mm thick, preferably 0.2 to 1 thick, most preferably 0.3 mm thick. Alternatively, the gusset side walls may be varied throughout, for example some regions may be thicker than others to aid coupling of the air delivery tube to the gusset, or some regions of lesser thickness than others to promote flexibility in that region.

In this embodiment, the base of the gusset may be coupled directly to the air delivery tube 20 in use.

In another embodiment, as shown in FIG. 17-2, headgear connectors 240 may be provided to the sealing portion 210 for attaching headgear. As illustrated, the headgear connectors may extend from a trampoline-type base 282 which allows the sealing portion to flex, stretch, and/or bounce relative to the headgear connectors and hence the headgear to alleviate pressure in use. Such arrangement enhances adjustability along with the gusset. Preferably, headgear connectors 240 may be between the sealing portion 210 and the flexible base 282 to permit decoupling of tube forces from the sealing portion 210.

Furthermore, an additional trampoline-type arrangement 283 may be provided to the base of the gusset 281 to allow additional adjustability of the air delivery tube to relative to the gusset.

3.2.6 Tube Decoupling Mechanism

Figure 41:
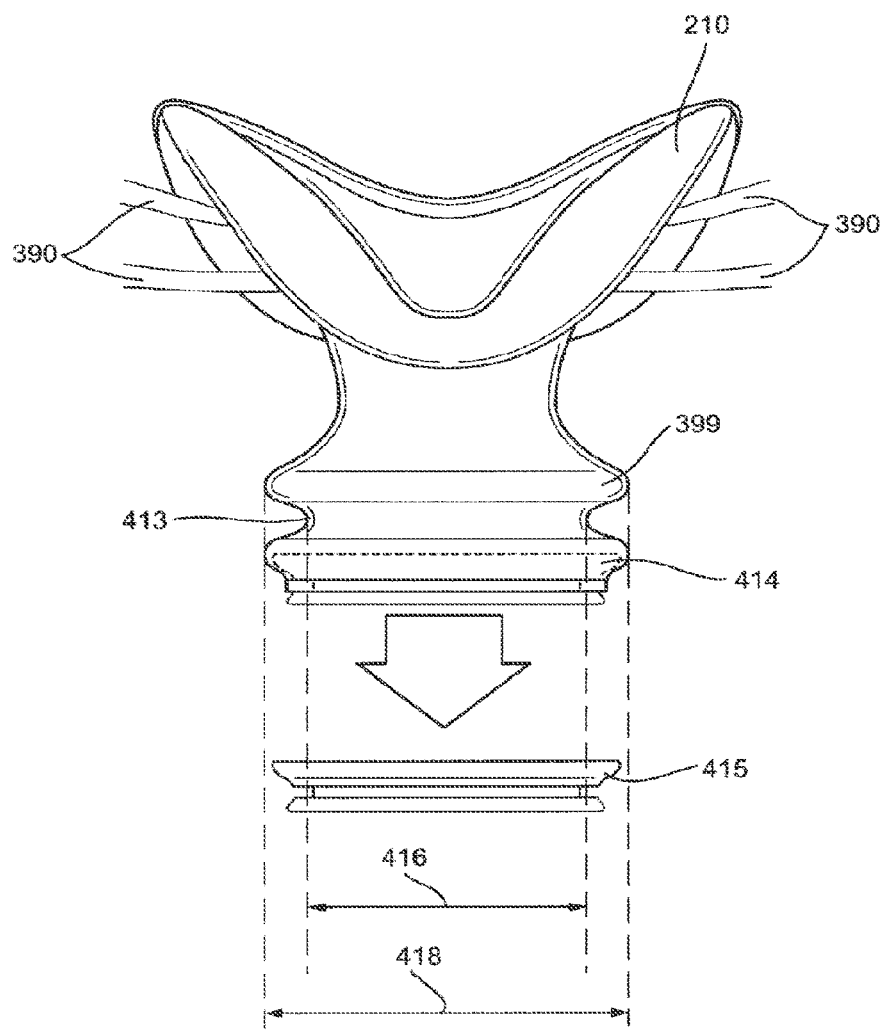
FIG. 41 is a side view of a tube decoupling mechanism according to an embodiment of the present technology.

The sealing portion 210 may be provided with a spring portion 413 (FIG. 41) to absorb or take up tube drag forces. The spring portion 413 may have a width 416 that is less than the width 418 of the sealing portion (cradle) connection portion 399 and the swivel connection portion 414. The swivel connection portion 414 may connect to a swivel ring 415 such as the embodiment described above. FIG. 41 also shows headgear straps 390 attached to the sealing portion 210 to support the mask in position on the patient's head.

3.2.7 Swivel Ring Diffuse Venting

Figures 1, 42:
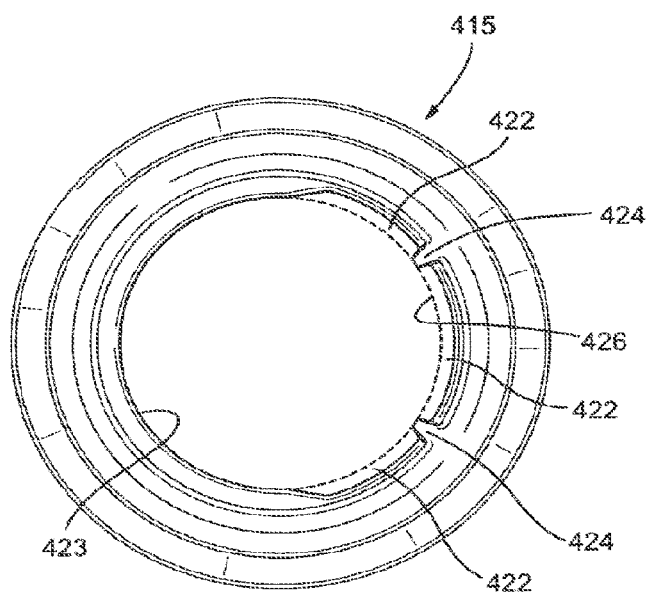
Figures 2, 42:
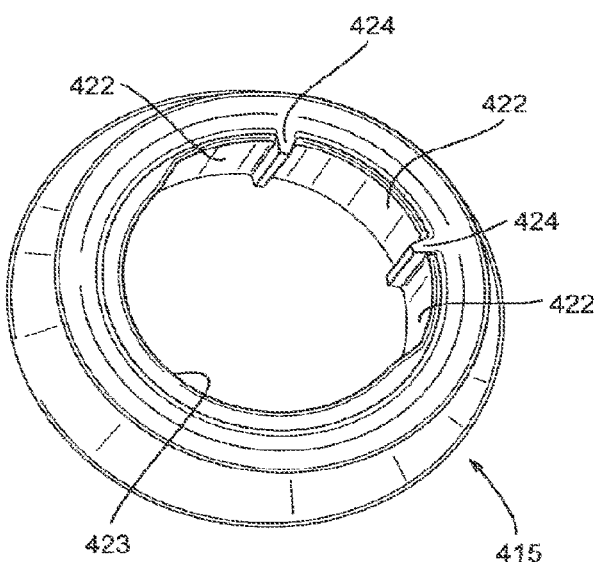
Figures 3, 42:
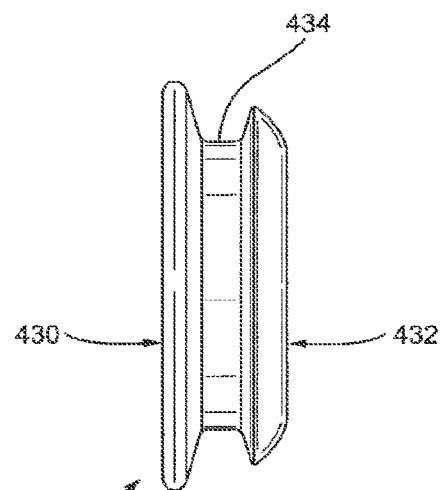
Figures 4, 42:
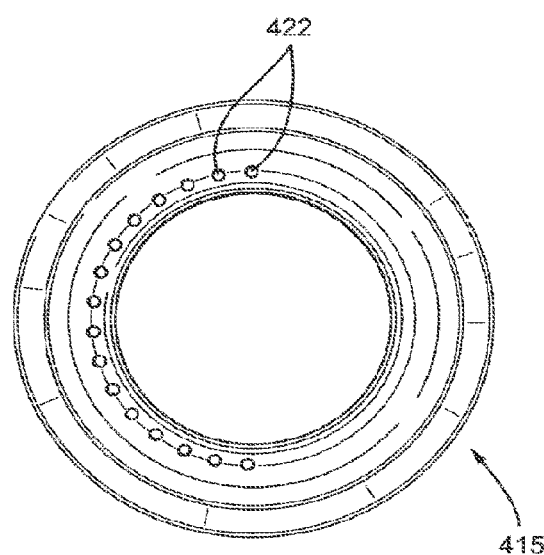
Figures 5, 42:
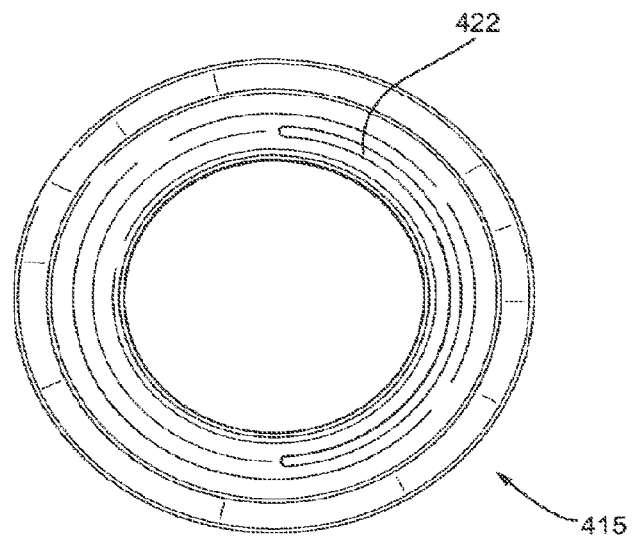
Figures 6, 42:
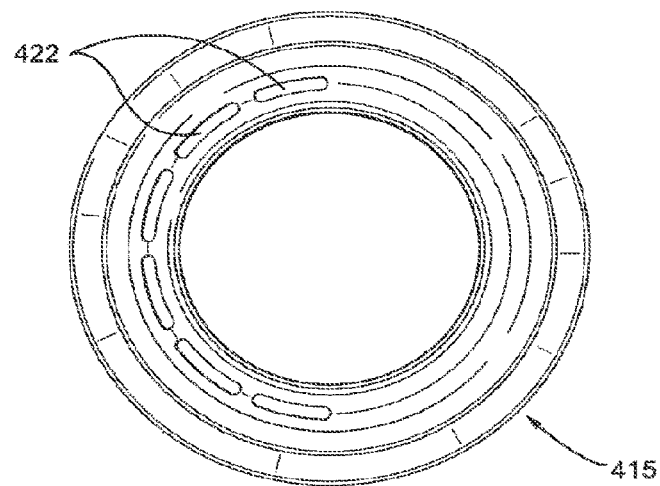
Figures 7, 42:
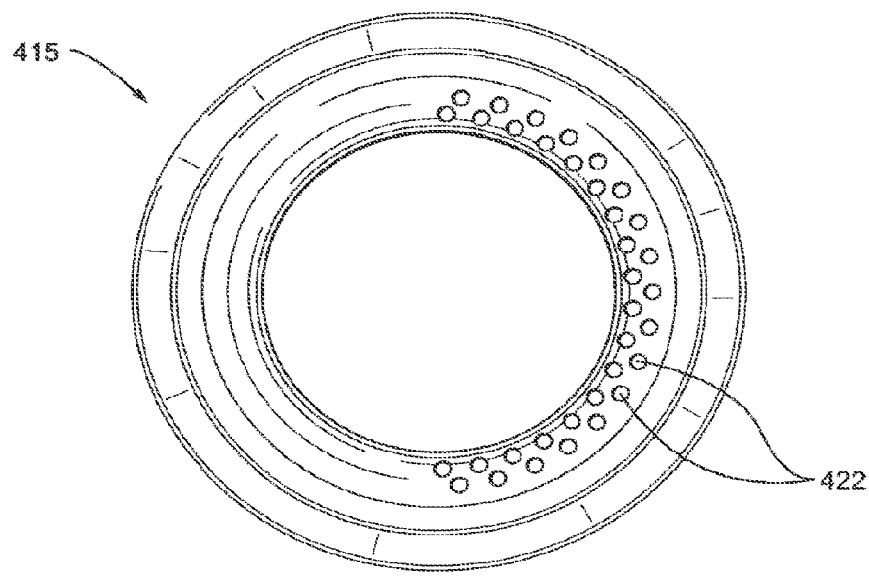
Figures 8, 42:
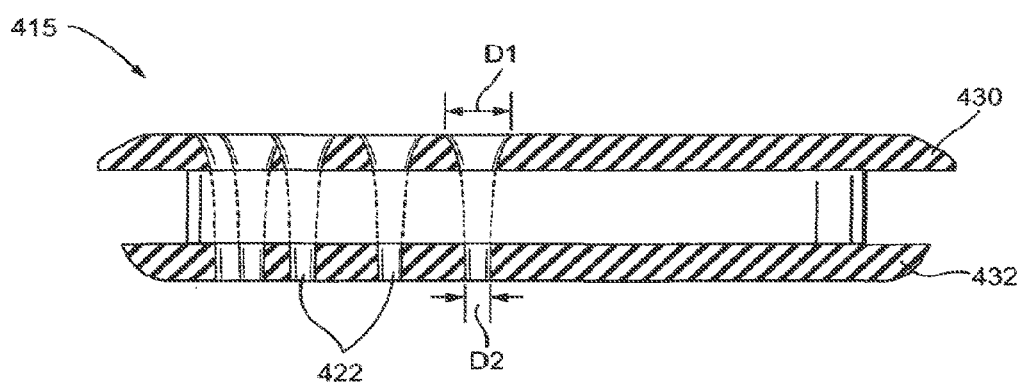

The swivel ring 415 may include one or more gas washout vents 422. The gas washout vents 422 may take provided as one or more aperture, hole, slot or scallop. FIGS. 42-1 and 42-2 illustrate a swivel ring 415 with one or more gas washout vents 422 cut out of the inner wall that interfaces with an elbow wall 426 (shown in dashed lines), to form one or more vent slots or gas washout vents 422 that enable expired gases to pass through and exit from the mask to atmosphere. There may be one or more vent slots or gas washout vents 422 (3 shown), which are formed between the support walls 424. The elbow wall 426 interfaces with the inner wall 423 of the swivel ring 415 and also the support walls 424. The support walls 424 prevent the elbow from accidental disassembly.

FIG. 42-3 illustrates where the swivel ring 415 connects to the sealing portion 210 at cradle flange 430 and to the elbow at elbow flange 432. The swivel ring 415 is inserted into an aperture in the sealing portion 210 and is retained by an interference fit with the flanges on either side of the sealing portion interference web 434. The sealing portion interference web 434 may be U-shaped, although other shapes may be used. In an example, the swivel ring 415 may be structured similar to that shown in PCT/AU2008/001557 filed Oct. 22, 2008, which is incorporated herein by reference in its entirety.

FIG. 42-4 illustrates alternative gas washout vents 422 where there is an array of small holes provided as the gas washout vents 422 within the swivel ring 415. The gas washout vents 422 (e.g., from 5-50, or about 15) may be about 0.5-1.0 mm, e.g., 0.7 mm, in diameter.

FIG. 42-5 illustrates alternative gas washout vents 422 where there is a single vent slot provided as the gas washout vent 422 in the swivel ring 415. FIG. 42-6 illustrates another alternative gas washout vents 422 where there are multiple vent slots provided as gas washout vents 422 in the swivel ring 415 (e.g., more than 2, or about 5-20).

FIG. 42-7 illustrates an array of vent holes provided as gas washout vents 422 arranged about the swivel ring 415. As illustrated, two rows of vent holes are provided as the gas washout vents 422, with the vent holes from each row being offset or staggered from one another. The vent holes may be positioned or arranged in other configurations.

FIG. 42-8 illustrates an exemplary cross section of the vent holes provided as gas washout vents 422 shown in FIG. 42-7. The diameter] of the vent holes varies from the entrance to the exit in this embodiment, e.g., the vent holes tapers along their length. The diameter D 1 of the vent holes on the side of the swivel ring 415 facing the sealing portion 210 is greater than the diameter D2 on the other side of the swivel ring 415. The diameters D1 and D2 could also be the same, or the diameter D2 could be greater than the diameter D1. The diameter of the vent holes may be about 0.5-1.0 mm. Preferably, the diameter of the vent holes may be about 0.7 mm.

In all of the above venting examples, the venting is directed downwards and therefore away from the patient's face, and along the elbow or air delivery tube. The vent holes 422 are also arranged on only half or a portion of the swivel ring 415 so that air may avoid being directed towards the patient's chest in use.

3.2.8 Vent Direction

Figure 43:
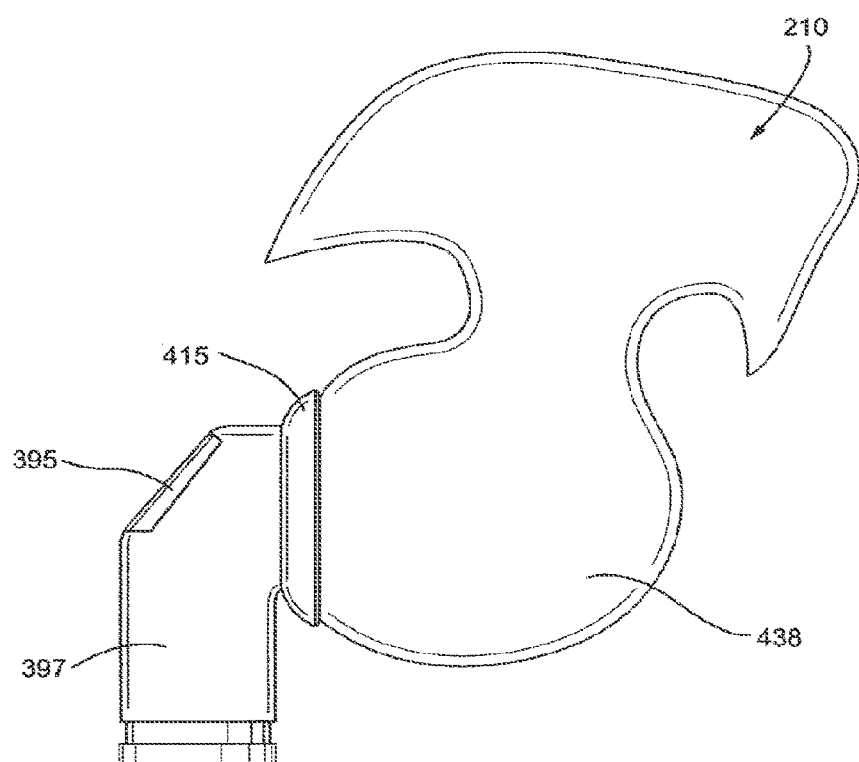
FIG. 43 is a side view of a system including a plenum according to an embodiment of the present technology.

As illustrated in FIG. 43, the direction of air expelled from the vent 395 may be modified by positioning the attachment of the elbow 397 to the sealing portion 210 using a plenum 438. The plenum 438 may attach the sealing portion 210 in an upwards position so as to engage with a patient's nose in use. The plenum 438 may attach via swivel ring 415 to elbow 397 in a location where it will avoid contacting the patient and direct air away from the patient when in use. The plenum 397 may further absorb tube drag forces by buckling or compressing when the tube drag force is applied, rather than dislodging or moving the sealing portion 210 from its sealed position.

3.3 Frame

FIGS. 1-9 to 1-14 show the suspension system 215 connected to the frame 220 (without sealing portion 210 provided to the suspension system 215), and FIGS. 1-15 to 1-18 show the suspension system 215 connected to the frame 220 (with sealing portion 210 provided to the suspension system 215). In the illustrated embodiment, the suspension system 215 includes connection ring 217 adapted to be push fit into channel 227 on frame 220. Alternatively, suspension system 215 may be connected to frame 220 by other removable means, e.g., such as clips, hooks, zip locks or any other suitable means. Also, suspension system 215 may be attached to frame 220 by permanent means, e.g., including but not limited to insert molding, co-molding, gluing, etc.

Frame 220 may be generally more rigid than suspension system 215 and sealing portion 210 to support and stabilize sealing portion 210 and/or suspension system 215. Frame 220 may be made from, including but not limited to, silicone, TPE, polycarbonate, polypropylene, foam, gel, nylon etc.

As best shown in FIG. 1-10, frame 220 may include an aperture 226 adapted to connect to an elbow 230 or to an air delivery tube 20. Frame 220 may connect to elbow 230 or air delivery conduit 20 by a snap fit, tongue and groove mechanism or any other removable or non-removable connection. Exemplary connections are disclosed in U.S. Patent Publication No. US 2009-0044808, which is incorporated herein by reference in its entirety.

3.3.1 Headgear Attachments

In the illustrated embodiments, frame 220 includes headgear attachments or connectors 240 to removably attach headgear 150 and/or headgear rigidizers 160 to the mask 200, as shown in FIGS. 1-1 and 1-9 to 1-18. Headgear attachments 240 may be made from, e.g., including but not limited to: silicone, TPE, polycarbonate or any other suitable material. Headgear attachments may be molded with frame 220. Alternatively, headgear attachments may be provided to the suspension system 215 and/or sealing portion 210 as described below. Alternatively, headgear attachments may be attached to any part of the mask 200 by, e.g., including but not limited to: gluing, push clip, snap fit, etc.

As illustrated in FIGS. 61 to 64-2 and 67, the patient interface 459 may be secured to the patient with headgear 484. The headgear 484 may extend in use from the headgear connectors 456 between the patients eyes and ears on each side of the patients head and connect at the top portion of the patient's head. An adjustable connector 500 may allow the adjustment of the headgear to fit the patient. The headgear 484 may include a back of head portion 485 that wraps around the back of the patient's head.

In an embodiment, headgear attachments may include those disclosed in U.S. Patent Application Publication No. 2009/0044808 published 19 Feb. 2009, which is incorporated herein by reference in its entirety.

3.3.1.1 Orientation

In the illustrated embodiment, the headgear connectors 240 extend generally perpendicular to the longitudinal axis of frame 220 as shown in FIG. 1-12, e.g., indicated with f3. As shown in FIG. 1-1, the rigidizers 160 are rotatably coupled to respective headgear connectors (as described in U.S. Patent Application Publication No. 2009/0044808 incorporated herein by reference) to allow adjustment to suit the nasolabial angle for a large range of patients. In addition, such arrangement allows adjustment of the suspension system to move the suspension system away from the patient's top lip.

3.3.1.2 Alternative Positioning

In an alternative embodiment, headgear connectors may be provided closer to the sealing portion to improve stability of the seal as it eliminates or reduces the length of the moment arm. For example, FIG. 10 illustrates headgear connectors 240 provided to the sealing portion 210 directly.

In another embodiment, the headgear connectors may be positioned so that the headgear straps/rigidizers extend under the nostril engagement flaps 214 in use. For example, as shown in FIG. 11, the headgear connectors 240 may be provided to the suspension system 215. In use, the headgear straps 190/rigidizers 160 are positioned under the nostril engagement flaps 214, which straps/rigidizers act as stops to prevent further deformation of the flaps and/or urge the flaps upwards in use. The straps/rigidizers are positioned to engage specific regions of the flap and allow remaining portions of the sealing portion to bend or conform in use. As illustrated, a strut 284 may be placed under the flaps for engaging the straps/rigidizers.

In another embodiment illustrated in FIG. 47-3, a patient interface 459 includes headgear connectors 456. The headgear connectors 456 may include tabs 458. The tabs 458 may provide connection points for connecting headgear. The headgear connectors 456 may be molded together with the stem 454. Alternatively, headgear connectors 456 may be removably attachable to stem 454 and/or the supporting portion 453. For example, headgear connectors 456 may be clipped, wrapped or otherwise connected to the stem 454.

Headgear connectors 456 may have a hardness of about durometer 20 to 80 Shore A, preferably about 20 to 60 Shores A, and most preferably about 40 Shore A. The geometry of the supporting portion 453 may be adjusted to be molded with the headgear connectors 456.

The position of the headgear tabs 458 relative to the sealing portion 450 is important. If the headgear tabs 458 are too low, i.e. further away from the sealing portion 450, they may not provide enough stability. The greater the distance from the sealing portion 450 to the headgear tabs 458, the longer the lever arm and hence a greater tendency for movement of the sealing portion 450. If the headgear tabs 458 are too close to the top of the sealing portion 450, the sealing portion 450 may hinge inwards beyond what is required for seal, and increase the force on the patient's nose. There could also cause a possibility of occlusion of the patient nares. Accordingly, the headgear tabs 458 should be 1 to 10 mm from the sealing portion. Preferably, the headgear tabs 458 should be about 2 to 5 mm from the sealing portion.

Further details of such headgear connectors and tabs are disclosed in PCT/AU2008/001557, filed Oct. 22, 2008, which is incorporated by reference herein in its entirety.

3.3.2 Sealing Portion Support

Figures 1, 2, 3, 4, 5, 6, 7, 8, 9, 10, 11, 12, 13, 14, 15, 16, 17, 18:
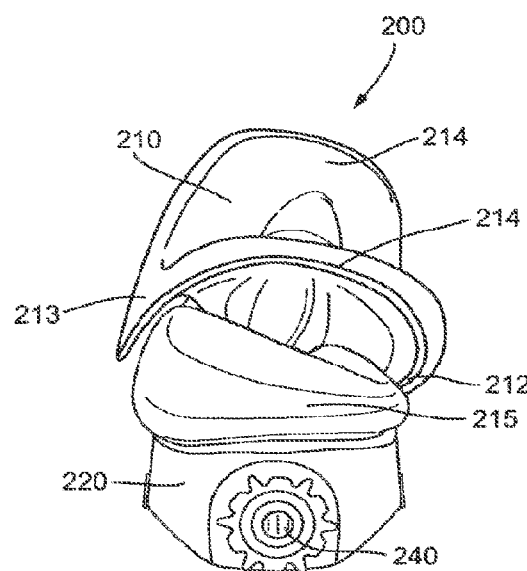
Figures 1, 2:
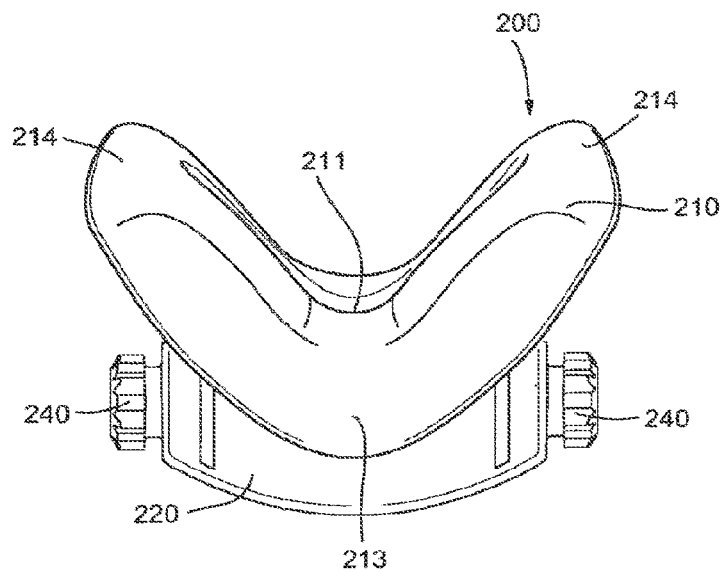
Figure 2:
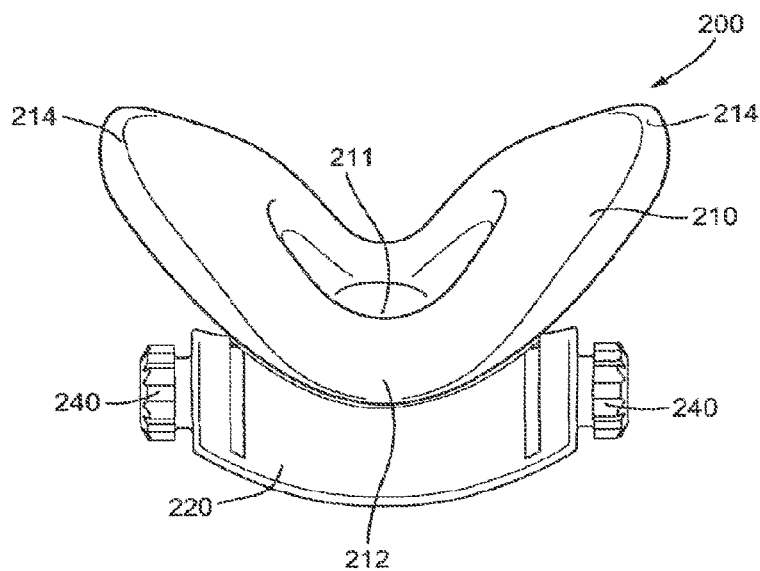
Figures 2, 3:
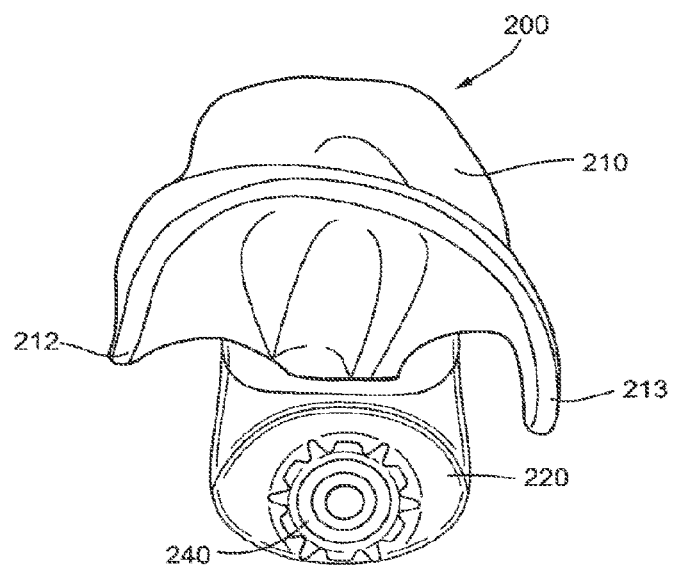
Figures 2, 3, 4:
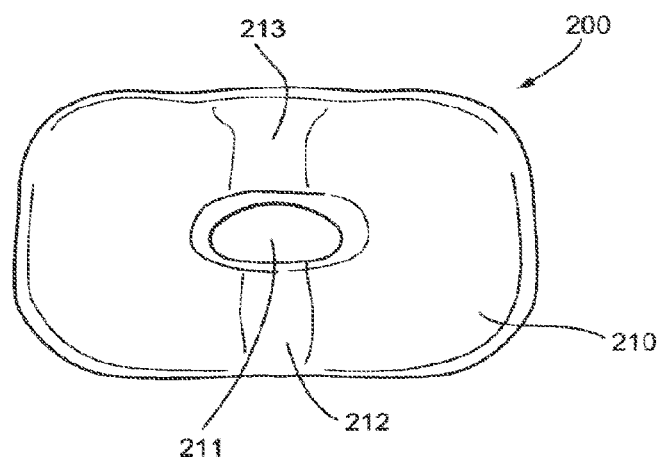
Figures 2, 3, 4, 5:
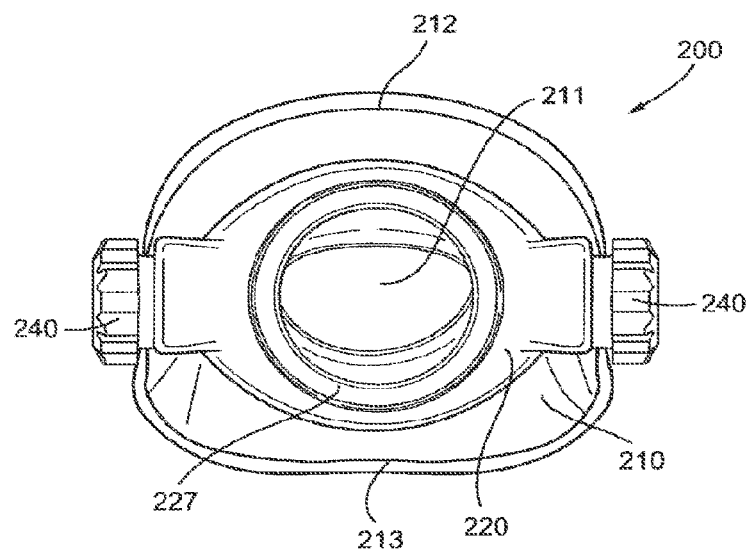
Figures 2, 3, 4, 5, 6:
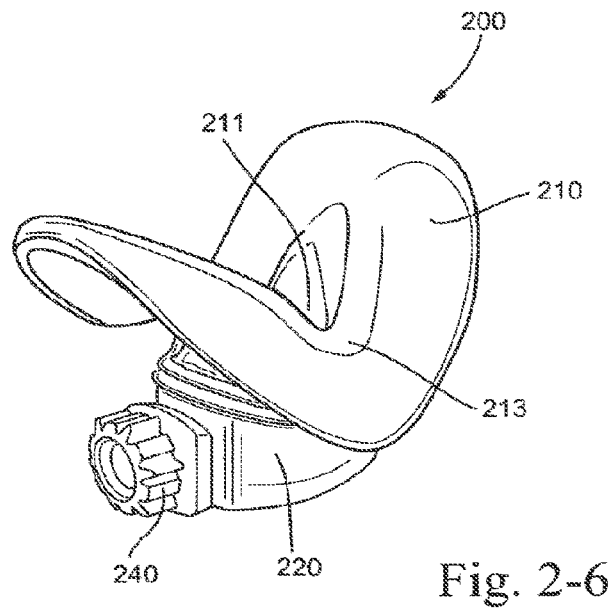
Figures 2, 3, 4, 5, 6, 7, 7A:
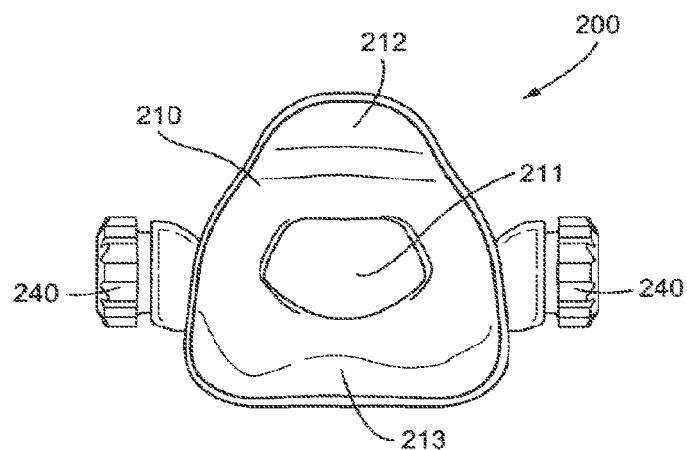
Figures 2, 3, 4, 5, 6, 7, 7B:
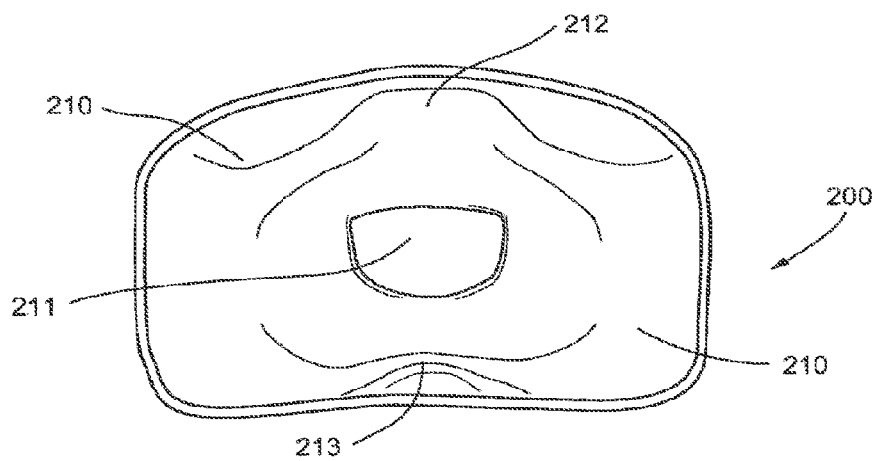
Figures 2, 3, 4, 5, 6, 7, 8, 8A:
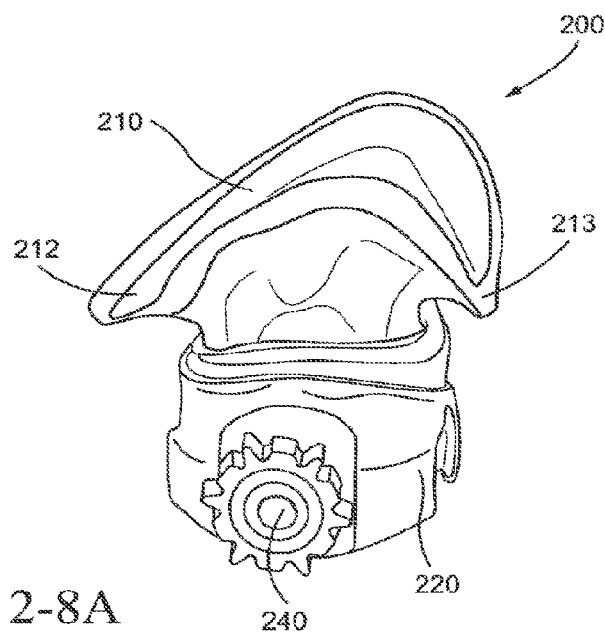
Figures 2, 3, 4, 5, 6, 7, 8, 8B:
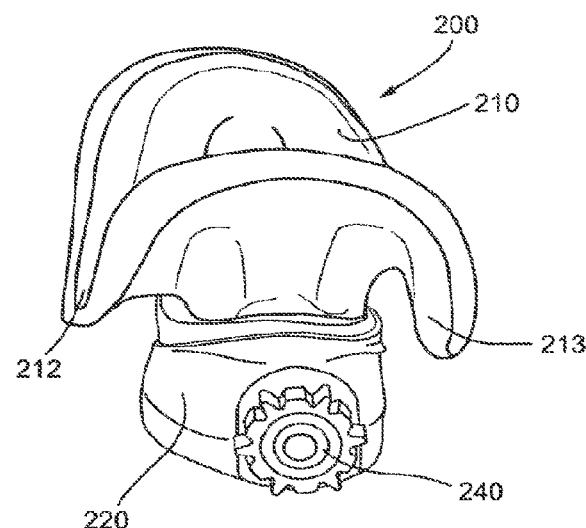
Figures 2, 3, 4, 5, 6, 7, 8, 9, 9A:
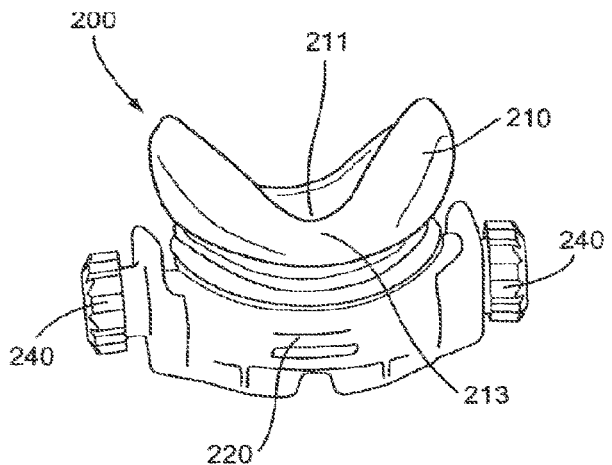
Figures 2, 3, 4, 5, 6, 7, 8, 9, 9B:
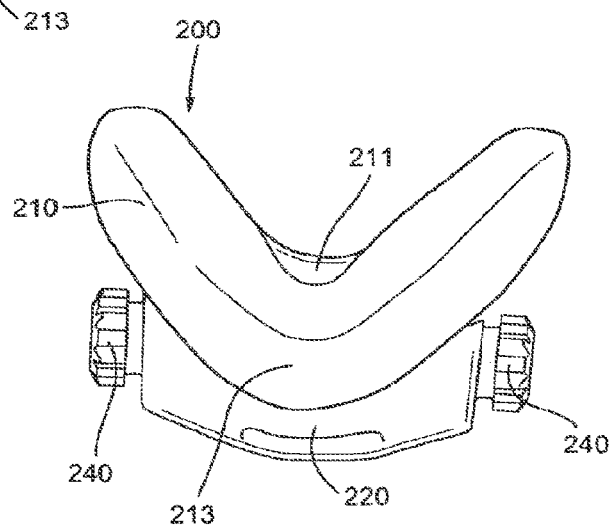
Figures 2, 3, 4, 5, 6, 7, 8, 9, 10:
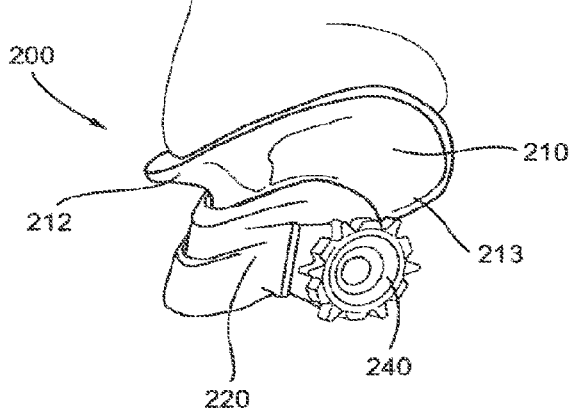
Figures 2, 3, 4, 5, 6, 7, 8, 9, 10, 11:
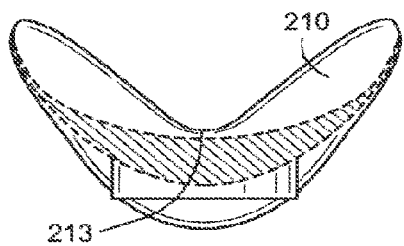
Figures 1, 3:
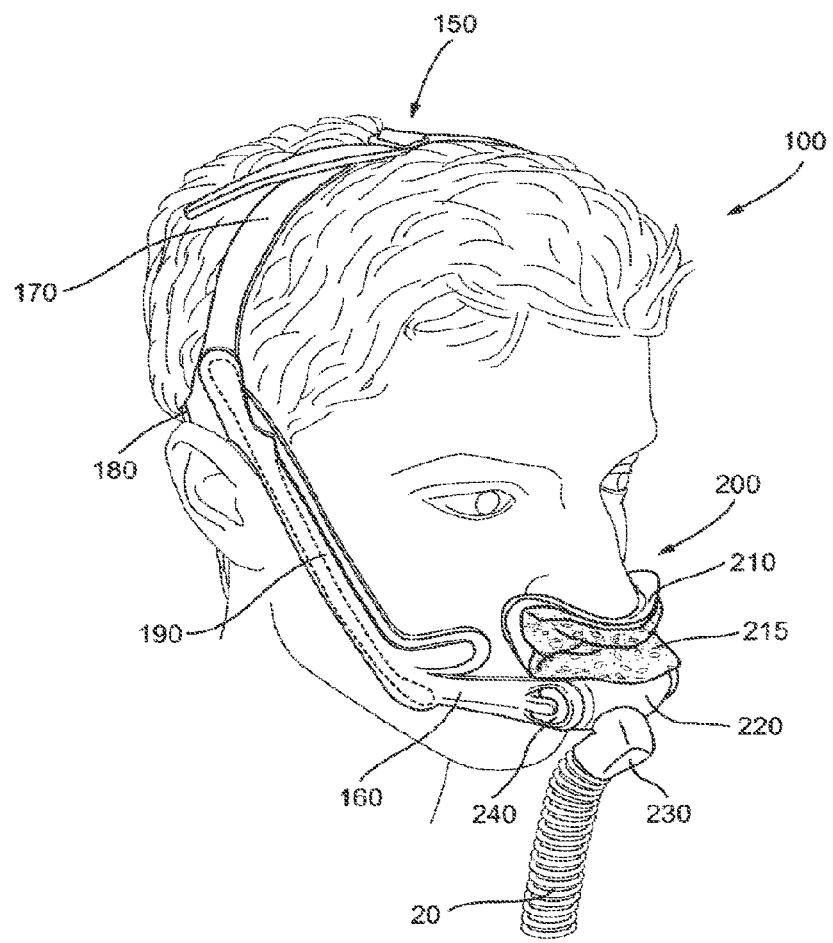
Figures 2, 3:
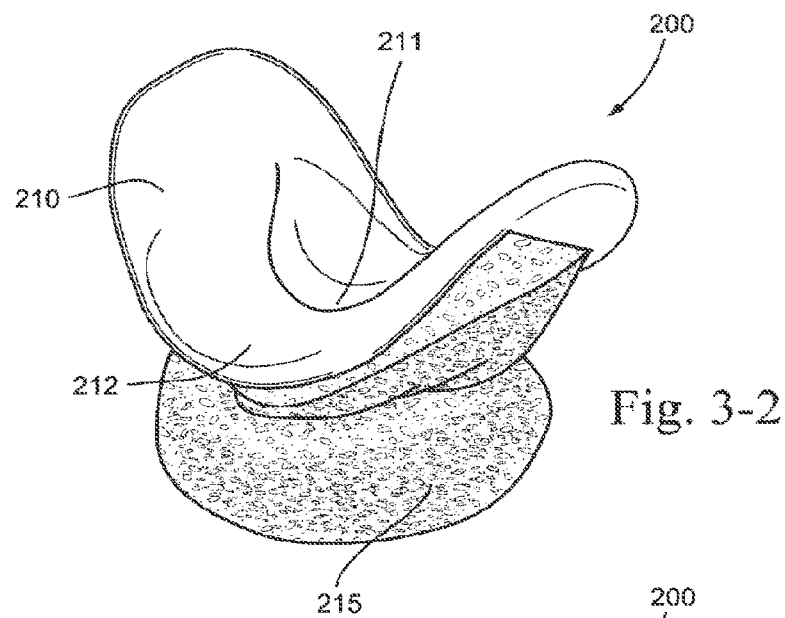
Figure 3:
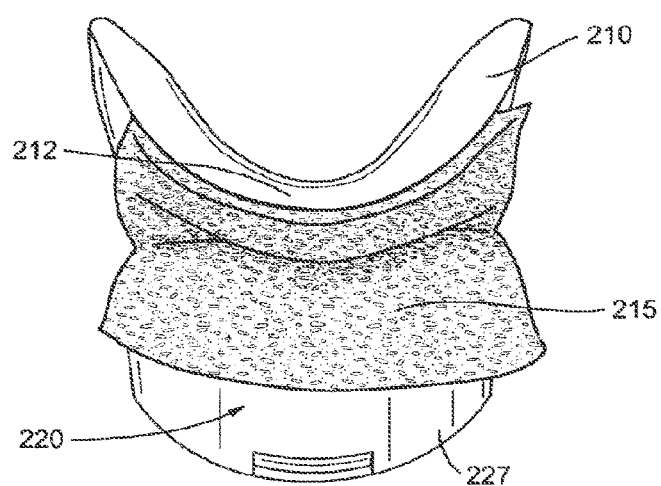
Figures 3, 4:
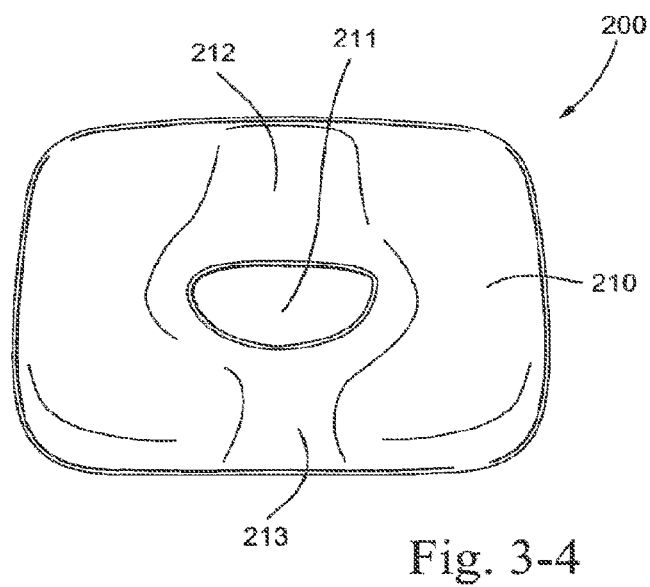
Figures 3, 4, 5:
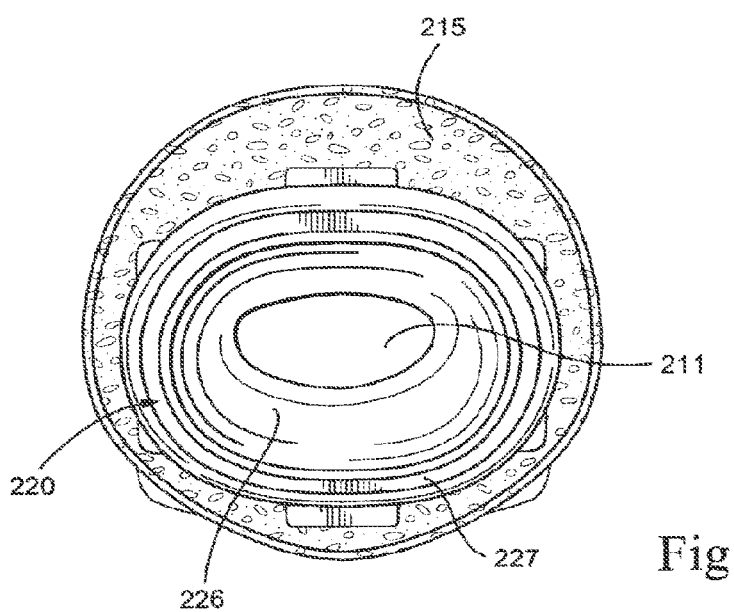
Figures 3, 4, 5, 6:
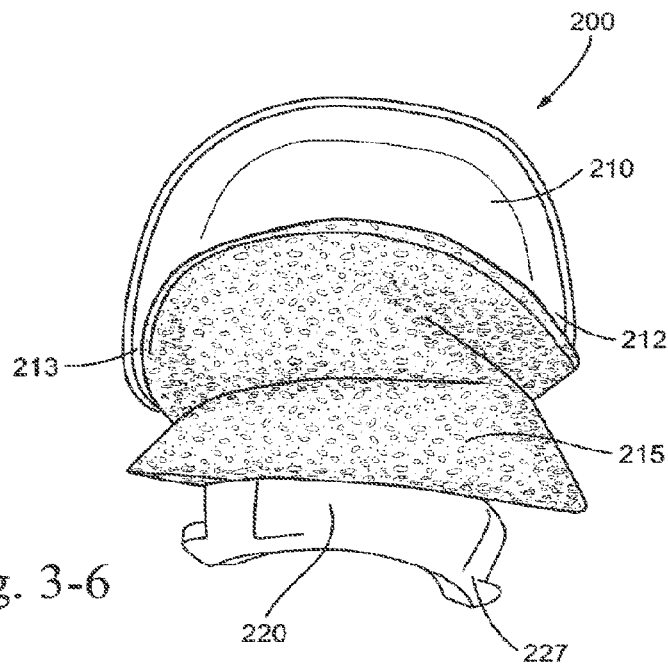
Figures 1, 4:
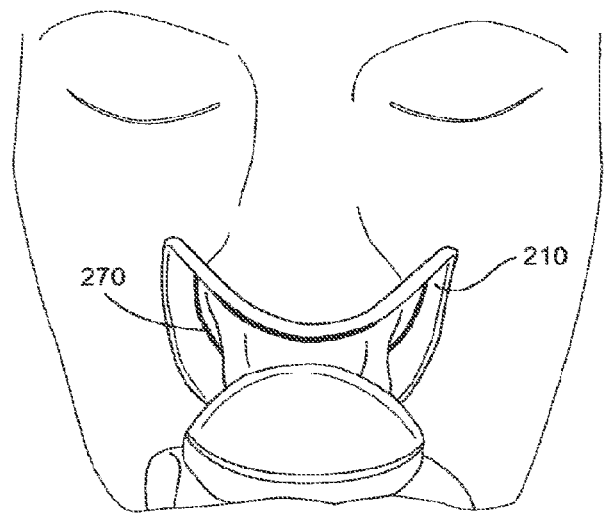
Figures 2, 4:
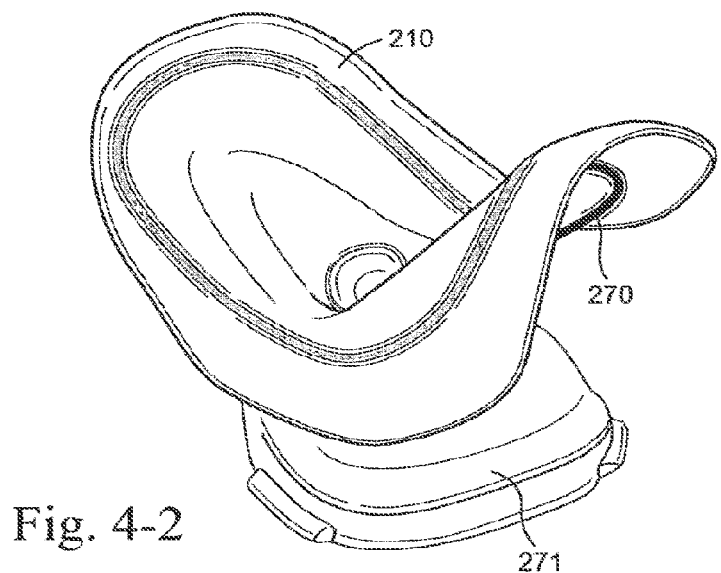
Figures 3, 4:
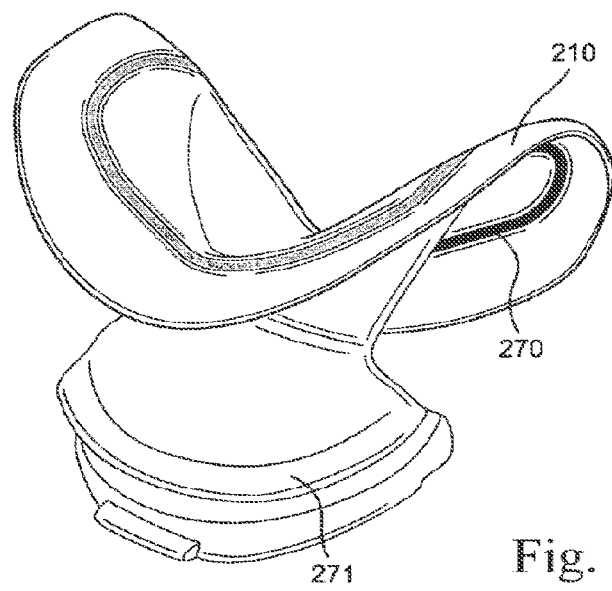
Figure 4:
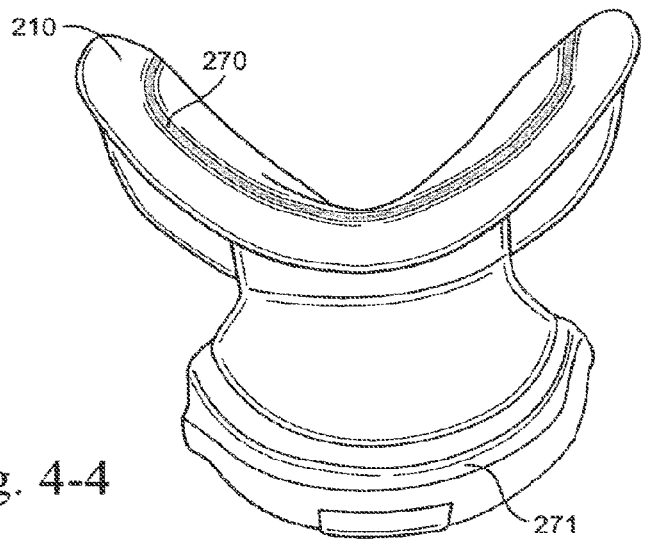
Figures 4, 5:
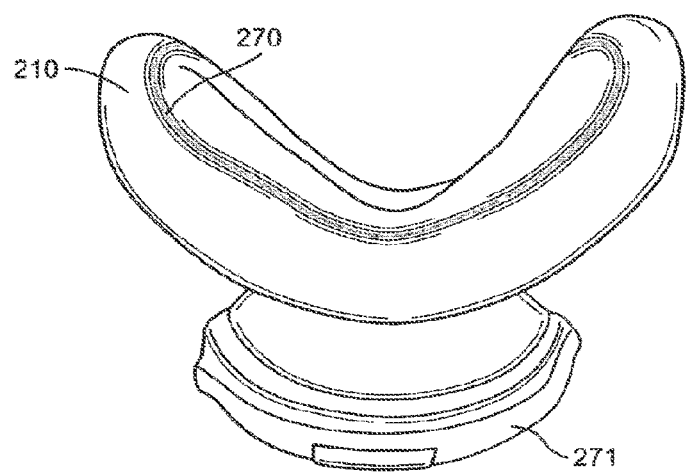
Figures 4, 5, 6:
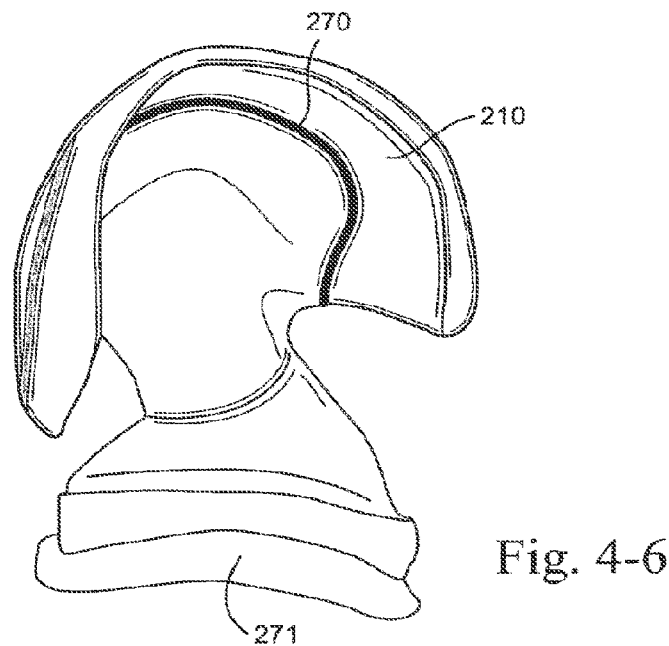
Figures 4, 5, 6, 7:
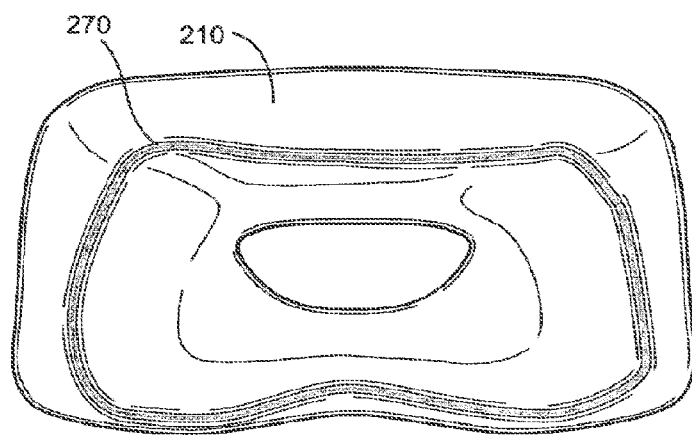
Figures 4, 5, 6, 7, 8:
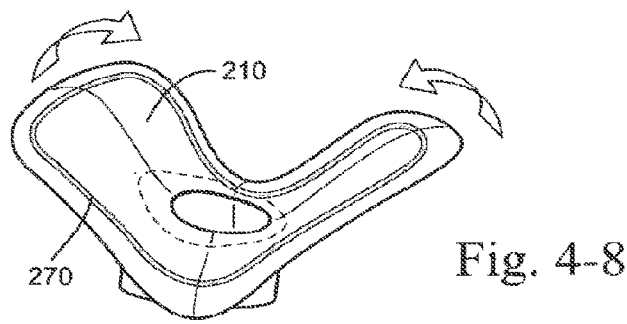
Figures 4, 5, 6, 7, 8, 9:
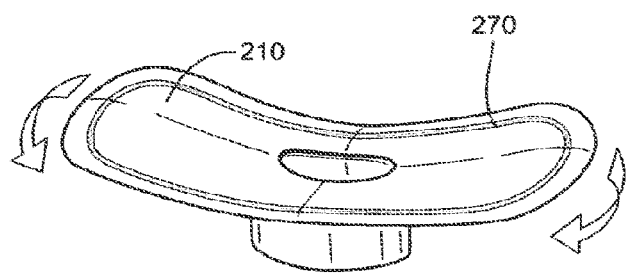
Figures 1, 5:
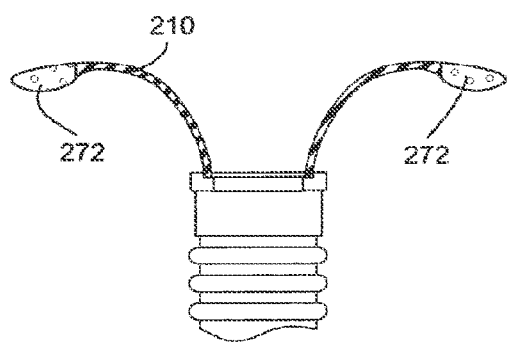
Figures 2, 5:
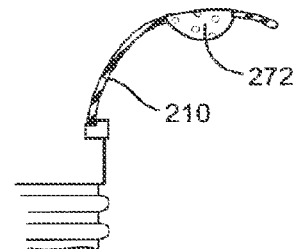
Figures 1, 6:
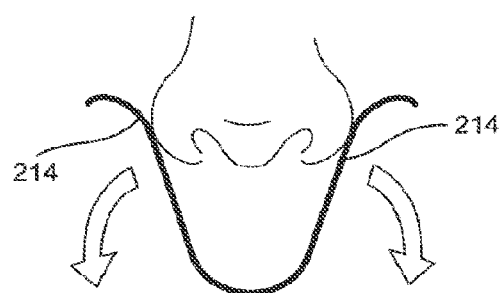
Figures 2, 6:
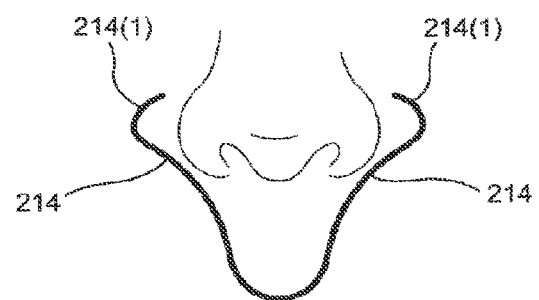
Figures 1, 7:
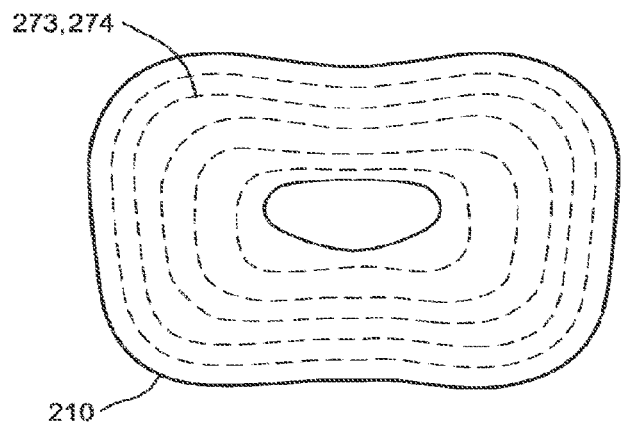
Figures 2, 7:
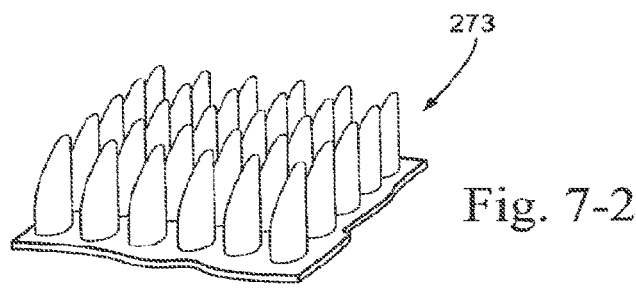
Figures 3, 7:
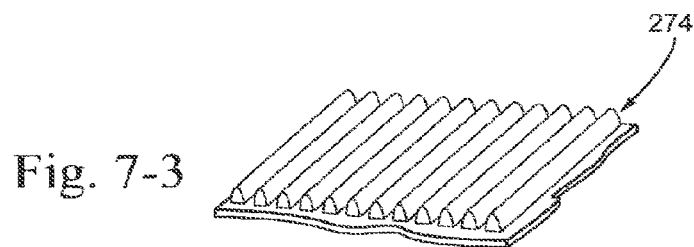
Figures 1, 8:
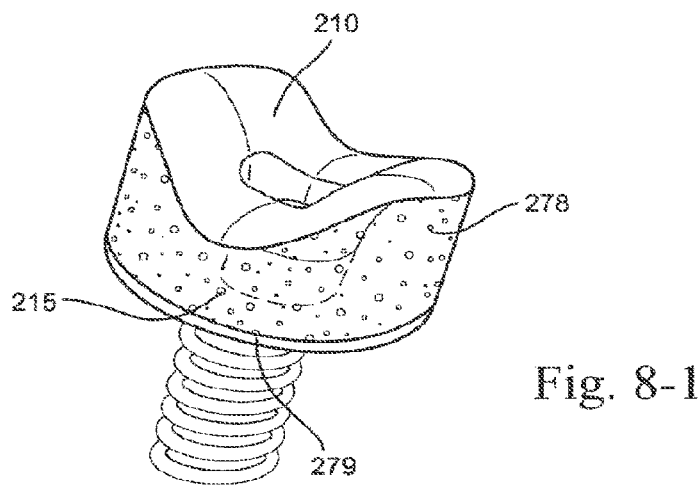
Figures 2, 8:
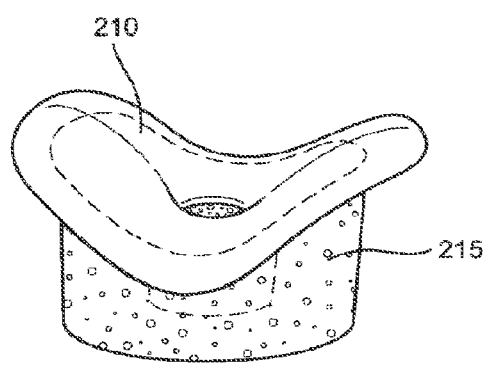
Figures 3, 8:
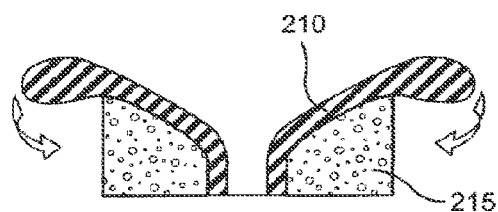
Figures 1, 9:
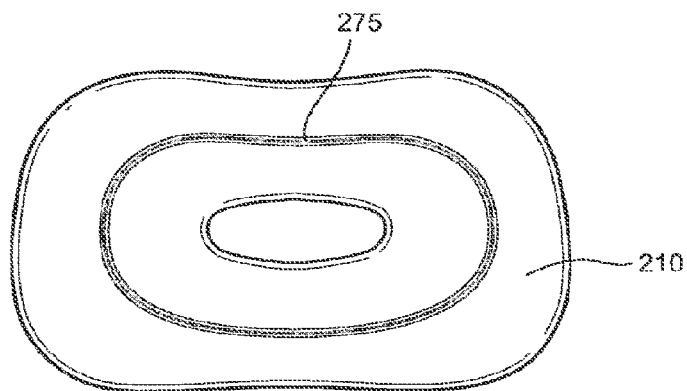
Figures 2, 9:
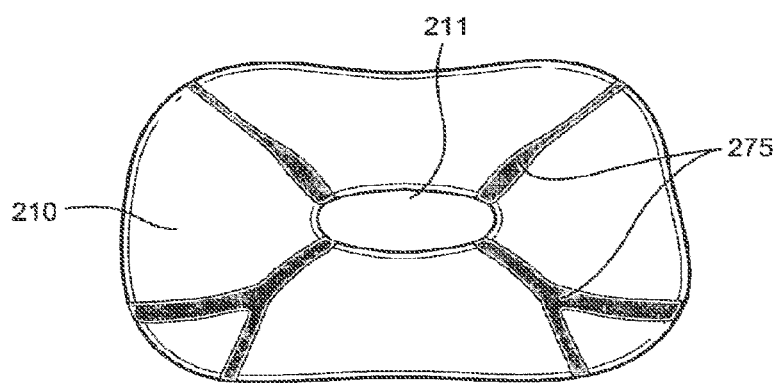
Figure 10:
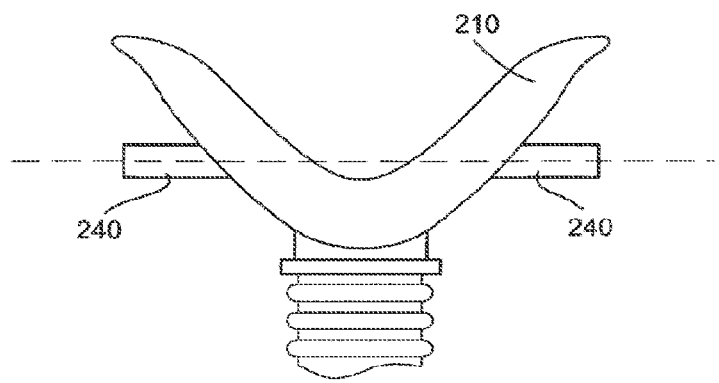
Figure 11:
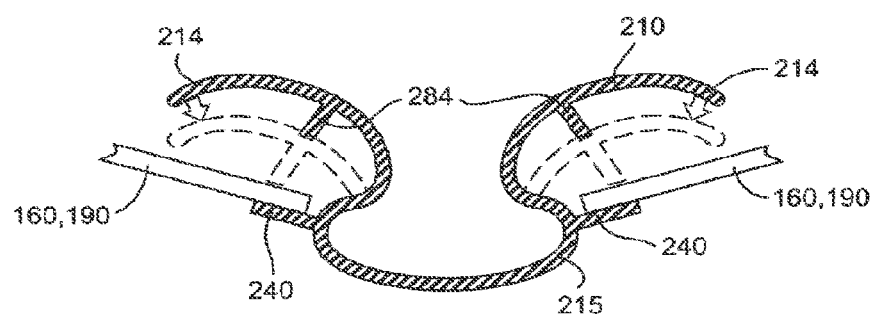
Figure 12:
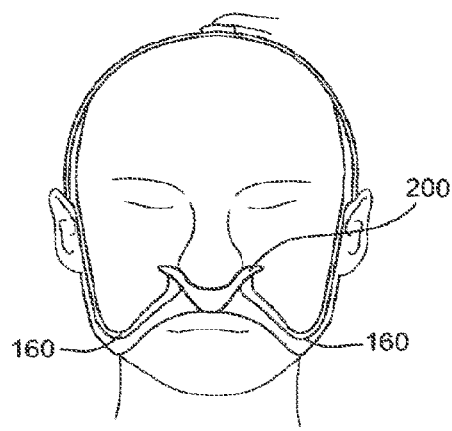
Figures 1, 13:
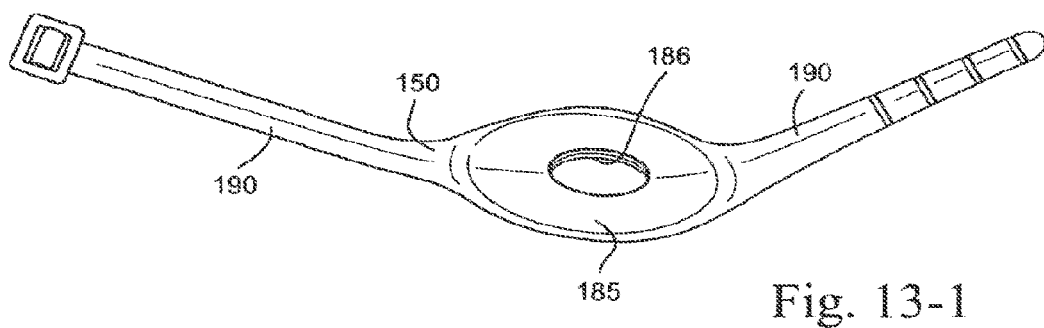
Figures 2, 13:
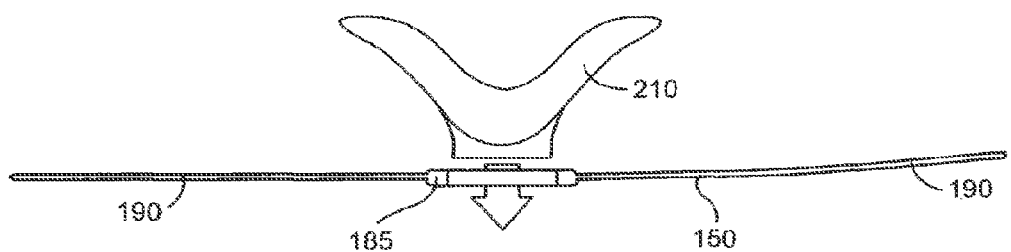
Figures 3, 13:
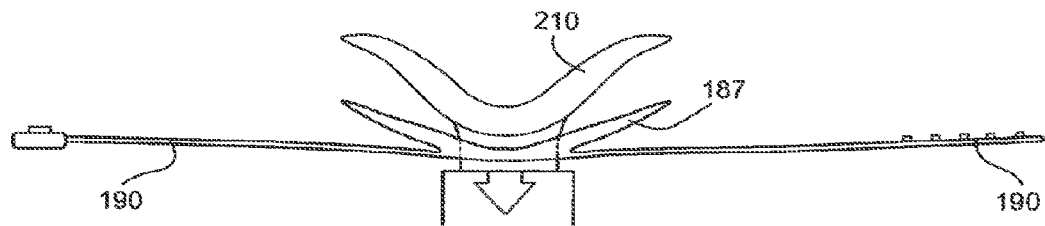
Figures 4, 13:
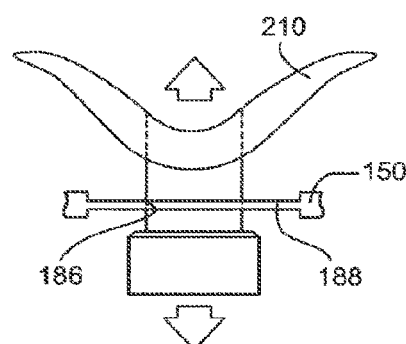
Figures 5, 13:
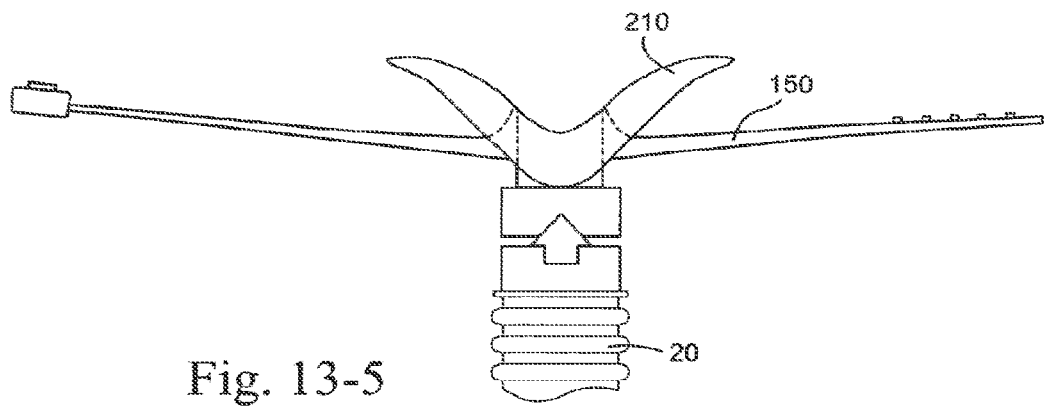
Figures 1, 14:
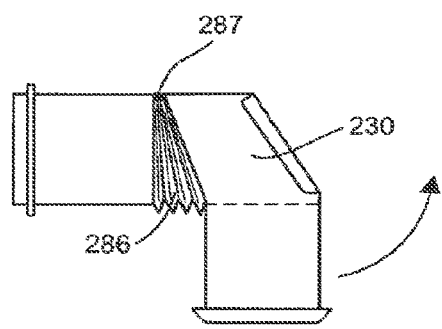
Figures 2, 14:
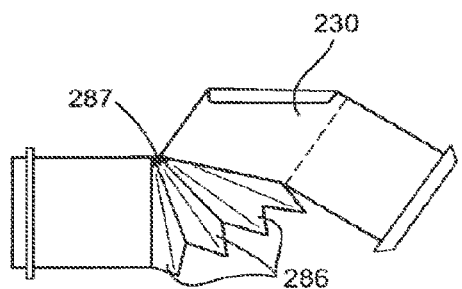
Figures 3, 14:
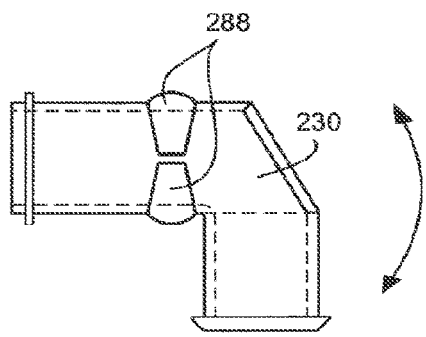
Figures 4, 14:
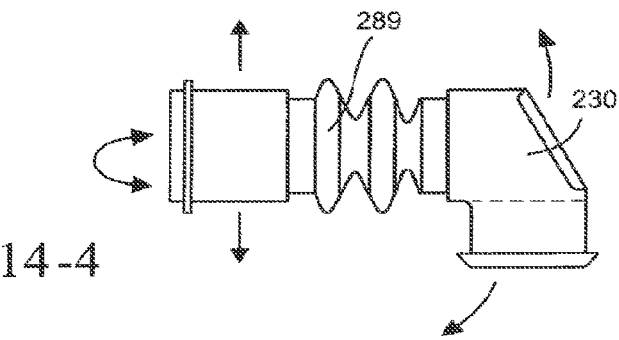
Figure 15:
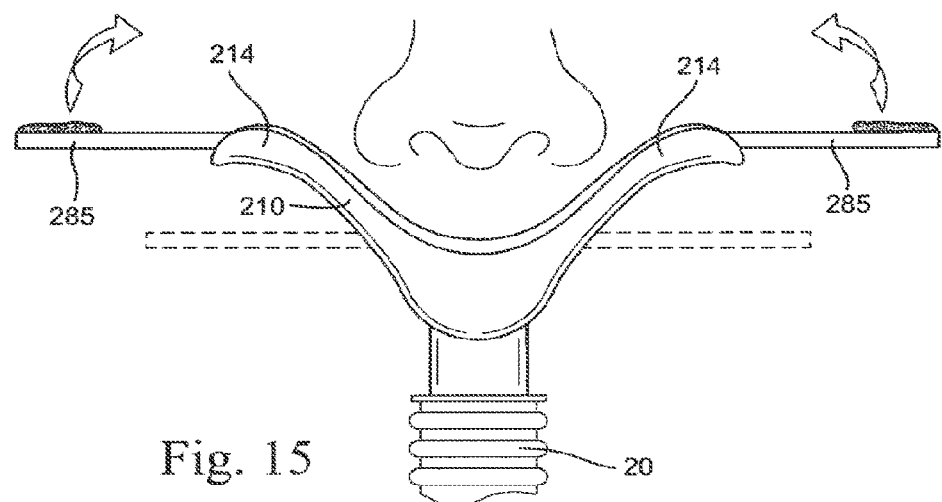
Figures 1, 16:
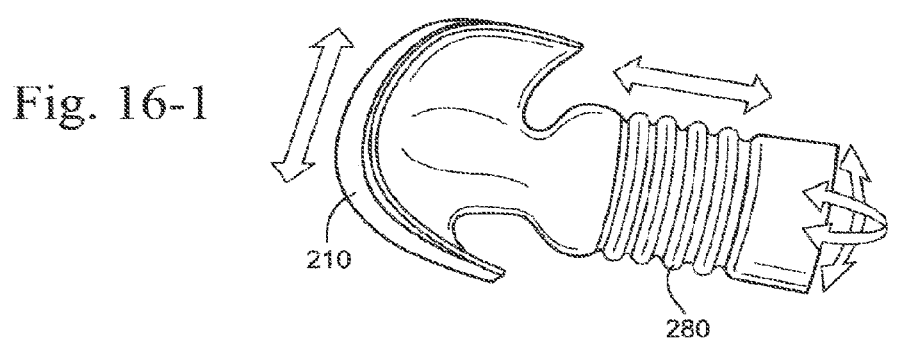
Figures 2, 16:
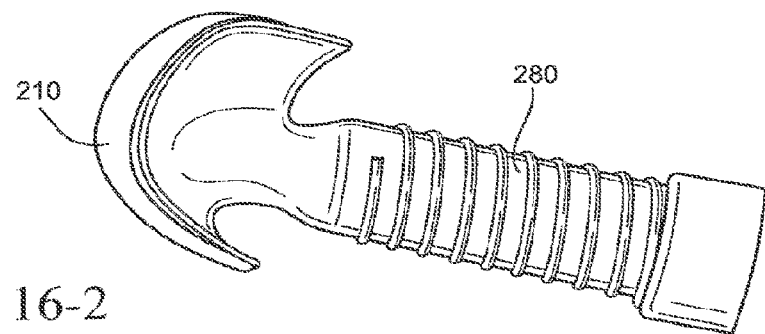
Figures 1, 17:
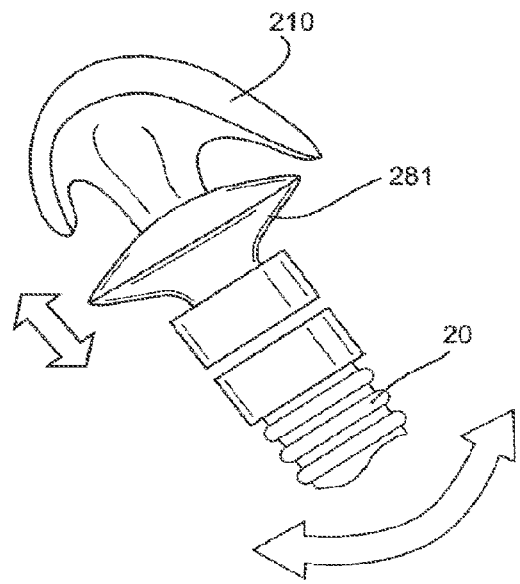
Figures 2, 17:
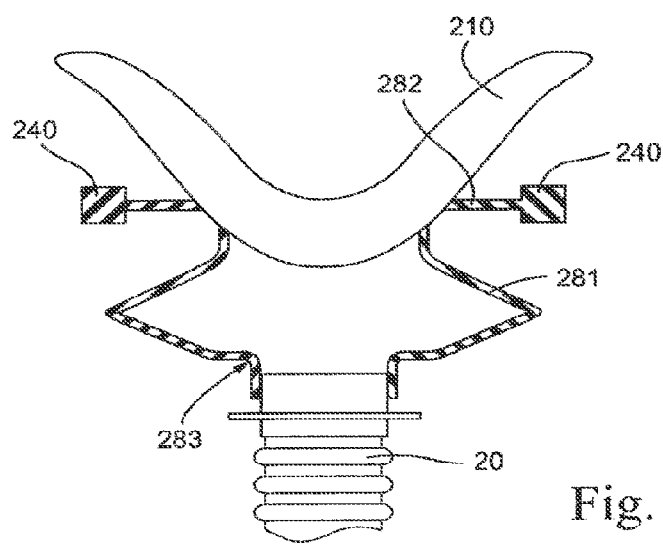
Figures 1, 18:
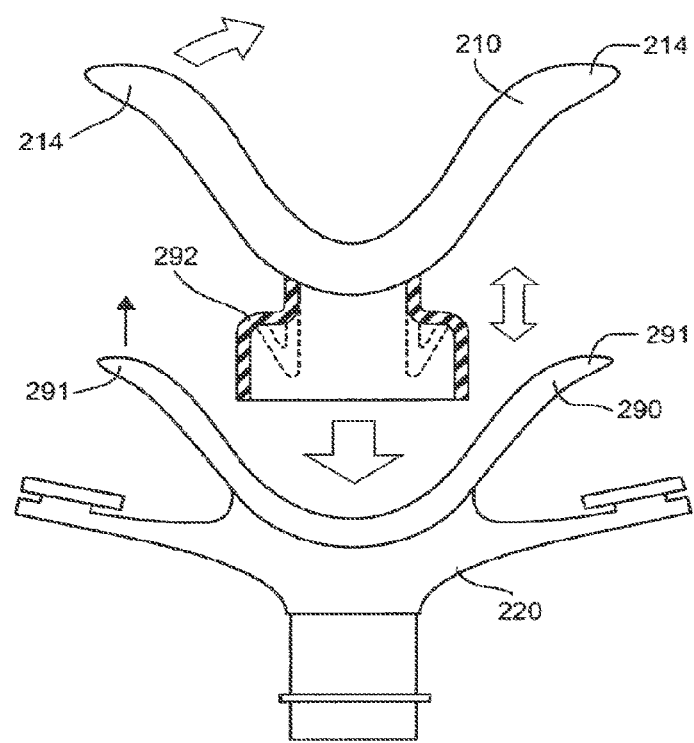
Figures 2, 18:
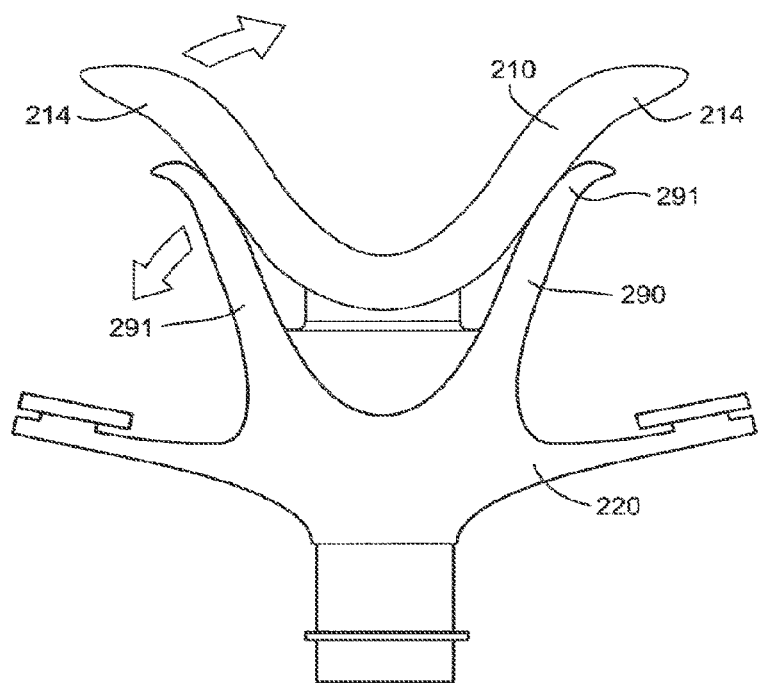

In an embodiment, as shown in FIGS. 18-1 and 18-2, the frame 220 may include an exoskeleton or support arrangement 290 structured to urge the nostril engagement flaps 214 towards the nostrils in use. As illustrated, the fingers 291 provided by the exoskeleton 290 will support and shape the sealing portion when engaged therewith. That is, the exoskeleton is constructed of a more rigid material than the sealing portion, so that the fingers may flex/deform, but to a less extent than the sealing portion so that the fingers will urge or pinch the sealing portion on the patient's nose.

In an embodiment, the base of the sealing portion may include a rolling membrane 292 adapted to fit into the exoskeleton so as to provide some adjustability of the sealing portion to relative to the exoskeleton (e.g., compress or expand).

In an embodiment, the sealing portion and exoskeleton may be provided as a one-piece molding or may be formed separately and attached to one another.

4. Headgear

As best shown in FIG. 1-1, headgear 150 may include side straps 190, top strap 1 70, back strap 180 and rigidizers 160 provided to respective side straps 190 (e.g., stitched onto respective side straps).

In the illustrated embodiment, the rigidizers provide end portions adapted to engage respective headgear connectors 240 on the frame, e.g., with a snap fit, as shown in FIG. 1-1. However, the rigidizers may be coupled to respective headgear connectors in other suitable manners, e.g., rigidizers include openings adapted to receive respective lug-like headgear connectors.

In an embodiment, headgear 150 may include headgear disclosed in U.S. Patent Application Publication No. 2009/0044808 published 19 Feb. 2009, which is incorporated herein by reference in its entirety.

The rigidizers may be configured to add support to selected areas of the mask. For example, the rigidizers may provide cheek supports (like those disclosed in U.S. Patent Application Publication No. 2009/0044808) and/or the rigidizers may be configured to engage lower cheek or chin portions for supporting/locating the mask in use (see FIG. 12).

In an alternative embodiment, headgear straps may be constructed of silicone and rigidizers may be co-molded into respective silicone straps.

In the illustrated embodiment, the headgear provides a two-point connection to the mask. However, other arrangements are possible, e.g., three-point, or more.

4.1 One-Piece Headgear

FIGS. 13-1 and 13-2 illustrate headgear 150 constructed in one piece, e.g., cut from material as a one-piece structure. As illustrated, the headgear 150 includes a central portion 185 and side straps 190 adapted to engage one another, e.g., via a buckle arrangement. The central portion 185 includes an opening 186 for receiving and supporting a sealing portion 210. As shown in FIG. 13-3, the headgear may include a contoured portion 187 surrounding the opening 186 which is adapted to support the sealing portion in use.

In an embodiment, as shown in FIG. 13-4, the region 188 surrounding the opening 186 may be configured to provide a trampoline-type arrangement to the sealing portion 210 which allows the sealing portion to flex, stretch, and/or bounce relative to the headgear 150 to alleviate pressure in use. For example, the region surrounding the opening may be thinner than the remaining portions of the headgear.

In another embodiment, as shown in FIG. 13-5, the headgear 150 may be formed in one piece with the sealing portion 210.

In each of the above arrangements, the air delivery tube 20 may be connected directly to the base of the sealing portion 210.

4.2 Adhesive Headgear

As shown in FIG. 15, instead of headgear, adhesive strips 285 may be provided to respective nostril engagement flaps 214 to adhere the sealing portion 210 directly onto the patient's face. However, the strips may be provided to a lower portion of the sealing portion, e.g., as indicated in dashed lines in FIG. 15. Examples are disclosed in U.S. patent application Ser. No. 12/478,537, filed Jun. 4, 2009, which is incorporated herein by reference in its entirety.

4.3 Other Headgear

FIG. 86 illustrates headgear 484 that includes a strap 527 and a back strap 529. The strap 527 includes slots 531 for attaching to headgear connectors 456 (FIG. 47-2), and an adjustable connector 500. The strap 527 could connect to the headgear connectors 456 by other connecting structure, e.g., utilizing hook and loop type connectors.

The strap 527 is configured to extend in use between the patient's eyes and ears and connect at the top of the patient's head with the adjustable connector 500. The flexible tube 486 may be attached to the strap 527 in the area of the adjustable connector 500 of strap 527 by a tube clip or other retention means, to hold the flexible tube 486 in place at the top of the patients head.

Back strap 529 is configured to extend in use around the back of the patient's head to assist in maintaining the strap 527 in position. The back straps may include a connector 500 for connecting at the back of the patient's head, or alternatively may be a single piece strap. The strap 527 and the back strap 529 may be silicone or other suitable material, such as elastic or TPE.

FIGS. 87-89 illustrate headgear 533 that includes two side portions 535 and a rear portion 524 connected to each of the side portions 535. The side portions 535 each contain a first slot for connecting to the headgear connectors 456 (FIG. 47-2), and a second slot 537 for connecting to the rear portion 524. The rear portion 524 may have an end portion 526 that threads through the second slot 537. The end portion 526 may be formed with a hook-type material, for connecting to a loop-type material 528.

The side portions 535 may be formed from a silicone material, which may be molded. The silicone material may reduce the visual bulk of the side portions 535 by giving them a more streamlined appearance. The rear portion 524 may be formed from a softer material to provide comfort to the patient, such as a soft polymeric material, e.g., TPE or thermoplastic urethane (TPU).

The rear portion 524 may include one or more rigidizer or stiffener to help maintain the shape of the headgear and also secure and position the headgear in relation to the patient's crown and/or occiput. The one or more rigidizer may be constructed of a rigid or semi-rigid material structured to add rigidity or stiffness to the headgear and anchor the headgear in position in use. The rigidizer may be able to bend or deform along its length but resist or prevent stretching of the headgear in the lengthwise direction of the rigidizer. The rigidizers may be substantially inextensible. The rear portion 524 may wrap around a crown of the patients head. The rigidizer may be resilient. The rear portion may be thermoformed and/or ultrasonically die cut, such as disclosed in PCT/AU2009/001605, filed Dec. 10, 2009. The headgear disclosed in PCT/AU2009/001605 may be utilized with the present technology disclosed in this application, and PCT/AU2009/001605 is hereby incorporated by reference in its entirety.

FIGS. 90 to 93 illustrate headgear 539 that is formed in one piece. The headgear 539 covers over the front of the patient interface in area 541 and covers the headgear connectors 456 to give a more streamlined appearance. Rigidizers may be included in or on the headgear 539 for added stability.

FIG. 94 illustrates headgear 543, which is similar to headgear 539 in that it covers over the front of the patient interface in area 541. However, headgear 543 includes cutout portions 545 that allow the headgear tabs 532 to be visible on the outside of the headgear 543. This arrangement may assist in alignment of the headgear with the patient interface.

FIG. 110 illustrates headgear 484 that may be used with any of the embodiments herein, and includes a hook and loop attachment. A loop material 560 may be positioned on a first portion of the headgear 484, and a hook material 562 may be positioned on a second portion of the headgear 484. The hook material 562 and the loop material 560 fasten when pressed together, but allow a user to pull them apart when a certain amount of force is exerted.

A finger loop 558 may be included on the hook material 562 to aid the user in gripping and finding the end portion of the hook material 562. A buckle 590 may be attached to an end of the portion of the headgear 484 having the loop material 560 to aid in alignment and guide the hook material 562 portion of headgear 484 into position on the loop material 560. The buckle 590 and finger loop 558 may be interchanged, i.e., the buckle 590 at the end of the hook material 562 and the finger loop on the loop material 560 portion of the headgear 584.

5. Elbow

In FIG. 1-1, the elbow 230 (e.g., with swivel) is generally L-shaped and is adapted to connect the mask to the air delivery tube 20.

In an alternative embodiment, the elbow may be bendable or flexible to prevent or reduce tube drag in use. For example, as shown in FIGS. 14-1 and 14-2, an intermediate portion of the elbow 230 may include a series of corrugations 286 and a living hinge 287 to allow end portions of the elbow to pivot relative to one another in use. Such corrugated elbow may be molded in one piece (e.g., 2-shot mold, co-mold, insert mold) or may be an assembly (e.g., 2 or 3 part assembly).

In another embodiment, as shown in FIG. 14-3, a flexible region 288 may be incorporated into the elbow 230 to allow end portions of the elbow to move relative to one another in use. The flexible region may be constructed of resilient material (e.g., TPE, soft rubber) to allow the flexible region to compress and expand. Such elbow may be formed by molding, e.g., 2-shot mold, co-mold, insert mold.

Figure 38:
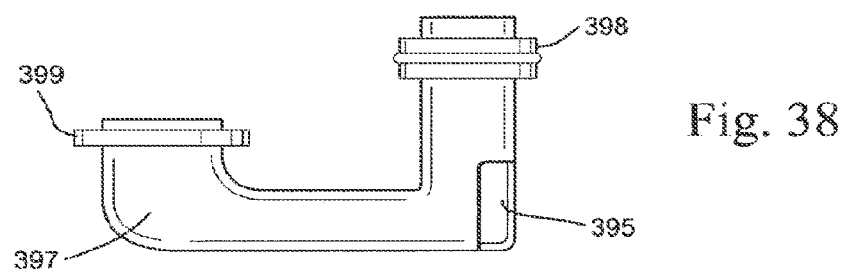
FIG. 38 is a side view of an elbow according to an embodiment of the present technology.

In another embodiment, a corrugated region 289 may be provided between end portions of the elbow 230 to allow the end portions to move relative to one another in any direction, e.g., compress, expand, bend, etc. Such elbow may be formed by molding, e.g., 2-shot mold, co-mold, insert mold. In another embodiment, as illustrated in FIG. 38, a generally L-shaped elbow 397 connects to a sealing portion or mask system at one end and to a tube at the other end, e.g., sealing portion connector 399 to a sealing portion or mask system, and tube connector 398 to a tube. A vent 395 may be positioned between the connectors. The elbow 397 is configured such that when the patient is wearing a mask, the elbow 397 moves the tube connector 398 away from the patients face and upwards of the mask, so that the tube may be positioned over the patients head in use. The vent 395 advantageously directs expired air away from the patients face in use. Connector 398 may attach the an air delivery tube and connector 399 may attach to a mask, such that the vent 395 is parallel to the patient and facing directly away from the patient's airways.

6. Sealing Portion without Suspension System

In an alternative embodiment, the mask 200 may be provided without a suspension system between the sealing portion 210 and the frame 220, i.e., sealing portion attached directly to frame as shown in FIGS. 2-1 to 2-6.

In such embodiment, sealing portion 210 may be removably connected to frame 220 by, e.g., including but not limited to: snap fit, tongue and groove, clips, etc. Alternatively, sealing portion 210 may be permanently connected to frame 220 by, e.g., including but not limited to: co-molding, insert molding, gluing, etc. In an alternative form, sealing portion 210 may be constructed in one piece with the frame 220.

6.1 Shape

Sealing portion 210 may be generally rectangular or elliptical when viewed from the top, as shown in FIG. 2-7B. In an alternative embodiment, sealing portion 210 may be generally triangular or trapezoidal when viewed from the top, as shown in FIG. 2-7 A. The embodiment of FIG. 2-7 A is structured to reduce the amount of excess material in the sealing portion 210 that may cause discomfort or be less obtrusive. This may also be to indicate alignment to the patient, i.e., the patient may be more likely to correctly align a triangular shaped sealing portion 210 as the nose is naturally shaped more like a triangle and thus the nose tip engagement portion 212 and upper lip engagement portion 213 are more likely to be oriented in their desired locations.

As shown in FIGS. 2-8B and 2-9B, the upper lip engagement portion 213 of the rectangular-shaped sealing portion is sufficiently long such that its free end overhangs at least a portion of the frame, e.g., to prevent engagement of the patient's upper lip with the frame in use. In addition, the upper lip engagement portion may be sufficiently long so as to accommodate a variety of nose and upper lip shapes (e.g., the embodiment shown in FIG. 2-8B may have a larger fit range of patient's than the embodiment shown in FIG. 2-8A). In the triangular-shaped sealing portion embodiment, as shown in FIGS. 2-8A and 2-9A, the length of the upper lip engagement portion 213 is shortened or abbreviated, e.g., to reduce the amount of excess material. FIG. 2-10 illustrates the triangular-shaped sealing portion embodiment engaged with patient's face in use.

FIG. 2-11 is a rear view of a sealing portion showing a portion of the upper lip engagement portion 213 to be removed (shaded section), e.g., with respect to the sealing portions of FIGS. 2-8B and 2-9B. The reduction of material in the upper lip engagement portion may improve comfort and appeal of the mask (i.e., more unobtrusive look) and may improve leak performance.

7. Alternative Mask to Tube Connections

FIGS. 57 to 85 and 95 to 101 illustrate various alternative mask to tube connections that may be utilized with the present technology.

7.1 Thin Membrane

Figure 57:
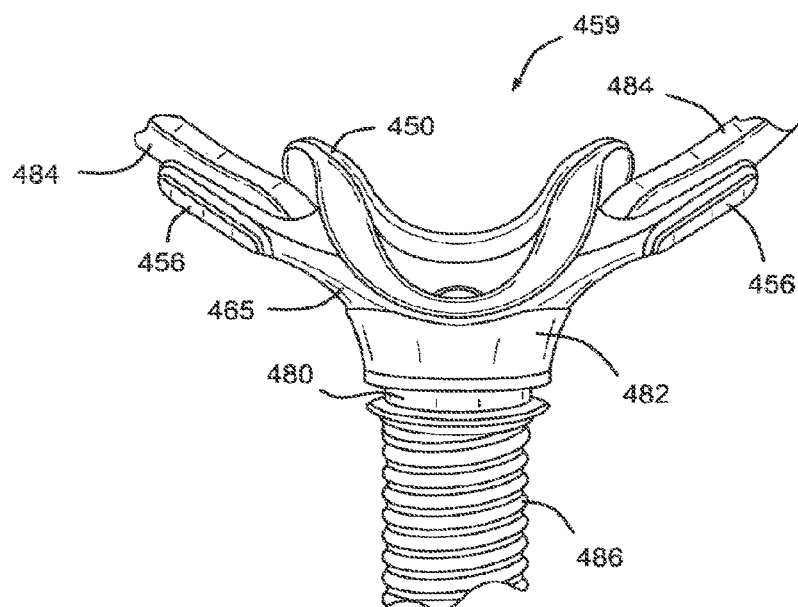
Figure 58:
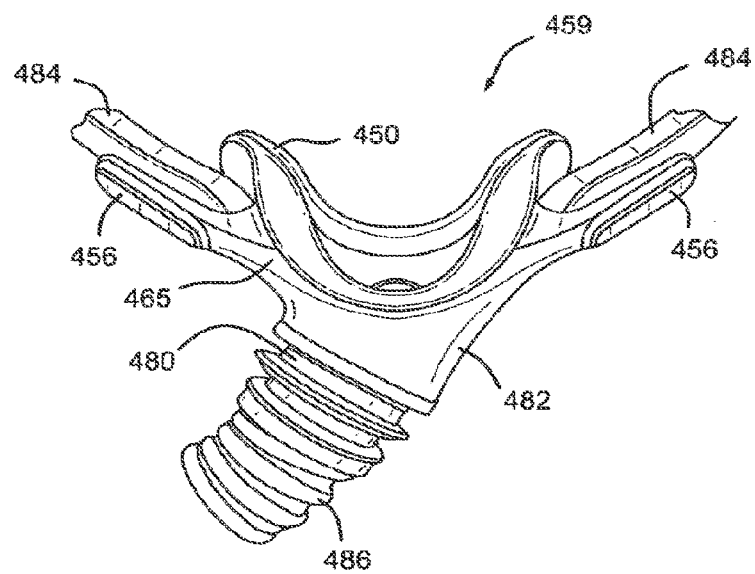

As illustrated in FIG. 57, thin membrane 482 may be disposed between the supporting membrane 465 and flexible tube 486. In this embodiment, headgear connectors 456 allow connection of headgear 484. As illustrated in FIG. 58, a degree of freedom of movement is provided between the support membrane 465 and the flexible tube 486 by thin membrane 482, which may join the flexible tube 486 to the patient interface 459 via swivel ring 480. Thin membrane 482 may stretch, flex or otherwise elastically deform to permit movement between the supporting membrane 465 and flexible tube 486. Thin membrane 482 may have a wall thickness that is less than the supporting membrane 465. Thin membrane 482 may have a wall thickness of about 0.2 to 5 mm. Preferably, thin membrane 482 may have a wall thickness of about 0.5 to 2 mm. Most preferably, thin membrane 482 may have a wall thickness of about 0.5 to 1 mm. Movement between the tube 486 and the sealing portion 450 may be limited by the length of the membrane 482, which may be adjusted based on a desired amount of movement. Any additional movement becomes a function of the flexible tubing.

7.2 Multi-Axis Elbow Assembly

FIGS. 59 to 64 illustrate a multi-axis elbow assembly 495 that creates additional degrees of freedom by allowing rotation in two separate planes, as shown by the arrows in FIG. 59, for example. The multi-axis elbow assembly 495 includes frame 491 which may be connected to thin membrane 482 or to support membrane 465, elbow 488 connected to frame 491, swivel assembly 494, swivel ring 492, and elbow 490.

The additional degrees of freedom provided by the multi-axis elbow assembly 495 have a marked impact on the functionality of the patient interface 459. For example, the multi-axis elbow assembly 495 allows the flexible tube 486 to easily be placed on either side of the patient's head, as illustrated in FIGS. 60 and 61, to be positioned along the nose and between the eyes of the patient as illustrated in FIG. 62, while being streamlined (not bow outward), while applying a moment to the patient interface that is almost zero. Additionally, as shown in FIGS. 63 and 64, the flexible tube 486 may also be positioned in a downward configuration or in an outward configuration, respectively. The multi-axis elbow assembly 495 allows the tube 486 to be placed in many different positions that may be utilized by a patient while not applying significant moment to the patient interface created by tube drag to provide an effective and comfortable seal with the patient.

7.3 Bellows Short Tube Decouple

A bellows or concertina tube decouple is illustrated in FIGS. 65-69. A series of bellows 502 connects to patient interface 459 at one end, and connects to a tube 506 at the other end. The tube 506 may have a swivel connector 504, which may be used to connect to a gas supply tube, for example. The bellows 502 includes a bore with a plurality of supportive rings that helps prevent air path occlusion under tight bending conditions, i.e. the bellows may have a thicker wall section than the portions of the bore without the bellows portions. Alternatively, the bellows and the bore may have a constant wall section. The length of the bellows may be selected to provide a decoupling function, to retain the seal of the patient interface 459 despite bending of the bellows 502. The bellows 502 thus provides a degree of freedom of movement between the patient interface 459 and the tube 506.

The bellows 506 may be molded as a unitary structure with the support membrane 465, or may be a separately, removably attachable element. The bellows 502 may be formed from a material with a hardness of about durometer 20 to 80 Shore A, preferably 20 to 60 Shore A and most preferably about 40 Shore A to match the support membrane 465 so that both parts may be molded together, and where the bellows 502 is a separate element, it may have a different hardness, such as about durometer 20-40 Shore A, preferably about 20 Shore A. Preferably, when a durometer of Shore A 40, a preferred thickness is about 0.3 mm.

The bellows 502 may have an internal bore of 8 to 20 mm, preferably 10 to 15 mm, most preferably 12 mm or 15 mm. A thin membrane may be used between the bellows 502 and the support membrane 465 of the patient interface 459.

The added flexibility of the bellows 502 allows the tubing 506 to be easily positioned overhead as illustrated in FIG. 67, to the side of the head, outward or downward with minimal force on the patient interface 459. The bellows 502 has a wide separation between rings to ensure adequate bending with the tube. The bellows 502 prevents occlusion of the air path when the tube bends sharply.

FIG. 69 illustrates various dimensions of the bellows rings and sidewall shown in FIG. 68. Each bellows ring has a height of e.g., 2 to 6 mm, preferably 3 to 5 mm, most preferably 5 mm, including the sidewall, and a width of, e.g., about 2 to 8 mm, preferably about 3 to 6 mm, most preferably about 4 mm. The radius RI of the curved portion between each bellows ring may be about 1 to 4 mm, preferably about 2 to 3 mm, most preferably about 2.5 mm, the separation between the rings of the bellows is, e.g., about 2 to 8 mm, preferably about 4 to 6 mm, most preferably about 5 mm, and the thickness of the side wall of the bellows ring is, e.g., 0.2 to 2 mm, preferably about 0.5 to 1.5 mm, most preferably about 0.3 mm. The radius of the bellows 502 measured from an inner side of the bottom of each curved portion between the bellows ring is, e.g., about 4 to 12 mm, preferably about 6 to 10 mm, most preferably about 7.5 mm. These values may be varied but have been found to provide improved impedance and overall tube/patient interface compatibility while providing a very flexible bellows at about durometer 20 to 60 Shore A, preferably about 40 Shore A.

7.4 Ball and Socket

FIG. 70 illustrates a patient interface 459 that connects to a flexible tube 486 via a ball and socket connection. The ball and socket connection includes a ball 508 and a socket connector 510. The ball 508, also illustrated in FIG. 71, may be connected to the flexible tube 486 by connector 507, also illustrated in FIG. 72. The socket connector 510 may be connected to the patient interface 459. The socket connector 510 may be a conventional elbow ring sized to accept the ball 508. The socket connector 510 may also include a diffuse vent allowing exhaled air from the patient to be vented.

The ball and socket connection provides decoupling of movement of the flexible tube 486 to relieve moment created on the patient interface 459 created tube drag. As the flexible tube 486 is moved about, the ball 508 may move about in socket connector 510.

FIGS. 73 and 74 illustrate the ball 508 connected to an elbow 509. The elbow 508 may connect to a flexible tube. The elbow 509 includes a bend, which may be, e.g., about 90° to 150°, preferably about 100° to 130°, most preferably about 110°, although other angles may be used. The elbow 509 may include a vent 511, which may include one or more vent holes 513 for venting exhaled air. The vent holes 513 may be an array of spaced apart vent holes. Preferably, the internal diameter of the bend is about 7 to 15 mm. Preferably, bend may have an internal diameter of less than 12 mm. Most preferably, bend may have an internal diameter of about 8 mm.

Ball 508 may preferably have outside diameter in the range of about 15 to 19 mm. Most preferably, ball 508 may have an outside diameter of about 17 mm.

Ball 508 may preferably have an internal diameter of about 7 to 15 mm. Preferably, ball 508 may have an internal diameter of less than 12 mm. Most preferably, ball 508 may have an internal diameter of about 8 mm.

As illustrated in FIG. 75, the vent may be in the form of a removable insert 517. The removable insert 517 may be attached to the elbow 509 by structure to lock it in place, such as lugs, tongue and groove, etc. The insert may be a mesh vent 515, as shown in FIG. 76.

FIG. 77 illustrates an embodiment in which the ball 508 includes a series of vent grooves 501. The vent grooves 501 may have a length to extend to both sides of the socket connector 510 in use, so that exhaled air may exit through the vent grooves 501. Vent grooves may have a length of about 2 to 50 mm. Preferably, vent grooves 519 may extend along the outer surface of the ball 508 to create a long vent flow path. A long vent flow path may reduce the noise of the exiting gases as the velocity of the air may decrease. Preferably, vent grooves 519 are distributed around ball 508 to diffuse the exiting air flow paths. Preferably, vent grooves 519 are molded on ball 508. Preferably, grooves 519 have a width of about 0.2 to 3 mm. Preferably, grooves 519 have a width of less than 1 mm. The thinner the groove, the slower the air flow and hence the quieter the vent. The grooves 519 may be generally linear or may have various other configurations. A curved or tortuous pathway is preferred as this may increase the length of the vent flow path and hence reduce the noise of the vent. The walls of ball 508 adjacent the grooves 519 may interface with the connector 510. Connector 510 may lie over the top of groove 519 and hence form a cover over grooves 519.

FIG. 111 illustrates an embodiment in which the ball 508 includes a series of curved vent grooves 564. The curved vent grooves 564 may also have a width of about 0.2 to 3 mm. Preferably, vent grooves 564 have a width of less than 1 mm. The ball 508 may be connected to a tube 486 or to an elbow 509 or other element.

FIG. 112 illustrates an embodiment in which the ball is a perforated ball 568, which includes a series of vent holes 570. The perforated ball 568 may allow the air to flow between a connector (such as connector 510) and the ball 568. The ball 508 may be connected to a tube 486 or to an elbow 509 or other element.

FIGS. 113-1 and 113-2 illustrate an embodiment with a ball 508 having vent grooves 570, in which a flow path barrier 592 may be removably attachable to the ball 508. The flow path barrier 592 may interface with a connector 510 to create a flow path between the barrier 592 and the connector 510.

FIG. 78 illustrates an alternative socket connector 521. The socket connector 521 includes vent grooves 523. The vent grooves 523 allow exhaled air to exit the patient interface. The vent grooves 523 may extend radially outwards (as shown). Alternatively, vent grooves 523 may extend axially. Alternatively, vent grooves 523 may extend along the inner surface of the inner wall of socket connector 521.

FIG. 79 illustrates the patient interface 459 utilizing the ball 508 and socket connector. The ball 508 may be freely moved in the socket connector providing a degree of freedom of movement, allowing the tub 486 to be placed in various positions.

7.5 Hybrid Elbow and Ball Joint

FIGS. 80 to 83 illustrate a hybrid elbow and ball joint. Elbow assembly 514 includes a swivel connector 512 and a socket connector 518. Ball assembly 516 includes a ball 522 and a swivel connector 520. The ball 522 mates with the socket connector 518.

The elbow assembly 514 may utilize an angle of, e.g., 90° to 150°, preferably about 100° to 130°, most preferably about 110°. The combination of the elbow assembly 516 with the ball joint provides multiple degrees of freedom of movement. For example, utilization of an elbow without the ball joint would either force the connected tubing to close to the patient's chin in the tube down position, or too far out in the tube up position. Utilizing the elbow assembly with the ball joint allows the tube to be place in more desirable positions.

FIG. 82 illustrates the elbow assembly 514 utilizing the ball assembly 516, with the flexible tubing 486 in the downward position. The ball 516 allows positioning of the flexible tube 486 away from and not in contact with the patient's face.

FIG. 83 illustrates the elbow assembly 514 utilizing the ball assembly 516, with the flexible tubing 486 in the upward position. The ball 516 allows positioning of the flexible tube 486 closer to the patient's face, to help prevent obstruction of vision.

7.6 Thin Membrane with Elbow

FIG. 84 illustrates the thin membrane 482 utilized with elbow assembly 514 and a swivel connector 512. The sealing portion 450 includes an aperture that exits at an angle downward from the horizontal, making it difficult to be able to achieve both the tube-up and tube-down positions. The thin membrane 482 is flexible to be able to adjust the exit angle to a more horizontal position. The thin membrane 482 thus allows the flexible tube 486 to hang downward without applying excess moment to the sealing portion 450, and also allows the flexible tube 486 to be properly positioned in the upward position.

7.7 Angled Elbow Ball Joint

FIG. 85 illustrates an angled elbow and ball joint assembly 525. The angled elbow ball joint assembly 525 includes an elbow 514, a ball 516, and a swivel connector 520 for connecting to the flexible tube 486. The angled elbow ball joint assembly 525 may include an angle of, e.g., 100° to 160°, preferably about 100° to 130°, most preferably about 110°. The ball 516 may be connected to a socket connector such as illustrated in FIG. 70. The ball 516 provides the freedom of movement that will allow the flexible tube 486 to be properly positioned in the upward or downward positions.

7.8 Ball and Socket Assembly

FIGS. 95 to 101 illustrate a ball and socket assembly 561 incorporated with a ball joint portion and swivel ring. Swivel ring 550 may interface with the mask or support membrane 465. Ball 552 is placed within the swivel (see FIG. 101) to allow 360° rotation of the ball joint portion 548 axial to the swivel ring 550, and to move in planes other than axial to the swivel ring 550. Alternatively, the swivel ring 550 may be omitted and the ball 552 may interface with the mask.

Connector 556 is adapted to connect to a flexible gas supply tube, so that gas may be supplied in the air passageway 560 in the direction of arrow 558. The air passageway may have an internal diameter of 11-15 mm, and the connector 556 may have the same internal diameter. A vent 554 may be incorporated into ball joint portion 548, to vent exhaled gas from a patient.

The swivel ring 550 may be manufactured in a mold and set. The swivel ring 550 may then be placed in a tool, where the ball joint portion 548 is molded about or within the swivel ring 550. As the material of the ball joint portion 548 cools down, it will shrink off of the swivel ring 550. The vent 554 may be molded into the ball joint portion 548.

7.9 Side Connected Tube

FIGS. 102 to 104 illustrate a patient interface 459 with a side connected flexible tube 486. In all of the embodiments, the patient interface 459 may include the sealing portion 450 and the support membrane 465, even if not specifically illustrated. Two apertures 538 are located on each side of the patient interface 459, and allow connection of the flexible tube 486 on either side of the patient interface 456, extending towards the side (laterally). A plurality of vent holes 544 may also be included, for venting gas exhaled by the patient.

An elbow 542 may be connected to the end of the flexible tube 486, and be adapted for connection to the aperture 538. The elbow may include a swivel connector allowing the flexible tube 486 to be swiveled to different positions, such as an upward position along a side of the patient's face, as illustrated in FIG. 103, or a downward position, such as illustrated in FIGS. 102 and 104. A plug 540 may be utilized on an aperture 538 to which the flexible tube 486 is not connected, to seal the aperture 538.

The side connected tube presents a streamlined appearance and moves the tube 486 away from the face of the patient. The side connected tube also decouples tube drag forces from the sealing portion 450. Further details of the side connecting interface are disclosed in U.S. application Ser. No. 12/377,801 filed Feb. 29, 2008, which is incorporated herein by reference in its entirety.

7.10 Two Side Connected Tubes

FIG. 105 illustrates a patient interface 459 which utilizes two side connected flexible tubes 548. A frame 546 may be utilized to support the patient interface 459. The flexible tubes 548 may have a smaller diameter than when one flexible tube is utilized. For example, the flexible tubes 548 may have half the diameter as when one tube is utilized. This may provide more comfort to the patient, particularly if the patient rolls over onto one of the tubes 548.

7.11 Rigid Frame Over Patient Interface

FIGS. 105 to 107 illustrate a rigid frame 546, which may be adapted to fit over and support the patient interface 459. For example, the rigid frame may be shaped to fit over the patient interface 459. The rigid frame 546 may include headgear connectors 456 for connecting to headgear 484.

The frame 546 may be formed from a rigid material to provide rigid support. Further details of the frame 546 are also disclosed in U.S. application Ser. No. 12/377,801, which is incorporated herein by reference in its entirety.

7.12 Headgear Cradle

FIGS. 108 and 109 illustrate a headgear cradle portion 552 adapted to connect to patient interface 459. The headgear cradle portion 552 may include an aperture 554 for connecting the headgear cradle portion 552 to the patient interface 459. The headgear cradle portion 552 may have apertures at its ends to receiver the headgear 484.

The headgear cradle portion 552 may also tactile ends 550 to enhance a patient's grip to ease in connecting and disconnecting of the headgear 484. The headgear 484 may use hook and loop material to connect. The headgear cradle portion 552 may also include a conformable pad 556 internal to the headgear cradle portion 552. The conformable pad 556 supports the patient interface 459 and provides decoupling between the patient interface 459 and the headgear cradle portion 552. The conformable pad 556 also provides a softened feel to the patient when using the patient interface 459.

7.13 Elbow with Lugs

FIG. 114 illustrates an embodiment in which a patient interface 459 connects to headgear 484 and an elbow 582. The patient interface includes a connector 578 having apertures 580. The headgear 484 has a headgear connector 557 shaped to interface with connector 578, by fitting over the outside of connector 578. The lugs 586 of the elbow 582 fit within the apertures 580. The elbow 582 is adapted to form an airtight connection with the connector 578. The headgear 484 may have apertures if needed near the headgear connector 557 to receive portions of the elbow 582 near the lugs 586.

7.14 Vented Elbow Assembly

FIGS. 115 and 116 illustrate a vented elbow assembly. The vented elbow assembly includes an elbow 509, a swivel ring 550 and a connector 556. The swivel ring 550 may be connected to a patient interface 459 or a support membrane 465, and the connector 556 may be connected to a flexible tube supplying gas.

The elbow 509 may include a series of vented grooves 558 for venting gas exhaled by the patient. The vented grooves 558 may be of different lengths, and may be arranged parallel or perpendicular to the direction of gas flow through the elbow 509.

8. Additional Embodiments

Figures 1, 23:
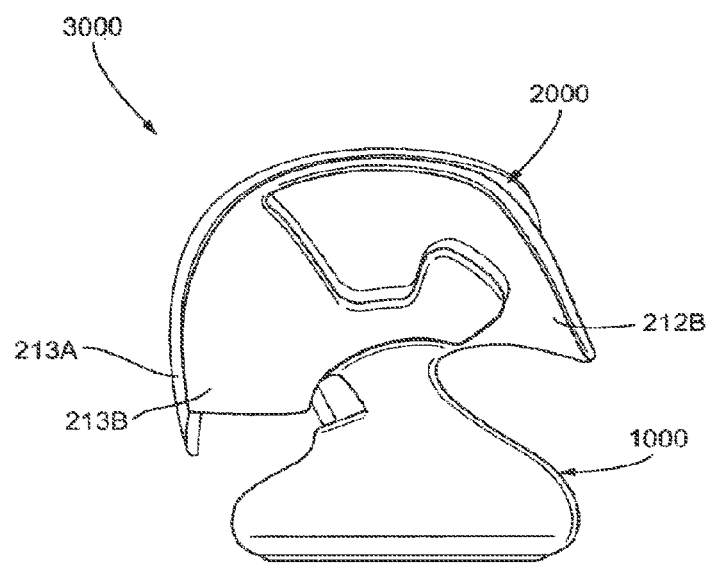
Figures 2, 23:
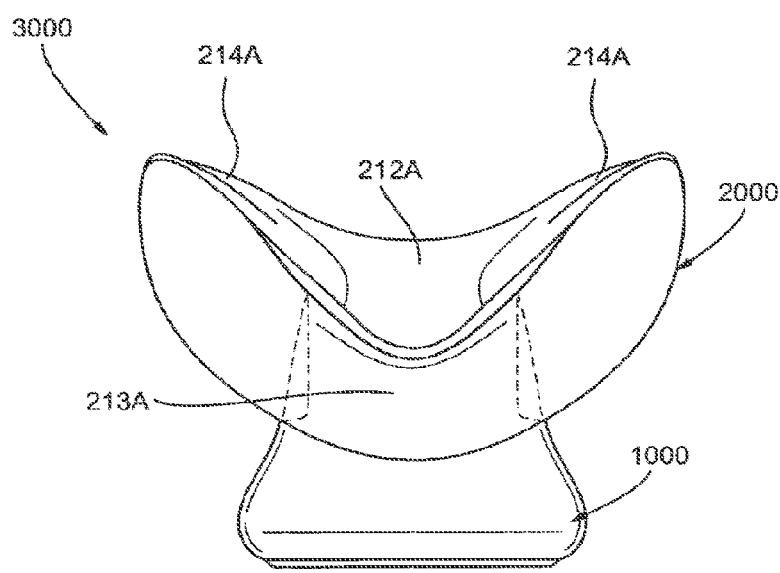
Figures 3, 23:
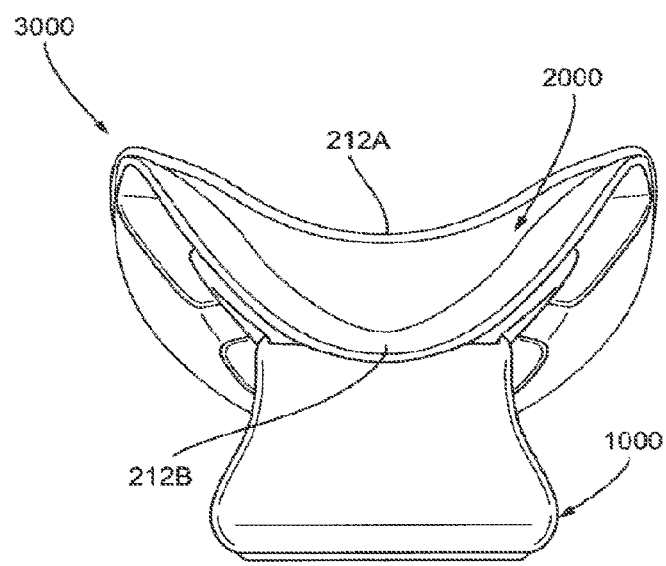
Figures 4, 23:
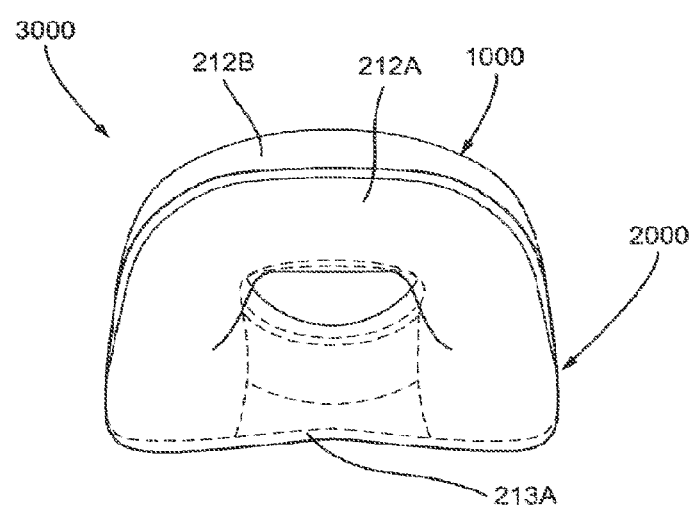
Figures 5, 23:
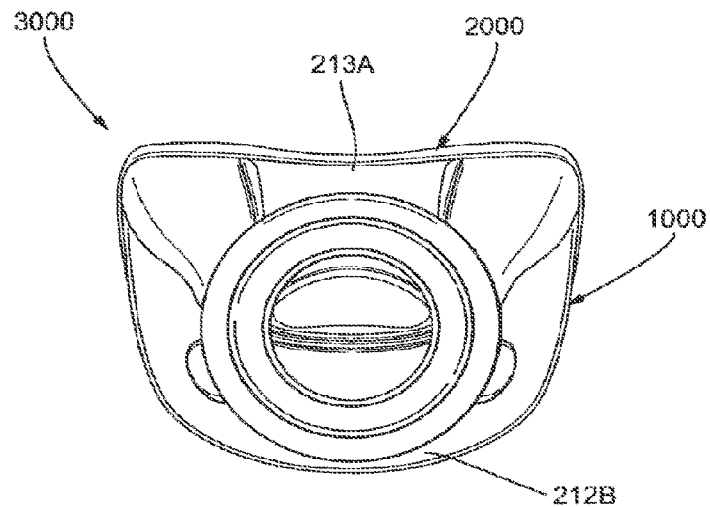
Figures 6, 23:
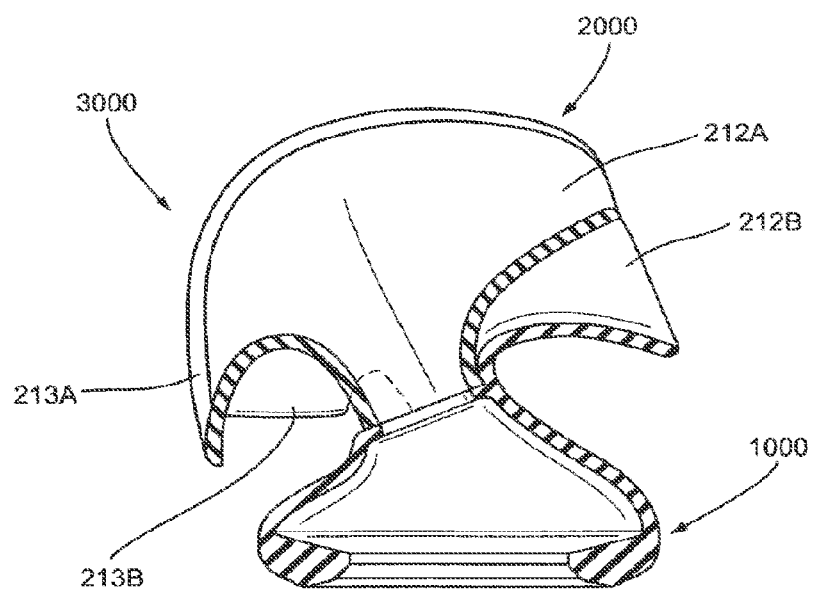
Figures 7, 23:
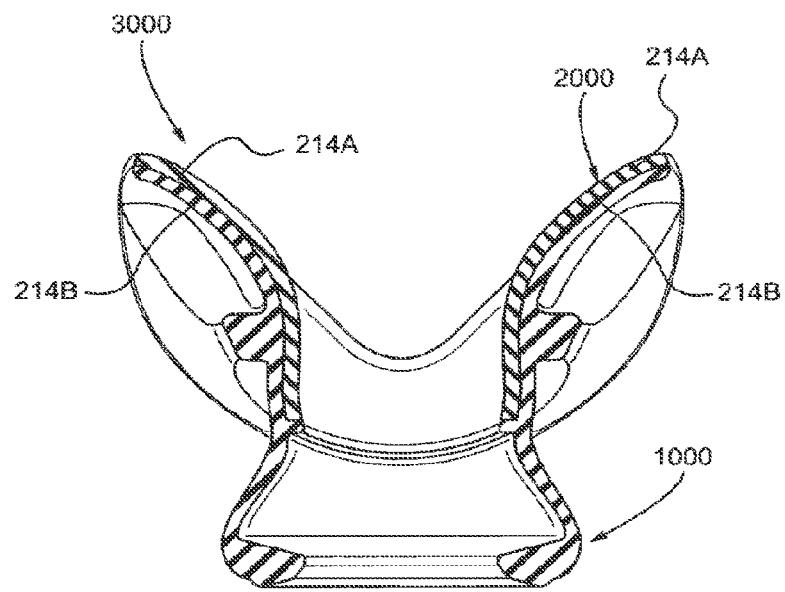

FIGS. 23-1 to 23-7 show an additional embodiment of the present technology. FIG. 23-1 shows a patient interface 3000 with an interfacing portion (also known as sealing portion) 2000 positioned above or on top of a supporting portion 1000. Supporting portion 1000 is shown in FIGS. 21-1 to 21-6. Supporting portion 1000 may have a nose tip portion 212B, nostril portions 214B, and an optional upper lip portion 213B. Regions underneath or on the non-patient contacting side may have ridges or thickened sections to provide additional support to interfacing portion 2000 when assembled, and to provide varying degrees of support to the sealing portion 210. Supporting portion 1000 may be constructed of a silicone with a hardness of about 20 to 90 Shore A, preferably about 40 Shore A. The supporting portion 1000 could also be made from polycarbonate, polypropylene, nylon, thermoplastic elastomer (TPE), Hytrel™, etc. The supporting portion 1000 may be about 1-15 mm thick, preferably 1.2 mm. As best shown in FIG. 21-4, upper lip portion 213 B may be cut out or removed.

Figures 1, 22:
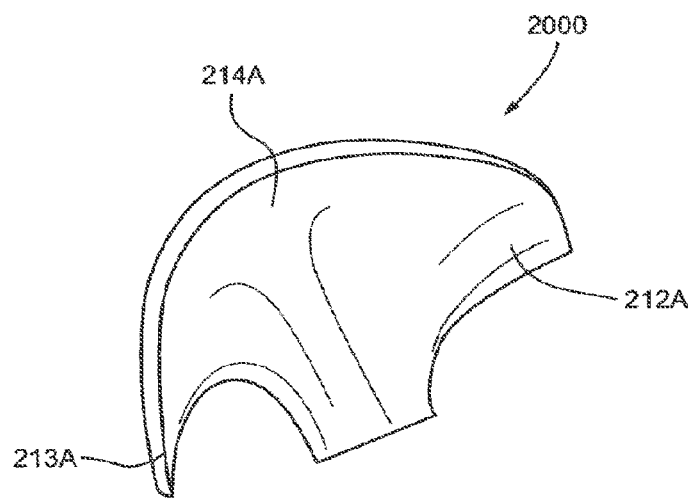
Figures 2, 22:
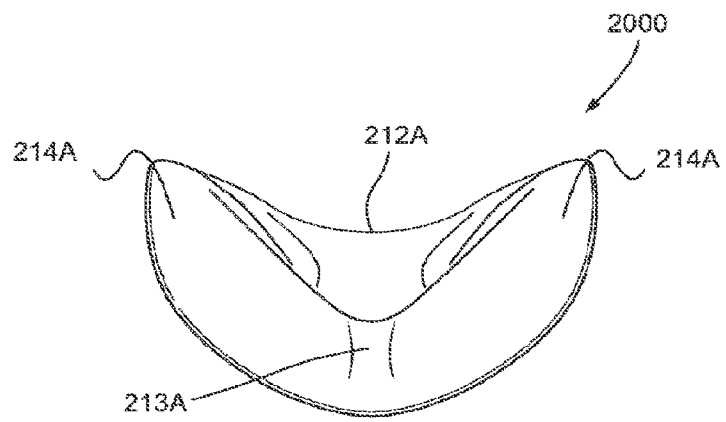
Figures 3, 22:
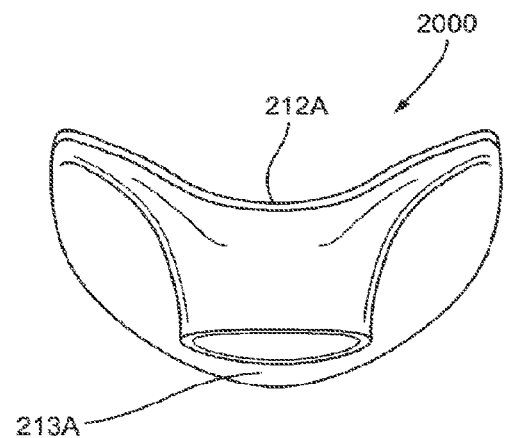
Figures 4, 22:
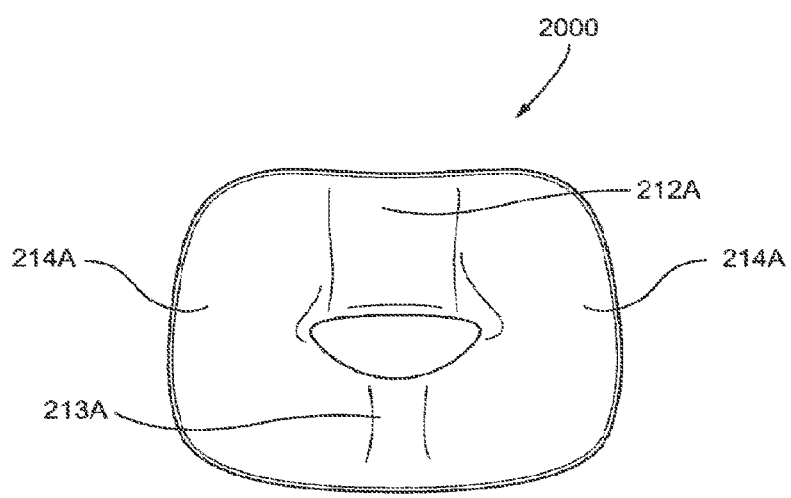

FIGS. 22-1 to 22-4 show interfacing portion 2000. Interfacing portion 2000 may have a nose engagement portion 212A, nostril engagement portions 214A, and an upper lip engagement portion 213A. Interfacing portion 2000 may engage with the patient in use. Interfacing portion 2000 may be made from a silicone, with a hardness of about 7 durometer on the Shore A scale. Alternatively, the hardness of the interfacing portion 2000 may be about 12 durometer on the Shore A scale. The thickness of interfacing portion 2000 may be about 1.2 mm. The interfacing portion 2000 may be made from other suitable materials such as nylon, a textile, TPE, etc. The interfacing portion may have a polished surface finish for tactility and to 'stick' or tack on to the patient's skin in use.

FIGS. 23-1 to 23-7 show interfacing portion 2000 attached to or positioned on top of support portion 1000. Interfacing portion 2000 may be co-molded, insert molded, glued or otherwise attached to support portion 1000. Interfacing portion 2000 may be permanently attached or removably attached.

As best show in FIGS. 23-3 and 23-6, nose engagement portion 212A may be raised or supported above nose portion 212B. This arrangement may be beneficial for allowing patient's noses to flex into nose engagement portion 212A, thereby allowing a greater fit range. Nose portion 212B supports the side walls of the interfacing portion 2000. As best shown in FIG. 23-5, upper lip engagement portion 213A is suspended over the gap at upper lip portion 213B. This allows flexibility of the patient interface 3000 at the patient's upper lip region, thereby allowing a greater range of fit.

FIG. 117 illustrates a patient interface 600. The patient interface 600 includes a sealing portion 600 for sealing with the patient's face, a supporting portion 608, and a connecting portion 610 for connecting to a supply of gas, such as a flexible tube. An optional gusset 604 may also be included.

Headgear may be attached to the patient interface 600 creating headgear vectors in an area such as position 606. This may be accomplished by disposing headgear connectors under the sealing portion 602 on the supporting portion 608, for example. An optional gusset 604 may be included between the sealing portion 602 and the supporting portion 608.

FIGS. 118-1, 118-2 and 118-3 illustrate a patient interface 612. The patient interface 612 includes a sealing portion 602, a supporting portion 616, a gusset 614 between the sealing portion 602 and the supporting portion 616, and a connecting portion 618 to a supply of gas, such as a flexible tube, and an aperture 620.

The sealing portion 602 interfaces and creates a seal with the face of the patient, typically with the upper lip and nose of the patient. The sealing portion 602 may include stiffened portions, such as portions of the sealing portion 602 that interface with the patient at regions of the patient's nose adjacent the nasal labial creases. The stiffened portions of the sealing portion 602 may be formed from a non-compressible material such as a gel or a material such as a high durometer silicone as compared to other portions of the sealing portion 602. Alternatively or in addition, structural support may be added such as ribs or thickened portions on sides of the sealing portion or on the supporting portion, such as in the embodiment of FIG. 52-5, and/or the gusset 614 may be filled with a stiff material to provide additional support.

Figures 1, 118:
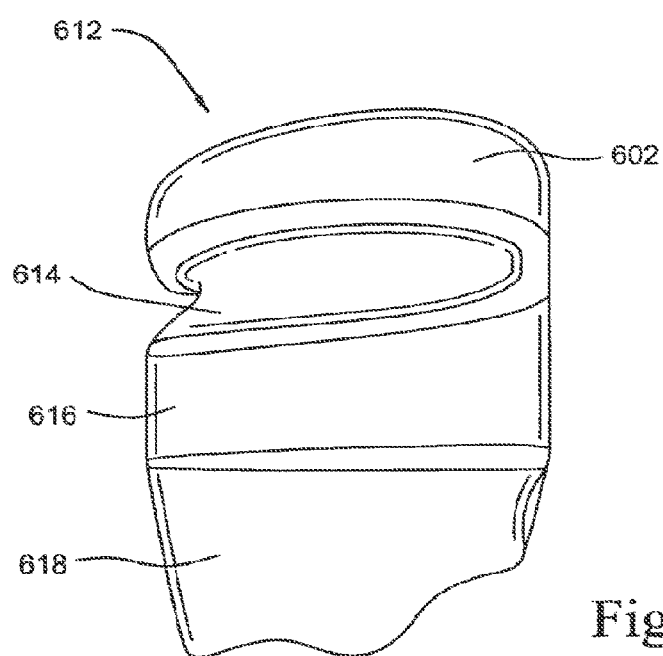
Figures 2, 118:
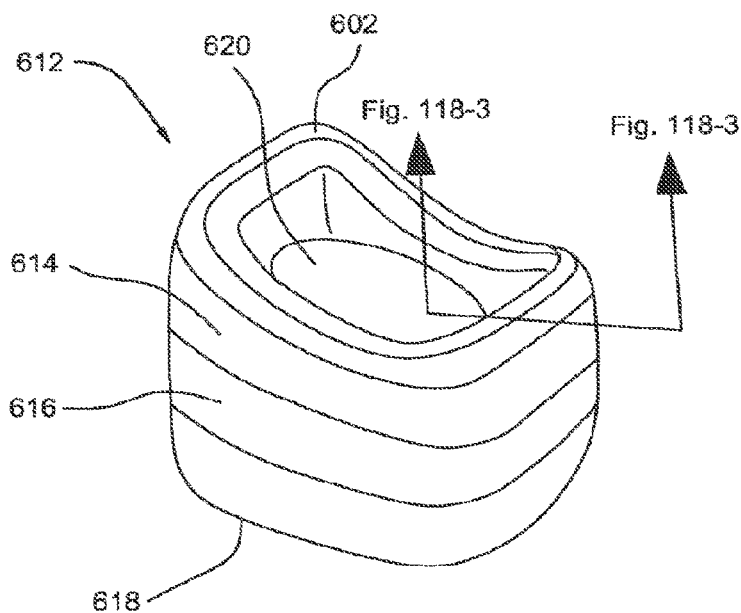
Figures 3, 118:
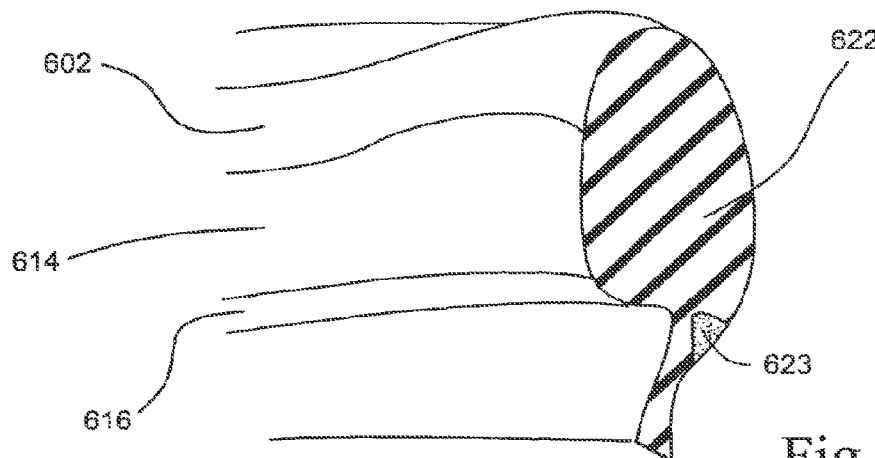

FIG. 118-3 illustrates a cross-sectional view that includes a gel filled pocket 622 in the corner region of the sealing portion 602, and such a gel filled pocket may be located in each corner region. The gel filled pocket 622 may be utilized to provide the stiffened portions and provide a more effective seal with the patient in use. A gel filling location 623 may be included allowing a user or patient to add or remove gel as needed.

FIG. 119 illustrates a top view of a sealing portion 602 of a patient interface. The sealing portion 602 may include an orifice 602 for delivering gas to the patient in use. The orifice 602 may have a substantially trapezoidal shape as illustrated, or may be a substantially triangular shape. These shapes are closer to the shape of a patient's nose, which allows a patient to more easily put the patient interface on in the correct orientation.

FIG. 120 illustrates a patient interface 630, which includes a sealing portion 632, a supporting portion 636, an optional gusset 638, and a connecting portion 640. The sealing portion 632 may be a single wall sealing portion, and in this embodiment may include a second sealing wall 634 underneath the sealing portion (forming a first sealing wall) to provide additional support.

FIG. 121 illustrates a patient interface 642, which includes a sealing portion 644, a supporting portion 652, and an optional gusset 650. In this embodiment, the front portion 648 (nose engaging portion) of the sealing portion 644 is curved downward making the sealing interface deeper and more curved. This shape allows the side walls of the sealing portion to flex outwards more with flatter noses, and allows more pointy noses to rest in the curvature provided by this shape.

FIGS. 122-1 and 122-3 illustrate cross-sectional views of the patient interface 600 or 642, with the addition of a soft, conformable support structure. A support structure 604 is provided below the sealing portion 602. The support structure 604 may be foam or another soft, conformable material, while the sealing portion 602 and support portion 606 are silicone or other similar material as described herein. The support structure 604 may fit into an indent formed in the side wall of the sealing portion 602 or in the supporting portion 606. The support structure 604 may have a varying width as illustrated, or may have a constant width. Three support structure 604 may be in the shape of a ring.

As illustrated in FIG. 122-3, the support structure 604 may provide an additional contact on the patient's upper lip in use, and because the material of the support structure 604 is soft and conformable, it may provide additional comfort to the patient in use. Additionally, the support structure 604 may assist in providing a seal with the patient's upper lip. FIG. 122-2 illustrates the support structure 604 with a sealing portion that curves outward at its outer edges.

The cross-section of the foam ring may vary in different regions. For example in a tip of nose region, the foam ring may have a small cross-section and be readily able to flex to fit different sizes of nose. In a side of nose region, e.g. adapted to be located adjacent a crease region of a face, the foam ring may be thicker.

The foam ring may incorporate different densities of foam and vary the level of support in different regions.

FIG. 123 illustrates a cross-sectional view of an inwardly curving sealing portion 620. The ends of the sealing portion 620 have been lengthened so as to seal against the sides (flares) of the patient's nose and provide side support 622, rather than sealing just on the underside of the nose. This provides a more effective seal.

FIGS. 124 and 125 illustrate a top view of a patient interface 630 having a sealing portion 636 that includes nasal prongs 634 disposed on an upper surface 640 of the sealing portion 636. The nasal prongs 634 are adapted to form a seal with the patient's nares in use. A supporting portion 638 may be optionally included under the sealing portion.

As illustrated in FIG. 125, the sealing portion 636 may include support portions 642 disposed adjacent to the nasal prongs 634. The support portions may be foam or another suitable material, and are disposed in an area of the sealing portion 636 that interfaces with an upper lip and corners of the nose of the patient in use, to provide support and secure the sealing portion 636 and the nasal prongs 634 in place.

It is believed that a patient interface in accordance with the present technology is more able to accommodate different sizes and shapes of faces and noses than prior designs. It is believed that a patient interface in accordance with the present technology may reduce the need for inventory in different sizes. It is believed that a patient interface in accordance with the present technology can provide improved comfort for patents, and improved compliance with their therapy.

While the technology has been described in connection with what are presently considered to be the most practical and preferred embodiments, it is to be understood that the technology is not to be limited to the disclosed embodiments, but on the contrary, is intended to cover various modifications and equivalent arrangements included within the spirit and scope of the technology. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A positive airway pressure system for treatment of sleep disordered breathing, comprising:
    a mask with a seal portion that is shaped to seal with a face of a patient around nares of the patient when the mask is worn by the patient, the seal portion defining a first aperture to provide pressurized air from an interior of the mask to a nose of the patient, the seal portion comprising a hanging flexible membrane that surrounds the first aperture and includes:
        a nose tip engagement portion shaped to contact a tip of the nose of the patient when the mask is worn by the patient and being flexible toward a distal portion of the mask when the nose tip engagement portion contacts the nose of the patient;
        an upper lip engagement portion shaped to contact an upper lip region of the patient, a base of the nose of the patient, or both the upper lip region of the patient and the base of the nose of the patient;
        a first nostril engagement flap portion located between the nose tip engagement portion and the upper lip engagement portion on a first side of the mask, the first nostril engagement flap portion including a first stiffer portion integrally formed with the first nostril engagement flap portion, the first stiffer portion being more stiff than each of the nose tip engagement portion and the upper lip engagement portion; and
        a second nostril engagement flap portion located between the nose tip engagement portion and the upper lip engagement portion on a second side of the mask opposite from the first side of the mask, the second nostril engagement flap portion including a second stiffer portion integrally formed with the second nostril engagement flap portion, the second stiffer portion being more stiff than each of the nose tip engagement portion and the upper lip engagement portion; and
    headgear structured to maintain the mask in position on the face of the patient when the mask is worn by the patient, the headgear including:
        a first side headgear portion attachable to the mask at the first side of the mask so that the first side headgear portion extends between a first eye of the patient and a first ear of the patient on a first side of a head of the patient when the mask is worn by the patient; and
        a second side headgear portion attachable to the mask at the second side of the mask so that the second side headgear portion extends between a second eye of the patient and a second ear of the patient on a second side of the head of the patient opposite from the first side of the head of the patient when the mask is worn by the patient.

2. The positive airway pressure system of claim 1, wherein the headgear includes:
    a top headgear portion that both connects to the first headgear portion above the first ear of the patient and connects to the second headgear portion above the second ear of the patient when the mask is worn by the patient, and that passes over a top of the head of the patient when the mask is worn by the patient; and
    a back headgear portion that both connects to the first headgear portion above the first ear of the patient and connects to the second headgear portion above the second ear of the patient when the mask is worn by the patient, and that passes around a back of the head of the patient when the mask is worn by the patient.

3. The positive airway pressure system of claim 1, wherein the mask is shaped to not extend into nostrils of the patient when the mask is worn by the patient.

4. The positive airway pressure system of claim 3, wherein the seal portion forms a nasal cradle, and the mask avoids contact with a nasal bridge region of the patient when the mask is worn by the patient.

5. The positive airway pressure system of claim 4, wherein the first nostril engagement flap portion and the second nostril engagement flap portion are angled with respect to each other in a V-shaped orientation at a first angle of about 75-95 degrees.

6. The positive airway pressure system of claim 5, wherein:
the seal portion includes an annular supporting wall;
the first nostril engagement flap portion extends away from the annular supporting wall; and
the second nostril engagement flap portion extends away from the annular supporting wall.

7. The positive airway pressure system of claim 1, wherein:
the mask is connectable to an air-delivery conduit to receive pressurized air through a second aperture that is spaced apart from the first aperture, wherein the mask includes an interior surface between the first aperture and the second aperture that is in communication with pressurized air when pressurized air is provided to the mask from the air-delivery conduit; and
the hanging flexible membrane is a continuous extension of the interior surface that is in communication with pressurized air when pressurized air is provided to the mask from the air-delivery conduit.

8. The positive airway pressure system of claim 7, wherein the first aperture has a width of about 15-40 mm.

9. The positive airway pressure system of claim 8, wherein the first aperture has a height of about 5-15 mm, the width of the first aperture being greater than the height of the first aperture.

10. The positive airway pressure system of claim 9, wherein a length of the nose tip engagement portion between the first aperture and a periphery of the hanging flexible membrane is about 12-18 mm.

11. The positive airway pressure system of claim 1, wherein:
the first stiffer portion extends radially from the first aperture to a periphery of the hanging flexible membrane on the first side of the mask; and
the second stiffer portion extends radially from the first aperture to the periphery of the hanging flexible membrane on the second side of the mask.

12. The positive airway pressure system of claim 1, wherein:
the nose tip engagement portion includes a first flexible portion that is less stiff than each of the first stiffer portion and the second stiffer portion, the first flexible portion extending radially from the first aperture to a periphery of the hanging flexible membrane;
the upper lip engagement portion includes a second flexible portion that is less stiff than each of the first stiffer portion and the second stiffer portion, the second flexible portion extending radially from the first aperture to the periphery of the hanging flexible membrane; and
each of the first flexible portion and the second flexible portion are located between the first stiffer portion and the second stiffer portion.

13. The positive airway pressure system of claim 1, wherein the first stiffer portion and the second stiffer portion are more stiff than each of the nose tip engagement portion and the upper lip engagement portion due to both the first stiffer portion having a greater thickness than each of the nose tip engagement portion and the upper lip engagement portion and the second stiffer portion having greater thickness than each of the nose tip engagement portion and the upper lip engagement portion.

14. The positive airway pressure system of claim 1, wherein the hanging flexible membrane comprises varying materials, with the first stiffer portion and the second stiffer portion comprising a harder material than the nose tip engagement portion and the upper lip engagement portion.

15. The positive airway pressure system of claim 1, wherein:
the first stiffer portion is located within the seal portion to seal with a portion of the nose of the patient adjacent a first nasal labial crease of the patient when the mask is worn by the patient; and
the second stiffer portion is located within the seal portion to seal with a portion of the nose of the patient adjacent a second nasal labial crease of the patient when the mask is worn by the patient.

16. The positive airway pressure system of claim 1, wherein:
a thickness of the first stiffer portion is about 1-5 mm; and
a thickness of the second stiffer portion is about 1-5 mm.

17. The positive airway pressure system of claim 16, wherein:
the first stiffer portion has a radius of curvature of between about 2.4 mm-6 mm; and
the second stiffer portion has a radius of curvature of between about 2.4 mm-6 mm.

18. The positive airway pressure system of claim 1, wherein the first stiffer portion and the second stiffer portion define portions of the hanging flexible membrane having the greatest stiffness.

19. The positive airway pressure system of claim 1, wherein:
the mask includes a frame to which the seal portion is attached;
the first side headgear portion is attachable to the mask at a first side of the frame;
the second side headgear portion is attachable to the mask at a second side of the frame opposite from the first side of the frame;
the hanging flexible membrane is formed of silicone; and
the frame is more rigid than the hanging flexible membrane and is formed of a material different from silicone.

20. The positive airway pressure system of claim 1, wherein the mask is connectable to a first air delivery conduit at the first side of the mask and a second air delivery conduit at the second side of the mask.

21. The positive airway pressure system of claim 1, wherein the headgear includes means for connecting the first side headgear portion to the mask at the first side of the mask and means for connecting the second side headgear portion to the mask at the second side of the mask.

22. The positive airway pressure system of claim 21, wherein the seal portion includes means for varying stiffness among different portions of the hanging flexible membrane.

23. The positive airway pressure system of claim 22, wherein the mask includes a frame that is more rigid than the hanging flexible membrane, and the mask includes means for connecting the frame to the hanging flexible membrane.

24. The positive airway pressure system of claim 1, wherein the first aperture is shaped to provide pressurized air from the interior of the mask to both nares of the patient.

25. A positive airway pressure system for treatment of sleep disordered breathing, comprising:
a mask with a seal portion that is shaped to seal with a face of a patient around nares of the patient when the mask is worn by the patient, the seal portion defining a first aperture to provide pressurized air from an interior of the mask to a nose of the patient, the seal portion comprising a hanging flexible membrane that surrounds the first aperture and includes:
  a nose tip engagement portion shaped to contact a tip of the nose of the patient when the mask is worn by the patient and being flexible toward a distal portion of the mask when the nose tip engagement portion contacts the nose of the patient;
  an upper lip engagement portion shaped to contact an upper lip region of the patient, a base of the nose of the patient, or both the upper lip region of the patient and the base of the nose of the patient;
  a first nostril engagement flap portion located between the nose tip engagement portion and the upper lip engagement portion on a first side of the mask, the first nostril engagement flap portion including a first integrally molded thickened region that is more rigid than the nose-tip engagement portion; and
  a second nostril engagement flap portion located between the nose tip engagement portion and the upper lip engagement portion on a second side of the mask opposite from the first side of the mask, the second nostril engagement flap portion including a second integrally molded thickened region that is more rigid than the nose-tip engagement portion, and
headgear structured to maintain the mask in position on the face of the patient when the mask is worn by the patient, the headgear including:
  a first side headgear portion attachable to the mask at the first side of the mask so that the first side headgear portion extends between a first eye of the patient and a first ear of the patient on a first side of a head of the patient when the mask is worn by the patient; and
  a second side headgear portion attachable to the mask at the second side of the mask so that the second side headgear portion extends between a second eye of the patient and a second ear of the patient on a second side of the head of the patient opposite from the first side of the head of the patient when the mask is worn by the patient.

26. The positive airway pressure system of claim 25, wherein:
  the mask is shaped to not extend into nostrils of the patient when the mask is worn by the patient; and
  the seal portion forms a nasal cradle, and the mask avoids contact with a nasal bridge region of the patient when the mask is worn by the patient.

27. A positive airway pressure system for treatment of sleep disordered breathing, comprising:
  a mask with a seal portion that is shaped to seal with a face of a patient around nares of the patient when the mask is worn by the patient, the seal portion defining a first aperture to provide air from an interior of the mask to a nose of the patient, the mask being shaped to not extend into nostrils of the patient when the mask is worn by the patient and being shaped to avoid contact with a nasal bridge region of the patient, the mask defining a second aperture that is spaced apart from the first aperture and through which the mask is adapted to receive pressurized air from an air-delivery conduit that is attachable to the mask at the second aperture, the mask including an interior surface between the first aperture and the second aperture that is in communication with pressurized air when pressurized air is provided to the mask through the second aperture from the air-delivery conduit, wherein the seal portion comprises a hanging flexible membrane that surrounds the first aperture and includes:
    a nose tip engagement portion shaped to contact a tip of the nose of the patient when the mask is worn by the patient and being flexible toward a distal portion of the mask when the nose tip engagement portion contacts the nose of the patient;
    an upper lip engagement portion shaped to contact an upper lip region of the patient, a base of the nose of the patient, or both the upper lip region of the patient and the base of the nose of the patient;
    a first nostril engagement flap portion located between the nose tip engagement portion and the upper lip engagement portion on a first side of the mask, the first nostril engagement flap portion including a first stiffer portion that is more stiff than the nose tip engagement portion and more stiff than the upper lip engagement portion; and
    a second nostril engagement flap portion located between the nose tip engagement portion and the upper lip engagement portion on a second side of the mask opposite from the first side of the mask, the second nostril engagement flap portion including a second stiffer portion that is more stiff than the nose tip engagement portion and more stiff than the upper lip engagement portion,
    wherein the hanging flexible membrane is a continuous extension of the interior surface that is in communication with pressurized air when pressurized air is provided to the mask from the air-delivery conduit; and
  headgear structured to maintain the mask in position on the face of the patient when the mask is worn by the patient, the headgear including:
    a first side headgear portion attachable to the mask at the first side of the mask so that the first side headgear portion extends between a first eye of the patient and a first ear of the patient on a first side of a head of the patient when the mask is worn by the patient;
    a second side headgear portion attachable to the mask at the second side of the mask so that the second side headgear portion extends between a second eye of the patient and a second ear of the patient on a second side of the head of the patient opposite from the first side of the head of the patient when the mask is worn by the patient;
    a top headgear portion that both connects to the first headgear portion above the first ear of the patient and connects to the second headgear portion above the second ear of the patient when the mask is worn by the patient, and that passes over a top of the head of the patient when the mask is worn by the patient; and
    a back headgear portion that both connects to the first headgear portion above the first ear of the patient and connects to the second headgear portion above the second ear of the patient when the mask is worn by the patient, and that passes around a back of the head of the patient when the mask is worn by the patient.

28. The positive airway pressure system of claim 27, wherein:
  the first stiffer portion extends radially from the first aperture to a periphery of the hanging flexible membrane on the first side of the mask; and the second stiffer portion extends radially from the first aperture to the periphery of the hanging flexible membrane on the second side of the mask.

\* \* \* \* \*

UNITED STATES PATENT AND TRADEMARK OFFICE
CERTIFICATE OF CORRECTION

PATENT NO. : 10,974,009 B2
APPLICATION NO. : 16/922354
DATED : April 13, 2021
INVENTOR(S) : Adam Francis Barlow et al.

It is certified that error appears in the above-identified patent and that said Letters Patent is hereby corrected as shown below:

On the Title Page

Column 1, (72) Inventors, Line 9, please replace "Stuebiger, Sydeny (AU); Peter Ross" with -- Stuebiger, Sydney (AU); Peter Ross --.

Page 2, Column 1, (30) Foreign Application Priority Data, please replace "201902359" with -- 2010902359 --.

In the Specification

In Column 1, Line 15, please replace "200902524" with -- 2009902524 --.

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*